US009914735B2

(12) United States Patent
Dahmann et al.

(10) Patent No.: US 9,914,735 B2
(45) Date of Patent: Mar. 13, 2018

(54) HETEROARYL SYK INHIBITORS

(71) Applicant: Boehringer Ingelheim International GmbH, Ingelheim am Rhein (DE)

(72) Inventors: Georg Dahmann, Biberach (DE); Matthias Hoffmann, Mittelbiberach (DE); Jasna Klicic, Geneva (CH); David James Lamb, Mittelbiberach (DE); Clive McCarthy, Wantage (GB); Spencer Charles R. Napier, Abingdon (GB); Karen Parrish, Abingdon (GB); John Scott, Abingdon (GB); Jennifer L. Swantek Fitzgerald, Ridgefield, CT (US); Edward Walker, Didcot (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/027,518

(22) PCT Filed: Mar. 12, 2015

(86) PCT No.: PCT/EP2015/055228
§ 371 (c)(1),
(2) Date: Apr. 6, 2016

(87) PCT Pub. No.: WO2015/140051
PCT Pub. Date: Sep. 24, 2015

(65) Prior Publication Data
US 2016/0244446 A1    Aug. 25, 2016

Related U.S. Application Data

(60) Provisional application No. 61/955,487, filed on Mar. 19, 2014.

(51) Int. Cl.
| | |
|---|---|
| A61K 31/4184 | (2006.01) |
| C07D 487/04 | (2006.01) |
| C07D 413/12 | (2006.01) |
| C07D 417/12 | (2006.01) |
| C07D 498/04 | (2006.01) |
| C07D 513/04 | (2006.01) |

(Continued)

(52) U.S. Cl.
CPC .......... *C07D 487/04* (2013.01); *A61K 31/416* (2013.01); *A61K 31/4184* (2013.01); *A61K 31/427* (2013.01); *A61K 31/437* (2013.01); *A61K 31/444* (2013.01); *A61K 31/454* (2013.01); *A61K 31/4545* (2013.01); *A61K 31/496* (2013.01); *A61K 31/519* (2013.01); *A61K 31/5377* (2013.01); *A61K 31/55* (2013.01); *A61K 45/06* (2013.01); *C07D 401/14* (2013.01); *C07D 403/12* (2013.01); *C07D 403/14* (2013.01); *C07D 413/12* (2013.01); *C07D 417/12* (2013.01);

(Continued)

(58) Field of Classification Search
USPC ................. 514/210.21, 217, 230.5
See application file for complete search history.

(56) References Cited

U.S. PATENT DOCUMENTS

| | | |
|---|---|---|
| 2011/0201608 A1 | 8/2011 | Hoffmann et al. |
| 2011/0263549 A1 | 10/2011 | Fiegen et al. |

(Continued)

FOREIGN PATENT DOCUMENTS

| | | |
|---|---|---|
| JP | 2011529931 A | 12/2011 |
| WO | 0183485 A1 | 11/2001 |

(Continued)

OTHER PUBLICATIONS

International Search Report and Written Opinion for corresponding application PCT/EP2015/055228, dated May 6, 2015.

(Continued)

*Primary Examiner* — Pancham Bakshi
(74) *Attorney, Agent, or Firm* — Marc Began; Philip I. Datlow

(57) ABSTRACT

The invention relates to new substituted heteroaryls of formula (1), wherein A is selected from the group consisting of N and CH, D is CH, E is selected from the group consisting of C and N, T is C, G is selected from the group consisting of C and N, and wherein each of the broken (dotted) double bonds in ring 1 are selected from either a single bond or a double bond under the proviso that all single and double bonds of ring 1 are arranged in such a way that they all form together with ring 2 an aromatic ring system, and wherein $R^1$, M and $R^3$ are defined according to claim 1, and to the above compounds for the treatment of a disease selected from the group consisting of asthma, COPD, allergic rhinitis, allergic dermatitis, lupus erythematodes, lupus nephritis and rheumatoid arthritis.

10 Claims, No Drawings

(51) Int. Cl.

| | |
|---|---|
| *A61K 31/416* | (2006.01) |
| *A61K 31/427* | (2006.01) |
| *A61K 31/437* | (2006.01) |
| *A61K 31/444* | (2006.01) |
| *A61K 31/454* | (2006.01) |
| *A61K 31/4545* | (2006.01) |
| *A61K 31/496* | (2006.01) |
| *A61K 31/5377* | (2006.01) |
| *A61K 31/55* | (2006.01) |
| *A61K 45/06* | (2006.01) |
| *C07D 401/14* | (2006.01) |
| *C07D 403/12* | (2006.01) |
| *C07D 403/14* | (2006.01) |
| *C07D 417/14* | (2006.01) |
| *C07D 471/04* | (2006.01) |
| *C07D 519/00* | (2006.01) |
| *A61K 31/519* | (2006.01) |

(52) U.S. Cl.
CPC ......... *C07D 417/14* (2013.01); *C07D 471/04* (2013.01); *C07D 498/04* (2013.01); *C07D 513/04* (2013.01); *C07D 519/00* (2013.01)

(56) References Cited

U.S. PATENT DOCUMENTS

| | | |
|---|---|---|
| 2012/0028939 A1 | 2/2012 | Hoffmann et al. |
| 2013/0029949 A1 | 1/2013 | Hoffmann et al. |
| 2015/0038488 A1* | 2/2015 | Currie ............. C07D 401/14 514/211.06 |
| 2015/0065489 A1 | 3/2015 | Hoffmann et al. |
| 2017/0008896 A1 | 1/2017 | Dahmann et al. |
| 2017/0073333 A1 | 3/2017 | Hoffmann et al. |

FOREIGN PATENT DOCUMENTS

| | | | |
|---|---|---|---|
| WO | 2010015520 A1 | 2/2010 | |
| WO | 2010027500 A1 | 3/2010 | |
| WO | 2011092128 A1 | 8/2011 | |
| WO | 2012123312 A1 | 9/2012 | |
| WO | 2013014060 A1 | 1/2013 | |
| WO | 2013182546 A1 | 12/2013 | |
| WO | 2015017610 A1 | 2/2015 | |
| WO | WO 2015/017610 A1 * | 2/2015 | ........... C07D 401/14 |
| WO | 2015140054 A1 | 9/2015 | |

OTHER PUBLICATIONS

ClinicalTrials.gov, identifier NCT00952588, last updated on Feb. 13, 2014: https://clinicaltrials.gov/ct2/show/results/NCT00952588?term=AZD1152&rank=7&sect=X430156#othr <https://clinicaltrials.gov/ct2/show/results/NCT00952588?term=AZD1152&rank=7&sect=X430156%23othr>.

Gilliland et al., "The roles of FLT3 in hematopoiesis and leukemia", Blood, 2002, 100, pp. 1532-1542.

Wander et al., "The evolving role of FLT3 inhibitors in acute myeloid leukemia: quizartinib and beyond", Ther Adv Hematol., 2014, 5:, pp. 65-77.

Yang et al., "AZD1152, a novel and selective aurora B kinase inhibitor, induces growth arrest, apoptosis, and sensitization for tubulin depolymerizing agent or topoisomerase II inhibitor in human acute leukemia cells in vitro and in vivo", Blood, 2007, vol. 110 No. 6, pp. 2034.

Thoma et al., "0rally bioavailable Syk inhibitors with activity in a rat PK/PD model", Bioorganic & Medicinal Chemistry Letters, 2016, vol. 25. No. 20., pp. 4642-4647.

* cited by examiner

HETEROARYL SYK INHIBITORS

The invention relates to new substituted heteroaryls of formula 1

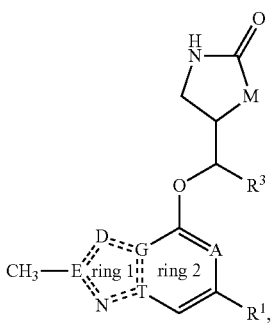

or of formula 1'

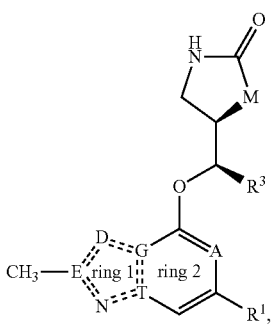

wherein
A is selected from the group consisting of N and CH
D is CH,
E is selected from the group consisting of C and N,
T is C,
G is selected from the group consisting of C and N,
and wherein each of the broken (dotted) double bonds in ring 1 are selected from either a single bond or a double bond under the proviso that all single and double bonds of ring 1 are arranged in such a way that they all form together with ring 2 an aromatic ring system,
and wherein
M, $R^3$ and $R^1$ are defined as in claim 1. Further the invention relates to the above compounds of formula 1 or of formula 1' for the treatment of a disease selected from the group consisting of asthma, COPD, allergic rhinitis, allergic dermatitis, lupus erythematodes, lupus nephritis and rheumatoid arthritis.

1. BACKGROUND TO THE INVENTION

1.1 SYK-Inhibitors

The present invention describes new compounds that inhibit the protein kinase Syk (spleen tyrosine kinase), the preparation and formulation thereof and their use for preparing a medicament.

Syk is an intracellular tyrosine kinase that has an important mediator function in the signal transduction of different receptors in B-cells, mast cells, monocytes, macrophages, neutrophils, T-cells, dendritic cells and epithelial cells. The receptors in which Syk performs an important function in signal transduction include for example the receptors for IgE (FcεRI) and IgG (FcγR1) on mast cells and B cells, the B-cell receptor (BCR) and the T-cell receptor (TCR) on B- and T-cells, the ICAM1 receptor (ICAM1R) on epithelial cells of the respiratory tract, the DAP12-receptor on natural killer cells, dendritic cells and osteoclasts, the dectin 1-receptor on a subpopulation of T-helper cells (Th-17 cells), as well as the integrin receptors for β1-, β2- and β3-integrins on neutrophils, monocytes and macrophages (Wong et al.; Expert Opin. Investig. Drugs (2004) 13(7), 743-762; Ulanova et al.; Expert Opion. Ther. Target (2005) 9(5); 901-921; Wang et al.; J. Immunol. (2006) 177, 6859-6870; Leib und Gut-Landmann et al.; Nature Immunology (2007) 8, 630-638; Slack et al., European J. Immunol. (2007) 37, 1600-1612). The molecular processes are described best for the signal transduction of the FcεRI. In mast cells the binding of IgE to FcεRI causes the cross-linking of IgE-receptors and the recruiting and activation of Lyn (a tyrosine kinase from the Src family). Active Lyn phoshorylates so-called ITAM motifs, which are present in many of the receptors listed above, and thereby generates binding sites for the SH2-domain of Syk. As a result of the binding to the ITAM motif Syk is activated and then phosphorylates various substrates which are needed for the release of allergic and inflammatory mediators such as e.g. histamine and β-hexosamidase (βHA), as well as for the synthesis of lipid mediators, such as e.g. prostaglandins and leukotrienes.

In view of its central function in different signal transduction pathways Syk has been discussed as a therapeutic target for different diseases such as e.g. allergic rhinitis, asthma, autoimmune diseases, rheumatoid arthritis, osteopenia, osteoporosis, COPD and various leukaemias and lymphomas (Wong et al.; Expert Opin. Investig. Drugs (2004) 13(7), 743-762; Ulanova et al.; Expert Opin. Ther. Target (2005) 9(5); 901-921; Sigh and Masuda. Annual Reports in Medicinal Chemistry (2007) Vol 42; 379-391; Bajpai et al.; Expert Opin. Investig. Drugs (2008) Vol 15 (5); 641-659; Masuda and Schmitz; PPT (2008) Vol 21; 461-467; Riccaboni et al., Drug Discovery Today (2010) Vol 00 (0); 517-530; Efremov and Luarenti, Expert Opin Investig Drugs. (2011) 20(5):623-36).

Allergic rhinitis and asthma are diseases associated with allergic reactions and inflammatory processes and involving different cell types such as e.g. Mast cells, eosinophils, T-cells and dendritic cells. After exposure to allergens has occurred, the high affinity immunoglobulin receptors for IgE (FcεRI) and IgG (FcγR1) are activated and induce the release of pro-inflammatory mediators and bronchoconstrictors. An inhibitor of the Syk kinase activity should thus be able to inhibit these steps.

Rheumatoid arthritis (RA) is an autoimmune disease in which the bones and ligaments structures surrounding the joints are progressively destroyed. In the pathophysiology of RA, B-cells play a significant role, as has been demonstrated for example by the therapeutic use of rituximab, a B cell-depleting antibody. In addition to the function of Syk in the signal transduction of the BCR (which after being stimulated also induces the release of pro-inflammatory mediators), Syk also plays an important part in the maturation and proliferation of B cells (Cheng et al. Nature (1995) 378, 303-306, Cornall et al., PNAS (2000) 97(4), 1713-1718). An inhibitor of the Syk kinase activity may thus offer a therapeutic option for the treatment of autoimmune diseases such as RA and diseases with an increased proliferation of B cells, such as e.g. B-cell lymphomas.

Chronic obstructive pulmonary disease (COPD) is characterised by a successive deterioration in lung function and chronic inflammation of the airways, which is initiated and produced by noxious substances of all kinds and contributes to the maintenance of the course of the disease. At a cellular level, in COPD there is in particular a multiplication of T-lymphocytes, neutrophils, granulocytes and macrophages. In particular, there is an increase in the number of CD8-positive lymphocytes, that is directly connected with the impairment of lung function. Another characteristic of COPD are acute deteriorations in lung function (exacerbations), characterised by viral (e.g. Rhinovirus), or bacterial (e.g. *Streptococcus pneumoniae, Haemophilus influenzae* and *Moraxella catarrhalis*) infections.

In view of the pro-inflammatory function of Syk in macrophages, T-cells and neutrophils as described above (see: Wong et al.; Expert Opin. Investig. Drugs (2004) 13(7), 743-762; and references cited therein) an inhibitor of the Syk kinase activity could be a new therapeutic approach to the treatment of the inflammatory processes that underlie COPD. It has also been shown that Syk in epithelial cells of the respiratory tract is involved in the ICAM1R-mediated uptake and subsequent replication of the Rhinovirus and that a si-RNA against Syk blocks these steps (Wang et al.; J. Immunol. (2006) 177, 6859-6870; Lau et al.; J. Immunol. (2008) 180, 870-880). Thus, an inhibitor of the Syk kinase activity could also be used therapeutically in exacerbations caused by Rhinoviruses.

Various studies suggest that Syk is involved in the malignant transformation of lymphocytes (summarised in Sigh and Masuda, Annual Reports in Medicinal Chemistry (2007) Vol 42; 379-391). A TEL-Syk fusion protein with a constitutive Syk activity transformed B cells of a patient with myelodysplastic syndrome, a constitutively active ITK-Syk fusion protein was isolated from patients with peripheral T-cell lymphomas (PTCL). Moreover, constitutively active Syk was found in B-cell lymphoma cells of patients, especially in B-lineage acute lymphoblastic leukemia (B-ALL), follicular lymphoma (FL), diffuse large B-cell lymphoma (DLBCL), mantle cell lymphomas and B cell Non-Hodgkin Lymphomas (NHLs) as well as in acute myeloid leukemia (AML). On the basis of these data it seems that Syk is a proto-oncogene in haematopoietic cells and represents a potential target for the treatment of certain leukaemias and lymphomas.

Idiophathic thrombocytopenic purpura (ITP) is an autoimmune disease in which IgG autoantibodies against antigens present on platelets bind to and destroy platelets. Patients with ITP have an accelerated clearence of circulating IgG-coated platelets via macrophages in the spleen and the liver. In view of the pro-inflammatory FcγR-mediated function of Syk in macrophages an inhibitor of Syk is considered to have a therapeutic benefit in FcγR-mediated cytopenias like ITP. Indeed the Syk inhibitor R788 (R406) improved platelet counts in a single center, oben label study in patients with ITP (Podolanczuk et al; Blood (2009) 113, 3154-3169).

Bullous pemphigoid (Ujiie et al. Journal of Dermatology 2010; 37: 194-204) is a chronic, autoimmune, subepidermal, blistering skin disease that rarely involves mucous membranes. Bullous pemphigoid is characterized by the presence of immunoglobulin G (IgG) autoantibodies specific for the hemidesmosomal bullous pemphigoid antigens BP230 (BPAg1) and BP180 (BPAg2). Pemphigus vulgaris (Venugopal et al. Dermatol. Clin. 2011; 29:373-80) is a chronic blistering skin disease with skin lesions that are rarely pruritic, but which are often painful. Pemphigus vulgaris is an autoimmune disease caused by IgG autoantibodies directed against both desmoglein 1 and desmoglein 3 resulting in the loss of cohesion between keratinocytes in the epidermis. It is characterized by extensive flaccid blisters and mucocutaneous erosions. In both diseases IgG autoantibodies bind to Fc receptor gamma (FcRγ) and activate FcRγ and downstream signaling via Syk kinase. Thus, an inhibitor of the Syk kinase activity which blocks downstream signalling of the FcRg could be used therapeutically to treat patients with bullous pemphigoid and pemphigus vulgaris.

Systemic lupus erythematosus (SLE) is a chronic autoimmune disease which can affect basically any organ of the body. It is characterised by a multisystem inflammation of the microvascular and the presence of autoantibodies. FcγR-deficient mice are protected from several aspects of SLE in disease-related preclinical models, suggesting that an inhibitor of Syk can have a therapeutic benefit in SLE in view of the pro-inflammatory FcγR-mediated function of Syk in various cells.

1.2 Prior Art 1,6-Naphthyridines are known as SYK-inhibitors. For example U.S. Pat. No. 3,928,367, U.S. Pat. No. 4,017,500, U.S. Pat. No. 4,115,395 and U.S. Pat. No. 4,260,759 describe 5-amino-1,6-naphthyridines with an antifungal and antibacterial activity. Further, WO 9918077 describes 5-piperazinyl-1,6-naphthyridines as serotonin antagonists. Additionally, U.S. Pat. No. 7,321,041 describes substituted 1,6-naphthyridines as SYK-inhibitors, however these 1,6-naphthyridines have a completely different substitution pattern from the compounds according to the invention. Also WO 2011092128 discloses 1,6-naphthyridines which are substituted in 5- and in 7-position.

In WO 2012/167733, WO 2012/167423 and in WO 2012/123312 other naphthryidine derivatives such as pyrido[3,4-b]pyrazines which were also substituted in 5- and in 7-position have been disclosed as SYK-inhibitors.

Additionally, WO 01/83485 discloses substituted imidazopyrimidines and triazolopyrimidines as SYK-inhibitors, whereas WO 2008/113469 discloses substituted imidazo- and triazolopyrimidines as GSK 3β-inhibitors.

Also quinolones are known as SYK-inhibitors. For instance, WO 2006038041 and WO 2013014060 both disclose quinoline-compounds which are substituted in the 5- and 7-position, however the substitution pattern—in particular in the 7-position—is completely different from the one of the compounds of formula 1 of the instant invention.

Surprisingly it has now been found that the compounds of formulas 1 and 1' and in particular the compounds of formulas 1a, 1a', 1c, 1c', are particularly suitable for the treatment of respiratory complaints, allergic diseases, osteoporosis, gastrointestinal diseases, autoimmune diseases, inflammatory diseases and diseases of the peripheral or central nervous system, particularly for the treatment of asthma, allergic rhinitis, rheumatoid arthritis, allergic dermatitis, lupus erythematosus (SLE) and COPD, in particular because all these compounds of the present invention show the following desired capacities:

high SYK inhibition (reflected by "low" $IC_{50}$-values with respect to SYK-inhibition)

very low inhibition of the kinase Aurora B (reflected by "high" $IC_{50}$-values with respect to inhibition of AURB)

low inhibition of the kinase FLT-3 (reflected by "high" $IC_{50}$-values with respect to inhibition of FLT-3)

low inhibition of the kinase GSK3β (reflected by "high" $IC_{50}$-values with respect to inhibition of GSK3β)

This was completely surprising for a person skilled in the art, since the compounds of formula 1 and 1' of the instant invention have several significant structural differences compared to the previously known prior art compounds. For instance the compounds of formula 1 and 1' of the instant invention differ from the previously known 1,6-naphthyridines, quinolones, pyrido[3,4-b]pyrazines, imidazopyrimidines and triazolopyrimidines therein that they combine the following features:

they all possess diverse core modifications in the central bicyclic heteroaromatic ring system (for instance core modifications resulting in benzopyrazoles etc.)
that they all have a methyl-group-substitution attached to position E in formula 1 and/or 1' and
that they all possess a residue of formula T

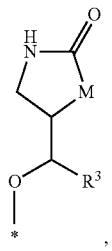

T preferably a residue of formula T'

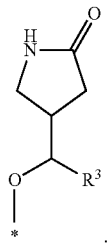

T'

2. DESCRIPTION OF THE INVENTION

The present invention concerns compounds of formula 1 wherein
A is selected from the group consisting of N and CH
D is CH
E is selected from the group consisting of C and N,
T is C
G is selected from the group consisting of C and N,
and wherein each of the broken (dotted) double bonds in ring 1 are selected from either a single bond or a double bond under the proviso that all single and double bonds of ring 1 are arranged in such a way that they all form together with ring 2 an aromatic ring system,
and wherein
M is selected from the group consisting of —CH$_2$—, —O—, —NH— and —N(C$_{1-4}$-alkyl)-;
R$^3$ is selected from the group consisting of methyl and ethyl;
Het is selected from the group consisting of
a five- to six-membered monocyclic heterocycle with 1, 2, 3 or 4 heteroatoms each independently from one another selected from N, S and O,
and a nine- to eleven-membered bicyclic heterocycle with 1, 2, 3 or 4 heteroatoms each independently from one another selected from N, S and O;
Hetaryl is selected from the group consisting of
a five- to six-membered monocyclic heteroaromate with 1, 2, 3 or 4 heteroatoms each independently from one another selected from N, S and O;
and a nine- to eleven-membered bicyclic heteroaromate with 1, 2, 3 or 4 heteroatoms each independently from one another selected from N, S and O;
and wherein
R$^1$ is selected from the group consisting of
C$_{6-10}$-aryl, Het and Hetaryl;
which is optionally further substituted by one, two or three substituents Z,
whereby each Z is a substituent selected from the group consisting of
—OH, oxo, —CN, halogen, —C$_{1-6}$-alkyl, —O—C$_{1-6}$-alkyl, —C$_{1-6}$-haloalkyl, three- to seven-membered cycloalkyl, Het, Hetaryl, —CO—N(CH$_3$)$_2$, —CO—NHCH$_3$, —CO—NH$_2$, —(C$_{1-3}$-alkylene)-O—(C$_{1-3}$-alkyl), —O-Het,
which is optionally further substituted by one, two or three substituents X,
whereby each X is selected from the group consisting of halogen, —OH, oxo, —C$_{1-4}$-alkyl, —O—C$_{1-4}$-alkyl, —C$_{1-4}$-haloalkyl, —O—(C$_{1-4}$-alkylene)-Het, Het, Hetaryl, —NH$_2$, —NH(CH$_3$), —N(CH$_3$)$_2$,
whereby substituent X is optionally further substituted by one, two or three substituents of a group selected from oxo, —OH, halogen and C$_{1-3}$-alkyl,
and the pharmaceutically acceptable salts of the aforementioned compounds.

A preferred embodiment of the instant invention relates to the aforementioned compounds of formula 1'

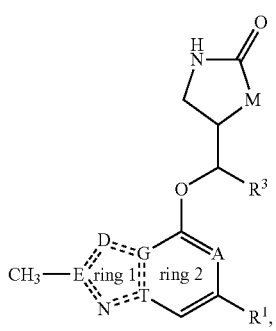

1

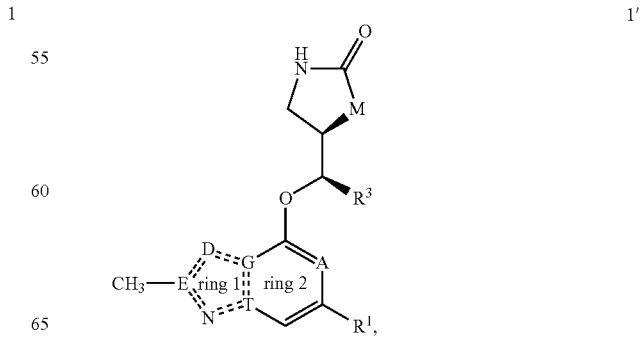

1' wherein residues A, D, E, T, G, Het, Hetaryl, $R^1$ and $R^3$ are defined as mentioned above, and the pharmaceutically acceptable salts of the aforementioned compounds.

In a further preferred embodiment the instant invention concerns the aforementioned compounds of formula 1 or of formula 1', wherein D is CH, and wherein E is N and wherein M is —CH$_2$— and wherein $R^3$ is methyl, and wherein

G is C (carbon)

$R^1$ is selected from the group consisting of phenyl, Het and Hetaryl;

which is optionally further substituted by one, two or three substituents Z, whereby each Z is a substituent selected from the group consisting of —OH, oxo, —CN, halogen, —C$_{1-6}$-alkyl, —O—C$_{1-6}$-alkyl, —C$_{1-6}$-haloalkyl, three- to seven-membered cycloalkyl, Het, Hetaryl, —CO—N(CH$_3$)$_2$, —CO—NHCH$_3$, —CO—NH$_2$, —(C$_{1-3}$-alkylene)-O—(C$_{1-3}$-alkyl), —O-Het, which is optionally further substituted by one, two or three substituents X, whereby each X is selected from the group consisting of halogen, oxo, —C$_{1-4}$-alkyl, —O—C$_{1-4}$-alkyl, —C$_{1-4}$-haloalkyl, —O—(C$_{1-4}$-alkylene)-Het, Het, Hetaryl, —NH$_2$, whereby substituent X is optionally further substituted by one, two or three substituents of a group selected from oxo, methyl, ethyl, n-propyl, isopropyl, n-butyl, isobutyl and tert-butyl, and the pharmaceutically acceptable salts of the aforementioned compounds.

In another preferred embodiment the instant invention relates to the aforementioned compounds of formula 1a

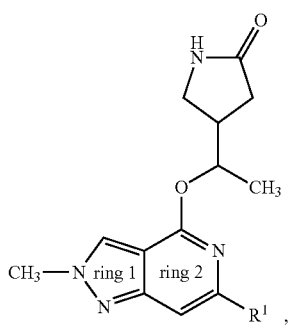

1a or of formula 1a'

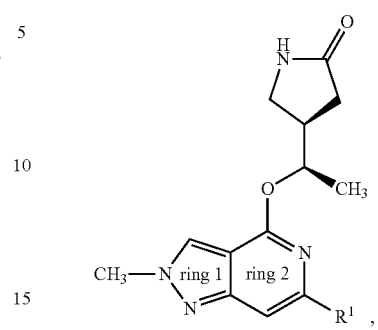

1a' wherein $R^1$ is selected from the group consisting of phenyl, Het and Hetaryl;

which is optionally further substituted by one, two or three substituents Z, whereby each Z is a substituent selected from the group consisting of —OH, oxo, —CN, halogen, —C$_{1-6}$-alkyl, —O—C$_{1-6}$-alkyl, —C$_{1-6}$-haloalkyl, three- to seven-membered cycloalkyl, Het, Hetaryl, —CO—N(CH$_3$)$_2$, —CO—NHCH$_3$, —CO—NH$_2$, —(C$_{1-3}$-alkylene)-O—(C$_{1-3}$-alkyl), —O-Het, which is optionally further substituted by one, two or three substituents X, whereby each X is selected from the group consisting of halogen, oxo, —C$_{1-4}$-alkyl, —O—C$_{1-4}$-alkyl, —C$_{1-4}$-haloalkyl, —O—(C$_{1-4}$-alkylene)-Het, Het, Hetaryl, —NH$_2$, whereby substituent X is optionally further substituted by one, two or three substituents of a group selected from oxo, methyl, ethyl, n-propyl, isopropyl, n-butyl, isobutyl and tert-butyl, and the pharmaceutically acceptable salts of the aforementioned compounds.

In a further preferred embodiment the invention relates to compounds of the above-mentioned formula 1a or of formula 1a', wherein $R^1$ is a) either selected from the group consisting of Het and Hetaryl;

which is optionally further substituted by one, two or three substituents Z, whereby each Z is a substituent selected from the group consisting of —OH, oxo, —CN, halogen, —C$_{1-6}$-alkyl, —O—C$_{1-6}$-alkyl, —C$_{1-6}$-haloalkyl, three- to seven-membered cycloalkyl, Het, Hetaryl, —CO—N(CH$_3$)$_2$, —CO—NHCH$_3$, —CO—NH$_2$, —(C$_{1-3}$-alkylene)-O—(C$_{1-3}$-alkyl), —O-Het, which is optionally further substituted by one, two or three substituents X, whereby each X is selected from the group consisting of halogen, oxo, —C$_{1-4}$-alkyl, —O—C$_{1-4}$-alkyl, —C$_{1-4}$-haloalkyl, —O—(C$_{1-4}$-alkylene)-Het, Het, Hetaryl, —NH$_2$, whereby substituent X is optionally further substituted by one, two or three substituents of a group selected from oxo, methyl, ethyl, n-propyl, isopropyl, n-butyl, isobutyl and tert-butyl, or wherein $R^1$ is b) phenyl, which is optionally further substituted by one, two or three substituents Z, whereby each Z is a substituent selected from the group consisting of, —CN, halogen, —C$_{1-6}$-alkyl, —(C$_{1-3}$-alkylene)-Hetaryl, —($C_{1-3}$-alkylene)-Het, —$C_{1-6}$-haloalkyl, three- to seven-membered cycloalkyl, Het, Hetaryl,
which is optionally further substituted by one, two or three substituents X,
whereby each X is selected from the group consisting of halogen, oxo and —$C_{1-4}$-alkyl,
and the pharmaceutically acceptable salts of the aforementioned compounds.

In another preferred embodiment the invention relates to compounds of the above-mentioned formula 1a or of formula 1a', wherein
$R^1$ is either
a monocyclic five- to six-membered heteroaromate with 1, 2 or 3 heteroatoms each independently from one another selected from the group consisting of N, O and S,
or a 9- to 11-membered bicyclic heteroaromate with 1, 2, 3 or 4 heteroatoms each independently from one another selected from the group consisting of N, O and S,
wherein this $R^1$-residue is attached to the rest of the molecule either via a C-atom or via an N-atom and is optionally further substituted by one, two or three substituents Z,
whereby each Z is a substituent selected from the group consisting of
—OH, oxo, —CN, halogen, -methyl, -ethyl, n-propyl, isopropyl, n-butyl, isobutyl, tert-butyl, —O—$C_{1-6}$-alkyl, —$C_{1-6}$-haloalkyl, three- to seven-membered cycloalkyl, Het, Hetaryl, —CO—N(CH$_3$)$_2$, —CO—NHCH$_3$, —CO—NH$_2$, —($C_{1-3}$-alkylene)-O—($C_{1-3}$-alkyl), —O-Het,
which is optionally further substituted by one, two or three substituents X,
whereby each X is selected from the group consisting of halogen, oxo, —$C_{1-4}$-alkyl, —O—$C_{1-4}$-alkyl, —$C_{1-4}$-haloalkyl, —O—($C_{1-4}$-alkylene)-Het, Het, Hetaryl, —NH$_2$,
whereby substituent X is optionally further substituted by one, two or three substituents of a group selected from oxo, methyl, ethyl, n-propyl, isopropyl, n-butyl, isobutyl and tert-butyl,
and the pharmaceutically acceptable salts of the aforementioned compounds.

In a further preferred embodiment the invention relates to the above compounds of the aforementioned formula 1a or formula 1a', wherein
$R^1$ is selected from the group consisting of pyridinyl, pyrimidinyl, pyrazinyl, pyrrolyl, imidazolyl, pyrazolyl, thiophenyl, furanyl, pyrazolopyridinyl, indazolyl, thiazolyl, imidazo-pyridinyl and indolyl,
wherein this $R^1$-residue is attached to the rest of the molecule either via a C-atom or via an N-atom and is optionally further substituted by one, two or three substituents Z,
whereby each Z is a substituent selected from the group consisting of
—OH, oxo, —CN, halogen, -methyl, -ethyl, n-propyl, isopropyl, n-butyl, isobutyl, tert-butyl, —O— methyl, —O-ethyl, O-propyl, O-butyl, —$C_{1-3}$-haloalkyl, three-, four, five- or six-membered cycloalkyl, Het, Hetaryl, —CO—N(CH$_3$)$_2$, —CO—NHCH$_3$, —CO—NH$_2$, —($C_{1-3}$-alkylene)-O—($C_{1-3}$-alkyl), —O-Het,
which is optionally further substituted by one, two or three substituents X,
whereby each X is selected from the group consisting of halogen, oxo, —$C_{1-4}$-alkyl, —O—$C_{1-4}$-alkyl, —$C_{1-4}$-haloalkyl, —O—($C_{1-4}$-alkylene)-Het, Het, Hetaryl, —NH$_2$,
whereby substituent X is optionally further substituted by one, two or three substituents of a group selected from oxo, methyl, ethyl, n-propyl, isopropyl, n-butyl, isobutyl and tert-butyl, and the pharmaceutically acceptable salts of the aforementioned compounds.

In another preferred embodiment the invention concerns the above compounds of the aformementioned formula 1a or of formula 1a', wherein
$R^1$ is phenyl,
which is optionally further substituted by one, two or three substituents Z,
whereby each Z is a substituent selected from the group consisting of
—OH, oxo, —CN, halogen, —$C_{1-6}$-alkyl, —O—$C_{1-6}$-alkyl, —$C_{1-6}$haloalkyl, three- to seven-membered cycloalkyl, Het, Hetaryl, —CO—N(CH$_3$)$_2$, —CO—NHCH$_3$, —CO—NH$_2$, —($C_{1-3}$-alkylene)-O—($C_{1-3}$-alkyl), —O-Het,
which is optionally further substituted by one, two or three substituents X,
whereby each X is selected from the group consisting of halogen, oxo, —$C_{1-4}$-alkyl, —O—$C_{1-4}$-alkyl, —$C_{1-4}$-haloalkyl, —O—($C_{1-4}$-alkylene)-Het, Het, Hetaryl, —NH$_2$,
whereby substituent X is optionally further substituted by one, two or three substituents of a group selected from oxo, methyl, ethyl, n-propyl, isopropyl, n-butyl, isobutyl and tert-butyl, and the pharmaceutically acceptable salts of the aforementioned compounds.

In a particularly preferred embodiment the instant invention relates to the above compounds of the aforementioned formula 1a or formula 1a', which is selected from the group consisting of

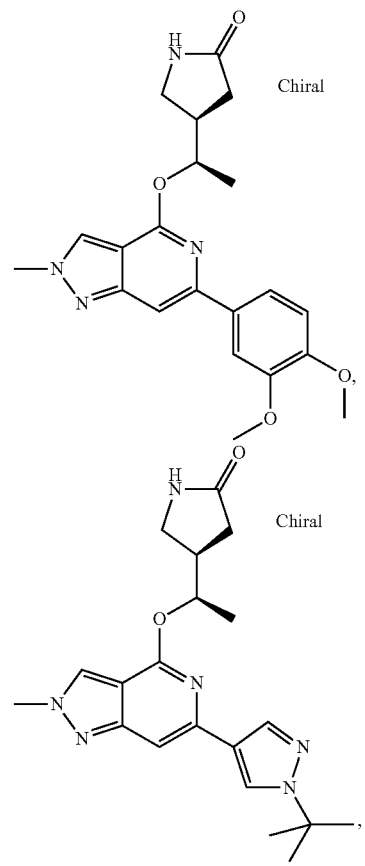

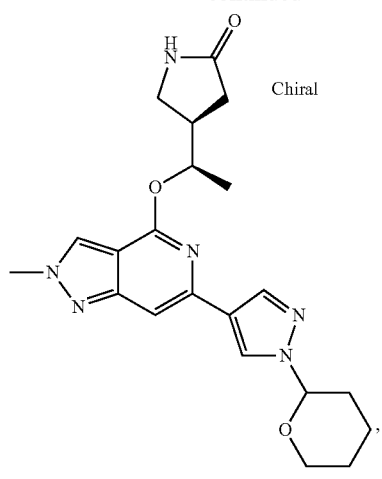
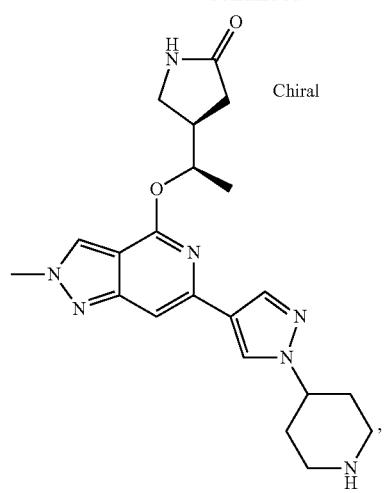
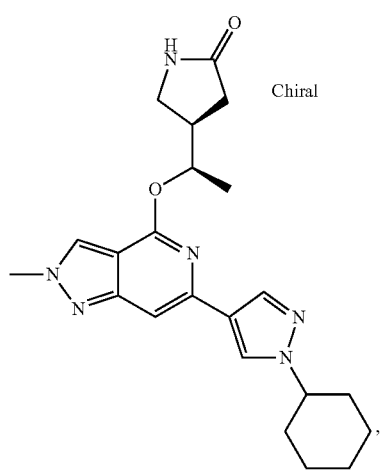
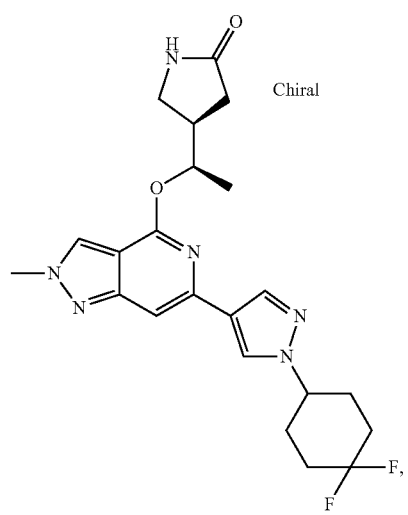
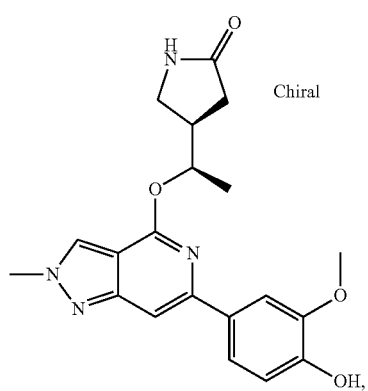
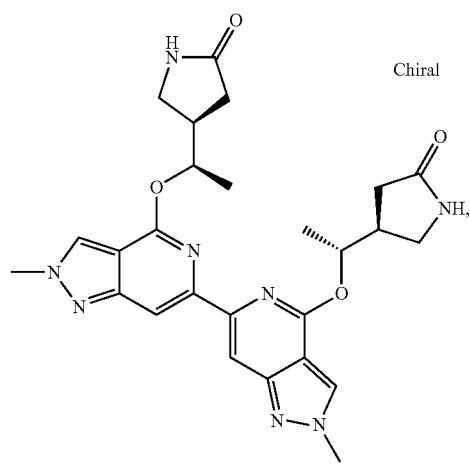

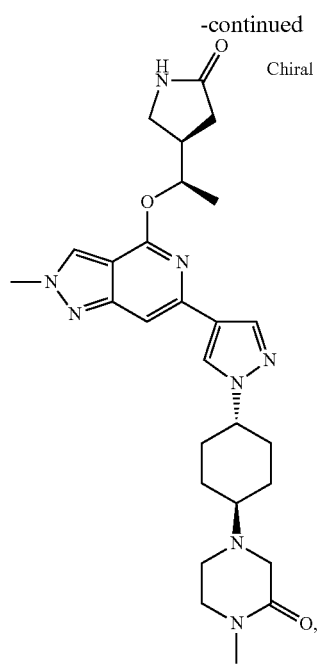
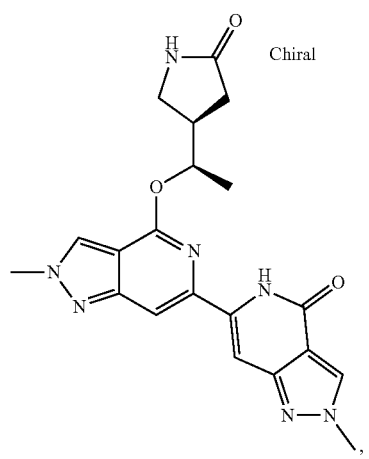
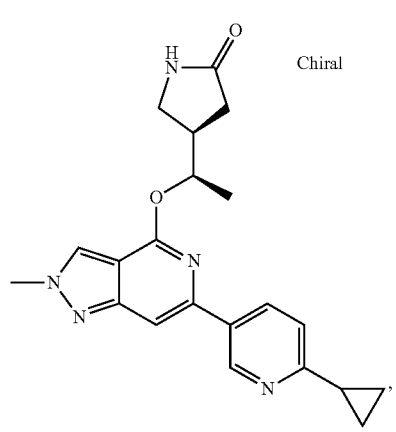
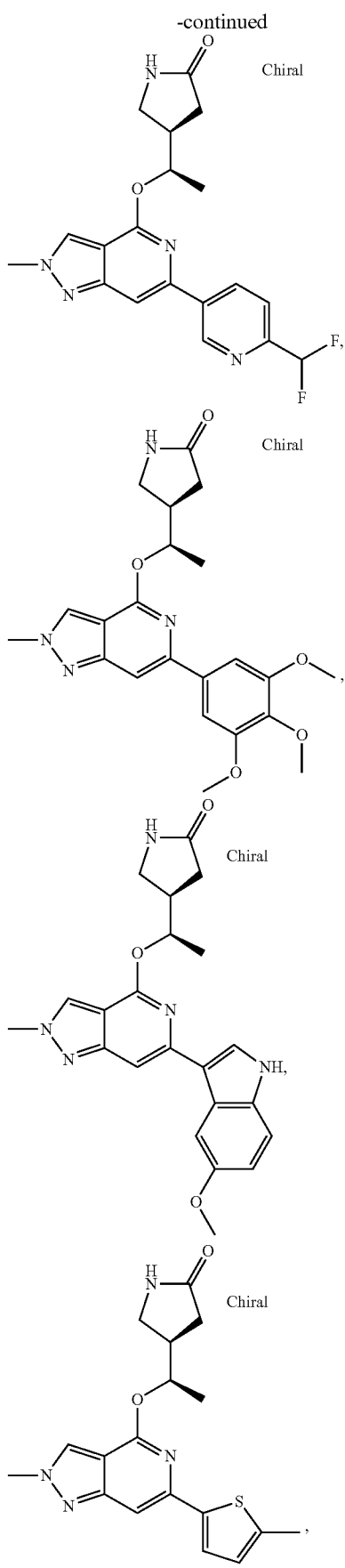

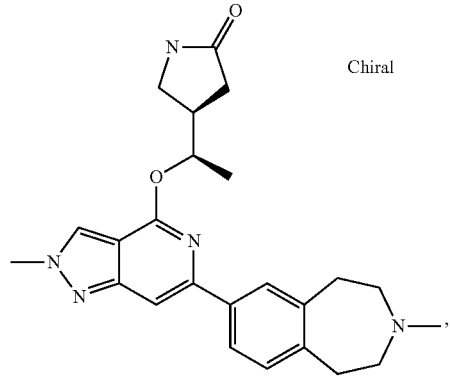
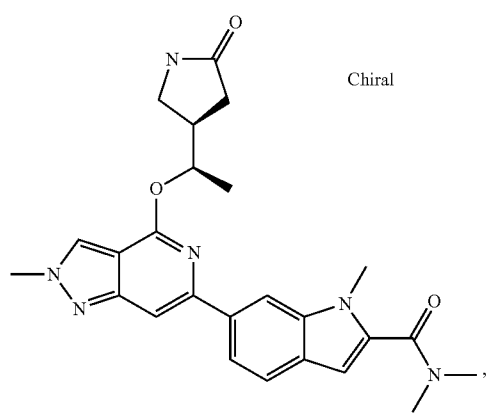
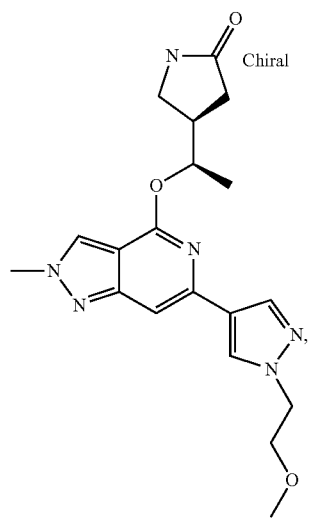
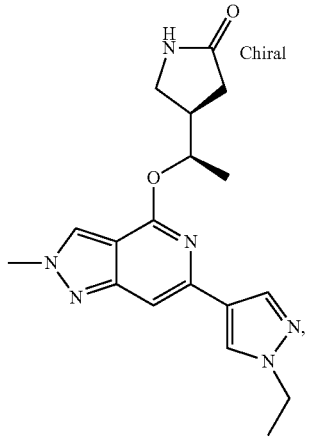
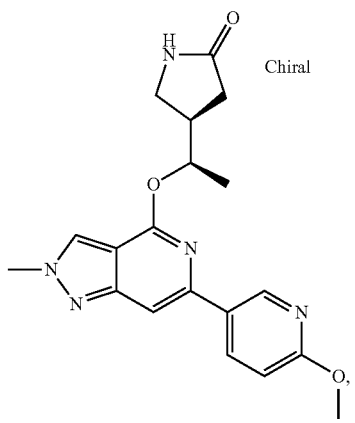
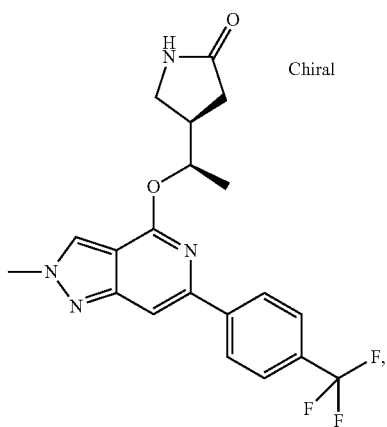
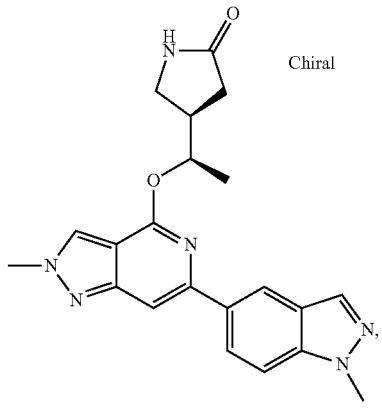

-continued
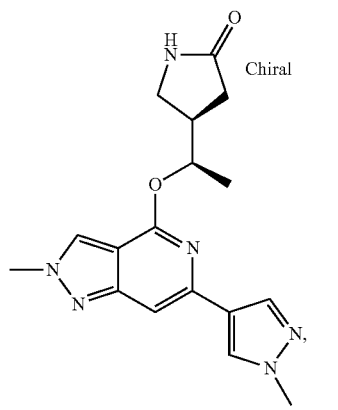
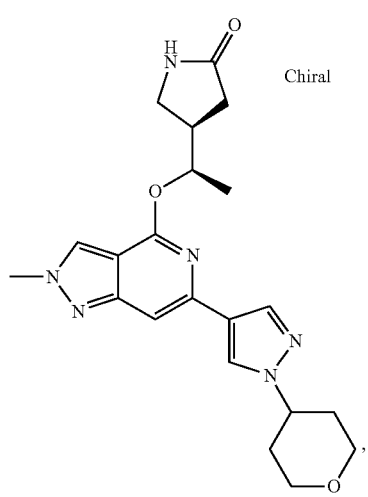
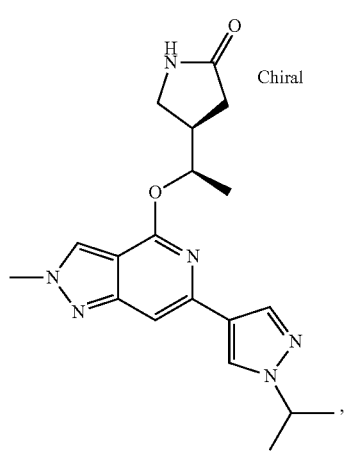
-continued
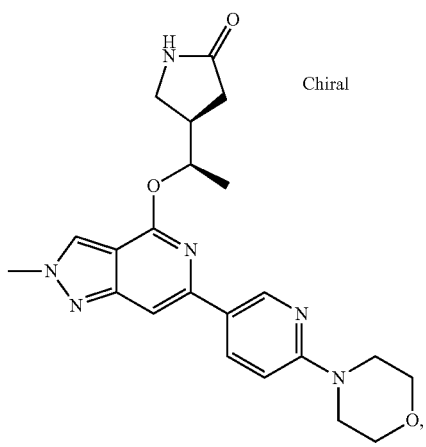
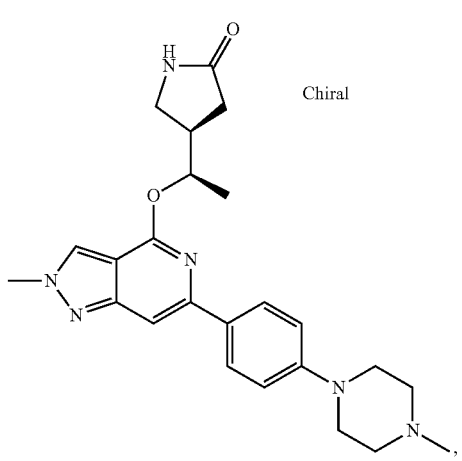
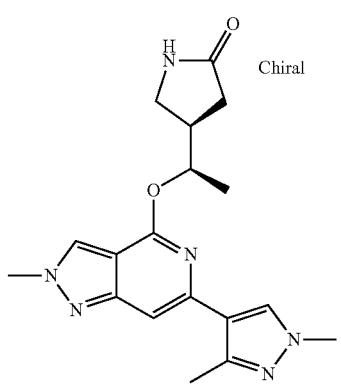
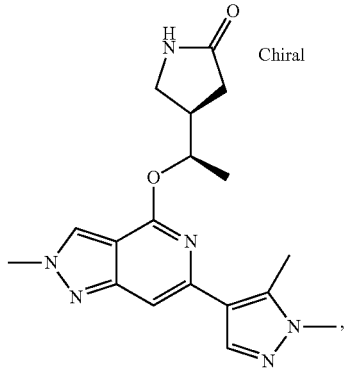

-continued
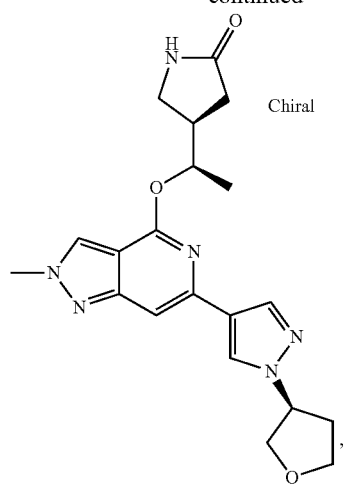
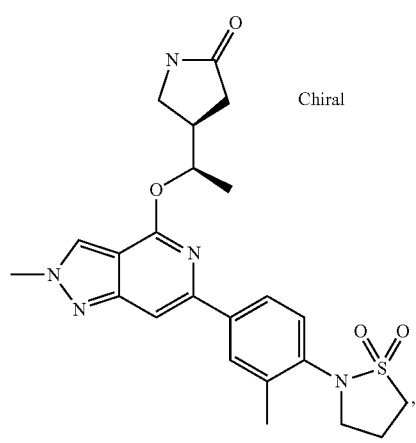
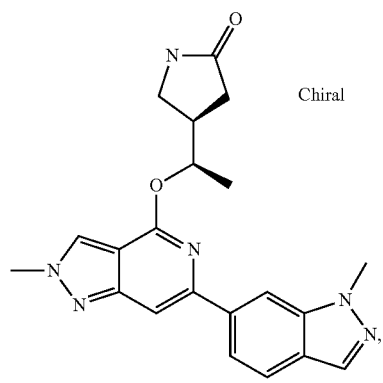
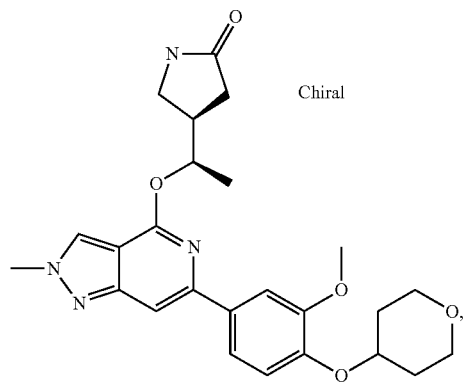
-continued
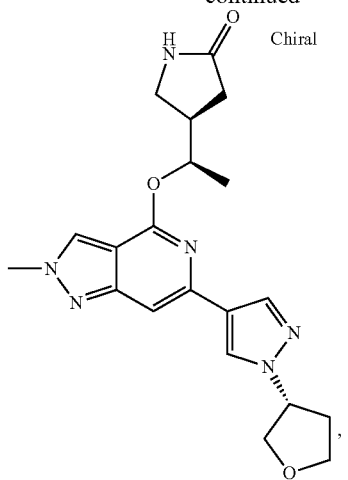
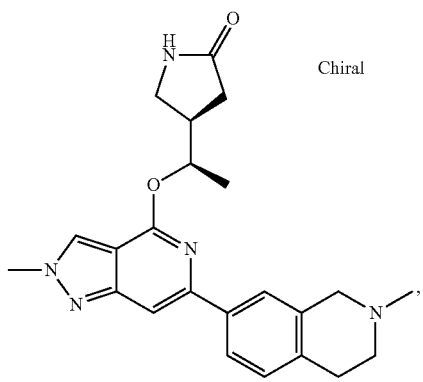
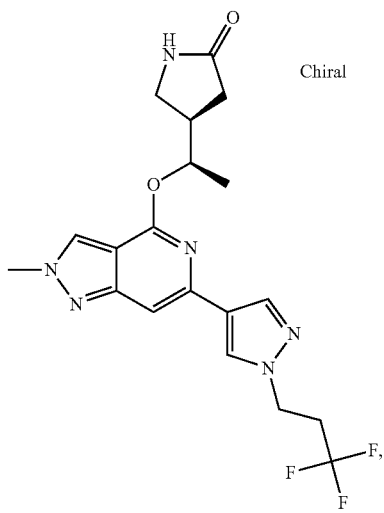

21
-continued
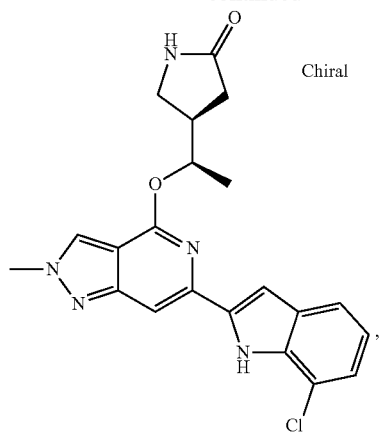
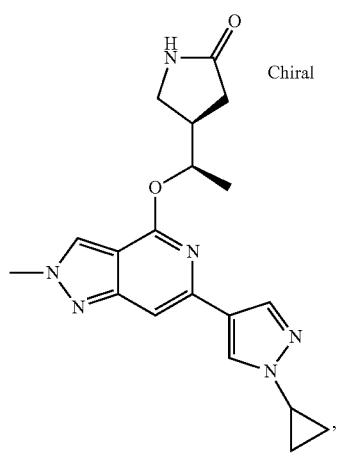
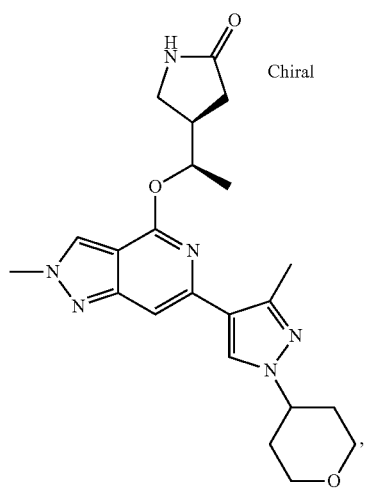
22
-continued
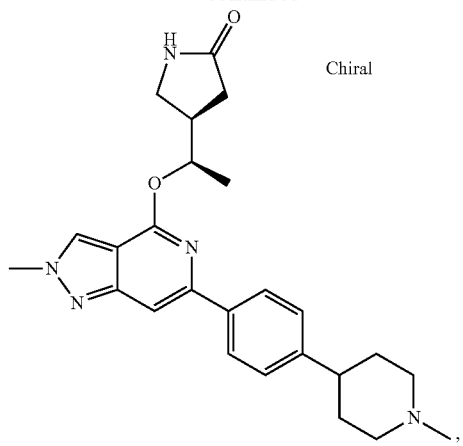
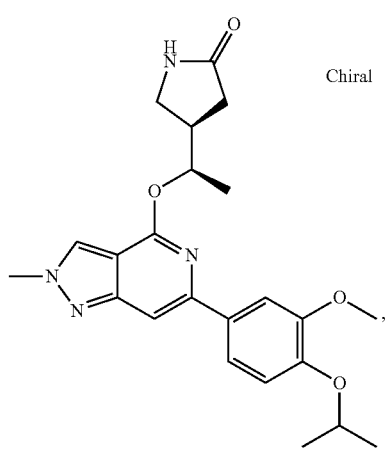
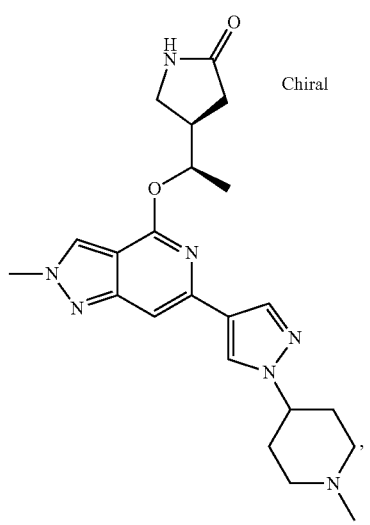

-continued

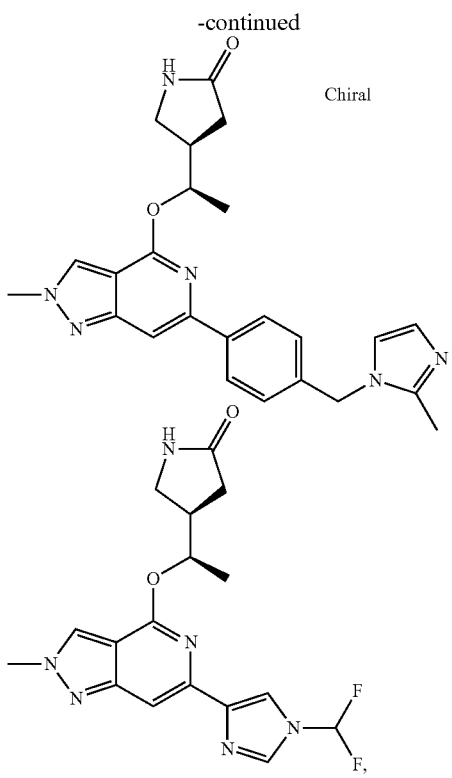

and the pharmaceutically acceptable salts of the aforementioned compounds.

In another preferred embodiment the instant invention concerns compounds of formula 1c

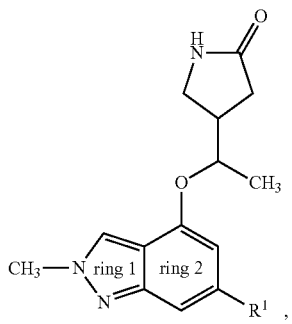

or of formula 1c'

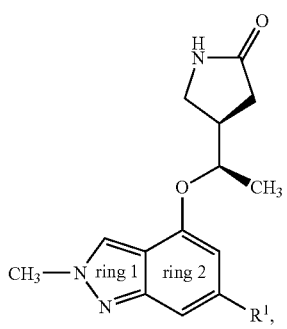

wherein
R$^1$ is selected from the group consisting of
phenyl, Het and Hetaryl;
which is optionally further substituted by one, two or three substituents Z,
whereby each Z is a substituent selected from the group consisting of
—OH, oxo, —CN, halogen, —C$_{1-6}$-alkyl, —O—C$_{1-6}$-alkyl, —C$_{1-6}$-haloalkyl, three- to seven-membered cycloalkyl, Het, Hetaryl, —CO—N(CH$_3$)$_2$, —CO—NHCH$_3$, —CO—NH$_2$, —(C$_{1-3}$-alkylene)-O—(C$_{1-3}$-alkyl), —O-Het,
which is optionally further substituted by one, two or three substituents X,
whereby each X is selected from the group consisting of halogen, oxo, —C$_{1-4}$-alkyl, —O—C$_{1-4}$-alkyl, —C$_{1-4}$-haloalkyl, —O—(C$_{1-4}$-alkylene)-Het, Het, —NH$_2$,
whereby substituent X is optionally further substituted by one, two or three substituents of a group selected from oxo, methyl, ethyl, n-propyl, isopropyl, n-butyl, isobutyl and tert-butyl, and the pharmaceutically acceptable salts of the aforementioned compounds.

In a further preferred embodiment the invention relates to the above compounds of the aforementioned formula 1c or formula 1c', wherein R$^1$ is
a) either selected from the group consisting of Het and Hetaryl;
which is optionally further substituted by one, two or three substituents Z,
whereby each Z is a substituent selected from the group consisting of —OH, oxo, —CN, halogen, —C$_{1-6}$-alkyl, —O—C$_{1-6}$-alkyl, —C$_{1-6}$-haloalkyl, three- to seven-membered cycloalkyl, Het, Hetaryl, —CO—N(CH$_3$)$_2$, —CO—NHCH$_3$, —CO—NH$_2$, —(C$_{1-3}$-alkylene)-O—(C$_{1-3}$-alkyl), —O-Het,
which is optionally further substituted by one, two or three substituents X,
whereby each X is selected from the group consisting of halogen, oxo, —C$_{1-4}$-alkyl, —O—C$_{1-4}$-alkyl, —C$_{1-4}$-haloalkyl, —O—(C$_{1-4}$-alkylene)-Het, Het, Hetaryl, —NH$_2$,
whereby substituent X is optionally further substituted by one, two or three substituents of a group selected from oxo, methyl, ethyl, n-propyl, isopropyl, n-butyl, isobutyl and tert-butyl,
or wherein R$^1$ is
b) phenyl,
which is optionally further substituted by one, two or three substituents Z,
whereby each Z is a substituent selected from the group consisting of, —CN, halogen, —C$_{1-6}$-alkyl, —(C$_{1-3}$-alkylene)-Hetaryl, —(C$_{1-3}$-alkylene)-Het, —C$_{1-6}$-haloalkyl, three- to seven-membered cycloalkyl, Het, Hetaryl,
which is optionally further substituted by one, two or three substituents X,
whereby each X is selected from the group consisting of halogen, oxo and —C$_{1-4}$-alkyl,
and the pharmaceutically acceptable salts of the aforementioned compounds.

In another preferred embodiment the invention relates to the above compounds of the aforementioned formula 1c or formula 1c', wherein
R$^1$ is either
a monocyclic five- to six-membered heteroaromate with 1, 2 or 3 heteroatoms each independently from one another selected from the group consisting of N, O and S, or a 9- to 11-membered bicyclic heteroaromate with 1, 2, 3 or 4 heteroatoms each independently from one another selected from the group consisting of N, O and S, wherein this $R^1$-residue is attached to the rest of the molecule either via a C-atom or via an N-atom and is optionally further substituted by one, two or three substituents Z, whereby each Z is a substituent selected from the group consisting of —OH, oxo, —CN, halogen, -methyl, -ethyl, n-propyl, isopropyl, n-butyl, isobutyl, tert-butyl, —O—$C_{1-6}$-alkyl, —$C_{1-6}$-haloalkyl, three- to seven-membered cycloalkyl, Het, Hetaryl, —CO—N(CH$_3$)$_2$, —CO—NHCH$_3$, —CO—NH$_2$, —($C_{1-3}$-alkylene)-O—($C_{1-3}$-alkyl), —O-Het, which is optionally further substituted by one, two or three substituents X, whereby each X is selected from the group consisting of halogen, oxo, —$C_{1-4}$-alkyl, —O—$C_{1-4}$-alkyl, —$C_{1-4}$-haloalkyl, —O—($C_{1-4}$-alkylene)-Het, Het, —NH$_2$, whereby substituent X is optionally further substituted by one, two or three substituents of a group selected from oxo, methyl, ethyl, n-propyl, isopropyl, n-butyl, isobutyl and tert-butyl, and the pharmaceutically acceptable salts of the aforementioned compounds.

In a further preferred embodiment the invention relates to the above compounds of the aforementioned formula 1c or formula 1c', wherein $R^1$ is selected from the group consisting of pyridinyl, pyrimidinyl, pyrazinyl, pyrrolyl, imidazolyl, pyrazolyl, thiophenyl, furanyl, pyrazolopyridinyl, indazolyl, thiazolyl, imidazo-pyridinyl and indolyl, wherein this $R^1$-residue is attached to the rest of the molecule either via a C-atom or via an N-atom and is optionally further substituted by one, two or three substituents Z, whereby each Z is a substituent selected from the group consisting of —OH, oxo, —CN, halogen, -methyl, -ethyl, n-propyl, isopropyl, n-butyl, isobutyl, tert-butyl, —O-methyl, —O-ethyl, O-propyl, O-butyl, —$C_{1-3}$-haloalkyl, three-, four, five- or six-membered cycloalkyl, Het, Hetaryl, —CO—N(CH$_3$)$_2$, —CO—NHCH$_3$, —CO—NH$_2$, —($C_{1-3}$-alkylene)-O—($C_{1-3}$-alkyl), —O-Het, which is optionally further substituted by one, two or three substituents X, whereby each X is selected from the group consisting of halogen, oxo, —$C_{1-4}$-alkyl, —O—$C_{1-4}$-alkyl, —$C_{1-4}$-haloalkyl, —O—($C_{1-4}$-alkylene)-Het, Het, —NH$_2$, whereby substituent X is optionally further substituted by one, two or three substituents of a group selected from oxo, methyl, ethyl, n-propyl, isopropyl, n-butyl, isobutyl and tert-butyl, and the pharmaceutically acceptable salts of the aforementioned compounds.

In a further preferred embodiment the instant invention concerns the above compounds of the aforementioned formula 1c or formula 1c', wherein $R^1$ is phenyl, which is optionally further substituted by one, two or three substituents Z, whereby each Z is a substituent selected from the group consisting of —OH, oxo, —CN, halogen, —$C_{1-6}$-alkyl, —O—$C_{1-6}$-alkyl, —$C_{1-6}$-haloalkyl, three- to seven-membered cycloalkyl, Het, Hetaryl, —CO—N(CH$_3$)$_2$, —CO—NHCH$_3$, —CO—NH$_2$, —($C_{1-3}$-alkylene)-O—($C_{1-3}$-alkyl), —O-Het, which is optionally further substituted by one, two or three substituents X, whereby each X is selected from the group consisting of halogen, oxo, —$C_{1-4}$-alkyl, —O—$C_{1-4}$-alkyl, —$C_{1-4}$-haloalkyl, —O—($C_{1-4}$-alkylene)-Het, Het, —NH$_2$, whereby substituent X is optionally further substituted by one, two or three substituents of a group selected from oxo, methyl, ethyl, n-propyl, isopropyl, n-butyl, isobutyl and tert-butyl, and the pharmaceutically acceptable salts of the aforementioned compounds.

In a particularly preferred embodiment the instant invention relates to the above compounds of the aforementioned formula 1c or formula 1c', which is selected from the group consisting of

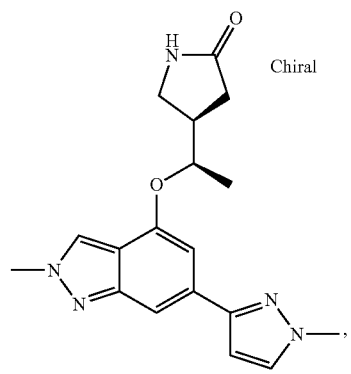

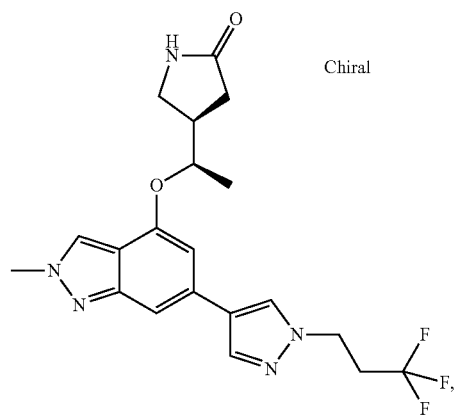

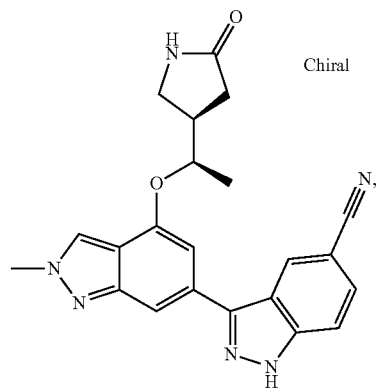

-continued
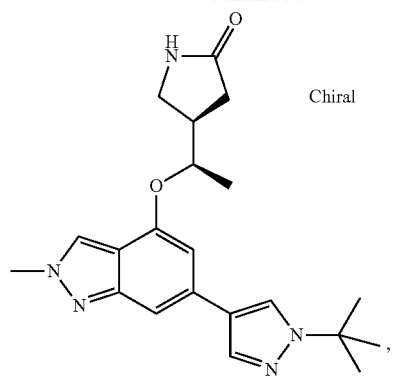
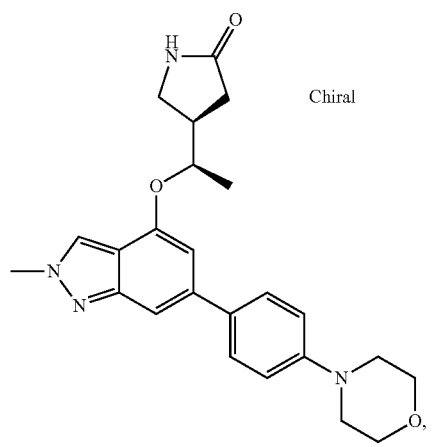
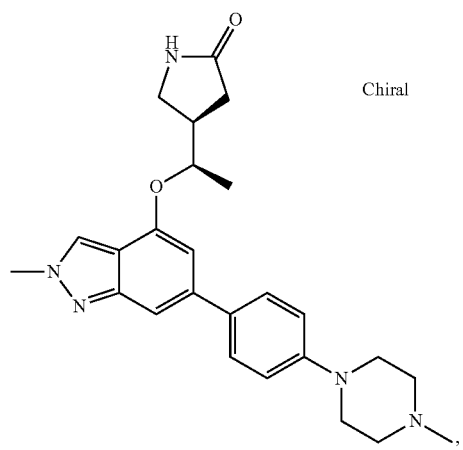
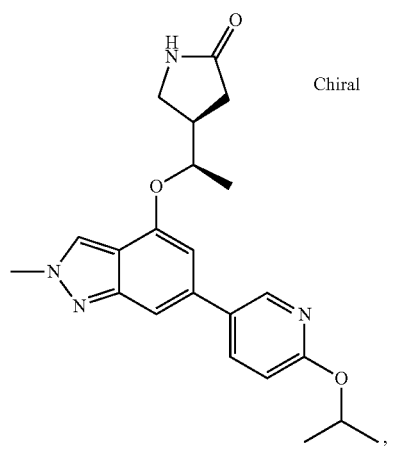
-continued
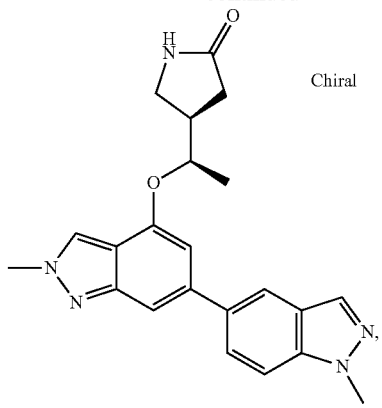
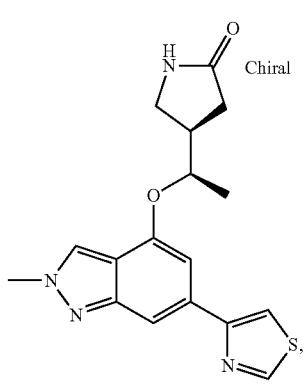
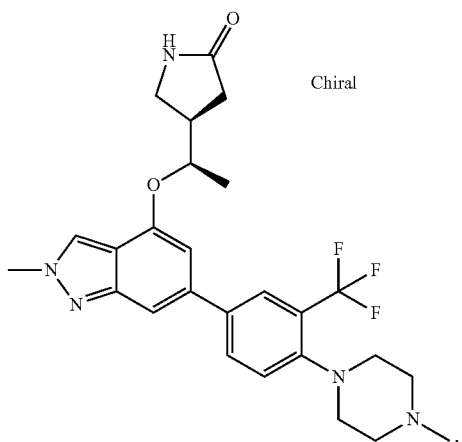
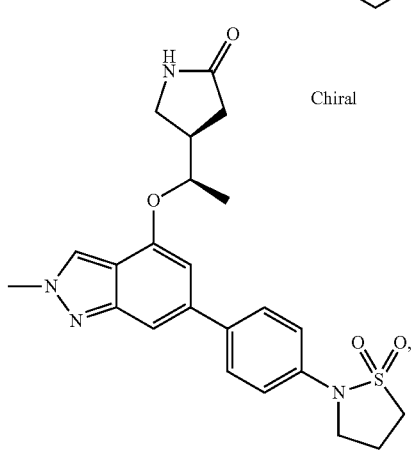

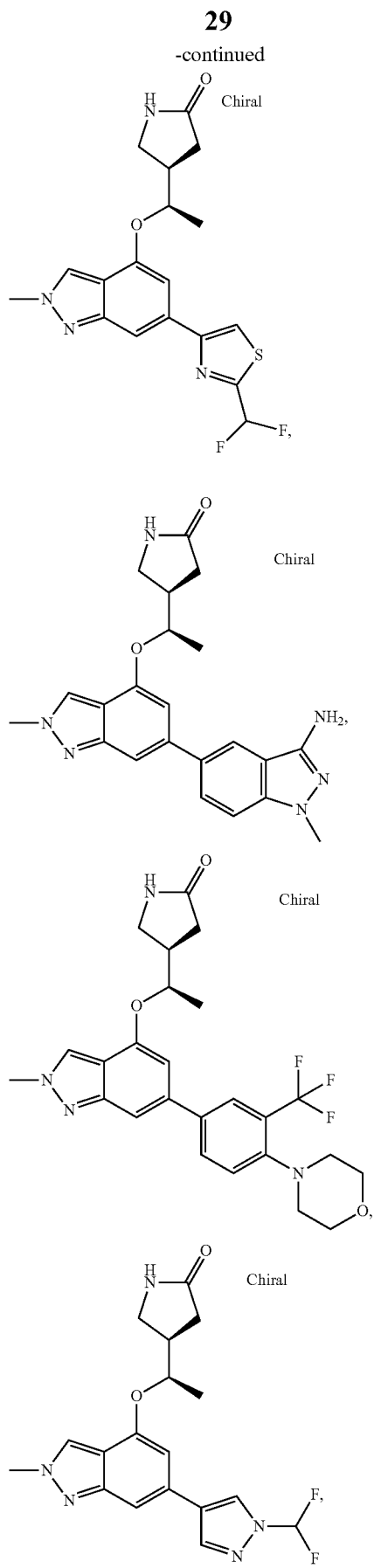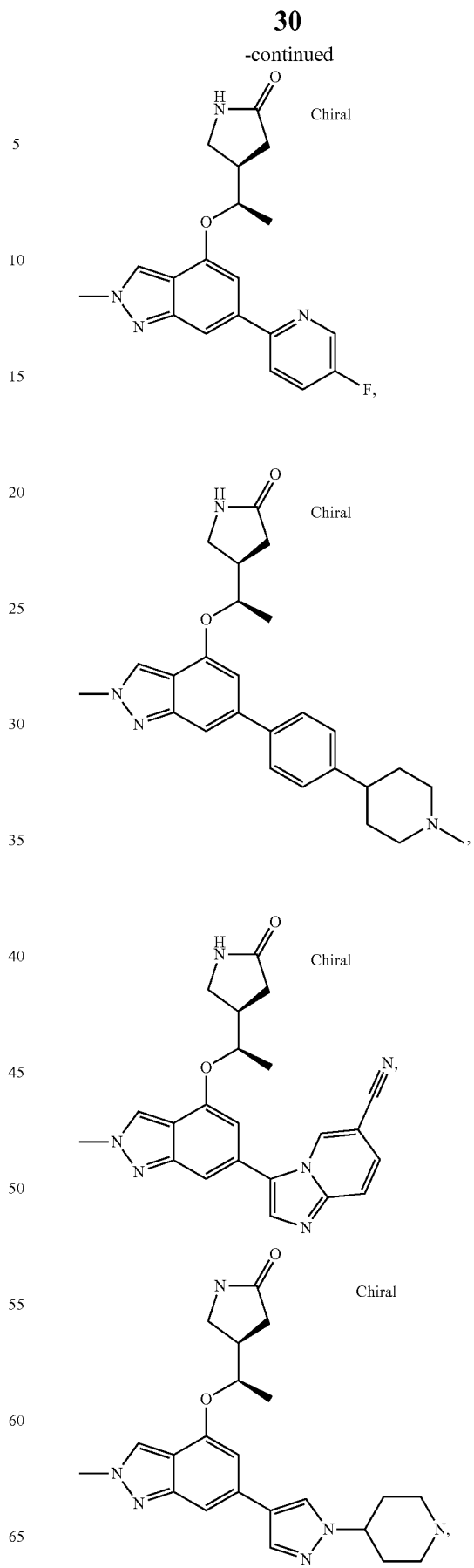

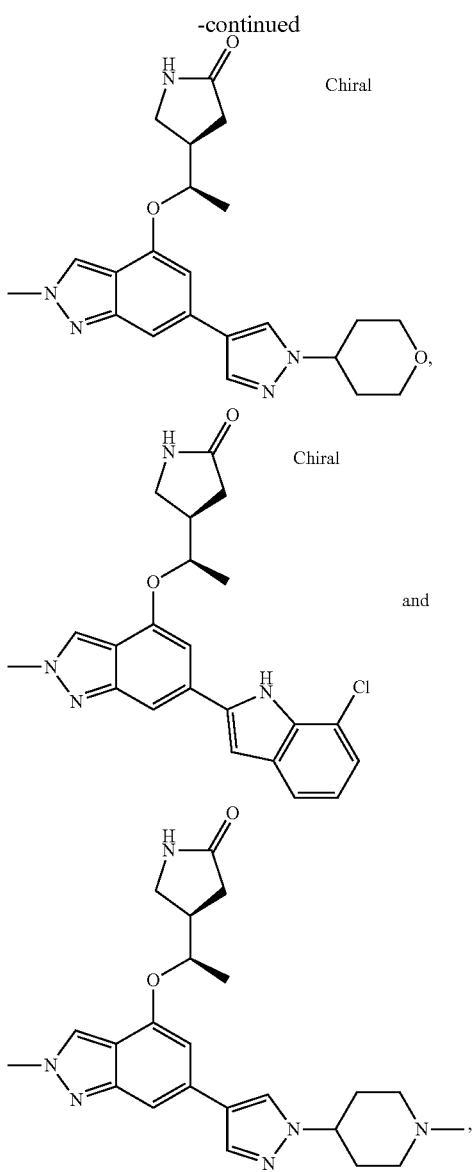

and the pharmaceutically acceptable salts of the aforementioned compounds.

In a further aspect the instant invention refers to an intermediate compound selected from the group consisting of formula 6

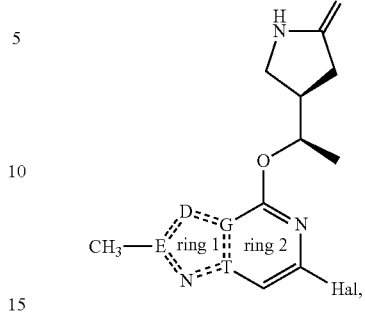

of formula 7

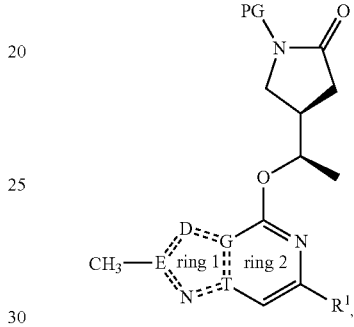

of formula 8

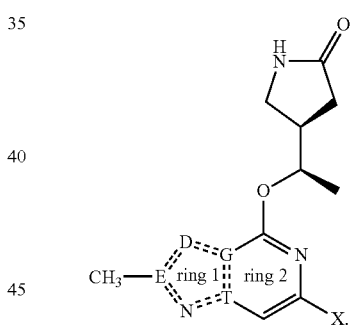

and of formula 11

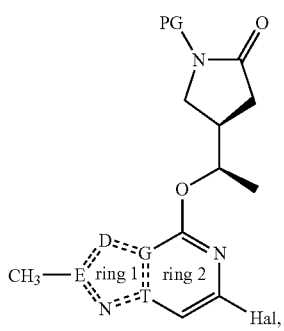

wherein E, D, G, T and $R^1$ are defined above or as defined in claim 1 and wherein Hal is Cl or Br and wherein PG is a protecting group selected from the group consisting of benzyl, 1-phenylethyl, 1-(4-methoxyphenyl)ethyl.

In a further aspect the instant invention refers to an intermediate compound selected from the group consisting of formula 5.1 and of formula 10.2

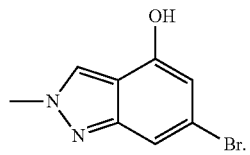

10.2

In a further aspect the instant invention refers to one of the aforementioned compounds of formula 1 or 1' (or of any of the sub-formulas 1a, 1a', 1c, 1c') for the treatment of a disease which can be treated by inhibition of the SYK enzyme.

In another preferred aspect the instant invention relates to one of the aforementioned compounds of formula 1 or 1' (or of any of the sub-formulas 1a, 1a', 1c, 1c') for the treatment of a disease selected from the group consisting of allergic rhinitis, asthma, COPD, adult respiratory distress syndrome, bronchitis, B-cell lymphoma, dermatitis and contact dermatitis, allergic dermatitis, allergic rhinoconjunctivitis, rheumatoid arthritis, anti-phospholipid syndrome, Berger's disease, Evans's syndrome, ulcerative colitis, allergic antibody-based glomerulonephritis, granulocytopenia, Goodpasture's syndrome, hepatitis, Henoch-Schönlein purpura, hypersensitivity vasculitis, immunohaemolytic anaemia, autoimmune haemolytic anemia, idiopathic thrombocytopenic purpura, Kawasaki syndrome, allergic conjunctivitis, lupus erythematodes, lupus nephritis, capsule cell lymphoma, neutropenia, non-familial lateral sclerosis, artheriosclerosis, Crohn's disease, multiple sclerosis, myasthenia gravis, osteoporosis, osteolytic diseases, osteopenia, psoriasis, Sjigren's syndrome, sclerodermy, T-cell lymphoma, urticaria/angiooedema, Wegener's granulomatosis and coeliac disease.

In another preferred aspect the instant invention concerns the aforementioned compounds of formula 1 or 1' (or of any of the sub-formulas 1a, 1a', 1c, 1c') for the treatment of a disease selected from the group consisting of asthma, COPD, allergic rhinitis, adult respiratory distress syndrome, bronchitis, allergic dermatitis, contact dermatitis, idiopathic thrombocytopenic purpura, rheumatoid arthritis, lupus erythematodes, lupus nephritis and allergic rhinoconjunctivitis.

In another particularly preferred aspect the instant invention concerns the aforementioned compounds of formula 1 or 1' (or of any of the sub-formulas 1a, 1a', 1c, 1c') for the treatment of a disease selected from the group consisting of asthma, COPD, allergic rhinitis, allergic dermatitis, lupus erythematodes, lupus nephritis and rheumatoid arthritis.

In another preferred aspect the instant invention concerns pharmaceutical formulations which contain one or more of the aforementioned compounds of formula 1 or 1' (or of any of the sub-formulas 1a, 1a', 1c, 1c') and a pharmaceutically acceptable excipient.

In another preferred aspect the instant invention concerns pharmaceutical formulations which contain one or more compounds of the aforementioned compounds of formula 1 or 1' (or of any of the sub-formulas 1a, 1a', 1c, 1c') in combination with an active substance selected from the group consisting of anticholinergics, betamimetics, corticosteroids, PDE4-inhibitors, EGFR-inhibitors, LTD4-antagonists, CCR3-inhibitors, iNOS-inhibitors, CRTH2-antagonists, HMG-CoA reductase inhibitors and NSAIDs.

3. TERMS AND DEFINITIONS USED

Unless stated otherwise, all the substituents are independent of one another. If for example a number of $C_{1-6}$-alkyl groups are possible substituents at a group, in the case of three substituents, for example, $C_{1-6}$-alkyl could represent, independently of one another, a methyl, an n-propyl and a tert-butyl.

Within the scope of this application, in the definition of possible substituents, these may also be presented in the form of a structural formula. An asterisk (*) in the structural formula of the substituent is to be understood as being the linking point to the rest of the molecule. Mor3eover, the atom of the substituent following the linking point is understood as being the atom in position number 1. Thus for example the groups N-piperidinyl (I), 4-piperidinyl (II), 2-tolyl (III), 3-tolyl (IV) and 4-tolyl (V) are represented as follows:

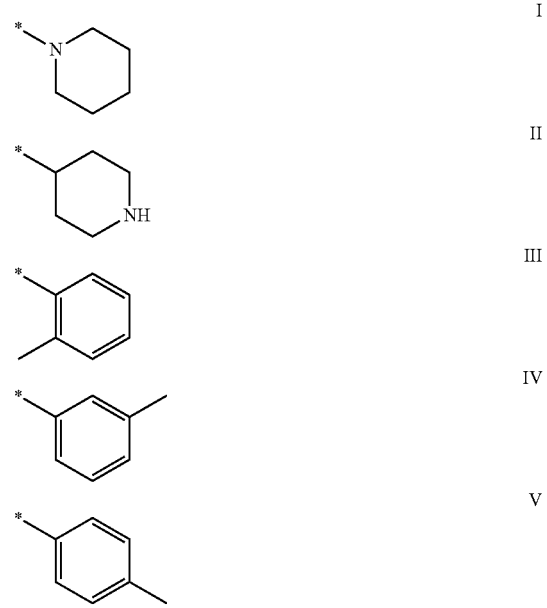

If there is no asterisk (*) in the structural formula of the substituent, each hydrogen atom may be removed at the substituent and the valency thus freed may serve as a binding site to the rest of a molecule. Thus, for example, VI

may represent 2-tolyl, 3-tolyl, 4-tolyl and benzyl.

Alternatively to the * within the scope of this application $X_1$ is also understood as being the linking point of the group $R^1$ to the structure of formula 1 and $X_2$ as being the linking point of the group $R^2$ to the structure of formula 1.

By the term "$C_{1-6}$-alkyl" (including those which are part of other groups) are meant branched and unbranched alkyl groups with 1 to 6 carbon atoms and by the term "$C_{1-3}$-alkyl" are meant branched and unbranched alkyl groups with 1 to 3 carbon atoms. "$C_{1-4}$-alkyl" accordingly denotes branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc., may also optionally be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples of these include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1, 3-dimethylpropylene or hexylene. Unless stated otherwise, the definitions propylene, butylene, pentylene and hexylene include all the possible isomeric forms of the groups in question with the same number of carbons. Thus, for example, propyl includes also 1-methylethylene and butylene includes 1-methylpropylene, 1,1-dimethylethylene, 1,2-dimethylethylene.

If the carbon chain is substituted by a group which together with one or two carbon atoms of the alkylene chain forms a carbocyclic ring with 3, 5 or 6 carbon atoms, this includes, inter alia, the following examples of the rings:

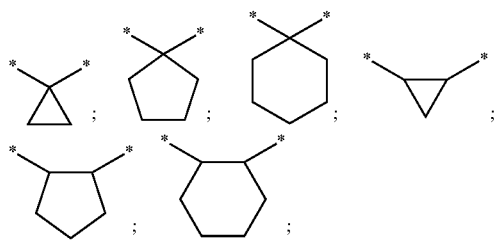

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples of these include: ethenylene, propenylene, 1-methylethenylene, butenylene, 1-methylpropenylene, 1,1-dimethylethenylene, 1, 2-dimethylethenylene, pentenylene, 1,1-dimethylpropenylene, 2,2-dimethylpropenylene, 1, 2-dimethylpropenylene, 1, 3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1, 1-dimethylethenylene, 1, 2-dimethylethenylene.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include: benzyl, 1- or 2-phenylethyl or 1- or 2-naphthylethyl. Unless otherwise stated, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—even though they are already included under "aryl-$C_{1-6}$-alkylene"-branched and unbranched alkylene groups with 1 to 6 carbon atoms, which are substituted by a heteroaryl.

If not specifically defined otherwise, a heteroaryl of this kind includes five- or six-membered heterocyclic aromatic groups or 5-10-membered, bicyclic heteroaryl rings which may contain one, two, three or four heteroatoms selected from among oxygen, sulphur and nitrogen, and contain so many conjugated double bonds that an aromatic system is formed. The following are examples of five- or six-membered heterocyclic aromatic groups or bicyclic heteroaryl rings:

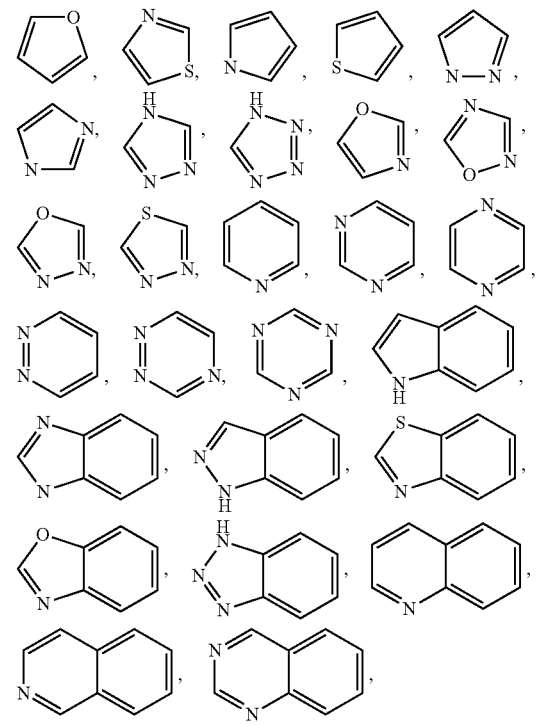

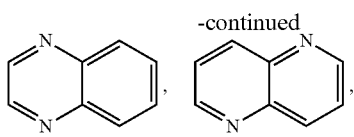

Unless otherwise stated, these heteroaryls may be substituted by one or more groups selected from among methyl, ethyl, iso-propyl, tert-butyl, hydroxy, fluorine, chlorine, bromine and iodine.

The following are examples of heteroaryl-$C_{1-6}$-alkylenes:

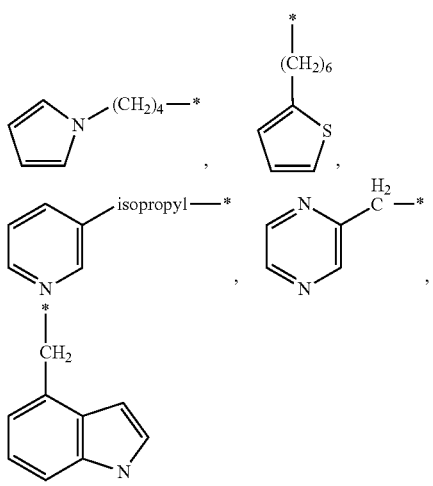

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms.

Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms, if not specifically defined otherwise. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

If not specifically defined otherwise, by the term "$C_{3-10}$-cycloalkyl" are also meant monocyclic alkyl groups with 3 to 7 carbon atoms and also bicyclic alkyl groups with 7 to 10 carbon atoms, or monocyclic alkyl groups which are bridged by at least one $C_{1-3}$-carbon bridge.

By the term "heterocyclic rings" or "heterocycle" are meant, unless stated otherwise, five-, six- or seven-membered, saturated, partially saturated or unsaturated heterocyclic rings which may contain one, two or three heteroatoms, selected from among oxygen, sulphur and nitrogen, while the ring may be linked to the molecule through a carbon atom or through a nitrogen atom, if there is one. Although included by the term "heterocyclic rings" or "heterocycles", the term "saturated heterocyclic ring" refers to five-, six- or seven-membered saturated rings. Examples include:

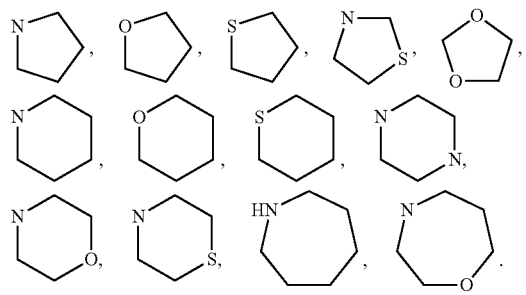

Although included by the term "heterocyclic rings" or "heterocyclic group", the term "partially saturated heterocyclic group" refers to five-, six- or seven-membered partially saturated rings which contain one or two double bonds, without so many double bonds being produced that an aromatic system is formed, unless specifically defined otherwise. Examples include:

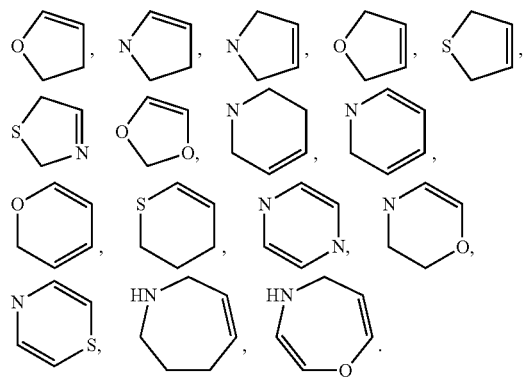

Although included by the term "heterocyclic rings" or "heterocycles", the term "heterocyclic aromatic rings", "unsaturated heterocyclic group" or "heteroaryl" refers to five- or six-membered heterocyclic aromatic groups or 5-10-membered, bicyclic heteroaryl rings which may contain one, two, three or four heteroatoms, selected from among oxygen, sulphur and nitrogen, and contain so many conjugated double bonds that an aromatic system is formed, unless not specifically defined otherwise. Examples of five- or six-membered heterocyclic aromatic groups include:

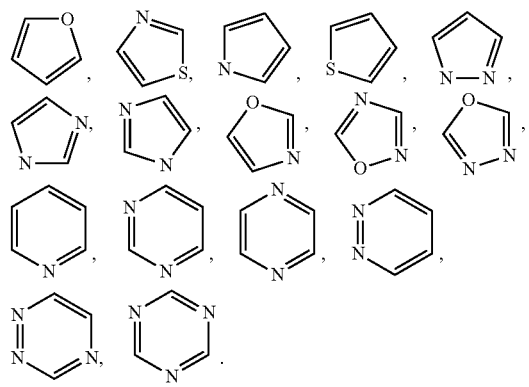

Unless otherwise mentioned, a heterocyclic ring (or heterocycle) may be provided with a keto group. Examples include:

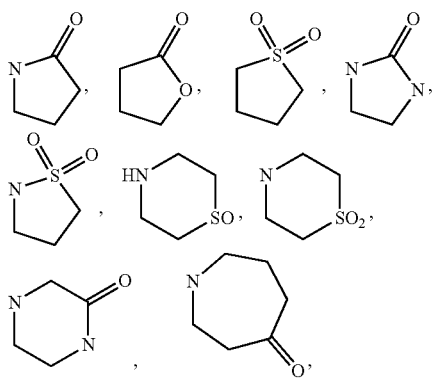

Although covered by the term "cycloalkyl", the term "bicyclic cycloalkyls" generally denotes eight-, nine- or ten-membered bicyclic carbon rings. Examples include

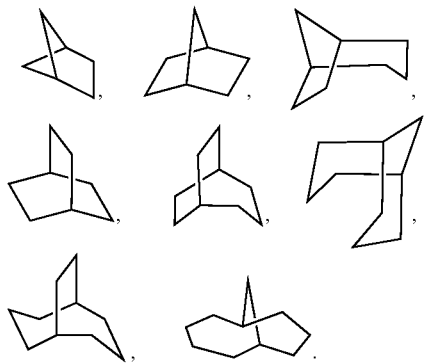

Although already included by the term "heterocycle", the term "bicyclic heterocycles" generally denotes eight-, nine- or ten-membered bicyclic rings which may contain one or more heteroatoms, preferably 1-4, more preferably 1-3, even more preferably 1-2, particularly one heteroatom, selected from among oxygen, sulphur and nitrogen, unless not specifically defined otherwise. The ring may be linked to the molecule through a carbon atom of the ring or through a nitrogen atom of the ring, if there is one. Examples include:

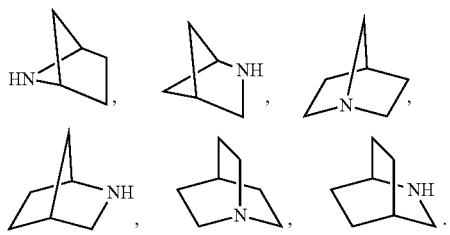

Although already included by the term "aryl", the term "bicyclic aryl" denotes a 5-10 membered, bicyclic aryl ring which contains sufficient conjugated double bonds to form an aromatic system. One example of a bicyclic aryl is naphthyl.

Although already included under "heteroaryl", the term "bicyclic heteroaryl" denotes a 5-10 membered, bicyclic heteroaryl ring which may contain one, two, three or four heteroatoms, selected from among oxygen, sulphur and nitrogen, and contains sufficient conjugated double bonds to form an aromatic system, unless specifically defined otherwise.

Although included by the term "bicyclic cycloalkyls" or "bicyclic aryl", the term "fused cycloalkyl" or "fused aryl" denotes bicyclic rings wherein the bridge separating the rings denotes a direct single bond. The following are examples of a fused, bicyclic cycloalkyl:

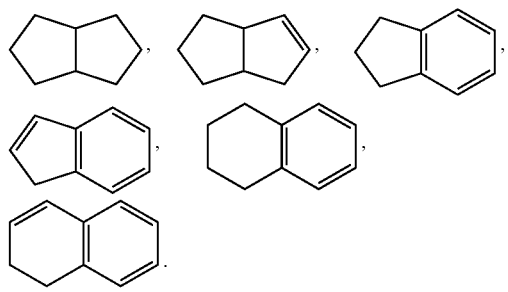

Although included by the term "bicyclic heterocycles" or "bicyclic heteroaryls", the term "fused bicyclic heterocycles" of "fused bicyclic heteroaryls" denotes bicyclic 5-10 membered heterorings which contain one, two, three or four heteroatoms, selected from among oxygen, sulphur and nitrogen and wherein the bridge separating the rings denotes a direct single bond. The "fused bicyclic heteroaryls" moreover contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

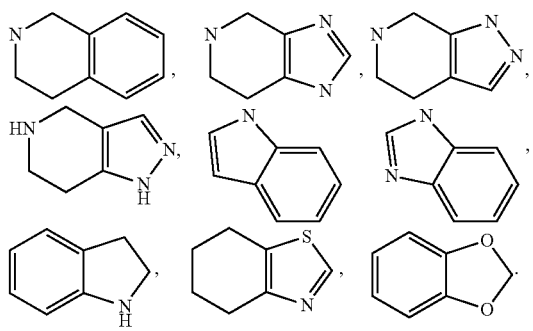

"Halogen" within the scope of the present invention denotes fluorine, chlorine, bromine or iodine. Unless stated to the contrary, fluorine, chlorine and bromine are regarded as preferred halogens.

Compounds of general formulas 1 or 1' may have acid groups, mainly carboxyl groups, and/or basic groups such as e.g. amino functions. Compounds of general formulas 1 or 1' may therefore be present as internal salts, as salts with pharmaceutically usable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically usable bases such as alkali metal or alkaline earth metal hydroxides or carbonates, zinc or ammonium hydroxides or organic amines such as e.g. diethylamine, triethylamine, triethanolamine, inter alia.

As mentioned previously, the compounds of formulas 1 or 1' may be converted into the salts thereof, particularly for pharmaceutical use into the physiologically and pharmacologically acceptable salts thereof. These salts may be present on the one hand as physiologically and pharmacologically acceptable acid addition salts of the compounds of formula 1 with inorganic or organic acids. On the other hand, the compound of formulas 1 or 1' when R is hydrogen may be converted by reaction with inorganic bases into physiologically and pharmacologically acceptable salts with alkali or alkaline earth metal cations as counter-ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. To prepare the alkali and alkaline earth metal salts of the compounds of formulas 1 or 1' wherein R denotes hydrogen, it is preferable to use the alkali and alkaline earth metal hydroxides and hydrides, of which the hydroxides and hydrides of the alkali metals, particularly sodium and potassium, are preferred, while sodium and potassium hydroxide are particularly preferred.

The compounds of general formulas 1 or 1' may optionally be converted into the salts thereof, particularly for pharmaceutical use into the pharmacologically acceptable acid addition salts with an inorganic or organic acid. Examples of suitable acids for this purpose include succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds of formula 1 in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The compounds of formula 1, 1a and 1c according to the invention may optionally be present as racemates, but may also be obtained as pure enantiomers, i.e. in the (R) or (S) form. Preferred are the compounds with the specific stereochemistry of formula 1', in particular the compounds with the specific stereochemistry of one of formulas 1a' and 1c'.

The invention relates to the compounds in question, optionally in the form of the individual optical isomers, diastereomers, mixtures of diastereomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The invention relates to the respective compounds of formulas 1 or 1' in the form of the pharmacologically acceptable salts thereof. These pharmacologically acceptable salts of the compounds of formulas 1 or 1' may also be present in the form of their respective hydrates (e.g. Monohydrates, dihydrates, etc.) as well as in the form of their respective solvates.

By a hydrate of the compound according to the formulas 1 or 1' is meant, for the purposes of the invention, a crystalline salt of the compound according to formulas 1 or 1', containing water of crystallisation.

By a solvate of the compound according to formulas 1 or 1' is meant, for the purposes of the invention, a crystalline salt of the compound according to formulas 1 or 1', which contains solvent molecules (e.g. Ethanol, methanol etc) in the crystal lattice.

The skilled man will be familiar with the standard methods of obtaining hydrates and solvates (e.g. recrystallisation from the corresponding solvent or from water).

4. METHODS OF PREPARATION

The Examples according to the invention were prepared as shown in Schemes 1, 2 or 3.

Scheme 1:

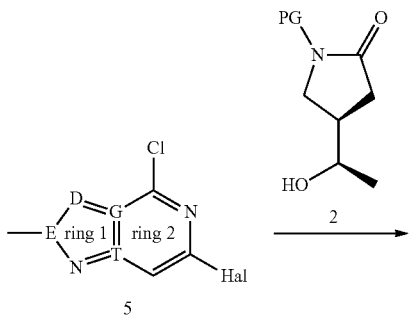

5

43 44
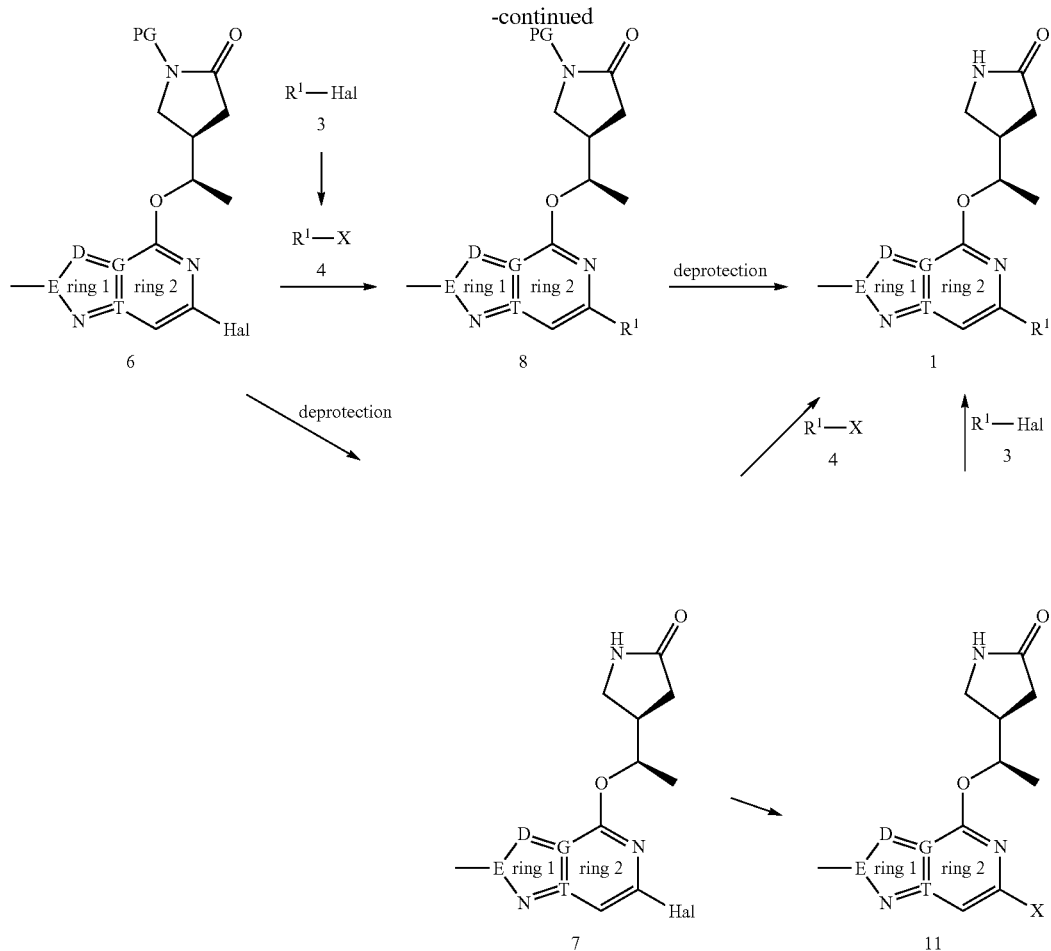
-continued
Building blocks applied in Scheme 1
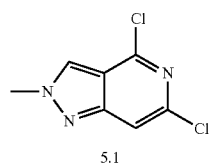
5.1
D is CH,
G is C or N
T is C
E is C or N, preferably N
Hal is Br or Cl
with X being —B(OH)$_2$, -boronic acid pinacolester, -trifluoroborate or —SnBu$_3$
PG is protecting group (e.g. benzyl, 1-phenylethyl, 1-(4-methoxyphenyl)ethyl)
and R$^1$ is as herein before defined.
Scheme 2:
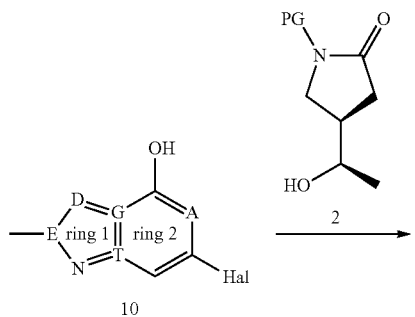

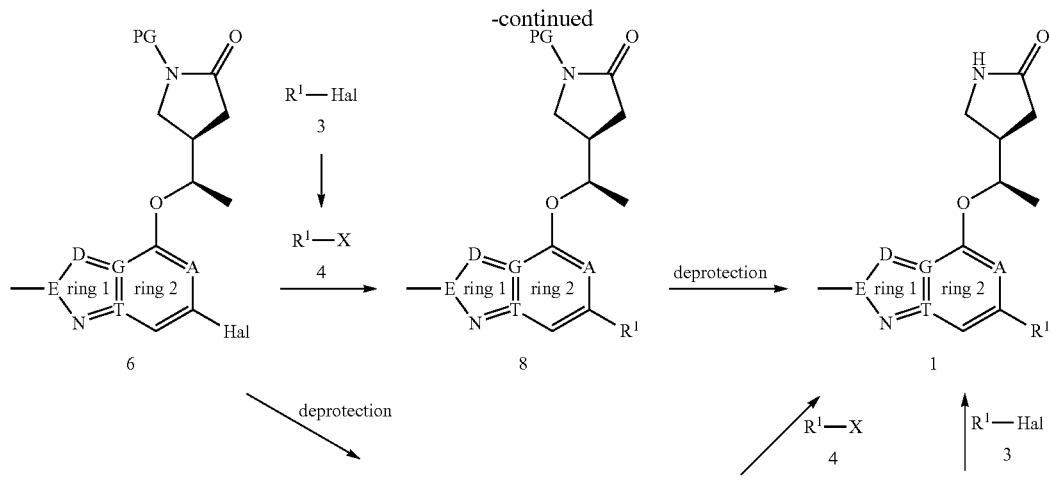

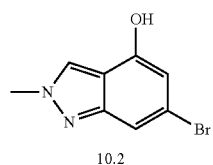

10.2

D is CH,

G is C or N

T is C

E is C or N, preferably N

A is CH or N

Hal is Br or Cl with X being —B(OH)$_2$, -boronic acid pinacolester, -trifluoroborate or —SnBu$_3$ PG is protecting group (e.g. benzyl, 1-phenylethyl, 1-(4-methoxyphenyl)ethyl)

and R$^1$ is as herein before defined.

4.1. Starting Materials of Formula 2, 3, 4, 5 and 10

4.1.1. Synthesis of Lactams 2 from Scheme 1 and 2

Synthesis of Synthesis of (R)-4-[(R)-1-Hydroxyethyl]-1-[(S)-1-(4-methoxyphenyl)-ethyl]-pyrrolidin-2-one 2.1 for Examples 1-3, 7-13, 17, 50-84 and (R)-4-[(S)-1-Hydroxyethyl]-1-[(S)-1-(4-methoxyphenyl)-ethyl]-pyrrolidin-2-one 2.2 for Examples 4-6, 14-16, 18-49.

Step 1: Synthesis of (1'R,3R/S)-1-(1'-(4-Methoxyphenylethyl))-5-oxo-3-pyrrolidine carboxylic acid (mixture of diastereoisomers)

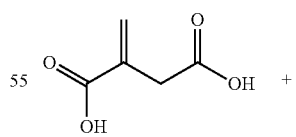

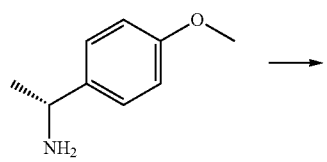

-continued

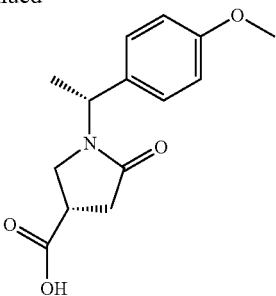

A suspension of 100 g of (R)-1-(4-methoxy-phenyl)-ethylamine and 95 g itaconic acid in 0.5 L 1-methyl-2-pyrrolidinone was heated to 80° C. for 1 hour. The solution was stirred for additional 4 hours at 120° C. The reaction mixture was cooled to 25° C. and poured into 1.5 L of demineralized water. The precipitate was filtered, washed with demineralized water and dried at 50° C.

Yield: 195 g (quantitative yield) solid as a mixture of diastereoisomers

Analysis (method G): $R_t$: 2.6 min and 2.7 min, (M+H)$^+$: 264

Step 2: Synthesis of (R/S)—N-Methoxy-5-oxo-1-[(S)-1-(4-methoxyphenyl)-ethyl]-pyrrolidine-3-carboxamide as a mixture of diastereoisomers

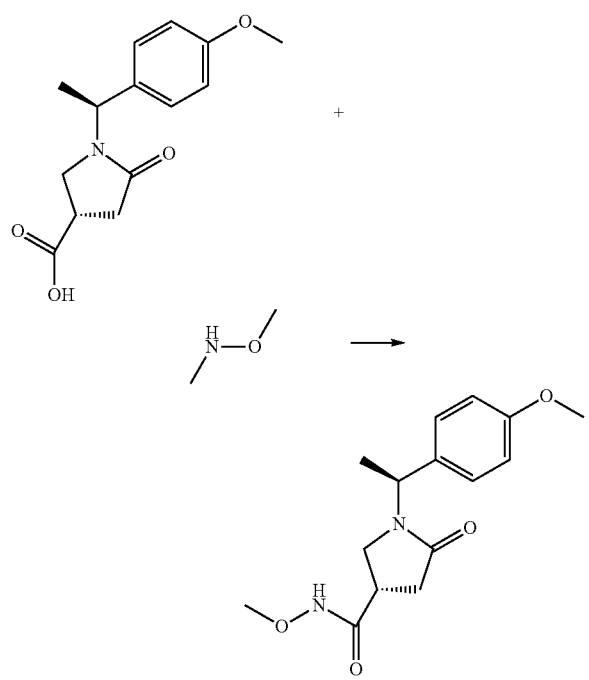

260 g of 1,1'-carbonyldiimidazole (CDI) were added to a solution of 285 g (1'R,3R/S)-1-(1'-(4-methoxyphenylethyl)-5-oxo-3-pyrrolidine carboxylic acid (mixture of diastereoisomers) in 1.4 L 2-methyltetrahydrofuran at 20° C. The suspension was stirred at 20° C. for 80 minutes. 235 mL ethyldiisopropylamine (DIPEA) and 130 g of N,O-dimethylhydroxylamine hydrochloride were added. The suspension was stirred for 3 hours at 20° C. Under cooling 850 mL 4M hydrochloric acid was added. The organic phase was separated and washed two times with 500 mL 1 N hydrochloric acid. The aqueous phase was reextracted two times with 500 mL ethyl acetate. The combined organic phases were dried over sodium sulfate. After filtration the solvent was evaporated under reduced pressure.

Yield: 271 g (82% of theory) of (R/S)—N-Methoxy-5-oxo-1-[(S)-1-(4-methoxyphenyl)-ethyl]-pyrrolidine-3-carboxamide (mixture of diastereoisomers) as an oil.

Analysis (method H): $R_t$: 11.1 min (41 area %) and 13.8 min (59 area %), (M+H)$^+$: 307

Step 3: Synthesis of (R/S)-4-Acetyl-1-[(S)-1-(4-methoxyphenyl)-ethyl]-pyrrolidine-2-one as a mixture of diastereoisomers

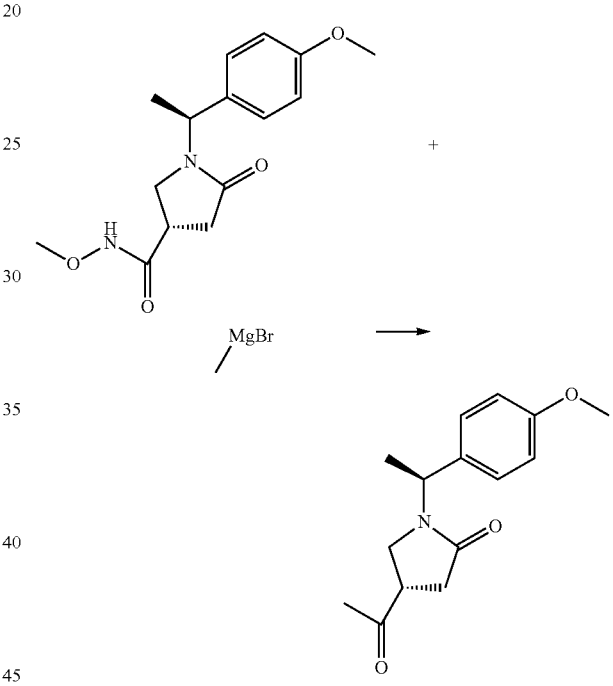

530 mL of a 3M solution of methylmagnesium bromide in diethylether were added slowly to a cooled solution of 271 g of (R/S)—N-methoxy-5-oxo-1-[(S)-1-(4-methoxyphenyl)-ethyl]-pyrrolidine-3-carboxamide (mixture of diastereoisomers) in 1.4 L of 2-methyltetrahydrofuran so that the temperature remained under 0°. After complete addition the temperature was kept for 75 minutes at 0° C. and then warmed up to 20° C. The suspension was stirred 16 hours at 20° C. Under cooling 650 mL of a 4M hydrochloric acid were added. The organic phase was separated and washed with 500 mL saturated sodium carbonate solution and with 500 mL saturated brine. The organic phase was dried over sodium sulfate. After filtration the solvent was evaporated under reduced pressure.

Yield: 188 g (81% of theory) of (R/S)-4-Acetyl-1-[(S)-1-(4-methoxyphenyl)-ethyl]-pyrrolidine-2-one (mixture of diastereoisomers) as an oil.

Analysis (method H): $R_t$: 7.4 min and 9.6 min, (M+H)$^+$: 262

Step 4: Crystallization of (R)-4-Acetyl-1-[(S)-1-(4-methoxyphenyl)-ethyl]-pyrrolidine-2-one under base induced epimerization conditions

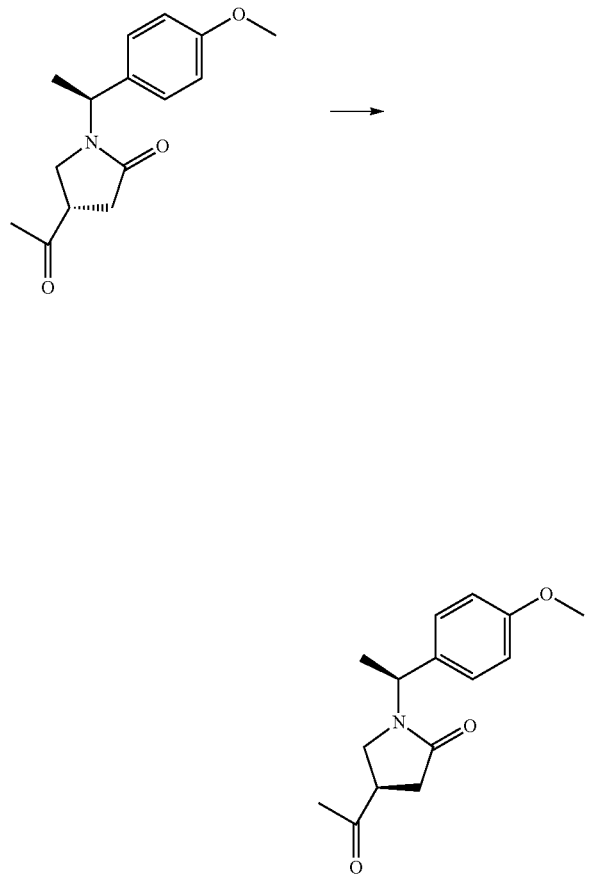

103 g of a mixture of diastereoisomers (R/S)-4-acetyl-1-[(S)-1-(4-methoxyphenyl)-ethyl]-pyrrolidine-2-one were dissolved in 155 mL 1-butanol at 25° C. 18 mL benzyltrimethylammonium hydroxide (40% solution in methanol) was added. The solution was stirred for 30 minutes at 25° C. The solution was cooled to 0° C. Precipitation started. The suspension was stirred for 15 minutes at 0° C. 100 mL n-heptane was added slowly and the suspension was stirred for 30 minutes at 0° C. The addition of 100 mL portions of n-heptane was repeated 4 times with subsequent stirring of the suspension at 0° C. for 30 minutes. The precipitate was isolated, washed with n-heptane and dried at 50° C.

Yield: 77.1 g of a beige solid (75% of theory) with a diastereoisomeric purity of ~95:5 (method H).

For further purification the crude product was dissolved in 310 mL 2-methyl-2-butanol at 40° C. (temperature <50° C.). The solution was slowly cooled to 0° C. Precipitation started. At 0° C. 385 mL of n-heptane were added and the suspension was stirred for 1 hour. The precipitate was filtrated, washed with n-heptane and dried at 50° C.

Yield: 68.7 g (67% of theory) of a colorless solid with a diastereoisomeric purity of >99:1.

Analysis (method H): $R_t$: 6.8 min, (M+H)$^+$: 262

Step 4: Crystallization of (R)-4-Acetyl-1-[(S)-1-(4-methoxyphenyl)-ethyl]-pyrrolidine-2-one under base induced epimerization conditions

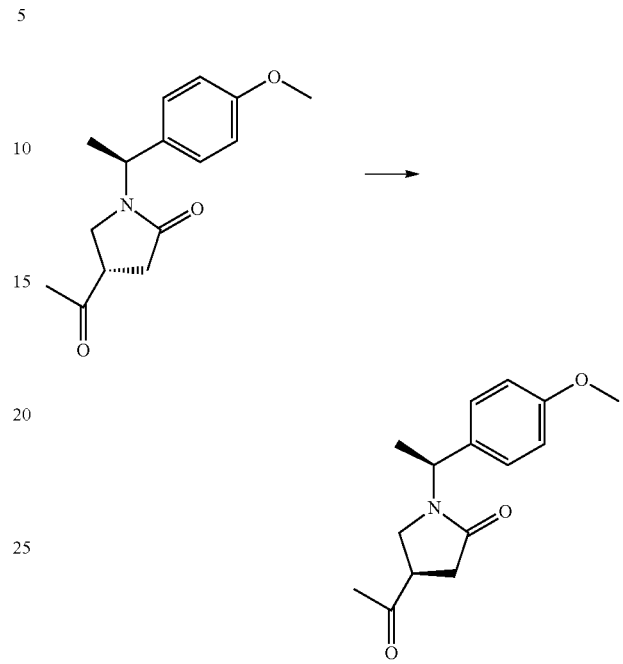

13.2 g of a mixture of diastereoisomers (R/S)-4-acetyl-1-[(S)-1-(4-methoxyphenyl)-ethyl]-pyrrolidine-2-one were dissolved in 18 mL of 1-butanol at 25° C. The solution was cooled to 3° C. and treated with 100 mg of (R)-4-Acetyl-1-[(S)-1-(4-methoxyphenyl)-ethyl]-pyrrolidine-2-one. The resulting mixture was agitated for 15 min at 3° C.; at which point, 2.3 mL benzyltrimethylammonium hydroxide (40% solution in methanol) were added. The solution was stirred for 30 minutes at 3° C. 64 mL n-heptane was added slowly over 1 h at 0 to 3° C. and the suspension was stirred for 60 minutes at 0° C. The precipitate was isolated, washed with n-heptane and dried at 3° C.

Yield: 10.6 g of a beige solid (80% of theory) with a diastereoisomeric purity of ~98:2 (method H).

Analysis (method H): $R_t$: 6.8 min, (M+H)$^+$: 262

Step 5: Synthesis of (R)-4-[(R)-1-Hydroxyethyl]-1-[(S)-1-(4-methoxyphenyl)-ethyl]-pyrrolidin-2-one 2.1

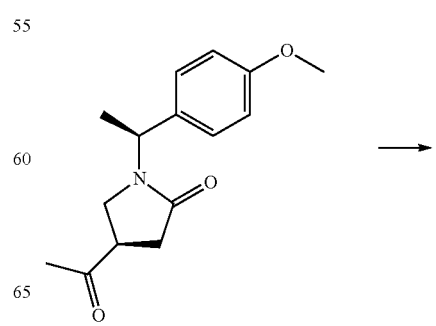

-continued

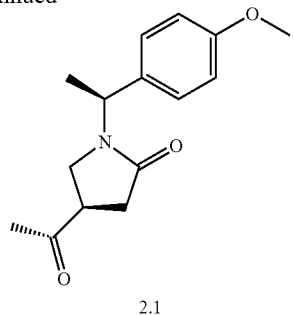

2.1

94.6 mg of dichloro (pentamethylcyclopentadienyl)-iridium(III) dimer and 105 mg of (S,S)—N-(p-toluenesulfonyl)-1,2-diphenylethylendiamine [(R,R)-TsDPEN] were dissolved in 20 mL of acetonitrile and subsequently charged to a slurry of 50 g of (R)-4-acetyl-1-[(S)-1-(4-methoxyphenyl)-ethyl]-pyrrolidine-2-one and 65 g of sodium formate in 500 mL of water at 25° C. The slurry was heated to 60° C. and agitated at this temperature while sparging with nitrogen for 3 h. The reaction was diluted at 60° C. with 500 mL of isopropyl acetate and subsequently cooled to ambient temperature. The layers were separated, and the organic portion was washed twice with 300 mL of water. The organic portion was concentrated to an oily solid. The residual material was crystallized three times from ethyl acetate and hexanes followed by drying in a vacuum oven with a nitrogen stream at 30° C.

25.4 g of a beige solid with a diastereomeric purity of >99:1

Step 5: Synthesis of (R)-4-[(S)-1-Hydroxyethyl]-1-[(S)-1-(4-methoxyphenyl)-ethyl]-pyrrolidin-2-one 2.2

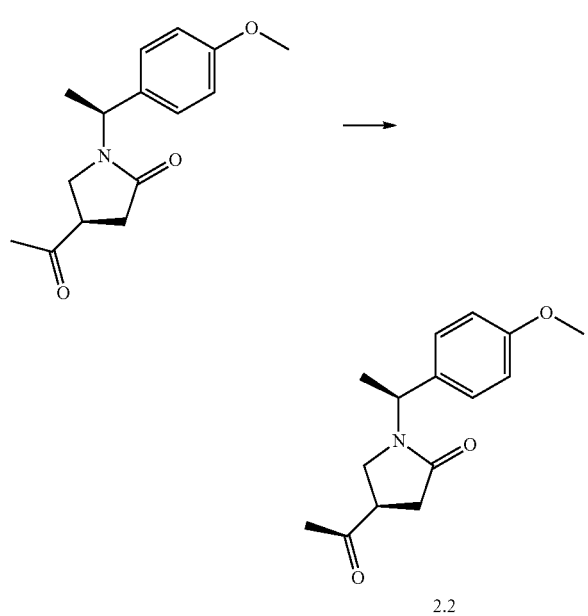

9.46 mg of dichloro (pentamethylcyclopentadienyl)-iridium(III) dimer and 10.52 mg of (R,R)—N-(p-toluenesulfonyl)-1,2-diphenylethylendiamine [(R,R)-TsDPEN] were dissolved in 1 mL of acetonitrile and subsequently charged to a slurry of 5 g of (R)-4-acetyl-1-[(S)-1-(4-methoxyphenyl)-ethyl]-pyrrolidine-2-one and 6.5 g of sodium formate in 50 mL of water at 25° C. The slurry was heated to 60° C. and agitated at this temperature while sparging with nitrogen for 3 h. The reaction was diluted at 60° C. with 50 mL of isopropyl acetate and subsequently cooled to ambient temperature. The layers were separated, and the organic portion was washed with 20 mL of water. The organic portion was concentrated to an oil. The oil was dissolved in 8 mL of isopropyl acetate at reflux. The solution was cooled to ambient temperature wherein crystallization occurred. The mixture was diluted dropwise with 10 mL of heptane at ambient temperature. The mixture was agitated for 30 minutes. The solids were collected by filtration, washed with a solution of 20 vol % isopropyl acetate in heptane and dried in a vacuum oven with a nitrogen stream at 55° C. 3.82 g of a beige solid with a diastereomeric purity of 99:1 Analysis (method I): $R_t$: 12.9 min, $(M+H)^+$: 264

Synthesis of [(1S)-1-[(3R)-1-[(1S)-1-(4-Methoxyphenyl)ethyl]-5-oxo-pyrrolidin-3-yl]ethyl]4-methyl-benzenesulfonate 2.3

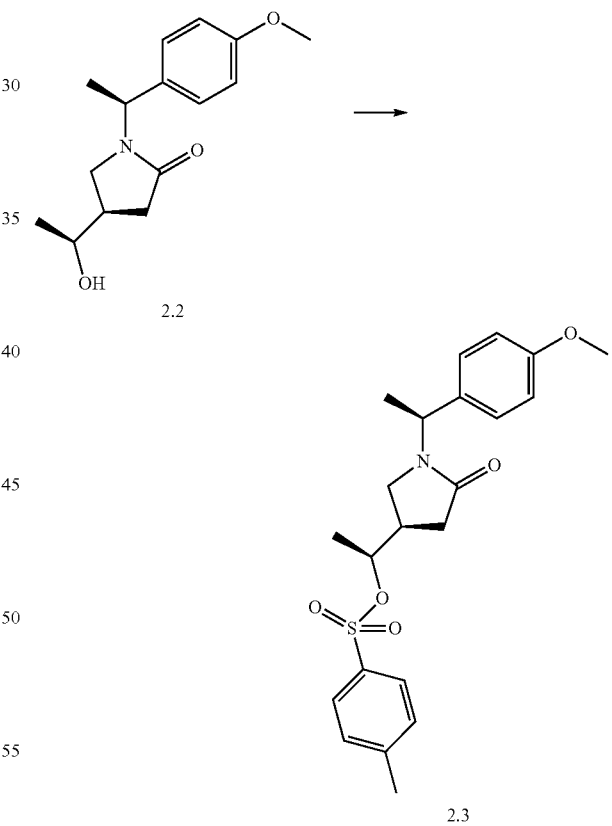

To a mixture of 20.0 g of (R)-4-[(S)-1-Hydroxyethyl]-1-[(S)-1-(4-methoxyphenyl)-ethyl]-pyrrolidin-2-one 2.2, 21.67 g p-toluenesulfonyl chloride and 0.92 g N,N-dimethylpyridin-4-amine was added 42 mL pyridine and 42 mL dichloromethane (DCM). The resulting mixture was stirred at 34° C. for 18 h under argon atmosphere. The reaction mixture was diluted with isopropyl acetate and washed with water and 2M hydrochloric acid. The combined organic phases were dried over magnesium sulfate, filtered and concentrated in vacuo. The residue was taken up in isopropyl acetate and n-heptane. The precipitate was filtered off, washed with n-heptane/isopropyl acetate and dried to yield 19.83 g of [(1S)-1-[(3R)-1-[(1S)-1-(4-methoxyphenyl)ethyl]-5-oxo-pyrrolidin-3-yl]ethyl] 4-methylbenzenesulfonate 2.3 as solid.

Analysis: HPLC-MS: $R_t$=0.680 min (method J), M+H=418

4.1.2. Synthesis of Boronic Acids, Boronic Esters, $BF_3$ Borates and Stannanes with Formula 4

X.1.2.1. Synthesis of $R^1$-Hal 3

Synthesis of 4-Bromo-1-tert-butyl-pyrazole 3.1 for Examples 2, 18

Step 1: Synthesis of 1-tert-Butyl-pyrazole

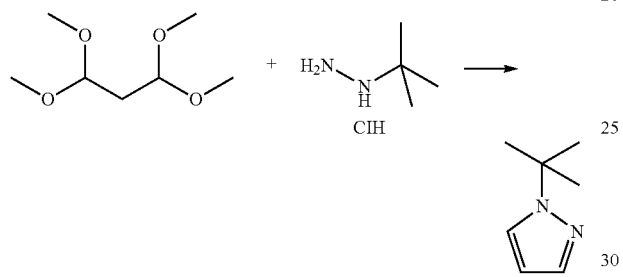

To a stirred mixture of 34.48 g of 1,1,3,3-tetramethoxypropane and 26.20 g tert.-butylhydrazine hydrochloride in 230 mL ethanol was added 40.0 mL conc. hydrochloric acid dropwise below 50° C., then the mixture was stirred under reflux for 2 h. The reaction mixture was diluted with water. The solvent was almost removed by destillation and the aqueous residue extracted with diethylether. The combined aqueous phases were basified with 10N sodium hydroxide solution and extracted with diethylether. The combined organic phases were washed with saturated brine, dried over sodium sulfate, filtered and concentrated in vacuo to yield 21.90 g of 1-tert-butyl-pyrazole as oil.

Analysis: HPLC-MS: $R_t$=0.412 min (method A), M+H=125

Step 2: Synthesis of 4-Bromo-1-tert-butyl-pyrazole

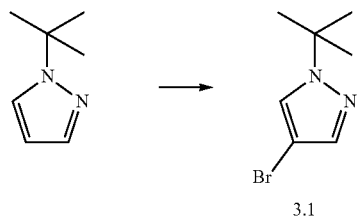

3.1

To a mixture of 21.9 g of 1-tert-butyl-pyrazole in 150 mL DCM was added 31.5 g N-bromosuccinimide in portions between 0 and 10° C. The resulting mixture was stirred for 30 min. The reaction mixture was allowed to reach ambient temperature. The precipitate was filtered off and washed with DCM. The combined organic extracts were washed with water and saturated brine, dried over magnesium sulfate, filtered and concentrated in vacuo to yield 34.0 g of 4-bromo-1-tert-butyl-pyrazole as oil.

Analysis: HPLC-MS: $R_t$=1.35 min (method B), M+H=203/205

Synthesis of trans 4-[4-(4-Bromo-pyrazol-1-yl)-cyclohexyl]-1-methyl-piperazin-2-one 3.2 for Example 12

The starting material 1-spiro[7-azoniabicyclo[2,2,1]heptane-7,4'-[1'-methyl-2'-oxo-4'-piperazinium]methane-sulphonate] was obtained as described in W2011092128.

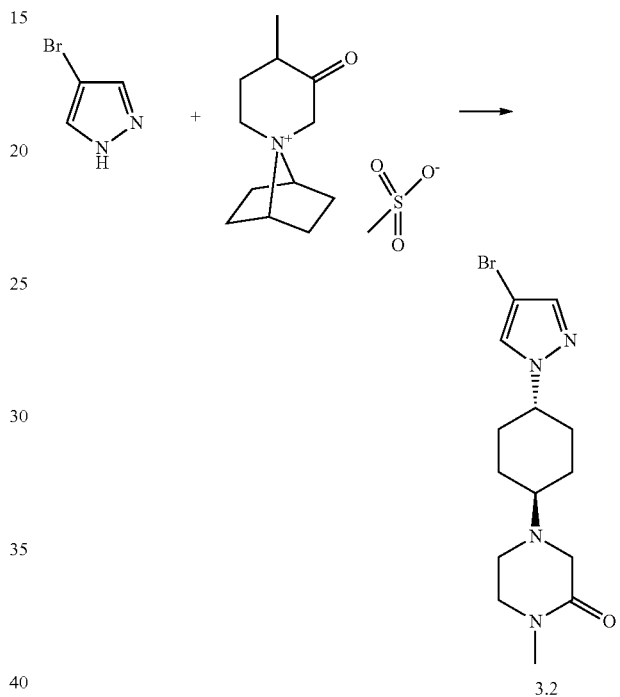

3.2

To a solution of 506 mg of 4-bromopyrazole in 7.5 mL dimethylacetamide (DMA) was added 91 mg sodium hydride (NaH). The resulting mixture was stirred at room temperature for 10 min, before 1.0 g of 1-spiro[7-azoniabicyclo[2,2,1]heptane-7,4'-[1'-methyl-2'-oxo-4'-piperazinium]methane-sulphonate] was added and the mixture was stirred at 100° C. for 40 min. Additional 70 mg NaH were added and the reaction mixture was stirred at 120° C. for 40 min. The solvent was removed by destillation and the residue taken up in MeOH and purified by rpHPLC (XbridgeC18, acetonitrile/water, ammonia) to yield after lyophilisation 850 mg of trans 4-[4-(4-bromo-pyrazol-1-yl)-cyclohexyl]-1-methyl-piperazin-2-one as solid.

Analysis: HPLC-MS: $R_t$=0.45 min (method C), M+H=341/343 Synthesis of 5-Bromo-2-(difluoromethyl)pyridine 3.3 for Example 51

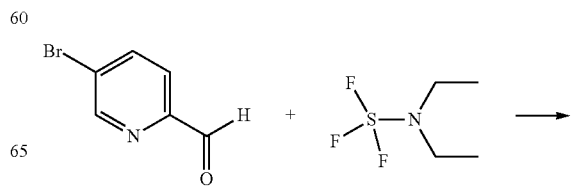

-continued

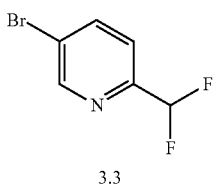

3.3

A solution of 1 g of 5-bromopyridine-2-carbaldehyde in 50 mL DCM was cooled to −70° C., then 1.55 mL diethylaminosulfurtrifluoride were added dropwise over 20 minutes. The suspension was stirred for 30 minutes at room temperature, then 10 mL water were added at 0° C. followed by slow addition of 20 mL saturated NaHCO₃ (gas formation). The phases were separated and 2 mL of 4M HCl in dioxane were added to the organic phase which was concentrated in vacuo to provide 1.06 g product as yellow solid.

Analysis: HPLC-MS: $R_t$=0.72 min (method D), M+H=208/210.

Synthesis of 7-Bromo-3-methyl-1,2,4,5-tetrahydro-3-benzazepine 3.4 for Example 55

7-Bromo-3-methyl-1,2,4,5-tetrahydro-3-benzazepine can be obtained as described in Shah, Unmesh; Lankin, Claire M.; Boyle, Craig D.; Chackalamannil, Samuel; Greenlee, William J.; Neustadt, Bernard R.; Cohen-Williams, Mary E.; Higgins, Guy A.; Ng, Kwokei; Varty, Geoffrey B.; Zhang, Hongtao; Lachowicz, Jean E. Bioorganic and Medicinal Chemistry Letters, 2008, 18, 4204-4209.

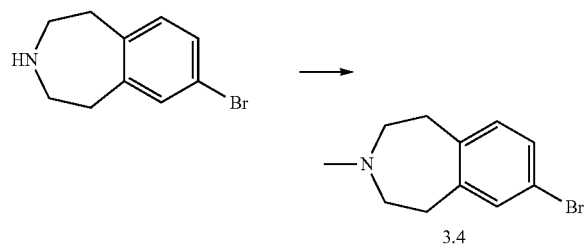

Synthesis of 6-Bromo-N,N,1-trimethyl-indole-2-carboxamide 3.5 for Example 56

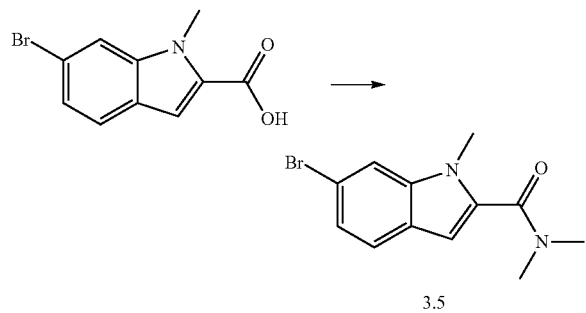

A mixture of 0.68 g of 6-bromo-1-methyl-indole-2-carboxylic acid, 1.1 g of 2-(1H-7-azabenzotriazol-1-yl)-1,1,3,3-tetramethyluroniumhexafluorophosphat (HATU) and 0.55 mL triethylamine in 2 mL N-methyl-2-pyrrolidinon (NMP) and 3 mL tetrahydrofuran (THF) was stirred at room temperature for 2 h followed by addition of 4.0 mL 2M dimetylamine solution in THF. The reaction mixture was stirred at room temperature for 30 min. The reaction mixture was diluted with DCM and washed with saturated aqueous sodium bicarbonate solution. The combined organic phases were concentrated in vacuo. The crude material was purified by flash chromatography (DCM→DCM: methanol 90:10) to yield 0.66 g of 6-bromo-N,N, 1-trimethyl-indole-2-carboxamide 3.5 as oil.

Analysis: HPLC-MS: $R_t$=0.85 min (method E), M+H=281/283

Synthesis of 4-Bromo-1-[(3S)-tetrahydrofuran-3-yl]pyrazole 3.6 for Example 70

Step 1: Synthesis of [(3R)-Tetrahydrofuran-3-yl] 4-methylbenzenesulfonate

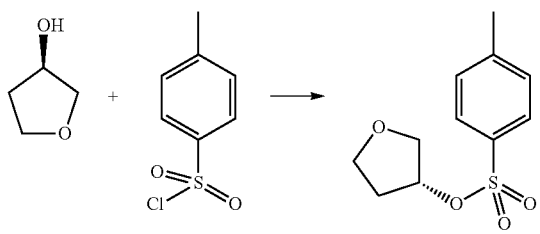 [SMILES: O[C@@H]1CCOC1 ; Cc1ccc(S(=O)(=O)Cl)cc1 ; Cc1ccc(S(=O)(=O)O[C@@H]2CCOC2)cc1]

To a solution of 25.43 g (R)-tetrahydro-furan-3-ol in 60 mL pyridine and 250 mL DCM was added 73.0 g of 4-methyl-benzenesulfonyl chloride followed by 1.0 g N,N-dimethylpyridin-4-amin. The reaction mixture was stirred at room temperature overnight. The reaction mixture was diluted with DCM and washed with 2M hydrochloric acid and water. The combined organic phases were dried over sodium sulfate, filtered and concentrated in vacuo. The crude material was purified by flash chromatography (DCM→DCM: methanol 95:5) to yield 59.46 g [(3R)-tetrahydrofuran-3-yl] 4-methylbenzenesulfonate as oil.

Analysis: MS: M+H=243

Step 2: Synthesis of 4-Bromo-1-[(3S)-tetrahydrofuran-3-yl]pyrazole 3.6

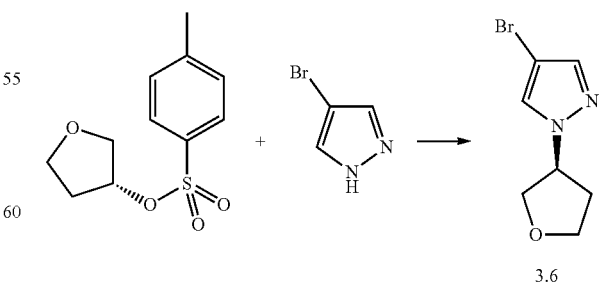

A mixture of 650 mg [(3R)-tetrahydrofuran-3-yl] 4-methylbenzenesulfonate, 400 mg 4-bromo-1H-pyrazole and 1.40 g cesium carbonate in 10 mL N,N-dimethylformamide (DMF) was stirred at 65° C. for 6 h. Additional 20 mg 4-bromo-1H-pyrazole were added and the reaction mixture was stirred at 65° C. overnight. The reaction mixture was diluted with ethyl acetate and washed with brine. The combined organic phases were dried over sodium sulfate, filtered and concentrated in vacuo. The crude material was purified by flash chromatography (cyclohexane/ethyl acetate 9:1→1:1) to yield 476 mg of 4-bromo-1-[(3S)-tetrahydrofuran-3-yl]pyrazole 3.6 as solid.

Analysis: MS: M+H=217/219

Synthesis of
4-Bromo-1-[(3R)-tetrahydrofuran-3-yl]pyrazole 3.7 for Example 74

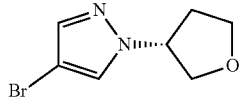

3.7

This intermediate was prepared from (S)-tetrahydrofuran-3-ol in two steps according to the preparation of 4-bromo-1-[(3S)-tetrahydrofuran-3-yl]pyrazole 3.6.

Analysis: MS: M+H=217/219

Synthesis of
4-Bromo-5-methyl-1-tetrahydropyran-4-yl-pyrazole 3.8 for Example 79

Step 1: Synthesis of
5-Methyl-1-tetrahydropyran-4-yl-pyrazole

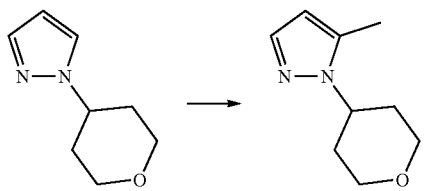

To a stirred mixture of 2.26 g of 1-tetrahydropyran-4-ylpyrazole in 20 mL THF was added 11.14 mL of 1.6M N-butyllithium solution in hexane dropwise at −50° C. under argon atmosphere. The mixture was stirred between −20° to −15° C. for 1.5 h, before 1.11 mL methyl iodide were added dropwise. The resulting mixture was stirred between −20° to −15° C. for 1.5 h. 10 mL water were added dropwise and the mixture was allowed to reach ambient temperature. The reaction mixture was diluted with water, followed by extraction with ethyl acetate. The combined organic phases were dried over magnesium sulfate, filtered and concentrated in vacuo. The residue was purified by rpHPLC (basic) to yield after lyophilisation 1.51 g of 5-methyl-1-tetrahydropyran-4-yl-pyrazole as solid.

Analysis: HPLC-MS: $R_t$=0.61 min (method F), M+H=167

Step 2: Synthesis of
4-Bromo-5-methyl-1-tetrahydropyran-4-yl-pyrazole 3.8

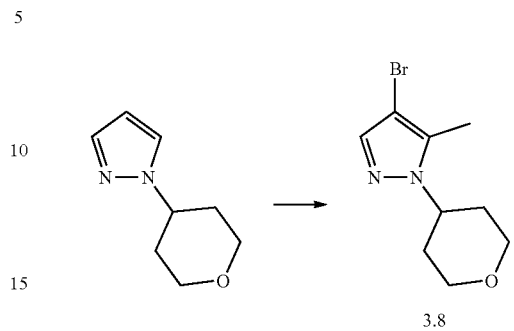

3.8

To a mixture of 1.0 g of 5-methyl-1-tetrahydropyran-4-yl-pyrazole in 20 mL THF and 20 mL ethyl acetate was added 1.09 g bromosuccinimide in portions between 10 and 20° C. The reaction mixture was stirred at room temperature for 30 min and then quenched with saturated aqueous potassium carbonate solution. The solvent was evaporated and the residue was purified by rpHPLC (basic) to yield after lyophilisation 1.20 g of 4-bromo-5-methyl-1-tetrahydropyran-4-yl-pyrazole 3.8 as solid.

Analysis: HPLC-MS: $R_t$=0.65 min (method F), M+H=245/247

Synthesis of
4-(4-Bromophenyl)-1-methyl-piperidine 3.9 for Example 80

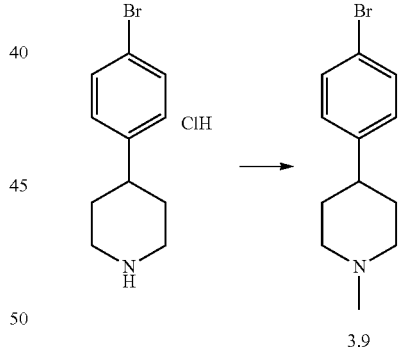

3.9

To a mixture of 100 mg of 4-(4-bromophenyl)-piperidine hydrochlorid and 100 mg sodium acetate in 3 mL DCM and 0.5 mL methanol was added 50 µL formaldehyde (aqueous 37%). The resulting mixture was stirred at room temperature for 10 min, before 155 mg sodium triacetoxyborohydride were added. The reaction mixture was stirred for 2 h and quenched with saturated aqueous sodium bicarbonate solution, followed by extraction with DCM. The combined organic phases were concentrated in vacuo to yield 88 mg of 4-(4-bromophenyl)-1-methyl-piperidine 3.9 as solid.

Analysis: HPLC-MS: $R_t$=0.38 min (method J), M+H=254/256

Synthesis of 4-(4-Bromo-3-trifluoromethyl-phenyl)-1-methyl-piperidine 3.10 for Example 32

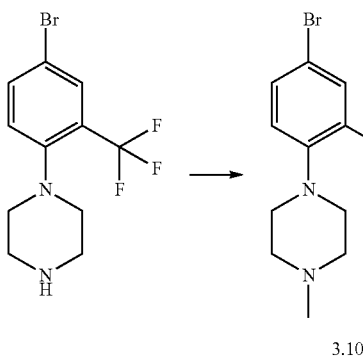

3.10

To a solution of 640 mg of 4-(4-bromo-3-trifluoromethyl-phenyl)-piperidine in 16.3 mL DCM and 2.9 mL methanol was added 6.40 mL formaldehyde (aqueous 37%). The resulting mixture was stirred at ambient temperature for 1 h, before cooled to 0° C. and 1.02 g sodium triacetoxyborohydride were added in portions. Then the reaction was allowed to warm to ambient temperature and was stirred for 1 h. The reaction mixture was quenched with saturated aqueous potassium carbonate solution, followed by extraction with DCM. The combined organic phases were dried over sodium sulfate, filtered and concentrated in vacuo. The crude material was purified by flash chromatography (heptane/ethyl acetate/methanol) to yield 650 mg of 4-(4-bromo-3-trifluoromethyl-phenyl)-1-methyl-piperidine 3.10 as oil.

Analysis: HPLC-MS: $R_t$=1.37 min (method K), M+H=323/325

Synthesis of 4-(4-Bromo-2-trifluoromethyl-phenyl)-morpholine 3.11 for Example 38

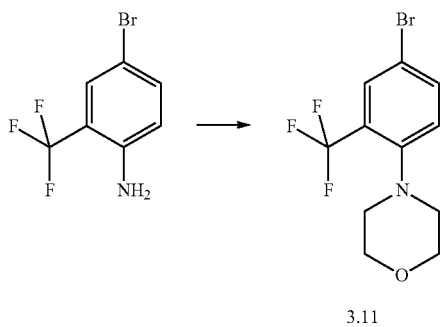 [SMILES: Nc1ccc(Br)cc1C(F)(F)F ; FC(F)(F)c1cc(Br)ccc1N1CCOCC1]

3.11

A mixture of 1.0 g of 4-bromo-2-(trifluoromethyl)aniline, 786 µL bis(2-bromoethyl)ether and 1.45 mL diisopropylamine in 3 mL DMA was stirred in a sealed tube at 140 CC for 2 days. The reaction mixture was poured into water and extracted with TBME. The combined organic extracts were washed with saturated aqueous sodium bicarbonate solution, dried over sodium sulfate, filtered and concentrated in vacuo. The crude material was purified by flash chromatography (heptane/ethyl acetate/methanol) to yield 833 mg (84% per HPLC) of 4-(4-bromo-2-trifluoromethyl-phenyl)-morpholine 3.11 as oil.

Analysis: HPLC-MS: $R_t$=2.37 min (method K), M+H=310/312

Synthesis of 4-Bromo-1-(4,4-difluorocyclohexyl)pyrazole 3.12 for Example 10

Step 1: Synthesis of N'-(4,4-difluoro-cyclohexylidene)-hydrazinecarboxylic acid tert-butyl ester

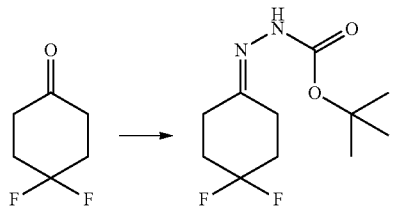

A solution of 0.99 g hydrazinecarboxylic acid tert-butyl ester in 5 mL methanol was added dropwise to a solution of 1.0 g of 4,4-difluoro-cyclohexanone in 5 mL methanol. The resulting mixture was stirred at room temperature for 1 h. The solvent was removed by destillation to yield 1.76 g N'-(4,4-difluoro-cyclohexylidene)-hydrazinecarboxylic acid tert-butyl ester as solid.

Analysis: MS: M+H=249

Step 2: Synthesis of N'-(4,4-difluoro-cyclohexyl)-hydrazinecarboxylic acid tert-butyl ester

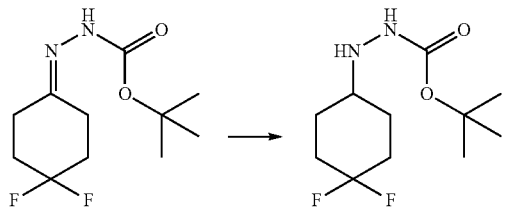 [SMILES: CC(C)(C)OC(=O)NN=C1CCC(F)(F)CC1 ; CC(C)(C)OC(=O)NNC1CCC(F)(F)CC1]

A mixture of 8.0 g N'-(4,4-difluoro-cyclohexylidene)-hydrazinecarboxylic acid tert-butyl ester and 800 mg palladium on carbon in 48 mL methanol was hydrogenated at 40° C. for 16 h at 10 bar. The catalyst was removed by filtration and the solvent was evaporated in vacuo to yield 7.82 g of N'-(4,4-difluoro-cyclohexyl)-hydrazinecarboxylic acid tert-butyl ester.

Analysis: MS: M−H=249

Step 3: Synthesis of (4,4-Difluoro-cyclohexyl)-hydrazine Hydrochlorid

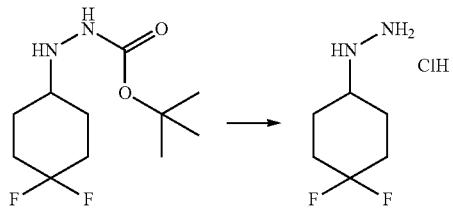 [SMILES: CC(C)(C)OC(=O)NNC1CCC(F)(F)CC1 ; NNC1CCC(F)(F)CC1 ; Cl]

To a mixture of 5.0 g of N'-(4,4-difluoro-cyclohexyl)-hydrazinecarboxylic acid tert-butyl ester in 20 mL DCM was added 40 mL 6M hydrochloric acid in isopropanol and the resulting mixture was stirred at room temperature for 12 h. The solvent was evaporated and the residue triturated with toluene. The precipitate was filtered off and dried to yield 3.72 g of (4,4-difluoro-cyclohexyl)-hydrazine hydrochlorid as solid.

Analysis: ESI-MS: M+H=151

Step 4: Synthesis of 1-(4,4-difluorocyclohexyl)pyrazole

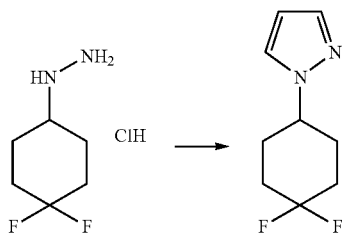 [SMILES: NNC1CCC(F)(F)CC1 ; Cl ; FC1(F)CCC(n2cccn2)CC1]

To a mixture of 2.04 g of (4,4-difluoro-cyclohexyl)-hydrazine hydrochlorid in 15 mL ethanol was added 3.50 mL conc. hydrochloric acid followed by 1.80 g 1,1,3,3-tetramethoxypropane, then the mixture was refluxed for 1h. The reaction mixture was diluted with water, ethanol was removed by destillation. The residue was alkalized with aqueous sodium hydroxid solution (30%) and extracted with diethylether. The combined organic phases were dried over magnesium sulfate, filtered and concentrated in vacuo to yield 2.02 g of 1-(4,4-difluorocyclohexyl)pyrazole as oil.

Analysis: HPLC-MS: $R_t$=0.46 min (method C), M+H=187

Step 5: Synthesis of 4-Bromo-1-(4,4-difluorocyclohexyl)pyrazole

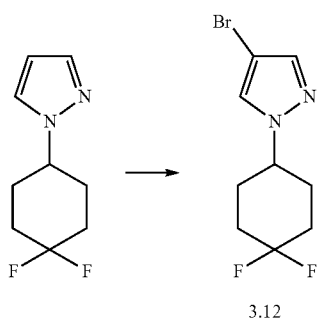 [SMILES: FC1(F)CCC(n2cccn2)CC1 ; FC1(F)CCC(n2cc(Br)cn2)CC1]

3.12

To a solution of 2.0 g of 1-(4,4-difluorocyclohexyl)pyrazole in 5 mL DCM was added 0.55 mL bromine at 0° C. and the mixture was stirred at room temperature for 15 min. The solvent was removed by destillation and the residue taken up in DCM and washed with semi saturated brine. The combined organic phases were dried over sodium sulfate, filtered and concentrated in vacuo to yield 2.81 g of 4-bromo-1-(4,4-difluorocyclohexyl)pyrazole 3.12 as solid.

Analysis: HPLC-MS: $R_t$=0.60 min (method C), M+H=265/267

Synthesis of 4-Bromo-1-(difluoromethyl) imidazole 3.13 for Example 83

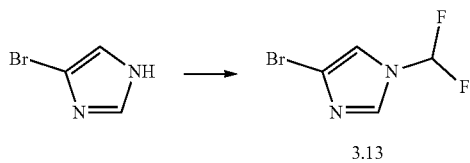 [SMILES: Brc1c[nH]cn1 ; FC(F)n1cnc(Br)c1]

3.13

Into a mixture of 10.0 g of 4-bromo-1H-imidazole in 60 mL DMF was passed 30 g chlorodifluoromethane under dry ice cooling, then 15.0 g potassium carbonate were added and the reaction mixture was heated to 110° C. overnight in a sealed tube (19 bar). Additional 30 g chlorodifluoromethane and 5 g potassium carbonate were added and the reaction mixture was heated to 110° C. overnight (9 bar). The reaction mixture was allowed to reach ambient temperature, then diluted with water and extracted with ethyl acetate. The combined organic extracts were washed with saturated brine, dried over magnesium sulfate, filtered and concentrated in vacuo. The residue was purified by rpHPLC (SunfireC18, acetonitrile/water trifluoroacetic acid) to yield 3.07 g 4-bromo-1-(difluoromethyl) imidazole.

Analysis: HPLC-MS: $R_t$=0.371 min (method J), M+H=197/199

The following bromides were commercially available:

3-Bromoimidazo[1,2-a]pyridine-6-carbonitrile 3.14 for Example 43,

4-Bromo-1-(3,3,3-trifluoro-propyl)pyrazole 3.15 for Example 15, 76

3-Bromo-1H-indazole-5-carbonitrile 3.16 for Example 16

2-Bromo-5-fluoro-pyridine 3.17 for Example 41

4-(4-Bromophenyl)-1-methyl-piperidine 3.18 for Example 42

2-(4-Bromo-2-methyl-phenyl)-1,2-thiazolidine 1,1-dioxide 3.19 for Example 71

7-Bromo-2-methyl-3,4-dihydro-1H-isoquinoline 3.20 for Example 75

4-Bromo-1-isopropoxy-2-methoxy-benzene 3.22 for Example 81

5-Bromo-1-methyl-indazol-3-amine 3.23 for Example 36, 2-(4-Bromophenyl)-1,2-thiazolidine 1,1-dioxide 3.24 for Example 33

4-Bromo-1-(difluoromethyl)pyrazole 3.25 for Example 40

4-Bromo-1-(tetrahydro-2H-pyran-2-yl)-1H-pyrazole 3.26 for Example 3

1-[(4-Bromophenyl)methyl]-2-methyl-1H-imidazole 3.27 for Example 17

4.1.3. Synthesis of compounds of formula 4 ($R^1$—X) (Scheme 1 and 2)

Synthesis of Tributyl-[2-(difluoromethyl)thiazol-4-yl]stannane 4.1 for Example 35

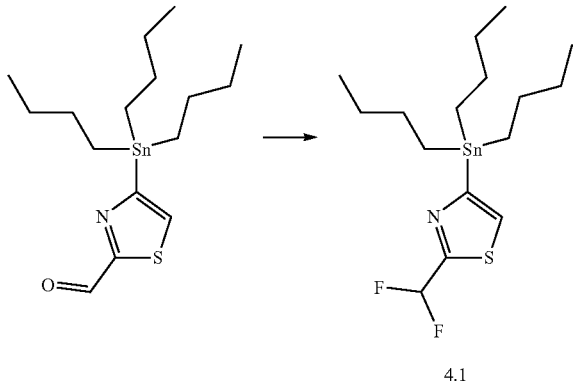 [SMILES: CCC[CH2][Sn]([CH2]CCC)([CH2]CCC)[c]1csc(C=O)n1 ; CCC[CH2][Sn]([CH2]CCC)([CH2]CCC)[c]1csc(C(F)F)n1]

4.1

To a mixture of 500 mg of 4-tributylstannylthiazole-2-carbaldehyde in 5 mL DCM was slowly added 1.01 mL 2.7M [bis(2-methoxyethyl)amino]sulfur trifluoride solution (in toluene) at 0° C., then the mixture was allowed to warm to ambient temperature and stirred for 2 h. The reaction mixture was diluted with DCM and washed with water. The combined organic phases were dried over sodium sulfate, filtered and concentrated in vacuo. The crude material was purified by flash chromatography (heptane/ethyl acetate/methanol) to yield 440 mg (82% per HPLC) tributyl-[2-(difluoromethyl)thiazol-4-yl]stannane 4.1 as oil.

Analysis: HPLC-MS: $R_t$=2.72 min (method M), M+H=425

The following stannane was commercially available:
Tributyl(thiazol-4-yl)stannane 4.2 for Example 29

Synthesis of 3-Methyl-7-(4,4,5,5-tetramethyl-1,3,2-dioxaborolan-2-yl)-1,2,4,5-tetrahydro-3-benzazepine 4.3 for Example 55

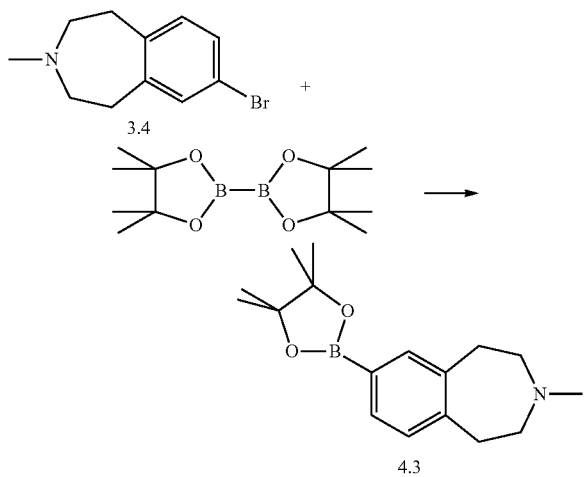

4.3

100 mg of 7-bromo-3-methyl-1,2,4,5-tetrahydro-3-benzazepine, 127 mg bis-(pinacolato)-diboron, 20 mg 1,1'-bis(diphenylphospino)ferrocenedichloropalladium(II) and 123 mg potassium acetate were suspended in 2 mL dioxane and the mixture stirred at 100° C. for 1.25 h. The mixture was diluted after cooling with dioxane, filtered through Celite, washed with dioxane and the solvent was evaporated in vacuo to yield 220 mg (92%, content 50%) 3-methyl-7-(4,4,5,5-tetramethyl-1,3,2-dioxaborolan-2-yl)-1,2,4,5-tetrahydro-3-benzazepine 4.3 as solid, which was used in the next step without further purification.

Analysis: HPLC-MS: $R_t$=0.45 min (method N), M+H=288

The following boronic esters were synthesized in analogy and were used without further purification:
1-Methyl-4-{4-[4-(4,4,5,5-tetramethyl-1,3,2-dioxaborolan-2-yl)-pyrazol-1-yl]-cyclohexyl}-piperazin-2-one 4.4 starting from 3.2 (for Example 12). Reaction conditions: 4 h, 100° C. Yield: 81% (content 36%). Analysis: HPLC-MS: $R_t$=0.41 min (method O), M+H=389
2-Difluoromethyl-5-(4,4,5,5-tetramethyl-1,3,2-dioxaborolan-2-yl)-pyridine 4.5 starting from 3.3 (for Example 51). Reaction conditions: 45 min, 100° C. Yield: 82% (content 40%). Analysis: HPLC: $R_t$=0.25 min (method N); MS: M+H=256
N,N,1-Trimethyl-6-(4,4,5,5-tetramethyl-1,3,2-dioxaborolan-2-yl)indole-2-carboxamide 4.6 starting from 3.5 (for Example 56). Reaction conditions: 3 h, 100° C. Yield: 84% (content 50%). Analysis: HPLC-MS: $R_t$=0.69 min (method N), M+H=329
1-[(3S)-Tetrahydrofuran-3-yl]-4-(4,4,5,5-tetramethyl-1,3,2-dioxaborolan-2-yl)pyrazole 4.7 starting from 3.6 (for Example 70). Reaction conditions: 3 h, 100° C. Yield: 59% (content 50%). Analysis: HPLC-MS: $R_t$=0.49 min (method N), M+H=265
2-[2-Methyl-4-(4,4,5,5-tetramethyl-1,3,2-dioxaborolan-2-yl)phenyl]-1,2-thiazolidine 1,1-dioxide 4.8 starting from 3.19 (for Example 71). Reaction conditions: 3 h, 100° C. Yield: 86% (content 50%). Analysis: HPLC-MS: $R_t$=0.64 min (method N), M+H=338
1-[(3R)-Tetrahydrofuran-3-yl]-4-(4,4,5,5-tetramethyl-1,3,2-dioxaborolan-2-yl)pyrazole 4.9 starting from 3.7 (for Example 74). Reaction conditions: 5 h, 100° C. Yield: 43% (content 38%). Analysis: HPLC-MS: $R_1$=0.54 min (method J), M+H=265
2-Methyl-7-(4,4,5,5-tetramethyl-1,3,2-dioxaborolan-2-yl)-3,4-dihydro-1H-isoquinoline 4.10 starting from 3.20 (for Example 75). Reaction conditions: 2 h, 100° C. Yield: 99% (content 43%). Analysis: HPLC-MS: $R_t$=0.41 min (method J), M+H=274
4-(4,4,5,5-Tetramethyl-1,3,2-dioxaborolan-2-yl)-1-(3,3,3-trifluoropropyl)pyrazole 4.11 starting from 3.15 (for Example 76). Reaction conditions: 4 h, 100° C. Yield: 29% (content 25%). Analysis: HPLC-MS: $R_t$=0.61 min (method J), M+H=291
1-Methyl-4-[4-(4,4,5,5-tetramethyl-1,3,2-dioxaborolan-2-yl)phenyl]piperidine 4.12 starting from 3.9 (for Example 80). Reaction conditions: 4 h, 100° C. Yield: 84% (content 50%). Analysis: HPLC-MS: $R_t$=0.47 min (method J), M+H=302
2-(4-Isopropoxy-3-methoxy-phenyl)-4,4,5,5-tetramethyl-1,3,2-dioxaborolane 4.13 starting from 3.22 (for Example 81). Reaction conditions: 3 h, 100° C. Yield: 87% (content 40%). Analysis: HPLC-MS: $R_t$=0.75 min (method J), M+H=293
2-[4-(4,4,5,5-Tetramethyl-1,3,2-dioxaborolan-2-yl)phenyl]-1,2-thiazolidine 1,1-dioxide 4.14 starting from 3.24 (for Example 33). Reaction conditions: 2.5 h, 80° C., in DMF. Yield: 68% (content 95%). Analysis: HPLC-MS: $R_t$=2.04 min (method K), M+H=324

The following examples were synthesized in analogy to the described example but using bis(triphenylphosphine)palladium(II) chloride (0.05 eq.) instead of 1,1'-bis(diphenylphospino)ferrocenedichloropalladium(II) as catalyst (see description above):

1-Methyl-5-(4,4,5,5-tetramethyl-1,3,2-dioxaborolan-2-yl)indazol-3-amine 4.15 starting from 3.23 (for Example 36). Reaction conditions: 1 h, 95° C. Yield: 89% (content 85%). Analysis: HPLC-MS: $R_t$=1.76 min (method K), M+H=274

1-Methyl-4-[4-(4,4,5,5-tetramethyl-1,3,2-dioxaborolan-2-yl)-2-(trifluoromethyl)phenyl]piperazine 4.16 starting from 3.10 (for Example 32). Reaction conditions: 1.5 h, 95° C. Yield: 61% (content 95%). Analysis: HPLC-MS: $R_t$=1.66 min (method K), M+H=371

1-(Difluoromethyl)-4-(4,4,5,5-tetramethyl-1,3,2-dioxaborolan-2-yl)pyrazole 4.17 starting from 3.25 (for Example 40). Reaction conditions: 2.5 h, 95° C. Yield: 70% (content 95%). Analysis: HPLC-MS: $R_t$=1.97 min (method K), M+H=245

4-[4-(4,4,5,5-Tetramethyl-1,3,2-dioxaborolan-2-yl)-2-(trifluoromethyl)phenyl]morpholine 4.18 starting from 3.11 (for Example 38). Reaction conditions: 1 h, 95° C. Yield: 99% (content 78%). Analysis: HPLC-MS: $R_t$=2.67 min (method K), M+H=358

Synthesis of 1-tert-Butyl-4-(4,4,5,5-tetramethyl-1,3,2-dioxaborolan-2-yl)pyrazole 4.19 for Examples 2,18

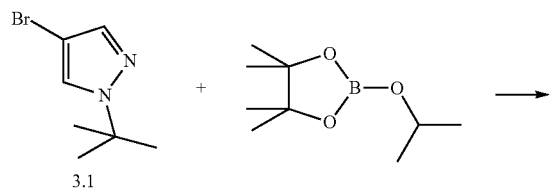

To a stirred mixture of 50 g of 4-bromo-1-tert-butylpyrazole 3.1 in 230 mL THF was added dropwise 100 mL 2.5M N-butyllithium solution in hexane under argon atmosphere below −60° C., then the mixture was stirred at this temperature for 5 min, before 52 mL 2-isopropoxy-4,4,5,5-tetramethyl-1,3,2-dioxaborolane were added dropwise below −60° C. The reaction mixture was allowed to reach ambient temperature. The mixture was cooled with an ice bath and diluted with aqueous phosphate buffer solution and water and neutralized with 2M aqueous hydrochloric acid. The organic solvent was removed by destillation and the residue was extracted with DCM. The combined organic extracts were washed with saturated brine, dried over sodium sulfate, filtered and concentrated in vacuo to yield 44.26 g of 1-tert-butyl-4-(4,4,5,5-tetramethyl-1,3,2-dioxaborolan-2-yl)pyrazole as solid.

Analysis: HPLC-MS: $R_t$=0.904 min (method F), M+H=251

Synthesis of 5-Methyl-1-tetrahydropyran-4-yl-4-(4,4,5,5-tetramethyl-1,3,2-dioxaborolan-2-yl)pyrazole 4.20 for Example 79

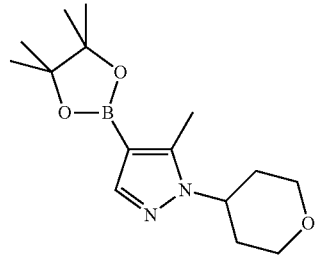

This intermediate was prepared from 4-bromo-5-methyl-1-tetrahydropyran-4-yl-pyrazole 3.8 according to the preparation of 1-tert-butyl-4-(4,4,5,5-tetramethyl-1,3,2-dioxaborolan-2-yl)pyrazole 4.19.

Yield: 94% of 4.20

Analysis: HPLC-MS: $R_t$=0.58 min (method J), M+H=293

Synthesis of 1-Methyl-4-[4-(4,4,5,5-tetramethyl-1,3,2-dioxaborolan-2-yl)pyrazol-1-yl]piperidine 4.21 for Example 49

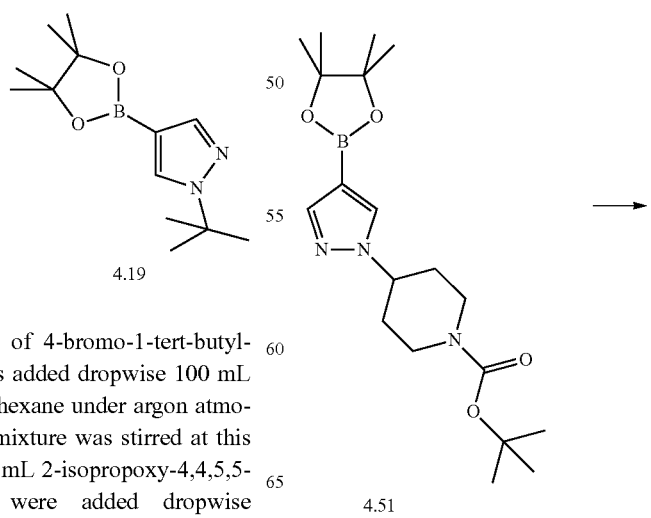

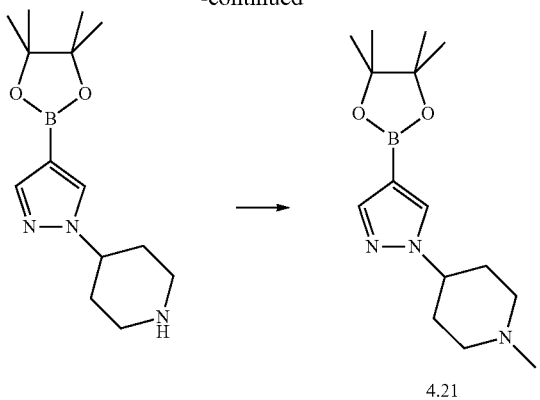

A mixture of 250 mg 4-[4-(4,4,5,5-tetramethyl-1,3,2-dioxaborolan-2-yl)-pyrazol-1-yl]piperidine-1-carboxylic acid tert-butyl ester 4.51 and 0.5 mL trifluoroacetic acid in 2 mL DCM was stirred at room temperature for 1 h. The solvent was removed by destillation and the residue taken up in 10 mL DCM, followed by addition of 494 µL formaldehyde (aqueous 37%). The reaction mixture was stirred at room temperature for 1 h, before 421 mg sodium triacetoxyborhydride were added. The resulting mixture was stirred at room temperature for 30 min, diluted with saturated aqueous sodium bicarbonate solution and extracted with DCM. The combined organic phases were dried over sodium sulfate, filtered and concentrated in vacuo to yield 99 mg of 1-methyl-4-[4-(4,4,5,5-tetramethyl-1,3,2-dioxaborolan-2-yl)pyrazol-1-yl]piperidine 4.21 as solid.

Analysis: HPLC-MS: $R_t$=1.25 min (method K), M+H=292

The following boronic acids, boronic esters and $BF_3$ borates were commercially available:
(3,4-Dimethoxyphenyl)boronic acid 4.22 for Example 1
2-Cyclopropyl-5-(4,4,5,5-tetramethyl-1,3,2-dioxaborolan-2-yl)pyridine 4.23 for Example 50
2-Methoxy-4-(4,4,5,5-tetramethyl-1,3,2-dioxaborolan-2-yl)phenol 4.24 for Examples 8, 73
(3,4,5-Trimethoxyphenyl)boronic acid 4.25 for Example 52
tert-Butyl-5-methoxy-3-(4,4,5,5-tetramethyl-1,3,2-dioxaborolan-2-yl)indole-1-carboxylate 4.26 for Example 53
1-(2-Methoxyethyl)-4-(4,4,5,5-tetramethyl-1,3,2-dioxaborolan-2-yl)pyrazole 4.27 for Example 57
1-Ethyl-4-(4,4,5,5-tetramethyl-1,3,2-dioxaborolan-2-yl)pyrazole 4.28 for Example 58
[6-(Trifluoromethyl)-3-pyridyl]boronic acid 4.29 for Examples 4, 61
(1-Methylindazol-5-yl)boronic acid 4.30 for Example 62
1-Methyl-4-(4,4,5,5-tetramethyl-1,3,2-dioxaborolan-2-yl)pyrazole 4.31 for Example 63
1-Tetrahydropyran-4-yl-4-(4,4,5,5-tetramethyl-1,3,2-dioxaborolan-2-yl)pyrazole 4.32 for Examples 47, 64
1-Isopropyl-4-(4,4,5,5-tetramethyl-1,3,2-dioxaborolan-2-yl)pyrazole 4.33 for Example 65
4-[5-(4,4,5,5-Tetramethyl-1,3,2-dioxaborolan-2-yl)-2-pyridyl]morpholine 4.34 for Example 66
1-Methyl-4-[4-(4,4,5,5-tetramethyl-1,3,2-dioxaborolan-2-yl)phenyl]piperazine 4.35 for Examples 26, 67
1,3-Dimethyl-4-(4,4,5,5-tetramethyl-1,3,2-dioxaborolan-2-yl)pyrazole 4.36 for Example 68
1,5-Dimethyl-4-(4,4,5,5-tetramethyl-1,3,2-dioxaborolan-2-yl)pyrazole 4.37 for Example 69
(1-Methylindazol-6-yl)boronic acid 4.38 for Example 72
7-Chloro-2-(4,4,5,5-tetramethyl-1,3,2-dioxaborolan-2-yl)-1H-indole 4.39 for Examples 48, 77
1-Cyclopropyl-4-(4,4,5,5-tetramethyl-1,3,2-dioxaborolan-2-yl)pyrazole 4.40 for Example 78
tert-Butyl 4-[4-(4,4,5,5-tetramethyl-1,3,2-dioxaborolan-2-yl)pyrazol-1-yl]piperidine-1-carboxylate 4.41 for Examples 9, 45, 82
Potassium 5-methyl-2-thiophenetrifluoroborate 4.42 for Example 54
Potassium 6-methoxy-3-pyridyltrifluoroborate 4.43 for Example 59
Potassium 4-(trifluoromethyl)phenyltrifluoroborate 4.44 for Example 60
5-Fluoro-2-(4,4,5,5-tetramethyl-1,3,2-dioxaborolan-2-yl)pyridine 4.45
(4-Morpholinophenyl)boronic acid 4.46 for Example 22
(1-Methylindazol-5-yl)boronic acid 4.47 for Examples 28
2-Isopropoxy-5-(4,4,5,5-tetramethyl-1,3,2-dioxaborolan-2-yl)pyridine 4.48 for Example 27
1-Methyl-3-(4,4,5,5-tetramethyl-1,3,2-dioxaborolan-2-yl)pyrazole 4.49 for Example 14
1-Cyclohexyl-4-(4,4,5,5-tetramethyl-1,3,2-dioxoborolan-2-yl)-1H-pyrazole 4.50 for Example 7
4-[4-(4,4,5,5-tetramethyl-1,3,2-dioxaborolan-2-yl)-pyrazol-1-yl]piperidine-1-carboxylic acid tert-butyl ester 4.51 for Example 49

4.1.4. Synthesis of Heterocyclic 5 and 10 from Scheme 1 and 2

Synthesis of 4,6-Dichloro-2-methyl-pyrazolo[4,3-c]pyridine 5.1 for Examples 1-3, 7-13, 17, 50-83

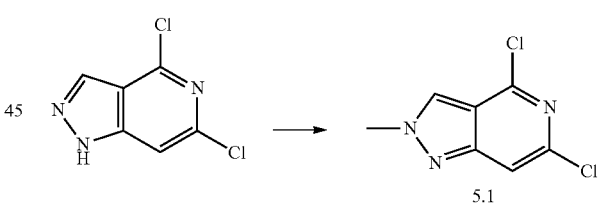

To a mixture of 9.5 g trimethyloxonium tetrafluoroborate in 300 mL DCM was added 10.0 g of 4,6-dichloro-3aH-pyrazolo[4,3-c]pyridine (commercially available from Sphinx Scientific Laboratory Corporation) under argon atmosphere. The reaction mixture was stirred at room temperature overnight. Additional 2.7 g trimethyl-oxonium tetrafluoroborate and 2.0 mL ethyldiisopropylamine (DIPEA) were added and the reaction mixture was stirred at room temperature overnight. The reaction mixture was diluted with water, filtered and the organic phase was concentrated in vacuo. The crude material was taken up in semi saturated aqueous sodium bicarbonate solution. The precipitate was filtered off, washed with water and dried to yield 8.2 g of 4,6-dichloro-2-methyl-pyrazolo[4,3-c]pyridine 5.1 as solid.

Analysis: HPLC-MS: $R_t$=0.45 min (method C), M+H=202/204

Synthesis of 6-Bromo-2-methyl-indazol-4-ol 10.2 for Examples 14-16, 18, 22, 26-29, 32, 33, 35, 36, 38, 40-43, 45, 47-49

Step 1: Synthesis of 6-Bromo-4-methoxy-2-methyl-indazole

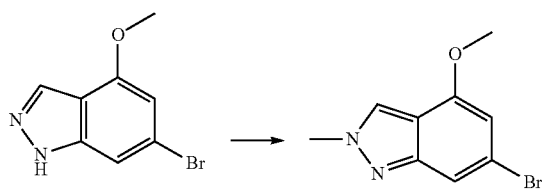

To a solution of 5.0 g of 6-bromo-4-methoxy-1H-indazole in 50 mL 1,4-dioxane was added 4.23 g trimethyloxonium tetrafluoroborate at room temperature. The reaction mixture was stirred at 40° C. for 3 h and left standing overnight. The reaction mixture was poured into water. The precipitate was filtered off, washed with water and dried to yield 4.26 g of 6-bromo-4-methoxy-2-methyl-indazole as solid.

Analysis: HPLC-MS: $R_t$=1.78 min (method K), M+H=241/243

Step 2: Synthesis of 6-Bromo-2-methyl-indazol-4-ol 10.2

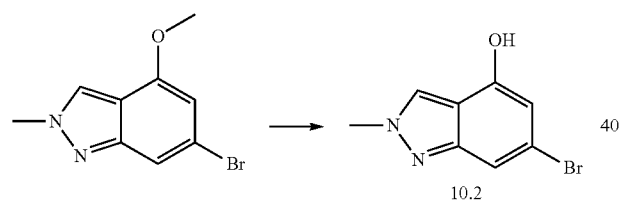

To a suspension of 4.26 g of 6-bromo-4-methoxy-2-methyl-indazole in 42.6 mL DCM was added 53.06 mL boron tribromide solution (1M in DCM) at 0° C. The reaction mixture was allowed to reach ambient temperature and stirred for 3 days. Additional 10 mL boron tribromide solution (1M in DCM) was added and the reaction mixture was stirred at room temperature for 8 h. The mixture was poured into water. The precipitate was filtered off and triturated with acetonitrile to yield 2.8 g of 6-bromo-2-methyl-indazol-4-ol 10.2 as solid. The acetonitrile filtrate was combined with the DCM layer and concentrated in vacuo. The residue was triturated with acetonitrile to yield 1.08 g of 6-bromo-2-methyl-indazol-4-ol 10.2 as solid. The two solids were combined to yield 3.88 g of 6-bromo-2-methyl-indazol-4-ol 10.2 as solid.

Analysis: HPLC-MS: $R_t$=1.49 min (method K), M+H=227/229

4.2. Synthesis of Intermediates 6, 7, 8 and 11 from Scheme 1 and 2

Synthesis of (4R)-4-[(1R)-1-(6-chloro-2-methyl-pyrazolo[4,3-c]pyridin-4-yl)oxyethyl]pyrrolidin-2-one (7) for Examples 1-3, 7-13, 17, 50-83

Step 1: Synthesis of (4R)-4-[(1R)-1-(6-chloro-2-methyl-pyrazolo[4,3-c]pyridin-4-yl)oxyethyl]-1-[(1S)-1-(4-methoxyphenyl)ethyl]pyrrolidin-2-one

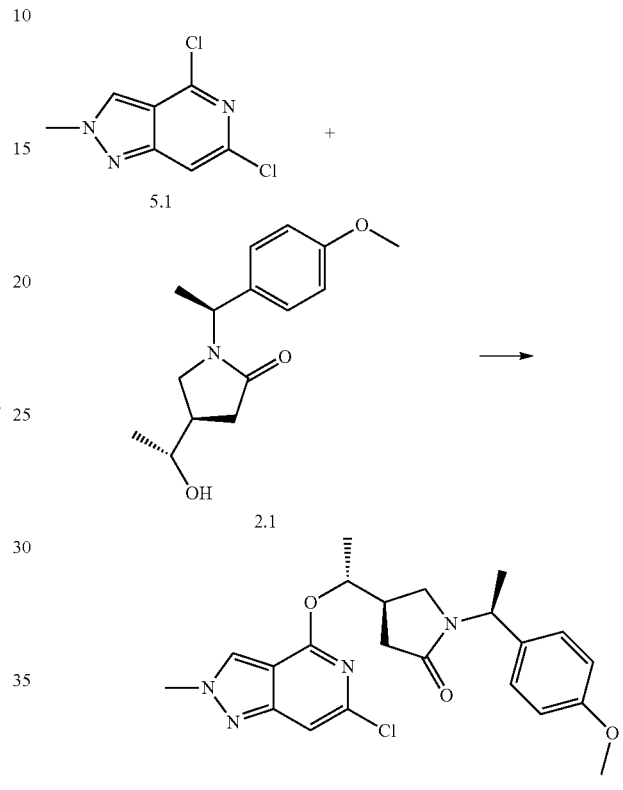

To a mixture of 20.0 g of 4,6-dichloro-2-methyl-pyrazolo[4,3-c]pyridine 5.1 and 30.1 g (R)-4-[(R)-1-hydroxyethyl]-1-[(S)-1-(4-methoxyphenyl)-ethyl]-pyrrolidin-2-one 2.1 in 1 L dioxane was added 4.51 g NaH in mineral oil (60%). The resulting mixture was stirred at 100° C. for 15 h. The solvent was removed by destillation to ⅓. The residue was taken up in DCM und washed with saturated ammonium chloride solution and water. The combined organic phases were dried over magnesium sulfate, filtered and concentrated in vacuo to yield 44.8 g (88% per HPLC) of (R)-4-[(R)-1-(6-chloro-2-methyl-2H-pyrazolo[4,3-c]pyridin-4-yloxy)-ethyl]-1-[(S)-1-(4-methoxy-phenyl)-ethyl]-pyrrolidin-2-one as solid.

Analysis: HPLC-MS: $R_t$=0.65 min (method J), M+H=429

Alternatively, 6.1 can be synthesized as following:

A solution of 20.0 g of 4,6-dichloro-2-methyl-pyrazolo[4,3-c]pyridine 5.1 and 25.4 g (R)-4-[(R)-1-hydroxyethyl]-1-[(S)-1-(4-methoxyphenyl)-ethyl]-pyrrolidin-2-one 2.1 in 250 mL dioxane was added to a slurry of 9.6 g NaH in mineral oil (60%) in 50 mL of dioxane at 20° C. The resulting mixture was stirred at 40° C. for 5.5 h. The mixture was cooled to ambient temperature and quenched by the slow addition of 36 mL of 4M HCl in dioxane. The reaction mixture was diluted with 200 mL of isopropyl acetate and water (100 mL). The layers were separated, and the aqueous portion was extracted with twice with 100 mL of isopropyl acetate. The organic portions were assayed to show 40.78 g of (4R)-4-[(1R)-1-(6-chloro-2-methyl-pyrazolo[4,3-c]pyridin-4-yl)oxyethyl]-1-[(1S)-1-(4-methoxyphenyl)ethyl]pyrrolidin-2-one in a solution mass of 796.3 g for a 99% yield. Purification of 6.1 can be conducted by concentration of a crude isopropyl acetate solution of 50 g 6.1 in vacuo to 200 mL wherein solids crystallized. 500 mL of heptane was slowly charged to the slurry at 20° C. and the mixture was agitated for 2 h. The solids were collected by filtration, washed with heptane, and dried at 30° C. 46.9 g of 6.1 was isolated as a beige solid in 92% recovery.

Step 2: Synthesis of (4R)-4-[(1R)-1-(6-chloro-2-methyl-pyrazolo[4,3-c]pyridin-4-yl)oxyethyl]pyrrolidin-2-one 7.1

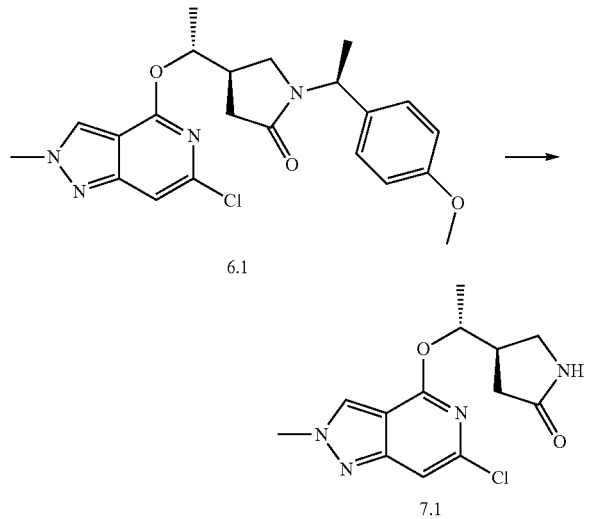

A mixture of 1.0 g of (R)-4-[(R)-1-(6-chloro-2-methyl-2H-pyrazolo[4,3-c]pyridin-4-yloxy)-ethyl]-1-[(S)-1-(4-methoxy-phenyl)-ethyl]-pyrrolidin-2-one 6.1 and 1 mL anisole in 5 mL trifluoroacetic acid (TFA) was stirred at 80° C. for 17 h. The solvent was removed by destillation. The residue was taken up in DCM and washed with saturated aqueous sodium bicarbonate solution. The combined organic phases were concentrated in vacuo and the residue was triturated with diethyl ether. The precipitate was filtered off and dried to yield 0.37 g of (R)-4-[(R)-1-(6-chloro-2-methyl-2H-pyrazolo[4,3-c]pyridin-4-yloxy)-ethyl]-pyrrolidin-2-one 7.1 as solid.
Analysis: HPLC-MS: $R_t$=0.47 min (method J), M+H=295

Synthesis of (4R)-4-[(1R)-1-(6-Bromo-2-methyl-indazol-4-yl)oxyethyl]pyrrolidin-2-one (7.5 for Examples 14-16, 18, 22, 26-29, 32, 33, 35, 36, 38, 40-43, 45, 47-49

Step 1: Synthesis of (4R)-4-[(1R)-1-(6-Bromo-2-methyl-indazol-4-yl)oxyethyl]-1-[(1S)-1-(4-methoxyphenyl)ethyl]pyrrolidin-2-one

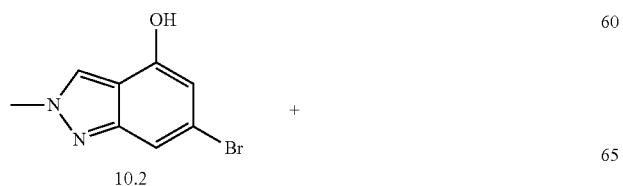

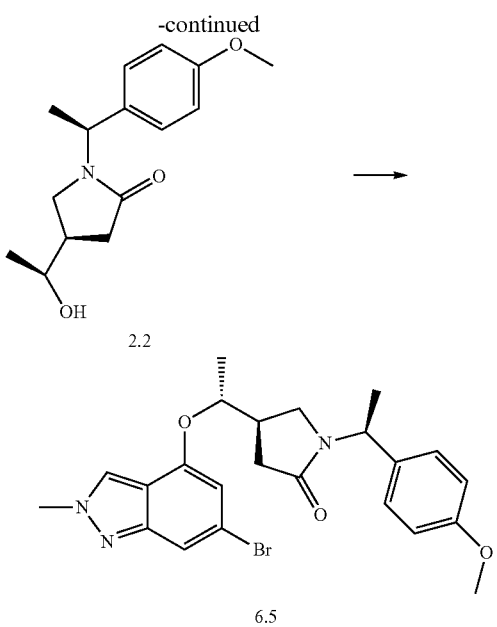

To a mixture of 1.46 g 6-bromo-2-methyl-indazol-4-ol 10.2, 1.86 g (R)-4-[(S)-1-hydroxyethyl]-1-[(S)-1-(4-methoxyphenyl)-ethyl]-pyrrolidin-2-one 2.2 and 5.06 g triphenylphosphine in 36.5 mL THF was added 4.44 g di-tert-butyl azodicarboxylate (DBAD) over 30 min. The resulting mixture was stirred at room temperature for 18 h. The solvent was evaporated and the residue triturated with TBME. The precipitate was filtered off and washed with TBME. The filtrate was concentrated in vacuo and the resulting residue was purified by flash chromatography (heptane/ethyl acetate/methanol) to yield 2.36 g (54% per HPLC) of (4R)-4-[(1R)-1-(6-bromo-2-methyl-indazol-4-yl)oxyethyl]-1-[(1S)-1-(4-methoxyphenyl)ethyl]pyrrolidin-2-one 6.5 as solid.
Analysis: HPLC-MS: $R_t$=2.00 min (method K), M+H=472/474

Step 2: Synthesis of (4R)-4-[(1R)-1-(6-Bromo-2-methyl-indazol-4-yl)oxyethyl]pyrrolidin-2-one 7.5

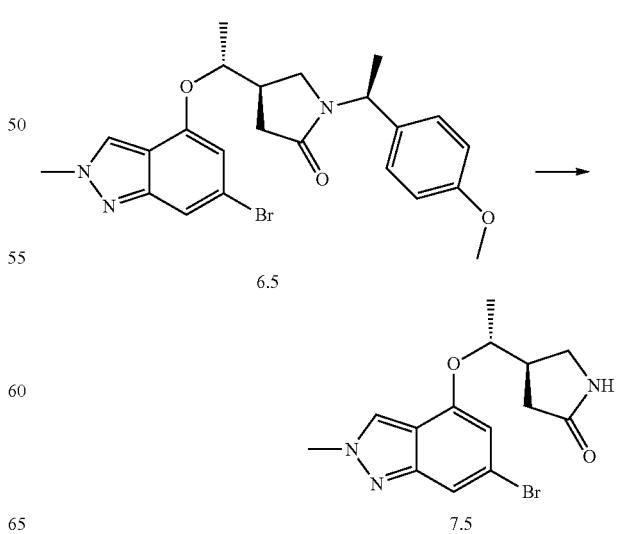

A mixture of 583 mg (63% per HPLC) of (4R)-4-[(1R)-1-(6-bromo-2-methyl-indazol-4-yl) oxyethyl]-1-[(1S)-1-(4-methoxyphenyl) ethyl] pyrrolidin-2-one 6.5 in 10 mL TFA was stirred at 70° C. for 18 h. The solvent was removed by destillation. The residue was taken up in DCM, poured into saturated aqueous sodium bicarbonate solution and extracted. The combined organic phases were dried over sodium sulfate, filtered and concentrated in vacuo. The crude material was purified by flash chromatography (heptane/ethyl acetate/methanol) to yield 321 mg (84% per HPLC) of (4R)-4-[(1R)-1-(6-bromo-2-methyl-indazol-4-yl) oxyethyl]pyrrolidin-2-one 7.5.

Analysis: HPLC-MS: $R_t$=1.63 min (method K), M+H=338/340

4.1.6. Synthesis of Boronic Acids and Boronic Esters 11 from Scheme 1 and 2

Synthesis of [2-Methyl-4-[(1R)-1-[(3R)-5-oxopyrrolidin-3-yl]ethoxy]pyrazolo[4,3-c]pyridin-6-yl]boronic acid 11.1 for Examples 3, 10, 13, 17, 83

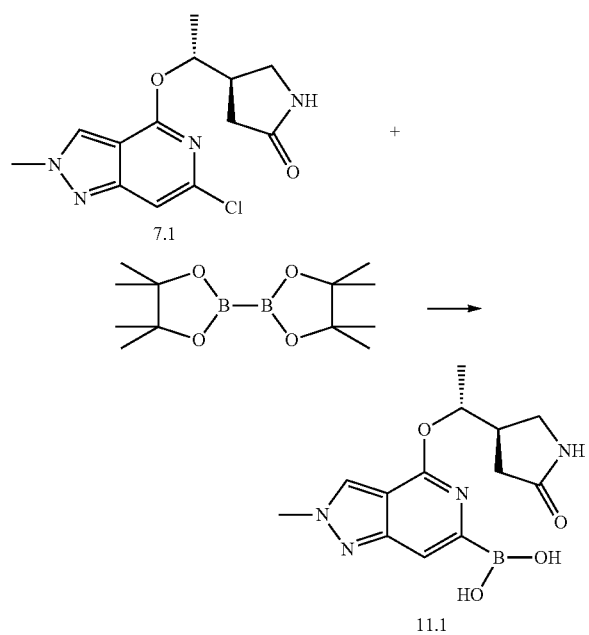

400 mg of (R)-4-[(R)-1-(6-chloro-2-methyl-2H-pyrazolo[4,3-c]pyridin-4-yloxy)-ethyl]-pyrrolidin-2-one 7.1, 620 mg bis-(pinacolato)-diboron, 122 mg 1,1'-bis(diphenylphosphino) ferrocenedichloropalladium(II) and 360 mg potassium acetate were suspended in 4 mL dioxane and the mixture stirred at 100° C. for 1 h. The mixture was diluted with dioxane, filtered through Celite, washed with dioxane and the solvent was evaporated in vacuo to yield 1.09 g (crude) [2-methyl-4-[(1R)-1-[(3R)-5-oxopyrrolidin-3-yl]ethoxy]pyrazolo[4,3-c] pyridin-6-yl]boronic acid 11.1 as oil, which was used in the next step without further purification.

Analysis: HPLC-MS: $R_t$=0.26 min (method S), M+H=305

Synthesis of (4R)-4-[(1R)-1-[2-Methyl-6-(4,4,5,5-tetramethyl-1,3,2-dioxaborolan-2-yl)indazol-4-yl]oxyethyl]pyrrolidin-2-one 11.3 for Examples 15, 16, 41, 42, 43

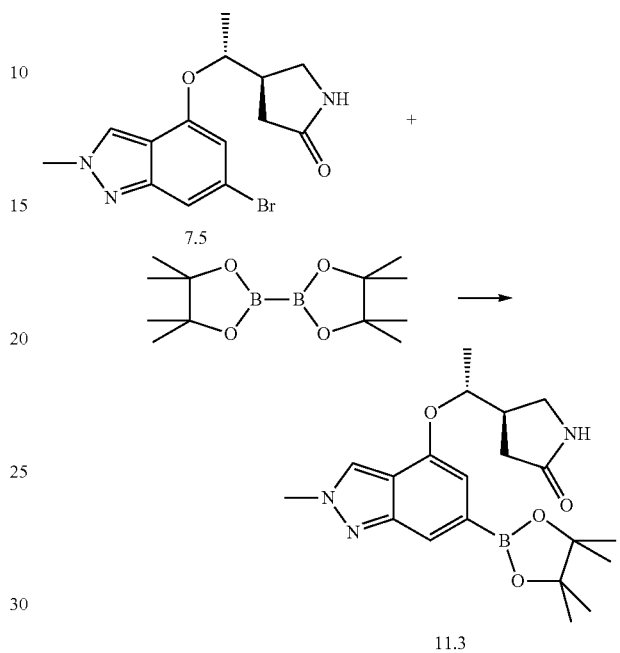

500 mg of (4R)-4-[(1R)-1-(6-bromo-2-methyl-indazol-4-yl)oxyethyl]pyrrolidin-2-one 7.5, 563 mg bis-(pinacolato)-diboron, 52 mg bis(triphenylphosphine)palladium(II) chloride and 435 mg potassium acetate were suspended in 5 mL dioxane and the resulting mixture was stirred at 95° C. for 1 h. The reaction mixture was allowed to reach ambient temperature, diluted with water and extracted with DCM. The combined organic phases were dried over sodium sulfate, filtered and concentrated in vacuo. The residue was purified by flash chromatography (heptane/ethyl acetate/methanol) to yield 505 mg (78% per HPLC) of (4R)-4-[(1R)-1-[2-methyl-6-(4,4,5,5-tetramethyl-1,3,2-dioxaborolan-2-yl)indazol-4-yl]oxyethyl]pyrrolidin-2-one 11.3.

Analysis: HPLC-MS: $R_t$=1.76 min (method K), M+H=387

4.3 Synthesis of the Patent Examples of Formula 1

Synthesis of (4R)-4-[(1R)-1-[6-(3,4-Dimethoxyphenyl)-2-methyl-pyrazolo[4,3-c]pyridin-4-yl]oxyethyl] pyrrolidin-2-one (Example 1)

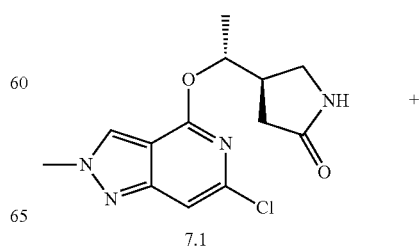

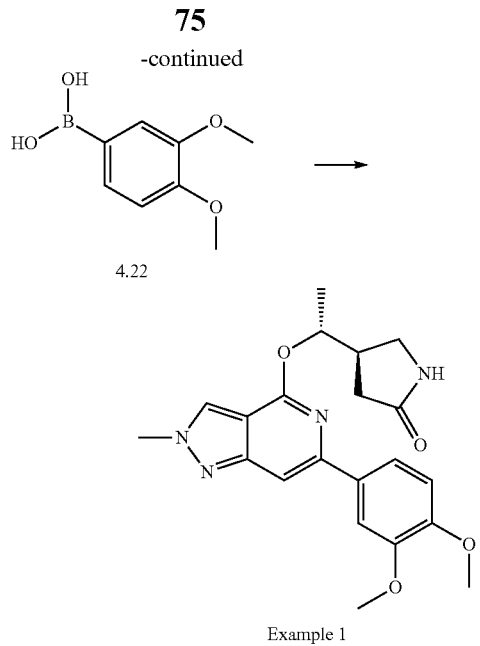

4.22

Example 1

A mixture of 150 mg (4R)-4-[(1R)-1-(6-chloro-2-methyl-pyrazolo[4,3-c]pyridin-4-yl)oxyethyl]pyrrolidin-2-one 7.1, 139 mg (3,4-dimethoxyphenyl)boronic acid 4.22, 17.9 mg bis(triphenylphosphine)palladium(II) chloride and 764 μL 2M aqueous sodium carbonat solution in 1.7 mL DMF was stirred at 90° C. for 20 h. The reaction mixture was allowed to reach ambient temperature and purified by rpHPLC to yield after lyophilisation 42 mg of Example 1.

Analysis: HPLC-MS: $R_t$=3.72 min (method T), M+H=397

Synthesis of (4R)-4-[(1R)-1-[6-(1-tert-Butylpyrazol-4-yl)-2-methyl-pyrazolo[4,3-c]pyridin-4-yl]oxyethyl]pyrrolidin-2-one (Example 2)

Step 1: Synthesis of (4R)-4-[(1R)-1-[6-(1-tert-Butylpyrazol-4-yl)-2-methyl-pyrazolo[4,3-c]pyridin-4-yl]oxyethyl]-1-[(1S)-1-(4-methoxyphenyl)ethyl]pyrrolidin-2-one

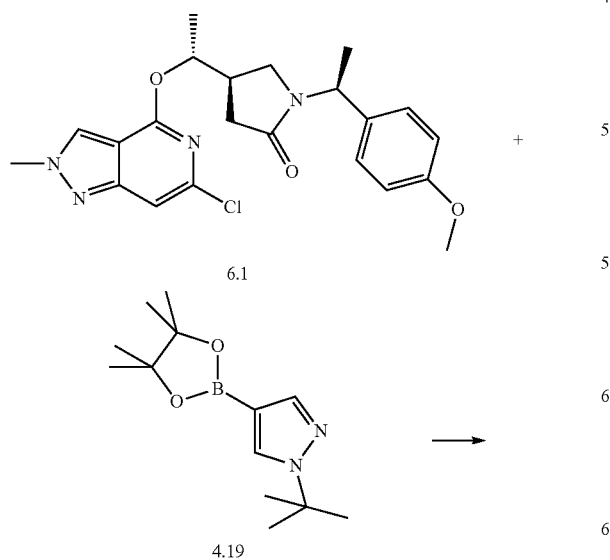

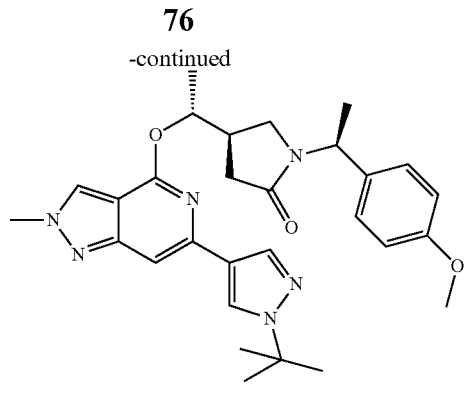

8.1

To a mixture of 1.0 g (4R)-4-[(1R)-1-(6-chloro-2-methyl-pyrazolo[4,3-c]pyridin-4-yl)oxyethyl]-1-[(1S)-1-(4-methoxyphenyl)ethyl]pyrrolidin-2-one 6.1, 790 mg 1-tert-butyl-4-(4,4,5,5-tetramethyl-1,3,2-dioxaborolan-2-yl) 4.19 and 170 mg 1,1'-bis(diphenylphospino) ferrocenedichloropalladium(II) (complex with DCM (1:1)) in 6 mL dioxane was added 5.0 mL 2M aqueous sodium carbonat solution. The resulting mixture was stirred in a sealed tube at 140° C. for 1h. The reaction mixture was poured into DCM. The precipitate was filtered off. The filtrate was concentrated in vacuo and the resulting residue was purified by flash chromatography (DCM/methanol=1/0→9/1) to yield 1.0 g (50% per NMR) of (4R)-4-[(1R)-1-[6-(1-tert-butylpyrazol-4-yl)-2-methyl-pyrazolo[4,3-c]pyridin-4-yl]oxyethyl]-1-[(1S)-1-(4-methoxyphenyl)ethyl]pyrrolidin-2-one 8.1 as oil.

Analysis: HPLC-MS: $R_t$=0.63 min (method C), M+H=517

Step 2: Synthesis of (4R)-4-[(1R)-1-[6-(1-tert-Butylpyrazol-4-yl)-2-methyl-pyrazolo[4,3-c]pyridin-4-yl]oxyethyl]pyrrolidin-2-one (Example 2)

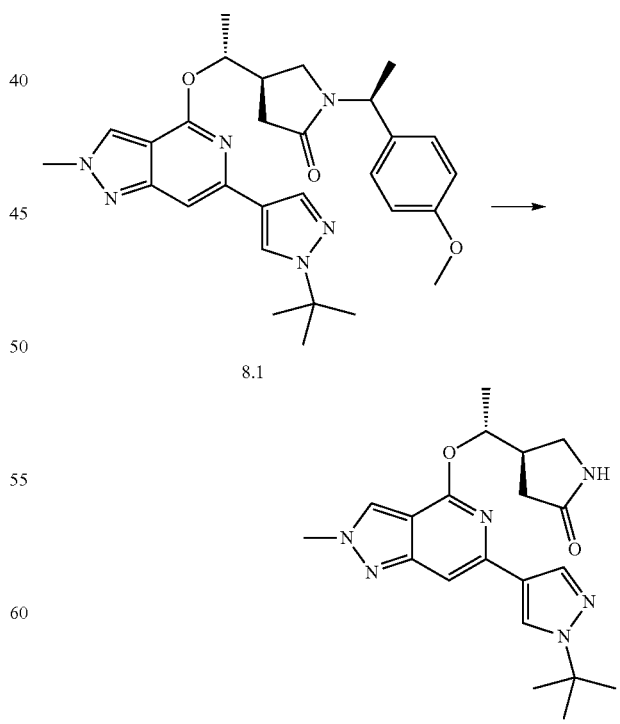

Example 2

A mixture of 3.90 g (36% per HPLC) of (4R)-4-[(1R)-1-[6-(1-tert-butylpyrazol-4-yl)-2-methyl-pyrazolo[4,3-c]pyridin-4-yl]oxyethyl]-1-[(1S)-1-(4-methoxyphenyl)ethyl]pyrrolidin-2-one 8.1 in 25 mL TFA was stirred at 80° C. for 3h. The reaction mixture was purified by rpHPLC (SunfireC18, acetonitrile/water, TFA and XbridgeC18, acetonitrile/water, ammonia) and the desired fractions were lyophilized. The residue was triturated with TBME and a small amount of acetone. The solvent was removed by destillation and the residue was dried to yield 410 mg of Example 2 as solid.

Analysis: HPLC-MS: $R_t$=0.52 min (method C), M+H=383

Alternatively, 8.1 can be synthesized as following:

Synthesis of Ethyl 3-amino-1-methyl-1H-pyrazole-4-carboxylate

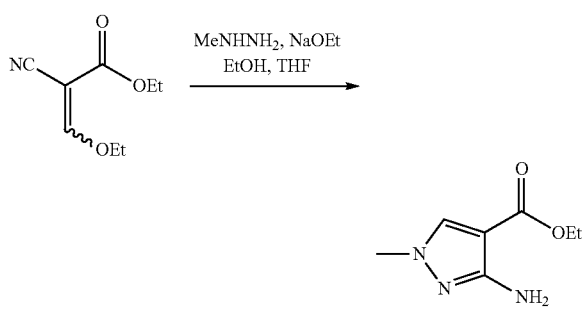

A solution of ethyl 2-cyano-3-ethoxyacrylate (5.0 g, 30 mmol) in anhydrous THF (10 mL) was charged dropwise to a mixture of sodium ethoxide (4.02 g, 59 mmol) and methylhydrazine (1.36 g, 30 mmol) in absolute ethanol (10 mL) at 0° C. under nitrogen. After aging the agitated mixture for 90 min, a solution of anhydrous hydrochloric acid (3.22 M in CPME, 28 mL, 90 mmol) was charged to the reaction dropwise. The reaction was then concentrated in vacuo to a solid, diluted with isopropyl acetate (20 mL) and concentrated to a solid. The crude paste was suspended in hot isopropyl acetate (75 mL) and filtered hot. The filtrate was concentrated in vacuo to approximately 15 mL wherein a solid crystallized upon cooling to ambient temperature. The mixture was diluted by the dropwise addition of heptane (30 mL). The mixture was agitated for 1h at ambient temperature. Ethyl 3-amino-1-methyl-1H-pyrazole-4-carboxylate was isolated by filtration, washed with heptane and dried under vacuum to provide 3.7 g as a yellow-orange solid in 74% yield. $^1$H NMR (500 MHz, DMSO-d$^6$) δ=7.87 (s, 1H), 5.3 (bs, 2H), 4.15 (q, J=7.2 Hz, 2H), 3.60 (s, 3H), 1.23 (t, J=7.2 Hz, 3H).

Synthesis of Ethyl 3-bromo-1-methyl-1H-pyrazole-4-carboxylate

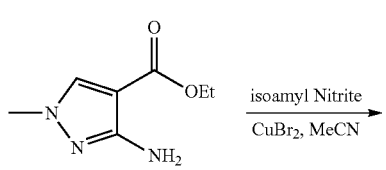

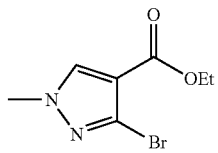

Isoamyl nitrite (420 mg, 3.6 mmol) was charged dropwise to an agitated mixture of ethyl 3-amino-1-methyl-1H-pyrazole-4-carboxylate (400 mg, 2.4 mmol) and copper (II) bromide (660 mg, 3.0 mmol) in anhydrous acetonitrile (10 mL) at ambient temperature. The reaction was agitated for one hour; at which point, the reaction was diluted with isopropyl acetate (100 mL). The mixture was washed with water (100 mL) and concentrated to an oily residue. Purification by silica gel chromatography with methyl t-butyl ether and hexanes provided ethyl 3-bromo-1-methyl-1H-pyrazole-4-carboxylate (350 mg) as a white solid in 64% yield. $^1$H NMR (500 MHz, CDCl$_3$) δ=7.83 (s, 1H), 4.30 (q, J=7.1 Hz, 2H), 3.90 (s, 3H), 1.35 (t, J=7.2 Hz, 3H).

Synthesis of 3-Bromo-1-methyl-1H-pyrazole-4-carboxylic acid

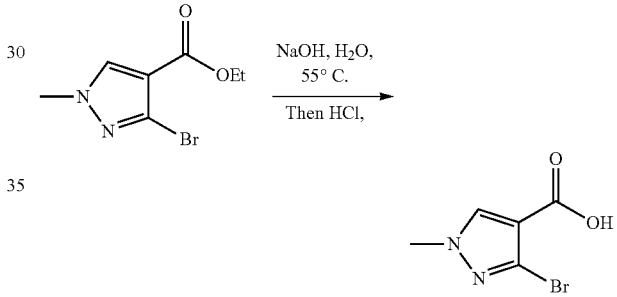

An aqueous solution of sodium hydroxide (2 M, 10 mL, 20 mmol) was charged to a mixture of ethyl 3-bromo-1-methyl-1H-pyrazole-4-carboxylate (2.0 g, 8.6 mmol) in ethanol (20 mL) at ambient temperature. The reaction was agitated at 50° C. for 1h; at which point, the reaction was cooled to ambient temperature. An aqueous solution of hydrochloric acid (3 M, 6.7 mL, 20 mmol) was charged dropwise to the reaction to induce crystallization. The solids of 3-bromo-1-methyl-1H-pyrazole-4-carboxylic acid were collected by filtration, washed with water followed by heptane, and dried to afford 1.4 g as a white solid in 79% yield. $^1$H NMR (400 MHz, DMSO-d$^6$) δ=12.59 (s, 1H), 8.27 (s, 1H), 3.85 (s, 3H).

Synthesis of 1-(1-(tert-Butyl)-1H-pyrazol-4-yl)ethan-1-one

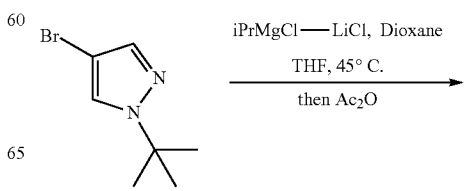

-continued

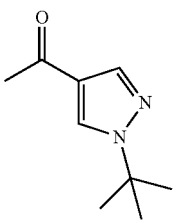

Isopropyl magnesium chloride lithium chloride complex (1.3 M in THF, 28.4 mL, 37 mmol) was charged to a solution of 4-bromo-1-(tert-butyl)-1H-pyrazole (5.0 g, 25 mmol) in anhydrous THF (25 mL) under argon at ambient temperature. Anhydrous dioxane (3.3 g, 37 mmol) was charged to the reaction, and the reaction was agitated at 45° C. for 4 h. The resulting mixture was cooled to ambient temperature and charged to an anhydrous solution of acetic anhydride (7.5 g, 73 mmol) in THF (25 mL) at −20° C. The resulting mixture was warmed to ambient temperature and concentrated to a residue. The mixture was dissolved in methyl t-butyl ether (50 mL) and washed with water (25 mL). The organic portion was concentrated to provide crude 1-(1-(tert-butyl)-1H-pyrazol-4-yl)ethan-1-one as an oil (7.6 g, 36 wt %) and 67% yield. Crystallization in a mixture of methyl t-butyl ether and heptane provided analytically pure material. $^1$H NMR (500 MHz, CDCl$_3$) δ=7.96 (s, 1H), 7.86 (s, 1H), 2.37 (s, 3H), 1.55 (s, 9H).

Synthesis of 6-(1-(tert-Butyl)-1H-pyrazol-4-yl)-2-methylpyrano[4,3-c]pyrazol-4(2H)-one

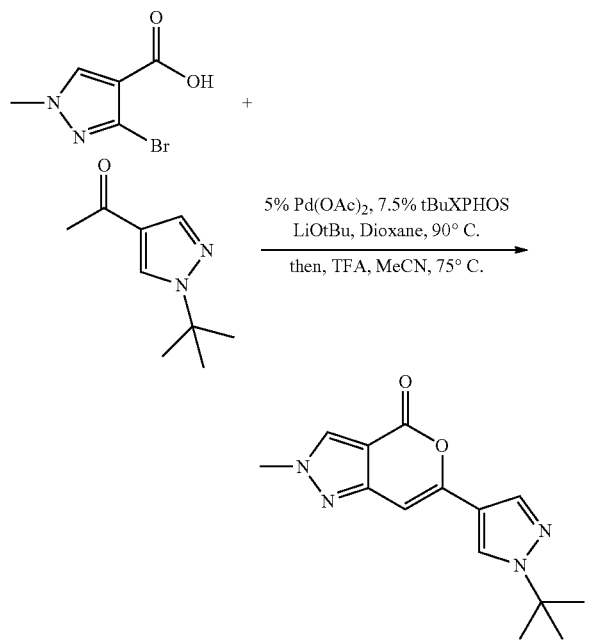

A mixture of lithium tert-butoxide (0.970 g, 12 mmol), palladium (II) acetate (27 mg, 0.12 mmol), and di-tert-butyl (2,4,6-trisopropylbiphenyl-2-yl)phosphine (77 mg, 18 mmol) in anhydrous and degassed 1,4 dioxane (4 mL) under argon was agitated at ambient temperature for 15 minutes. The mixture was heated to 90° C., and agitated at this temperature for 5 minutes. A solution of 3-bromo-1-methyl-1H-pyrazole-4-carboxylic acid (500 mg, 2.4 mmol) and 1-(1-(tert-Butyl)-1H-pyrazol-4-yl)ethan-1-one (490 mg, 2.9 mmol) in anhydrous and degassed 1,4-dioxane (7 mL) under argon was charged to the catalysts base slurry at 90° C. dropwise over 50 minutes. The reaction was agitated at 90° C. for 30 minutes. The reaction was cooled to ambient temperature and quenched by the addition of trifluoroacetic acid (5 mL). The reaction was concentrated to an oily solid. The mixture was suspended in a mixture of acetonitrile (20 mL) and trifluoroacetic acid (20 mL). The mixture was agitated at 75° C. for 14 h then concentrated to an oily solid. The mixture was suspended in isopropyl acetate (70 mL) and washed twice with water (40 mL). The organic portion was concentrated to a solid. Purification by silica gel chromatography with ethyl acetate and hexanes provided 6-(1-(tert-Butyl)-1H-pyrazol-4-yl)-2-methylpyrano[4,3-c]pyrazol-4(2H)-one as an orange solid (650 mg) in 98% yield. $^1$H NMR (500 MHz, CDCl$_3$) δ=8.06 (s, 1H), 7.94 (s, 1H), 7.84 (s, 1H), 6.68 (s, 1H), 4.04 (s, 3H), 1.60 (s, 9H).

Synthesis of 6-(1-(tert-Butyl)-1H-pyrazol-4-yl)-2-methyl-2,5-dihydro-4H-pyrazolo[4,3-c]pyridin-4-one

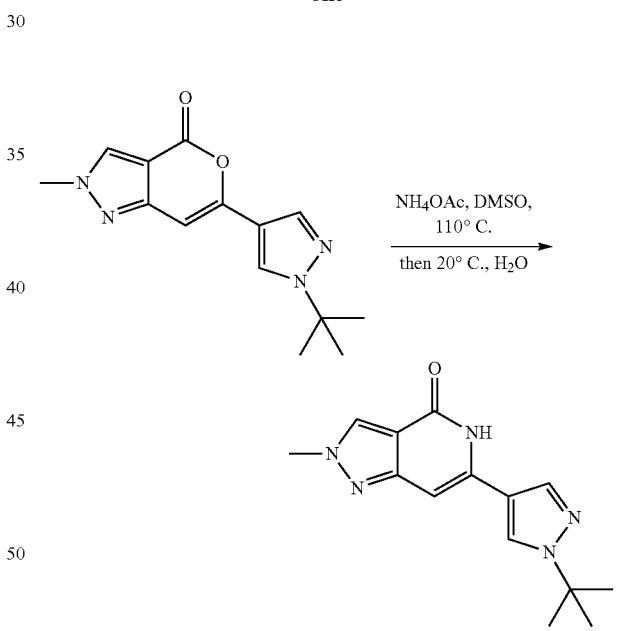

A mixture of 6-(1-(tert-Butyl)-1H-pyrazol-4-yl)-2-methylpyrano[4,3-c]pyrazol-4(2H)-one (980 mg, 3.6 mmol) and ammonium acetate (1.11 g, 14 mmol) in anhydrous DMSO (4 mL) was agitated at 110° C. for 4 h; at which point, additional ammonium acetate (1.11 g, 3.6 mmol) was charged to the reaction. After agitation for another 4 h at 110° C., the reaction was cooled to ambient temperature and diluted with water (20 mL). The solids of 6-(1-(tert-Butyl)-1H-pyrazol-4-yl)-2-methyl-2,5-dihydro-4H-pyrazolo[4,3-c]pyridin-4-one were isolated by filtration, washed with water, and dried to provide 880 mg for an 90% yield. $^1$H NMR (500 MHz, DMSO-d$^6$) δ=10.59 (s, 1H), 8.54 (s, 1H), 8.39 (s, 1H), 8.06 (s, 1H), 6.73 (s, 1H), 3.99 (s, 3H), 1.53 (s, 9H).

81

Synthesis of 6-(1-(tert-Butyl)-1H-pyrazol-4-yl)-4-chloro-2-methyl-2H-pyrazolo[4,3-c]pyridine

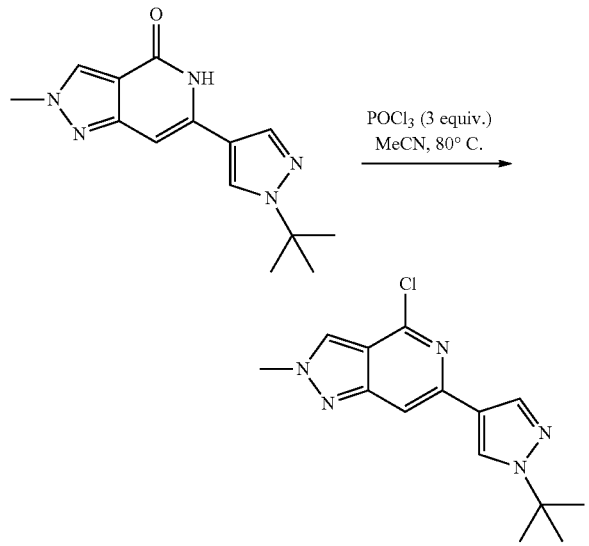

Phosphorous (V) oxychloride (848 mg, 5.53 mmol) was charged to a mixture of 6-(1-(tert-Butyl)-1H-pyrazol-4-yl)-2-methyl-2,5-dihydro-4H-pyrazolo[4,3-c]pyridin-4-one (500 mg, 1.84 mmol) in anhydrous acetonitrile (5 mL) under argon. The reaction was agitated at 75-80° C. for 3 h; at which point, the reaction was cooled to ambient temperature. The reaction slowly poured into a saturated sodium bicarbonate aqueous solution (45 mL). The mixture was agitated for 20 min and concentrated in vacuo to remove the acetonitrile solvent. The resulting aqueous slurry was diluted with isopropyl acetate (50 mL) and washed with water (2×20 mL). The organic portion was concentrated to an oil which solidified upon standing to provide 6-(1-(tert-Butyl)-1H-pyrazol-4-yl)-4-chloro-2-methyl-2H-pyrazolo[4,3-c]pyridine as a yellow solid (690 mg, 73 wt %) in 92% yield. Analytically pure material was obtained by crystallization in n-propanol and heptane. $^1$H NMR (500 MHz, CDCl$_3$) δ=8.08 (s, 1H), 8.00 (s, 1H), 7.95 (s, 1H), 7.52 (s, 1H), 4.20 (s, 3H), 1.62 (s, 9H).

Synthesis of (R)-4-((R)-1-((6-(1-(tert-Butyl)-1H-pyrazol-4-yl)-2-methyl-2H-pyrazolo[4,3-c]pyridin-4-yl)oxy)ethyl)-1-((S)-1-(4-methoxyphenyl)ethyl)pyrrolidin-2-one (8.1)

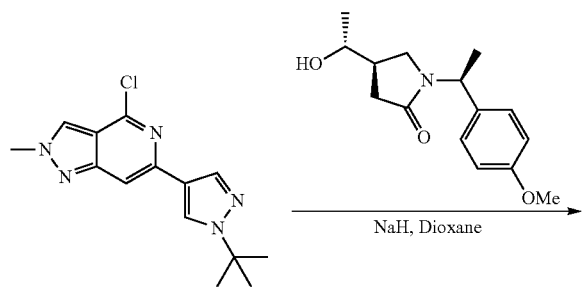

82

-continued

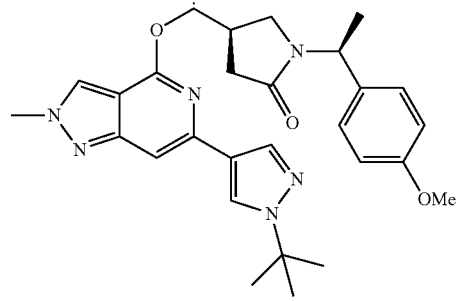

A mixture of (R)-4-((R)-1-hydroxyethyl)-1-((S)-1-(4-methoxyphenyl)ethyl)pyrrolidin-2-one (173 mg, 0.66 mmol), 6-(1-(tert-Butyl)-1H-pyrazol-4-yl)-4-chloro-2-methyl-2H-pyrazolo[4,3-c]pyridine (190 mg, 66 mmol) and sodium hydride (60 wt %, 66 mg, 1.6 mmol) in anhydrous 1,4 dioxane (3 mL) was agitated under argon at 50-70° C. for 18 h. The reaction mixture was cooled to ambient temperature and quenched by the slow addition of a hydrogen chloride solution (4 M in 1,4 dioxane, 0.245 mL, 0.98 mmol). The reaction was diluted with isopropyl acetate (20 mL) and water (20 mL). The layers were separated, and the aqueous portion was extracted twice with isopropyl acetate (20 ml). The combined organic layers were concentrated to an oil. Purification by silica gel chromatography with methanol and methyl tert-butyl ether provided (R)-4-((R)-1-((6-(1-(tert-Butyl)-1H-pyrazol-4-yl)-2-methyl-2H-pyrazolo[4,3-c]pyridin-4-yl)oxy)ethyl)-1-((S)-1-(4-methoxyphenyl)ethyl)pyrrolidin-2-one (185 mg) as a white foam in 55% yield. $^1$H NMR (500 MHz, CDCl$_3$) δ=7.94 (s, 1H), 7.89 (s, 1H), 7.76 (s, 1H), 7.20 (s, 1H), 7.10 (d, J=8.8 Hz, 2H), 6.57 (d, J=8.7 Hz, 2H), 5.48 (dddd, J=4.8, 6.1, 6.1, 6.1 Hz, 1H), 5.43 (q, J=7.0 Hz, 1H), 4.13 (s, 3H), 3.66 (s, 3H), 3.47 (t, J=9.0 Hz, 1H), 2.96 (dd, J=5.1, 9.8 Hz, 1H), 2.74-2.66 (m, 1H), 2.66-2.57 (m, 2H), 1.64 (s, 9H), 1.48 (d, J=7.1 Hz, 3H), 1.33 (d, J=6.2 Hz, 3H).

Synthesis of (4R)-4-[(1R)-1-[6-1-(tetrahydro-2H-pyran-2-yl)-1H-pyrazol-4-yl)-2-methyl-pyrazolo[4,3-c]pyridin-4-yl]oxyethyl]pyrrolidin-2-one (Example 3)

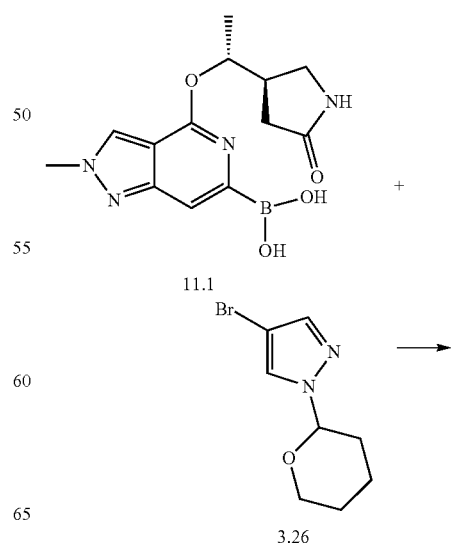

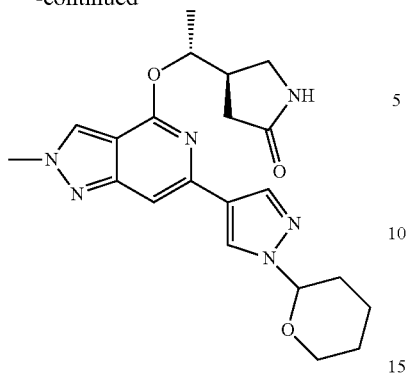

Example 3

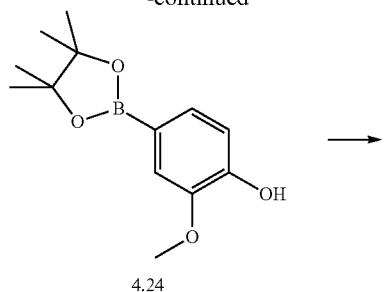

4.24

To a mixture of 50 mg [2-Methyl-4-[(1R)-1-[(3R)-5-oxopyrrolidin-3-yl]ethoxy]pyrazolo[4,3-c]pyridin-6-yl]boronic acid 11.1, 46.2 mg 4-Bromo-1-(tetrahydro-2H-pyran-2-yl)-1H-pyrazole 3.26 and 20 mg palladium-X-phos was added to 3 mL dioxane and 65 µL 5M aqueous sodium carbonat solution. The resulting mixture was heated at 110° C. for 14h. The mixture was cooled to ambient temperature aund purified via rpHPLC. The combined organic phases were lyophilized to provide example 3 in 21 mg.

Analysis: HPLC-MS: $R_t$=0.86 min (method Z1), M+H=411

Example 17 was synthesized in analogous manner to Example 3 using 1-[(4-bromophenyl)methyl]-2-methyl-1H-imidazole 3.27.

Analysis: HPLC-MS: $R_t$=0.73 min (method Z1), M+H=431

Synthesis of (4R)-4-[(1R)-1-[6-(4-Hydroxy-3-methoxy-phenyl)-2-methyl-pyrazolo[4,3-c]pyridin-4-yl]oxyethyl]pyrrolidin-2-one (Example 8)

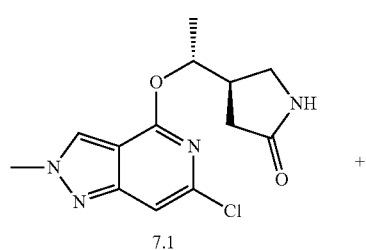

7.1

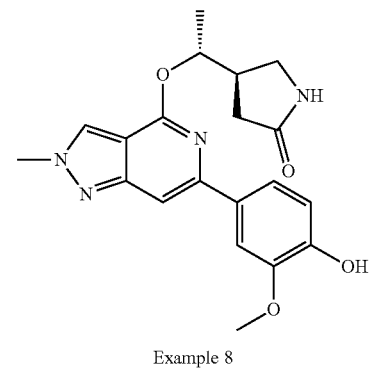

Example 8

To a mixture of 100 mg (4R)-4-[(1R)-1-(6-chloro-2-methyl-pyrazolo[4,3-c]pyridin-4-yl)oxyethyl]pyrrolidin-2-one 7.1, 110 mg 2-methoxy-4-(4,4,5,5-tetramethyl-1,3,2-dioxaborolan-2-yl)phenol 4.24 and 37 mg 1,1'-bis(diphenylphospino)ferrocene-dichloropalladium(II) (complex with DCM (1:1)) in 1 mL dioxane and 0.5 mL methanol was added 400 µL 2M aqueous sodium carbonat solution. The reaction mixture was stirred at 140° C. for 15 min under microwave irradiation. The reaction mixture was filtered through rpSiO₂, washed with methanol and purified by rpHPLC to yield after lyophilisation 80 mg (yield: 68%) of Example 8 as solid.

Analysis: HPLC-MS: $R_t$=0.47 min (method S), M+H=383

The following Examples were synthesized in analogous manner to Example 8.

| Example | Boronic acid/ester or BF₃ borates (corresponding to formula 4) | Yield | Analysis |
|---|---|---|---|
| Example 7 (R)-4-((R)-1-(6-(1-cyclohexyl-1H-pyrazol-4-yl)-2-methyl-2H-pyrazolo[4,3-c]pyridin-4-yloxy)ethyl)pyrrolidin-2-one | 1-Cyclohexyl-4-(4,4,5,5-tetramethyl-1,3,2-dioxoborolan-2-yl)-1H-pyrazole 4.50 | 50 mg (47%) | HPLC-MS: $R_t$ = 0.72 min (method U), M + H = 409 |
| Example 53 (4R)-4-[(1R)-1-[6-(5-methoxy-1H-indol-3-yl)-2-methyl-pyrazolo[4,3-c]pyridin-4-yl]oxyethyl]pyrrolidin-2-one | tert-butyl 5-methoxy-3-(4,4,5,5-tetramethyl-1,3,2-dioxaborolan-2-yl)indole-1-carboxylate 4.26 | 51 mg (51%) | HPLC-MS: $R_t$ = 0.64 min (method U), M + H = 406 ¹H NMR (DMSO, 400 MHz) δ = 1.42 (3H, d), |

-continued

| Example | Boronic acid/ester or BF₃ borates (corresponding to formula 4) | Yield | Analysis |
|---|---|---|---|
| | | | 2.20-2.36 (2H, m), 2.75-2.89 (1H, m), 3.12 (dd, 1H), 3.40 (1H, t), 3.82 (3H, s), 4.12 (3H, s), 5.58-5.68 (1H, m), 6.79 (1H, d), 7.32 (1H, d), 7.41 (1H, s), 7.53 (1H, s), 7.80 (1H, s), 7.96 (1H, s), 8.42 (s, 1H), 11.2 (1H, s). |
| Example 54 (4R)-4-[(1R)-1-[2-methyl-6-(5-methyl-2-thienyl)pyrazolo-[4,3-c]pyridin-4-yl]oxyethyl]-pyrrolidin-2-one | potassium 5-methyl-2-thiophene-trifluoroborate 4.42 | 36 mg (67%) | HPLC-MS: R$_t$ = 0.68 min (method V), M + H = 357 |
| Example 55 (4R)-4-[(1R)-1-[2-methyl-6-(3-methyl-1,2,4,5-tetrahydro-3-benzazepin-7-yl)pyrazolo-[4,3-c]pyridin-4-yl]oxyethyl]-pyrrolidin-2-one | 3-methyl-7-(4,4,5,5-tetramethyl-1,3,2-dioxaborolan-2-yl)-1,2,4,5-tetrahydro-3-benzazepine 4.3 | 29 mg (46%) | HPLC-MS: R$_t$ = 0.62 min (method V), M + H = 420 |
| Example 56 N,N,1-trimethyl-6-[2-methyl-4-[(1R)-1-[(3R)-5-oxopyrrolidin-3-yl]ethoxy]pyrazolo[4,3-c]pyridin-6-yl]indole-2-carboxamide | N,N,1-trimethyl-6-(4,4,5,5-tetramethyl-1,3,2-dioxaborolan-2-yl)indole-2-carboxamide 4.6 | 34 mg (49%) | HPLC-MS: R$_t$ = 0.59 min (method V), M + H = 461 |
| Example 59 (4R)-4-[(1R)-1-[6-(6-methoxy-3-pyridyl)-2-methyl-pyrazolo-[4,3-c]pyridin-4-yl]oxyethyl]-pyrrolidin-2-one | potassium 6-methoxy-3-pyridyl-trifluoroborate 4.44 | 37 mg (66%) | HPLC-MS: R$_t$ = 0.57 min (method V), M + H = 368 |
| Example 60 (4R)-4-[(1R)-1-[2-methyl-6-[4-(trifluoromethyl)phenyl]-pyrazolo[4,3-c]pyridin-4-yl]-oxyethyl]pyrrolidin-2-one | potassium 4-(trifluoromethyl)phenyltrifluoroborate 4.44 | 19 mg (31%) | HPLC-MS: R$_t$ = 0.75 min (method V), M + H = 405 |
| Example 64 (4R)-4-[(1R)-1-[2-methyl-6-(1-tetrahydropyran-4-yl-pyrazol-4-yl)pyrazolo[4,3-c]pyridin-4-yl]oxyethyl]-pyrrolidin-2-one | 1-tetrahydropyran-4-yl-4-(4,4,5,5-tetramethyl-1,3,2-dioxaborolan-2-yl)pyrazole 4.32 | 48 mg (76%) | HPLC-MS: R$_t$ = 0.57 min (method W), M + H = 411 |
| Example 65 (4R)-4-[(1R)-1-[6-(1-iso-propylpyrazol-4-yl)-2-methyl-pyrazolo[4,3-c]pyridin-4-yl]-oxyethyl]pyrrolidin-2-one | 1-isopropyl-4-(4,4,5,5-tetramethyl-1,3,2-dioxaborolan-2-yl)pyrazole 4.33 | 31 mg (55%) | HPLC-MS: R$_t$ = 0.61 min (method W), M + H = 369 ¹H NMR (DMSO, 400 MHz) δ = 1.35 (3H, d), 1.46 (6H, d), 2.20-2.32 (2H, m), 2.72-2.83 (1H, m), 3.12 (m, 1H), 3.38 (1H, t), 4.10 (3H, s), 4.48-4.59 (1H, m), 5.50-5.60 (1H, m), 7.30 (1H, s), 7.51 (1H, s), 7.99 (1H, s), 8.21 (1H, s), 8.41 (s, 1H). |
| Example 66 (4R)-4-[(1R)-1-[2-methyl-6-(6-morpholino-3-pyridyl)-pyrazolo[4,3-c]pyridin-4-yl]oxyethyl]pyrrolidin-2-one | 4-[5-(4,4,5,5-tetramethyl-1,3,2-dioxaborolan-2-yl)-2-pyridyl]-morpholine 4.34 | 49 mg (76%) | HPLC-MS: R$_t$ = 0.46 min (method W), M + H = 423 |
| Example 67 (4R)-4-[(1R)-1-[2-methyl-6-[4-(4-methylpiperazin-1-yl)phenyl]pyrazolo[4,3-c]pyridin-4-yl]oxyethyl]-pyrrolidin-2-one | 1-methyl-4-[4-(4,4,5,5-tetramethyl-1,3,2-dioxaborolan-2-yl)phenyl]-piperazine 4.35 | 20 mg (24%) | HPLC-MS: R$_t$ = 0.46 min (method W), M + H = 435 |

-continued

| Example | Boronic acid/ester or BF₃ borates (corresponding to formula 4) | Yield | Analysis |
| --- | --- | --- | --- |
| Example 68 (4R)-4-[(1R)-1-[6-(1,3-dimethylpyrazol-4-yl)-2-methyl-pyrazolo[4,3-c]pyridin-4-yl]oxyethyl]pyrrolidin-2-one | 1,3-dimethyl-4-(4,4,5,5-tetramethyl-1,3,2-dioxaborolan-2-yl)pyrazole 4.36 | 36 mg (67%) | HPLC-MS: $R_t = 0.52$ min (method W), M + H = 355 |
| Example 69 (4R)-4-[(1R)-1-[6-(1,5-dimethylpyrazol-4-yl)-2-methyl-pyrazolo[4,3-c]pyridin-4-yl]oxyethyl]pyrrolidin-2-one | 1,5-dimethyl-4-(4,4,5,5-tetramethyl-1,3,2-d ioxa borolan-2-yl)pyrazole 4.37 | 39 mg (72%) | HPLC-MS: $R_t = 0.52$ min (method W), M + H = 355 |
| Example 70 (4R)-4-[(1R)-1-[2-methyl-6-[1-[(3S)-tetrahydrofuran-3-yl]pyrazol-4-yl]pyrazolo[4,3-c]pyridin-4-yl]oxyethyl]-pyrrolidin-2-one | 1-[(3S)-tetrahydrofuran-3-yl]-4-(4,4,5,5-tetramethyl-1,3,2-dioxaborolan-2-yl)pyrazole 4.7 | 14 mg (23%) | HPLC-MS: $R_t = 0.55$ min (method W), M + H = 397 |
| Example 71 (4R)-4-[(1R)-1-[6-[4-(1,1-dioxo-1,2-thiazolidin-2-yl)-3-methyl-phenyl]-2-methyl-pyrazolo[4,3-c]pyridin-4-yl]oxyethyl]pyrrolidin-2-one | 2-[2-methyl-4-(4,4,5,5-tetramethyl-1,3,2-dioxaborolan-2-yl)phenyl]-1,2-thiazolidine 1,1-dioxide 4.8 | 42 mg (58%) | HPLC-MS: $R_t = 0.66$ min (method W), M + H = 470 |
| Example 72 (4R)-4-[(1R)-1-[2-methyl-6-(1-methylindazol-6-yl)pyrazolo[4,3-c]pyridin-4-yl]oxyethyl]pyrrolidin-2-one | (1-methylindazol-6-yl)boronic acid 4.38 | 34 mg (57%) | HPLC-MS: $R_t = 0.67$ min (method W), M + H = 391 |
| Example 74 (4R)-4-[(1R)-1-[2-methyl-6-[1-[(3R)-tetrahydrofuran-3-yl]pyrazol-4-yl]pyrazolo[4,3-c]pyridin-4-yl]oxyethyl]-pyrrolidin-2-one | 1-[(3R)-tetrahydrofuran-3-yl]-4-(4,4,5,5-tetramethyl-1,3,2-dioxaborolan-2-yl)pyrazole 4.9 | 13 mg (25%) | HPLC-MS: $R_t = 0.47$ min (method V), M + H = 397 |
| Example 75 (4R)-4-[(1R)-1-[2-methyl-6-(2-methyl-3,4-dihydro-1H-isoquinolin-7-yl)pyrazolo[4,3-c]pyridin-4-yl]oxyethyl]-pyrrolidin-2-one | 2-methyl-7-(4,4,5,5-tetramethyl-1,3,2-dioxaborolan-2-yl)-3,4-dihydro-1H-isoquinoline 4.10 | 18 mg (23%) | HPLC-MS: $R_t = 0.61$ min (method V), M + H = 406 |
| Example 76 (4R)-4-[(1R)-1-[2-methyl-6-[1-(3,3,3-trifluoropropyl)-pyrazol-4-yl]pyrazolo[4,3-c]pyridin-4-yl]oxyethyl]-pyrrolidin-2-one | 4-(4,4,5,5-tetramethyl-1,3,2-dioxaborolan-2-yl)-1-(3,3,3-trifluoro-propyl)pyrazole 4.11 | 17 mg (25%) | HPLC-MS: $R_t = 0.44$ min (method X), M + H = 423 |
| Example 77 (4R)-4-[(1R)-1-[6-(7-chloro-1H-indol-2-yl)-2-methyl-pyrazolo[4,3-c]pyridin-4-yl]oxyethyl]pyrrolidin-2-on | 7-chloro-2-(4,4,5,5-tetramethyl-1,3,2-dioxaborolan-2-yl)-1H-indole 4.39 | 27 mg (32%) | HPLC-MS: $R_t = 0.59$ min (method X), M + H = 410 |
| Example 78 (4R)-4-[(1R)-1-[6-(1-cyclopropylpyrazol-4-yl)-2-methyl-pyrazolo[4,3-c]pyridin-4-yl]oxyethyl]pyrrolidin-2-one | 1-cyclopropyl-4-(4,4,5,5-tetramethyl-1,3,2-dioxaborolan-2-yl)pyrazole 4.40 | 40 mg (51%) | HPLC-MS: $R_t = 0.40$ min (method X), M + H = 367 |
| Example 79 (4R)-4-[(1R)-1-[2-methyl-6-(3-methyl-1-tetrahydropyran-4-yl-pyrazol-4-yl)pyrazolo-[4,3-c]pyridin-4-yl]oxyethyl]-pyrrolidin-2-one | 5-methyl-1-tetrahydropyran-4-yl-4-(4,4,5,5-tetramethyl-1,3,2-dioxaborolan-2-yl)pyrazole 4.20 | 26 mg (28%) | HPLC-MS: $R_t = 0.39$ min (method Y), M + H = 425 |
| Example 80 (4R)-4-[(1R)-1-[2-methyl-6-[4-(1-methyl-4-piperidyl)-phenyl]pyrazolo[4,3-c]pyridin-4-yl]oxyethyl]pyrrolidin-2-one | 1-methyl-4-[4-(4,4,5,5-tetramethyl-1,3,2-dioxaborolan-2-yl)phenyl]-piperidine 4.12 | 24 mg (32%) | HPLC-MS: $R_t = 0.50$ min (method Y), M + H = 434 |
| Example 81 (4R)-4-[(1R)-1-[6-(4-isopropoxy-3-methoxy-phenyl)-2-methyl-pyrazolo-[4,3-c]pyridin-4-yl]oxyethyl]-pyrrolidin-2-one | 2-(4-isopropoxy-3-methoxy-phenyl)-4,4,5,5-tetramethyl-1,3,2-dioxaborolane 4.13 | 35 mg (35%) | HPLC-MS: $R_t = 0.51$ min (method Y), M + H = 425 |

The following examples were synthesized in analogy to Example 8 but using different reaction solvents:

| Example | Boronic acid/ester (corresponding to formula 4) | Yield Solvent | Analysis |
|---|---|---|---|
| Example 11 (4S)-4-[(1R)-1-[2-methyl-6-[2-methyl-4-[(1R)-1-[(3R)-5-oxopyrrolidin-3-yl]ethoxy]-pyrazolo[4,3-c]pyridin-6-yl]pyrazolo[4,3-c]pyridin-4-yl]oxyethyl]pyrrolidin-2-one | | 11 mg (9%) dioxane | HPLC-MS: $R_t$ = 0.463 min (method C) M + H = 519 |
| Example 12 1-methyl-4-[4-[4-[2-methyl-4-[(1R)-1-[(3R)-5-oxopyrrolidin-3-yl]ethoxy]pyrazolo[4,3-c]pyridin-6-yl]pyrazol-1-yl]-cyclohexyl]piperazin-2-one | trans 1-methyl-4-{4-[4-(4,4,5,5-tetramethyl-1,3,2-dioxaborolan-2-yl)-pyrazol-1-yl]-cyclohexyl}-piperazin-2-one 4.4 | 13 mg (10%) dioxane | HPLC-MS: $R_t$ = 0.423 min (method C) M + H = 521 |
| Example 62 (4R)-4-[(1R)-1-[2-methyl-6-(1-methylindazol-5-yl)pyrazolo[4,3-c]pyridin-4-yl]oxyethyl]pyrrolidin-2-one | (1-methylindazol-5-yl)boronic acid 4.30 | 33 mg (50%) DMA | HPLC-MS: $R_t$ = 0.55 min (method V), M + H = 391 $^1$H NMR (DMSO, 400 MHz) δ = 1.42 (3H, d), 2.20-2.38 (2H, m), 2.75-2.88 (1H, m), 3.18 (dd, 1H), 3.40 (1H, t), 4.08 (3H, s), 4.13 (3H, s), 5.59-5.68 (1H, m), 7.53 (1H, s), 7.65 (1H, s), 7.70 (1H, d), 7.80 (1H, s), 8.12 (1H, s), 8.16 (1H, d). |

Synthesis of (4R)-4-[(1R)-1-[2-Methyl-6-[1-(4-piperidyl)pyrazol-4-yl]pyrazolo[4,3-c]pyridin-4-yl]oxyethyl]pyrrolidin-2-one (Example 9)

Step 1: Synthesis of tert-Butyl 4-[4-[2-methyl-4-[(1R)-1-[(3R)-5-oxopyrrolidin-3-yl]ethoxy]pyrazolo[4,3-c]pyridin-6-yl]pyrazol-1-yl]piperidine-1-carboxylate

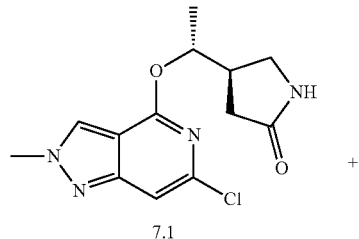

7.1

+

-continued

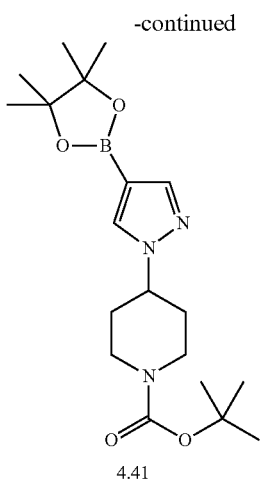

4.41

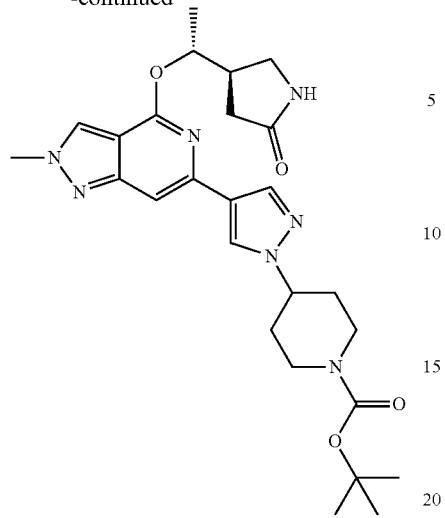

To a mixture of 100 mg (4R)-4-[(1R)-1-(6-chloro-2-methyl-pyrazolo[4,3-c]pyridin-4-yl)oxyethyl]pyrrolidin-2-one 7.1, 170 mg tert-butyl 4-[4-(4,4,5,5-tetramethyl-1,3,2-dioxaborolan-2-yl)pyrazol-1-yl]piperidine-1-carboxylate 4.41 and 37 mg 1,1'-bis(diphenylphospino)ferrocenedichloropalladium(II) (complex with DCM (1:1)) in 1 mL dioxane and 0.5 mL methanol was added 400 µL 2M aqueous sodium carbonat solution. The reaction mixture was stirred at 140° C. for 15 min under microwave irradiation. The reaction mixture was filtered through rpSiO$_2$, washed with methanol and purified by rpHPLC (XbridgeC18, acetonitrile/water, ammonia) to yield after lyophilisation 90 mg (80% per NMR) of tert-butyl 4-[4-[2-methyl-4-[(1R)-1-[(3R)-5-oxopyrrolidin-3-yl]ethoxy]pyrazolo-[4,3-c]pyridin-6-yl]pyrazol-1-yl]piperidine-1-carboxylate as solid.

Analysis: HPLC-MS: R$_t$=0.45 min (method J), M+H=510

Step 2: Synthesis of (4R)-4-[(1R)-1-[2-Methyl-6-[1-(4-piperidyl)pyrazol-4-yl]pyrazolo[4,3-c]pyridin-4-yl]oxyethyl]pyrrolidin-2-one (Example 9)

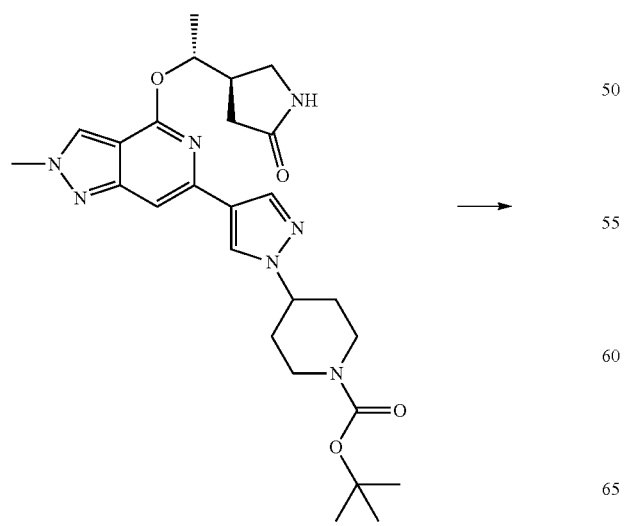

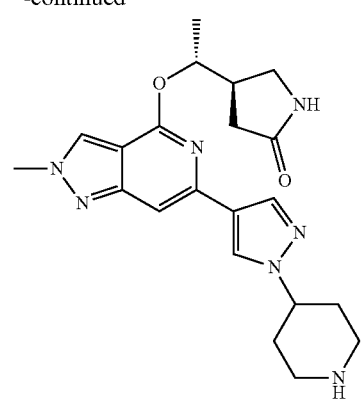

Example 9

A solution of 90 mg (80% per NMR) of tert-butyl 4-[4-[2-methyl-4-[(1R)-1-[(3R)-5-oxopyrrolidin-3-yl]ethoxy]pyrazolo[4,3-c]pyridin-6-yl]pyrazol-1-yl]piperidine-1-carboxylate in 2 mL TFA was stirred at room temperature for 15 min. The reaction mixture was purified by rpHPLC (SunfireC18, acetonitrile/water, TFA) to yield after lyophilisation 83 mg of Example 9 as solid.

Analysis: HPLC-MS: R$_t$=0.32 min (method J), M+H=410

Synthesis of (4R)-4-[(1R)-1-[6-[1-(4,4-Difluorocyclohexyl)pyrazol-4-yl]-2-methyl-pyrazolo[4,3-c]pyridin-4-yl]oxyethyl]pyrrolidin-2-one (Example 10)

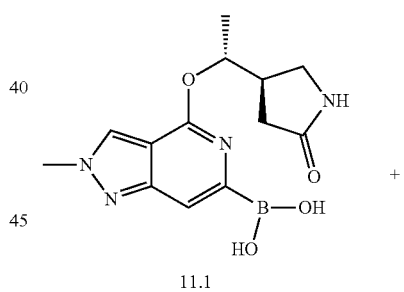

11.1

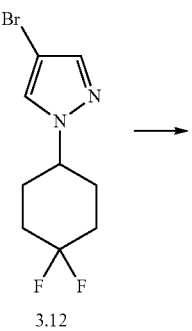

3.12

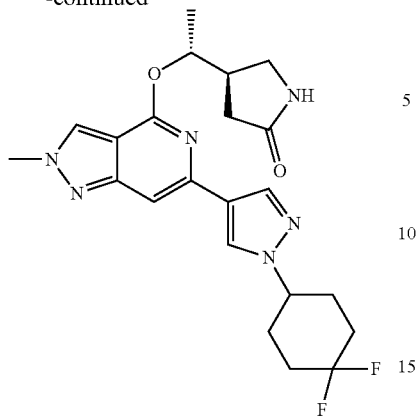

Example 10

A mixture of 100 mg [2-methyl-4-[(1R)-1-[(3R)-5-oxopyrrolidin-3-yl]ethoxy]pyrazolo[4,3-c]pyridin-6-yl]boronic acid 11.1, 87 mg 4-bromo-1-(4,4-difluoro-cyclohexyl)pyrazole 3.12, 27 mg 1,1'-bis(diphenylphospino)ferrocenedichloropalladium(II) (complex with DCM (1:1)) and 493 µL 2M aqueous sodium carbonat solution in 2 mL dioxane was stirred at 120° C. for 15 min under microwave irradiation. The reaction mixture was filtered and purified by rpHPLC to yield after lyophilisation 23 mg of Example 10 as solid.

Analysis: HPLC-MS: $R_t$=0.535 min (method C), M+H=445

$^1$H NMR (DMSO, 400 MHz) δ=1.38 (3H, d), 1.58 (9H, s), 2.00-2.20 (10H, m), 2.73-2.86 (1H, m), 3.11-3.16 (m, 1H), 3.38 (1H, t), 4.09 (3H, s), 4.39-4.49 (1H, m), 5.50-5.61 (1H, m), 7.31 (1H, s), 7.50 (1H, s), 8.00 (1H, s), 8.26 (1H, s), 8.40 (s, 1H).

Synthesis of (4R)-4-[(1R)-1-[2-Methyl-6-[1-(3,3,3-trifluoropropyl)pyrazol-4-yl]indazol-4-yl]oxyethyl]pyrrolidin-2-one (Example 15)

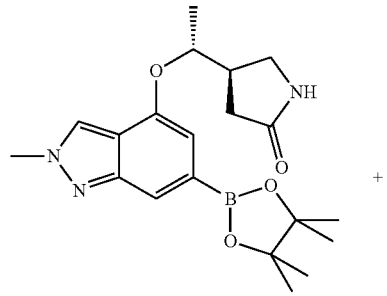

11.3

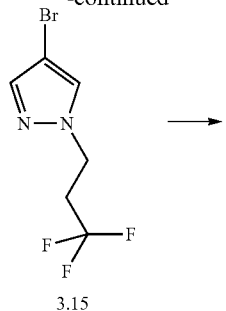

3.15

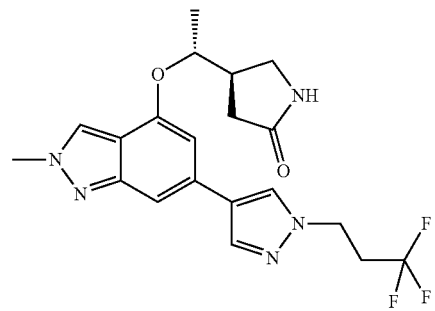

Example 15

To a mixture of 100 mg (4R)-4-[(1R)-1-[2-methyl-6-(4,4,5,5-tetramethyl-1,3,2-dioxaborolan-2-yl)indazol-4-yl]oxyethyl]pyrrolidin-2-one 11.3, 95 mg 4-bromo-1-(3,3,3-trifluoro-propyl)pyrazole 3.15 and 9.1 mg 1,1'-bis(triphenylphosphine)palladium(II) chloride in 1.5 mL ethanol (80% with toluene) was added 389 µL 2M aqueous sodium carbonat solution. The resulting mixture was stirred at 100° C. for 1 h under microwave irradiation. The reaction mixture was diluted with water and extracted with DCM. The combined organic phases were concentrated in vacuo. The crude residue was purified by flash chromatography (heptane/ethyl acetate/methanol) and by rpHPLC to yield 27 mg (yield: 25%) of Example 15 as solid.

Analysis: HPLC-MS: $R_t$=2.33 min (method R), M+H=422

The following Examples were synthesized in analogous manner to Example 15.

| Example | Bromide (corresponding to formula 3) | Yield | Analysis |
|---|---|---|---|
| Example 16 3-[2-methyl-4-[(1R)-1-[(3R)-5-oxopyrrolidin-3-yl]-ethoxy]indazol-6-yl]-1H-indazole-5-carbonitrile | 3-bromo-1H-indazole-5-carbonitrile 3.16 | 12 mg (12%) | HPLC-MS: $R_t$ = 2.20 min (method R), M + H = 401 |
| Example 41 (4R)-4-[(1R)-1-[6-(5-fluoro-2-pyridyl)-2-methyl-indazol-4-yl]oxyethyl]pyrrolidin-2-one | 2-bromo-5-fluoro-pyridine 3.17 | 19 mg (27%) | HPLC-MS: $R_t$ = 2.23 min (Method R), M + H = 355 |

-continued

| Example | Bromide (corresponding to formula 3) | Yield | Analysis |
|---|---|---|---|
| Example 42 (4R)-4-[(1R)-1-[2-methyl-6-[4-(1-methyl-4-piperidyl)-phenyl]indazol-4-yl]oxyethyl]-pyrrolidin-2-one | 4-(4-bromo-phenyl)-1-methyl-piperidine 3.18 | 34 mg (40%) | HPLC-MS: $R_t$ = 1.53 min (method R), M + H = 433 |
| Example 43 3-[2-methyl-4-[(1R)-1-[(3R)-5-oxopyrrolidin-3-yl]ethoxy]indazol-6-yl]imidazo[1,2-a]pyridine-6-carbonitrile | 3-bromoimidazo-[1,2-a]pyridine-6-carbonitrile 3.14 | 21 mg (26%) | HPLC-MS: $R_t$ = 1.65 min (method R), M + H = 401 |

Synthesis of (4R)-4-[(1R)-1-[2-Methyl-6-(4-morpholinophenyl)indazol-4-yl]oxyethyl]-pyrrolidin-2-one (Example 22)

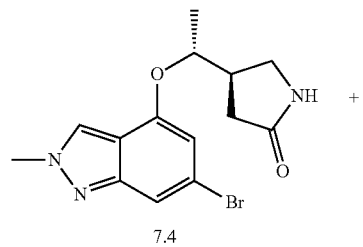

7.4

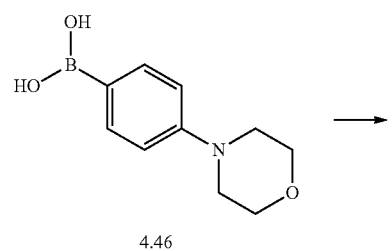

4.46

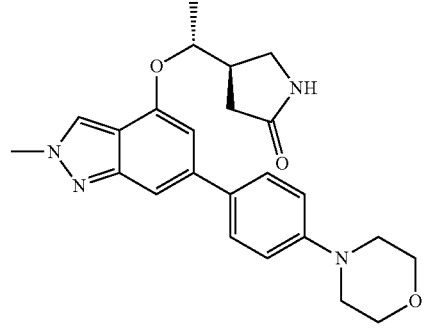

Example 22

To a mixture of 105 mg (4R)-4-[(1R)-1-(6-bromo-2-methyl-indazol-4-yl)oxyethyl]pyrrolidin-2-one 7.4, 96 mg (4-morpholinophenyl)boronic acid 4.46 and 10.9 mg 1,1'-bis(triphenylphosphine)palladium(II) chloride in 1.58 mL ethanol (80% with toluene) was added 466 µL 2M aqueous sodium carbonat solution. The resulting mixture was stirred at 95° C. for 1 h. The reaction mixture was diluted with water and extracted with DCM. The combined organic phases were concentrated in vacuo. The crude residue was purified by flash chromatography (heptane/ethyl acetate/methanol) and by rpHPLC to yield 74 mg (yield: 56%) of Example 22 as solid.

Analysis: HPLC-MS: $R_t$=2.35 min (method R), M+H=421

The following Examples were synthesized in analogous manner to Example 22, but with modified reaction time.

| Example | Boronic acid/ester (corresponding to formula 4) | Yield Reaction time | Analysis |
|---|---|---|---|
| Example 14 (4R)-4-[(1R)-1-[2-methyl-6-(1-methylpyrazol-3-yl)indazol-4-yl]oxyethyl]-pyrrolidin-2-one | 1-methyl-3-(4,4,5,5-tetramethyl-1,3,2-dioxaborolan-2-yl)pyrazole 4.49 | 49 mg (66%) 2 h | HPLC-MS: $R_t$ = 1.86 min (method R), M + H = 340 |
| Example 18 (4R)-4-[(1R)-1-[6-(1-tert-butylpyrazol-4-yl)-2-methyl-indazol-4-yl]oxyethyl]pyrrolidin-2-one | 1-tert-butyl-4-(4,4,5,5-tetramethyl-1,3,2-dioxaborolan-2-yl)pyrazole 4.19 | 95 mg (80%) 1 h | HPLC-MS: $R_t$ = 2.35 min (method R), M + H = 382 $^1$H NMR (DMSO, 500 MHz) δ = 1.28 (3H, d, J = 6.1 Hz), 1.56 (9H, s), 2.19-2.35 (2H, m), |

-continued

| Example | Boronic acid/ester (corresponding to formula 4) | Yield Reaction time | Analysis |
|---|---|---|---|
| | | | 2.74 (1H, h, J = 8.2 Hz), 3.12 (1H, dd, J = 9.6, 6.8 Hz), 3.37 (1H, t, J = 9.0 Hz), 4.08 (3H, s), 4.76 (1H, d, J = 6.0 Hz), 6.71 (1H, s), 7.34 (1H, s), 7.57 (1H, s), 7.91 (1H, s), 8.22 (1H, s), 8.29 (1H, s) |
| Example 26 (4R)-4-[(1R)-1-[2-methyl-6-[4-(4-methylpiperazin-1-yl)phenyl]indazol-4-yl]oxyethyl]pyrrolidin-2-one | 1-methyl-4-[4-(4,4,5,5-tetramethyl-1,3,2-dioxaborolan-2-yl)phenyl]-piperazine 4.35 | 97 mg (72%) 1.5 h | HPLC-MS: $R_t$ = 1.43 min (method R), M + H = 434 |
| Example 27 (4R)-4-[(1R)-1-[6-(6-isopropoxy-3-pyridyl)-2-methyl-indazol-4-yl]oxyethyl]pyrrolidin-2-one | 2-isopropoxy-5-(4,4,5,5-tetramethyl-1,3,2-dioxaborolan-2-yl)pyridine 4.48 | 78 mg (90%) 1.5 h | HPLC-MS: $R_t$ = 2.75 min (method R), M + H = 395 |
| Example 28 (4R)-4-[(1R)-1-[2-methyl-6-(1-methylindazol-5-yl)indazol-4-yl]oxyethyl]pyrrolidin-2-one | (1-methylindazol-5-yl)boronic acid 4.47 | 67 mg (78%) 1.5 h | HPLC-MS: $R_t$ = 2.30 min (method R), M + H = 390 |
| Example 32 (4R)-4-[(1R)-1-[2-methyl-6-[4-(4-methylpiperazin-1-yl)-3-(trifluoromethyl)phenyl]-indazol-4-yl]oxyethyl]pyrrolidin-2-one | 1-methyl-4-[4-(4,4,5,5-tetramethyl-1,3,2-dioxaborolan-2-yl)-2-(trifluoromethyl)phenyl]piperazine 4.16 | 75 mg (67%) 1 h | HPLC-MS: $R_t$ = 1.75 min (method R), M + H = 502 |
| Example 33 2-[4-(4,4,5,5-tetramethyl-1,3,2-dioxaborolan-2-yl)phenyl]-1,2-thiazolidine 1,1-dioxide | 2-[4-(4,4,5,5-tetramethyl-1,3,2-dioxaborolan-2-yl)phenyl]-1,2-thiazolidine 1,1-dioxide 4.14 | 45 mg (45%) 1 h | HPLC-MS: $R_t$ = 2.25 min (method R), M + H = 455 |
| Example 36 (4R)-4-[(1R)-1-[6-(3-amino-1-methyl-indazol-5-yl)-2-methyl-indazol-4-yl]oxyethyl]pyrrolidin-2-one | 1-methyl-5-(4,4,5,5-tetramethyl-1,3,2-dioxaborolan-2-yl)indazol-3-amine 4.15 | 66 mg (73%) 1 h | HPLC-MS: $R_t$ = 1.97 min (method R), M + H = 405 |
| Example 38 (4R)-4-[(1R)-1-[2-methyl-6-[4-morpholino-3-(trifluoromethyl)phenyl]indazol-4-yl]oxyethyl]pyrrolidin-2-one | 4-[4-(4,4,5,5-tetramethyl-1,3,2-dioxaborolan-2-yl)-2-(trifluoromethyl)-phenyl]morpholine 4.18 | 43 mg (40%) 1 h | HPLC-MS: $R_t$ = 3.11 min (method R), M + H = 489 |
| Example 40 (4R)-4-[(1R)-1-[6-[1-(difluoromethyl)pyrazol-4-yl]-2-methyl-indazol-4-yl]oxyethyl]pyrrolidin-2-one | 1-(difluoromethyl)-4-(4,4,5,5-tetramethyl-1,3,2-dioxaborolan-2-yl)pyrazole 4.17 | 53 mg (63%) 1 h | HPLC-MS: $R_t$ = 2.16 min (method R), M + H = 376 |
| Example 47 (4R)-4-[(1R)-1-[2-methyl-6-(1-tetrahydropyran-4-ylpyrazol-4-yl)indazol-4-yl]oxyethyl]pyrrolidin-2-one | 1-tetrahydropyran-4-yl-4-(4,4,5,5-tetramethyl-1,3,2-dioxaborolan-2-yl)pyrazole 4.32 | 68 mg (75%) 1.5 h | HPLC-MS: $R_t$ = 1.95 min (method R), M + H = 410 $^1$H NMR (DMSO, 500 MHz) δ = 1.29 (3H, d, J = 6.1 Hz), 1.92-2.08 (4H, m), 2.18-2.35 (2H, m), 2.75 (1H, dt, J = 14.9, 7.6 Hz), 3.12 (1H, dd, J = 9.5, 6.8 Hz), 3.38 (1H, t, J = 9.1 Hz), 3.48 (2H, td, J = 11.4, 3.1 Hz), 3.98 (2H, d, J = 11.2 Hz), 4.08 (3H, s), 4.40 (1H, tt, J = 10.1, 5.1 Hz), 4.74 (1H, p, J = 6.0 Hz), 6.69 (1H, s), 7.33 (1H, s), 7.58 (1H, s), 7.94 (1H, s), |

| Example | Boronic acid/ester (corresponding to formula 4) | Yield Reaction time | Analysis |
|---|---|---|---|
| Example 48 (4R)-4-[(1R)-1-[6-(7-chloro-1H-indol-2-yl)-2-methyl-indazol-4-yl]oxyethyl]-pyrrolidin-2-one | 7-chloro-2-(4,4,5,5-tetramethyl-1,3,2-dioxaborolan-2-yl)-1H-indole 4.39 | 65 mg (71%) 1 h under microwave irradiation | 8.23 (1H, s), 8.31 (1H, s) HPLC-MS: $R_t$ = 3.05 min (method R), M + H = 409/411 |
| Example 49 (4R)-4-[(1R)-1-[2-methyl-6-[1-(1-methyl-4-piperidyl)-pyrazol-4-yl]indazol-4-yl]-oxyethyl]pyrrolidin-2-one | 1-methyl-4-[4-(4,4,5,5-tetramethyl-1,3,2-dioxaborolan-2-yl)pyrazol-1-yl]piperidine 4.21 | 64 mg (68%) 1 h | HPLC-MS: $R_t$ = 1.25 min (method R), M + H = 423 |

Synthesis of (4R)-4-[(1R)-1-(2-methyl-6-thiazol-4-yl-indazol-4-yl)oxyethyl]pyrrolidin-2-one (Example 29)

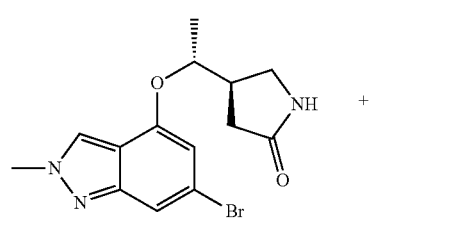

7.5

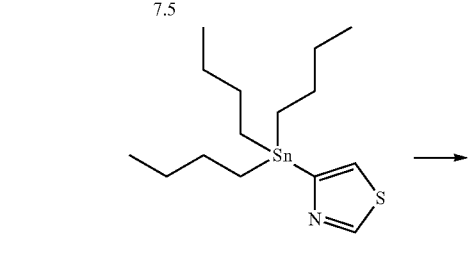

4.2

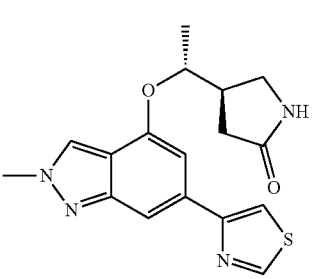

Example 29

A mixture of 75 mg (4R)-4-[(1R)-1-(6-bromo-2-methyl-indazol-4-yl)oxyethyl]pyrrolidin-2-one (9.2), 102 µL tributyl(thiazol-4-yl)stannane and 7.8 mg 1,1'-bis(triphenylphosphine) palladium(II) chloride in 1.5 mL dioxane was stirred at 95° C. for 18 h. The reaction mixture was concentrated in vacuo. The crude residue was purified by flash chromatography (heptane/ethyl acetate/methanol) and by rpHPLC to yield 13 mg (yield: 19%) of Example 29 as solid.

Analysis: HPLC-MS: $R_t$=1.98 min (method R), M+H=343

The following Example was synthesized in analogous manner to Example 29, but with modified reaction time.

| Example | Stannane (corresponding to formula 4) | Yield Reaction time | Analysis |
|---|---|---|---|
| Example 35 (4R)-4-[(1R)-1-[6-[2-(difluoromethyl)thiazol-4-yl]-2-methyl-indazol-4-yl]-oxyethyl]pyrrolidin-2-one | 2-difluoromethyl-4-tributylstannanyl-thiazole 4.1 | 49 mg (42%) 1 h | HPLC-MS: $R_t$ = 2.50 min (method R), M + H = 393 |

Synthesis of (4R)-4-[(1R)-1-[2-Methyl-6-[1-(4-piperidyl)pyrazol-4-yl]indazol-4-yl]oxyethyl]pyrrolidin-2-one (Example 45)

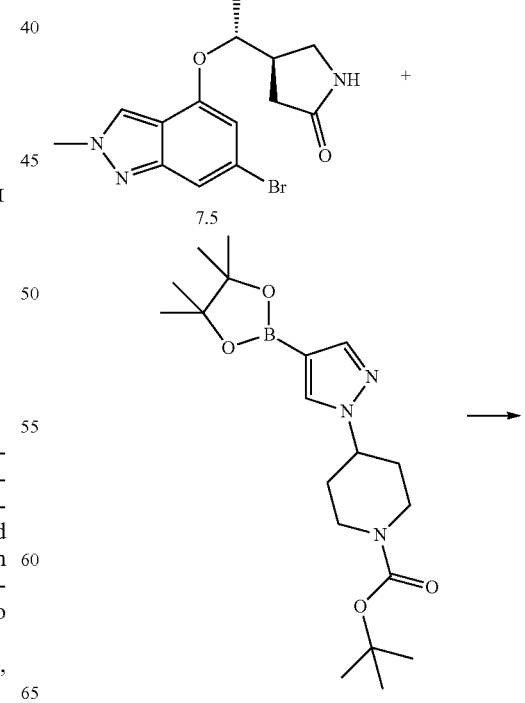

7.5

4.41

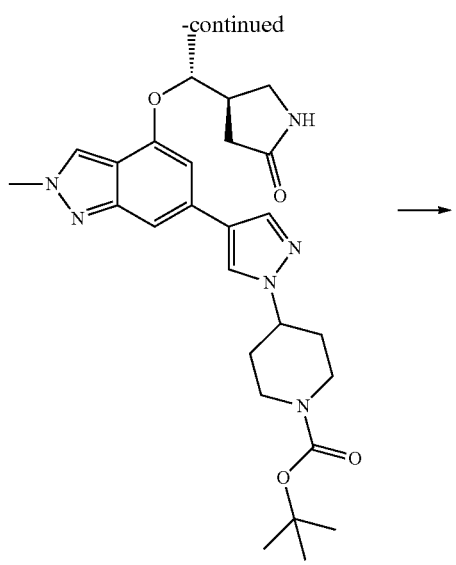

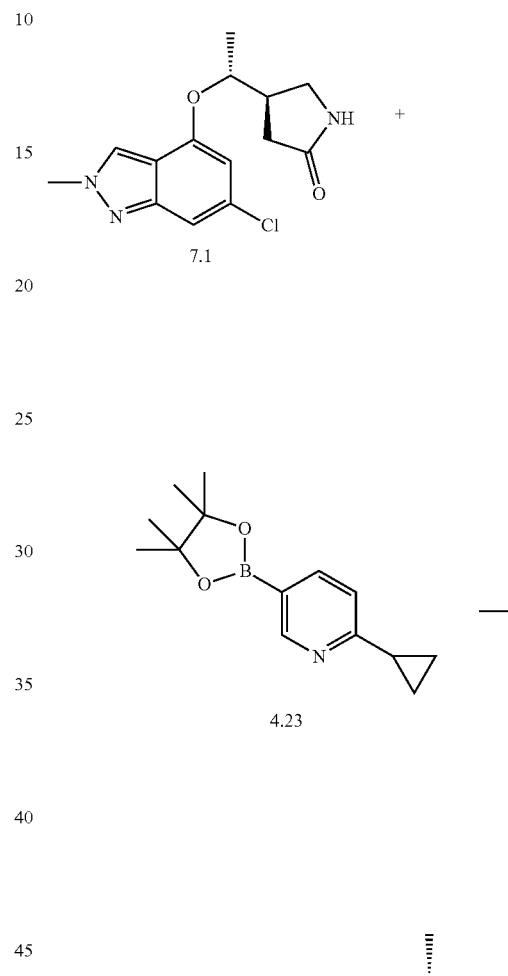

Example 45

To a mixture of 125 mg (4R)-4-[(1R)-1-(6-bromo-2-methyl-indazol-4-yl)oxyethyl]pyrrolidin-2-one 7.5, 167 mg tert-butyl 4-[4-(4,4,5,5-tetramethyl-1,3,2-dioxaborolan-2-yl)pyrazol-1-yl]piperidine-1-carboxylate 4.41 and 13 mg 1,1'-bis(triphenylphosphine)palladium (II) chloride in 1.88 mL ethanol (80% with toluene) was added 554 µL 2M aqueous sodium carbonat solution. The resulting mixture was stirred at 95° C. for 1 h. The reaction mixture was diluted with water and extracted with DCM. The combined organic phases were concentrated in vacuo. The crude residue was purified by flash chromatography (heptane/ethyl acetate/methanol). The residue was dissolved in 2 mL DCM, 500 µL TFA were added and the resulting mixture was stirred at room temperature for 1 h. The reaction mixture was purified by flash chromatography (DCM/methanol/ammonia) and by elution through a SCX (Biotage SCX-3) column and subsequent rpHPLC to yield 92 mg (yield: 61%) of Example 45 as solid.

Analysis: HPLC-MS: $R_t$=1.25 min (method R), M+H=409

Synthesis of (4R)-4-[(1R)-1-[6-(6-Cyclopropyl-3-pyridyl)-2-methyl-pyrazolo[4,3-c]pyridine-4-yl]oxy-ethyl]pyrrolidin-2-one (Example 50)

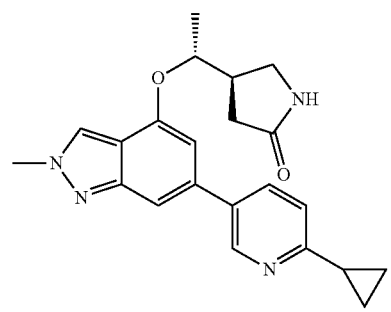

Example 50

To a mixture of 50 mg (4R)-4-[(1R)-1-(6-chloro-2-methyl-pyrazolo[4,3-c]pyridin-4-yl)oxyethyl]pyrrolidin-2-one 7.1, 94 mg 2-cyclopropyl-5-(4,4,5,5-tetramethyl-1,3,2-dioxaborolan-2-yl)pyridine 4.23 and 20 mg 1,1'-bis(triphenylphosphine)palladium(II) chloride in 1 mL DMA was added 400 µL 2M aqueous sodium carbonat solution. The reaction mixture was stirred at 130° C. for 25 min under microwave irradiation. The reaction mixture was filtered through rpSiO$_2$, washed with methanol and purified by rpHPLC to yield after lyophilisation 22 mg (yield: 37%) of Example 50 as solid.

Analysis: HPLC-MS: R$_t$=0.69 min (method U), M+H=378

The following Examples were synthesized in analogous manner to Example 50.

| Example | Boronic acid/ester (corresponding to formula 4) | Yield | Analysis |
| --- | --- | --- | --- |
| Example 2 (4R)-4-[(1R)-1-[6-(1-tert-butylpyrazol-4-yl)-2-methyl-pyrazolo[4,3-c]pyridin-4-yl]oxyethyl]pyrrolidin-2-one | 1-tert-butyl-4-(4,4,5,5-tetramethyl-1,3,2-dioxaborolan-2-yl)pyrazole 4.19 | 1.11 g (54%) | HPLC-MS: R$_t$ = 0.50 min (method C), M + H = 383 $^1$H NMR (DMSO, 400 MHz) δ = 1.38 (3H, d), 1.58 (9H, s), 2.20-2.34 (2H, m), 2.73-2.85 (1H, m), 3.11-3.19 (m, 1H), 3.38 (1H, t), 4.10 (3H, s), 5.50-5.60 (1H, m), 7.33 (1H, s), 7.52 (1H, s), 7.98 (1H, s), 8.26 (1H, s), 8.41 (s, 1H). |
| Example 51 (4R)-4-[(1R)-1-[6-[6-(difluoromethyl)-3-pyridyl]-2-methyl-pyrazolo[4,3-c]pyridin-4-yl]oxyethyl]pyrrolidin-2-one | 2-difluoromethyl-5-(4,4,5,5-tetramethyl-1,3,2-dioxaborolan-2-yl)-pyridine 4.5 | 24 mg (40%) | HPLC-MS: R$_t$ = 0.65 min (method U), M + H = 388 |
| Example 52 (4R)-4-[(1R)-1-[2-methyl-6-(3,4,5-trimethoxyphenyl)-pyrazolo[4,3-c]pyridin-4-yl]oxyethyl]pyrrolidin-2-one | (3,4,5-trimethoxy-phenyl)boronic acid 4.25 | 35 mg (54%) | HPLC-MS: R$_t$ = 0.67 min (method W), M + H = 427 |
| Example 57 (4R)-4-[(1R)-1-[6-[1-(2-methoxyethyl)pyrazol-4-yl]-2-methyl-pyrazolo[4,3-c]pyridin-4-yl]oxyethyl]pyrrolidin-2-one | 1-(2-methoxy-ethyl)-4-(4,4,5,5-tetramethyl-1,3,2-dioxaborolan-2-yl)pyrazole 4.27 | 36 mg (62%) | HPLC-MS: R$_t$ = 0.53 min (method W), M + H = 385 |
| Example 58 (4R)-4-[(1R)-1-[6-(1-ethylpyrazol-4-yl)-2-methyl-pyrazolo[4,3-c]pyridin-4-yl]oxyethyl]pyrrolidin-2-one | 1-ethyl-4-(4,4,5,5-tetramethyl-1,3,2-dioxaborolan-2-yl)pyrazole 4.28 | 31 mg (45%) | HPLC-MS: R$_t$ = 0.48 min (method V), M + H = 355 |
| Example 61 (4R)-4-[(1R)-1-[2-methyl-6-[6-(trifluoromethyl)-3-pyridyl]pyrazolo[4,3-c]pyridin-4-yl]oxyethyl]pyrrolidin-2-one | [6-(trifluoro-methyl)-3-pyridyl]boronic acid 4.29 | 15 mg (23%) | HPLC-MS: R$_t$ = 0.65 min (method V), M + H = 406 |
| Example 63 (4R)-4-[(1R)-1-[2-methyl-6-(1-methylpyrazol-4-yl)pyrazolo[4,3-c]pyridin-4-yl]oxyethyl]pyrrolidin-2-one | 1-methyl-4-(4,4,5,5-tetramethyl-1,3,2-dioxaborolan-2-yl)pyrazole 4.31 | 26 mg (50%) | HPLC-MS: R$_t$ = 0.44 min (method V), M + H = 341 |

Synthesis of (4R)-4-[(1R)-1-[6-(3-Methoxy-4-tetrahydropyran-4-yloxy-phenyl)-2-methyl-pyrazolo[4,3-c]pyridin-4-yl]oxyethyl]pyrrolidin-2-one (Example 73)

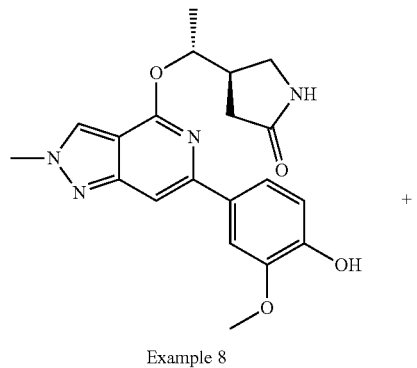
Example 8

+

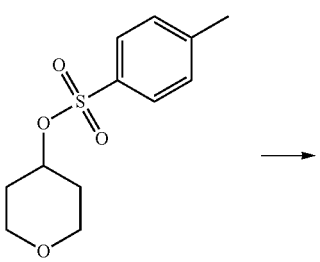

→

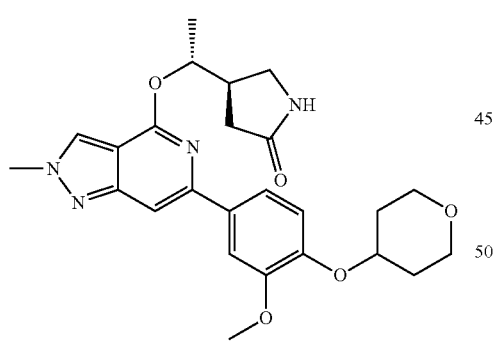
Example 73

A mixture of 68 mg of Example 8, 59 mg of tetrahydropyran-4-yl 4-methylbenzenesulfonate and 39 mg potassium carbonate in 2 mL DMF was stirred at 80° C. for 3 h and at 100° C. for 10 h. The reaction mixture was diluted with water and extracted with DCM. The combined organic phases were concentrated in vacuo. The resulting residue was purified by rpHPLC to yield after lyophilisation 37 mg of Example 73 as solid.

Analysis: HPLC-MS: $R_t$=0.70 min (method W), M+H=467

Synthesis of (4R)-4-[(1R)-1-[2-Methyl-6-[1-(1-methyl-4-piperidyl)pyrazol-4-yl]pyrazolo[4,3-c]pyridin-4-yl]oxyethyl]pyrrolidin-2-one (Example 82)

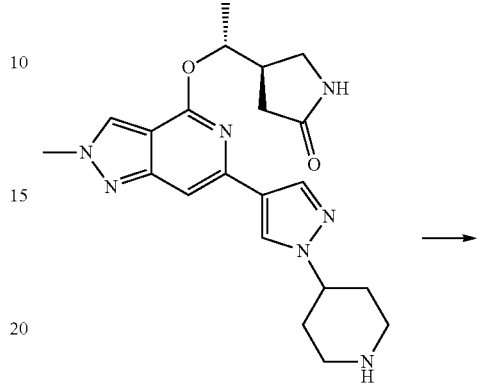
Example 9

→

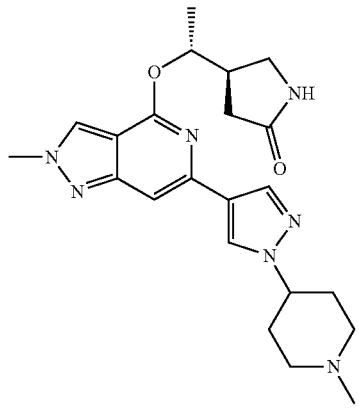
Example 82

To a mixture of 68 mg of Example 9 and 31 mg sodium acetate in 3 mL DCM and 0.5 mL methanol was added 17 µL formaldehyde (aqueous 37%). The resulting mixture was stirred at room temperature for 10 min, before 46 mg sodium triacetoxyborohydride was added. The reaction mixture was stirred for 1.75 h before quenched with water. The organic solvent was removed by destillation. The resulting residue was purified by rpHPLC to yield after lyophilisation 64 mg of Example 82 as solid.

Analysis: HPLC-MS: $R_t$=0.28 min (method X), M+H=424

Synthesis of (4R)-4-[(1R)-1-[6-[1-(Difluoromethyl)imidazol-4-yl]-2-methyl-pyrazolo[4,3-c]pyridin-4-yl]oxyethyl]pyrrolidin-2-one (Example 83) and 2-Methyl-6-[2-methyl-4-[(1R)-1-[(3R)-5-oxopyrrolidin-3-yl]ethoxy]pyrazolo[4,3-c]pyridin-6-yl]-5H-pyrazolo[4,3-c]pyridin-4-one (Example 13)

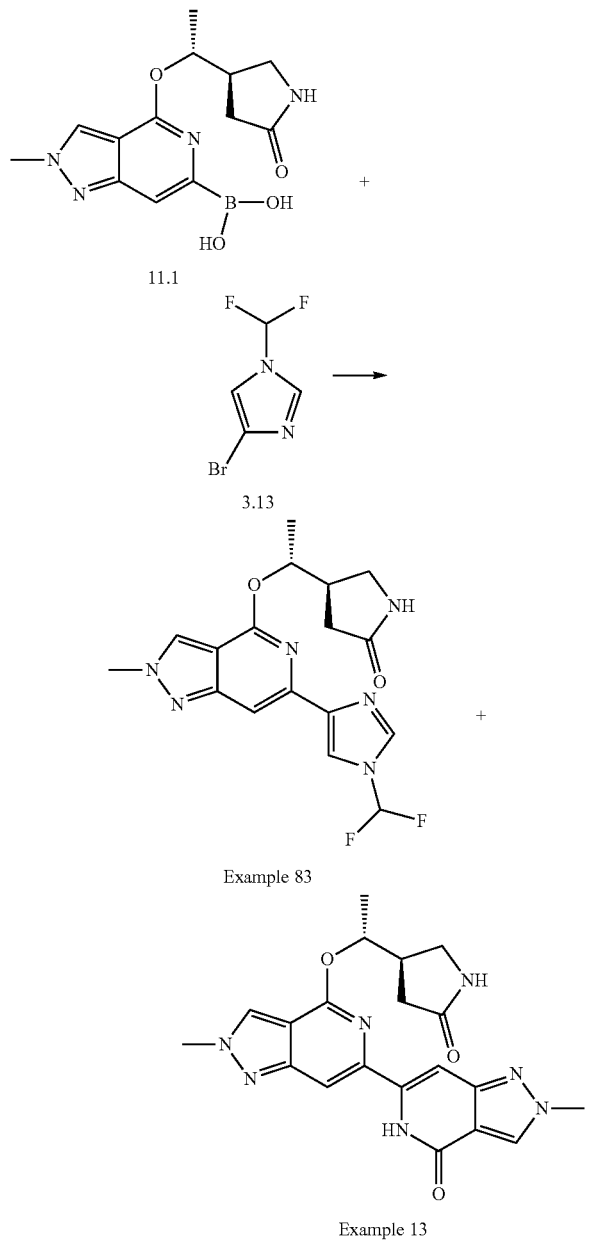

To a mixture of 300 mg (crude) [2-methyl-4-[(1R)-1-[(3R)-5-oxopyrrolidin-3-yl]ethoxy]pyrazolo[4,3-c]pyridin-6-yl]boronic acid 11.1, 60 mg 4-bromo-1-(difluoromethyl)imidazole and 41 mg 1,1'-bis(diphenylphospino)ferrocenedichloro palladium(II) (complex with DCM (1:1)) in 2 mL dioxane and 0.5 mL methanol was added 670 μL 2M aqueous sodium carbonat solution. The reaction mixture was stirred at 140° C. for 15 min under microwave irradiation. The reaction mixture was filtered through Agilent PL-Thiol MP-SPE, washed with methanol and purified by rpHPLC to yield after lyophilisation 9 mg of Example 83 and 4 mg of Example 13 as solids.

Analysis (Example 83): HPLC-MS: $R_t$=0.43 min (method C), M+H=377

Analysis (Example 13): HPLC-MS: $R_t$=0.38 min (method C), M+H=408

4.5 Analytical Methods

The Example compounds prepared according to the foregoing synthesis schemes were characterised by the following chromatographic methods and/or NMR spectroscopy.

4.5.1 Chromatographic Methods (HPLC-MS Methods)

Method A

| Column: Xbridge BEH C18, 2.1 × 30 mm, 1.7 μm | | | | |
|---|---|---|---|---|
| Column supplier: Waters | | | | |
| Gradient/Solvent Time [min] | % Sol [$H_2O$, 0.1% $NH_3$] | % Sol [Acetonitril] | Flow [ml/min] | Temp [° C.] |
| 0.00 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Method B:

| Column: Sunfire C18, 3 × 30 mm, 2.5 μm | | | | |
|---|---|---|---|---|
| Column Supplier: Waters | | | | |
| Gradient/Solvent Time [min] | % Sol [$H_2O$, 0.1% TFA] | % Sol [Methanol] | Flow [ml/min] | Temp [° C.] |
| 0.0 | 95 | 5 | 1.8 | 60 |
| 0.25 | 95 | 5 | 1.8 | 60 |
| 1.70 | 0 | 100 | 1.8 | 60 |
| 1.75 | 0 | 100 | 2.5 | 60 |
| 1.90 | 0 | 100 | 2.5 | 60 |

Method C:

| Column: Xbridge BEH C18, 2.1 × 30 mm, 1.7 μm | | | | |
|---|---|---|---|---|
| Column supplier: Waters | | | | |
| Gradient/Solvent Time [min] | % Sol [$H_2O$, 0.1% $NH_3$] | % Sol [Acetonitril] | Flow [ml/min] | Temp [° C.] |
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method D:

| Column: XBridge C18, 2.1 × 20 mm, 2.5 μm | | | | |
|---|---|---|---|---|
| Column Supplier: Waters | | | | |
| Gradient/Solvent Time [min] | % Sol [$H_2O$, 0.10% TFA] | % Sol [Methanol] | Flow [ml/min] | Temp [° C.] |
| 0.0 | 95 | 5 | 1.4 | 60 |
| 0.05 | 95 | 5 | 1.4 | 60 |
| 1.00 | 0 | 100 | 1.4 | 60 |
| 1.1 | 0 | 100 | 1.4 | 60 |

Method E:

| Column: Sunfire C18, 2.1 × 20 mm, 2.5 µm Column Supplier: Waters | | | | |
|---|---|---|---|---|
| Gradient/Solvent Time [min] | % Sol [H$_2$O, 0.10% TFA] | % Sol [Methanol] | Flow [ml/min] | Temp [° C.] |
| 0.00 | 99 | 1 | 1.3 | 60 |
| 0.15 | 99 | 1 | 1.3 | 60 |
| 1.10 | 0 | 100 | 1.3 | 60 |
| 1.25 | 0 | 100 | 1.3 | 60 |

Method F:

| Column: XBridge C18, 3 × 30 mm, 2.5 µm Column Supplier: Waters | | | | |
|---|---|---|---|---|
| Gradient/Solvent Time [min] | % Sol [H$_2$O, 0.1% NH$_3$] | % Sol [Acetonitril] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method G:
Eluent A: Water/0.2% KH$_2$PO$_4$ pH=3
Eluent B: Acetonitrile

| Time [min] | % A | % B | Flow rate [mL/min] |
|---|---|---|---|
| 0.00 | 80 | 20 | 1.50 |
| 5.00 | 20 | 80 | 1.50 |
| 8.00 | 20 | 80 | 1.50 |

The stationary phase used was a Inertsil C8-3 (GL Sciences), 5 µm; dimension: 100×4.0 mm, (column temperature: constant at 30° C.). Detection UV 220 nm.

Method H:
Eluent A: Hexane
Eluent B: 2-Propanol

| Time [min] | % A | % B | Flow rate [mL/min] |
|---|---|---|---|
| 00.00 | 90 | 10 | 1.0 |
| 20.00 | 90 | 10 | 1.0 |

The stationary phase used was a Chiralpak AD-H (Daicel), 5 µm; dimension: 150×4.6 mm, (column temperature: constant at 10° C.). Detection DAD 225 nm.

Method I:
Eluent A: Hexane
Eluent B: 2-Propanol

| Time [min] | % A | % B | Flow rate [mL/min] |
|---|---|---|---|
| 00.00 | 90 | 10 | 1.0 |
| 25.00 | 90 | 10 | 1.0 |

The stationary phase used was a Chiralpak AD-H (Daicel), 5 µm; dimension: 150×4.6 mm, (column temperature: constant at 10° C.). Detection DAD 225 nm.

Method J:

| Column: Sunfire C18, 2.1 × 30 mm, 2.5 µm Column Supplier: Waters | | | | |
|---|---|---|---|---|
| Gradient/Solvent Time [min] | % Sol [H$_2$O, 0.1% TFA] | % Sol [Acetonitril] | Flow [ml/min] | Temp [° C.] |
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

Method K:
Column: Waters Atlantis dC18 (2.1×50 mm, 3 µm column)
Flow rate: 1 mL/min
Solvent A: 0.1% Formic acid/water
Solvent B: 0.1% Formic acid/acetonitrile
Injection volume: 3 µL
Column temperature: 40° C.
UV Detection wavelength: 215 nm
Eluent: 0 to 2.5 minutes, constant gradient from 95% solvent A+5% solvent B to 100% solvent B; 2.5 to 2.7 minutes, 100% solvent B; 2.71 to 3.0 minutes, 95% solvent A+5% solvent B.
MS detection using Waters LCT Premier, QTof micro, ZQ or Shimadzu LCMS2010EV
UV detection using Waters 2996 photodiode array, Waters 2998 photodiode array, Waters 2487 UV or Shimadzu SPD-M20A PDA Method L:

| Column: XBridge C18, 4.6 × 30 mm, 3.5 µm Column Supplier: Waters | | | | |
|---|---|---|---|---|
| Gradient/Solvent Time [min] | % Sol [H$_2$O, 0.1% NH3] | % Sol [ACN] | Flow [ml/min] | Temp [° C.] |
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method M:
Column: Waters SymmetryShield RP8 (2.1×50 mm, 3.5 µm column)
Flow rate: 1 mL/min
Solvent A: 0.1% Formic acid/water
Solvent B: 0.1% Formic acid/acetonitrile
Injection volume: 3 µL
Column temperature: 40° C.
UV Detection wavelength: 215 nm
Eluent: 0 to 2.2 minutes, constant gradient from 95% solvent A+5% solvent B to 100% solvent B; 2.2 to 2.7 minutes, 100% solvent B; 2.71 to 3.0 minutes, 95% solvent A+5% solvent B.
MS detection using Waters LCT Premier, QTof micro, ZQ or Shimadzu LCMS2010EV
UV detection using Waters 2996 photodiode array, Waters 2998 photodiode array, Waters 2487 UV or Shimadzu SPD-M20A PDA Method N:

| Column: Xbridge BEH C18, 2.1 × 30 mm, 1.7 μm Column Supplier: Waters | | | | |
|---|---|---|---|---|
| Gradient/Solvent Time [min] | % Sol [H2O, 0.1% TFA] | % Sol [Acetonitril] | Flow [ml/min] | Temp [° C.] |
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

Method O:

| Column: Xbridge BEH Phenyl, 2.1 × 30 mm, 1.7 μm Column supplier: Waters | | | | |
|---|---|---|---|---|
| Gradient/Solvent Time [min] | % Sol [H2O, 0.1% NH3] | % Sol [Acetonitril] | Flow [ml/min] | Temp [° C.] |
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method P:
Column: Supelco Ascentis Express (2.1×30 mm, 2.7 μm column)
Flow rate: 1 ml/min
Solvent A: 0.1% Formic acid/water
Solvent B: 0.1% Formic acid/acetonitrile
Injection volume: 3 μL
Column temperature: 40° C.
UV Detection wavelength: 215 nm
Eluent: 0 to 1.5 minutes, constant gradient from 95% solvent A+5% solvent B to 100% solvent B; 1.5 to 1.6 minutes, 100% solvent B; 1.60 to 1.61 minutes, constant gradient from 100% solvent B to 95% solvent A+5% solvent B; 1.61 to 2.00 minutes, 95% solvent A+5% solvent B.
MS detection using Waters LCT Premier, QTof micro, ZQ or Shimadzu LCMS2010EV
UV detection using Waters 2996 photodiode array, Waters 2998 photodiode array, Waters 2487 UV or Shimadzu SPD-M20A PDA Method Q
Column: Atlantis d C18; 50×3 mm; 3μ
Flow rate: 0.6 ml/min
Solvent A: 0.1% Formic acid in water
Solvent B: 0.1% Formic acid in acetonitrile
Injection Volume: 5 μL
Column temperature: 35° C.
UV Detection wavelength: Spectra A max (with scan in the region of 200-400 nm)
Eluent: 0 to 3.5 minutes, constant gradient from 95% solvent A+5% solvent B to 100% solvent B; 3.5 to 3.8 minutes, 100% solvent B; 3.8 to 3.9 minutes, constant gradient from 100% solvent B to 95% solvent A+5% solvent B; 3.9 to 4.5 minutes, 95% solvent A+5% solvent B.
MS detection using Waters 3100, SQ detector, ES +ve and −ve modes (Cone voltage: 30V, Capillary voltage 3.0 KV)
UV detection using Waters 2996 photodiode array Method R:
Column: Phenomenex Kinetex-XB C18 (2.1×100 mm, 1.7 μm column)
Flow rate: 0.6 mL/min
Solvent A: 0.1% Formic acid/water
Solvent B: 0.1% Formic acid/acetonitrile
Injection volume: 3 μL
Column temperature: 40° C.
UV Detection wavelength: 215 nm
Eluent: 0 to 5.3 minutes, constant gradient from 95% solvent A+5% solvent B to 100% solvent B; 5.3 to 5.8 minutes, 100% solvent B; 5.80 to 5.82 minutes, constant gradient from 100% solvent B to 95% solvent A+5% solvent B; 5.82 to 7 mins, 95% solvent A+5% solvent B
MS detection using Waters SQD
UV detection using Waters Acquity photodiode array Method S:

| Column: Sunfire C18, 2.1 × 30 mm, 2.5 μm Column Supplier: Waters | | | | |
|---|---|---|---|---|
| Gradient/Solvent Time [min] | % Sol [H2O, 0.1% TFA] | % Sol [Acetonitril] | Flow [ml/min] | Temp [° C.] |
| 0.0 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Method T:
Column: Phenomenex Gemini C18 (2.0 mm×100 mm, 3 μm column)
Flow rate: 0.5 mL/min
Solvent A: 2 mM Ammonium bicarbonate modified to pH 10 with Ammonium Hydroxide/water
Solvent B: Acetonitrile
Injection volume: 3 μL
Column temperature: 40° C.
UV Detection wavelength: 215 nm
Eluent: 0 to 5.5 minutes, constant gradient from 95% solvent A+5% solvent B to 100% solvent B; 5.5 to 5.9 minutes, 100% solvent B; 5.90 to 5.92 minutes, constant gradient from 100% solvent B to 95% solvent A+5% solvent B; 5.92 to 9.00 minutes, 95% solvent A+5% solvent B.

Method U:

| Column: XBridge C18_3.0 × 30 mm, 2.5 μm Column producer: Waters Description: | | | | |
|---|---|---|---|---|
| Gradient/Solvent Time [min] | % Sol [H$_2$O 0.1% NH$_4$OH] | % Sol [Acetonitrile] | Flow [ml/min] | Temp [° C.] |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

Method V:

| Column: XBridge C18_3.0 × 30 mm, 2.5 μm Column producer: Waters | | | | |
|---|---|---|---|---|
| Gradient/Solvent Time [min] | % Sol [H$_2$O 0.1% NH$_4$OH] | % Sol [Acetonitrile] | Flow [ml/min] | Temp [° C.] |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

Method W:

| Column: Sunfire C18_3.0 × 30 mm, 2.5 µm | | | | |
|---|---|---|---|---|
| Column producer: Waters | | | | |
| Description: | | | | |
| Gradient/Solvent Time [min] | % Sol [H2O 0.1% TFA] | % Sol [Acetonitrile] | Flow [ml/min] | Temp [° C.] |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

Method X:

| Column: Sunfire C18_2.1 × 50 mm, 2.5 µm | | | | |
|---|---|---|---|---|
| Column producer: Waters | | | | |
| Description: | | | | |
| Gradient/Solvent Time [min] | % Sol [H$_2$O 0.1% TFA] | % Sol [Acetonitrile 0.08% TFA] | Flow [ml/min] | Temp [° C.] |
| 0.0 | 95.0 | 5.0 | 1.5 | 60.0 |
| 0.75 | 0.0 | 100.0 | 1.5 | 60.0 |
| 0.85 | 0.0 | 100.0 | 1.5 | 60.0 |

Method Y:

| Device description: Waters Acquity with 3100 MS | | | | |
|---|---|---|---|---|
| Column: XBridge BEH C18_3.0 × 30 mm, 1.7 µm | | | | |
| Column producer: Waters | | | | |
| Description: | | | | |
| Gradient/Solvent Time [min] | % Sol [H$_2$O 0.1% NH$_4$OH] | % Sol [Acetonitrile] | Flow [ml/min] | Temp [° C.] |
| 0.0 | 95.0 | 5.0 | 1.5 | 60.0 |
| 0.7 | 0.1 | 99.9 | 1.5 | 60.0 |
| 0.8 | 0.1 | 99.9 | 1.5 | 60.0 |
| 0.81 | 95.0 | 5.0 | 1.5 | 60.0 |
| 1.1 | 95.0 | 5.0 | 1.5 | 60.0 |

Method Z:

Column: Waters Atlantis dC18 (2.1×100 mm, 3 µm column)

Flow rate: 0.6 mL/min

Solvent A: 0.1% Formic acid/water

Solvent B: 0.1% Formic acid/acetonitrile

Injection Volume: 3 µL

Column temperature: 40° C.

UV Detection wavelength: 215 nm

Eluent: 0 to 5 minutes, constant gradient from 95% solvent A+5% solvent B to 100% solvent B; 5 to 5.4 minutes, 100% solvent B; 5.4 to 5.42 minutes, constant gradient from 100% solvent B to 95% solvent A+5% solvent B; 5.42 to 7.00 minutes, 95% solvent A+5% solvent B.

MS detection using Waters LCT Premier, QT of micro, ZQ or Shimadzu LCMS2010EV

UV detection using Waters 2996 photodiode array, Waters 2998 photodiode array, Waters 2487 UV or Shimadzu SPD-M20A PDA Method Z1:

| Method Name: | | | | |
|---|---|---|---|---|
| Column: Sunfire, 3 × 30 mm, 2.5 µm | | | | |
| Column Supplier: Waters | | | | |
| Gradient/Solvent Time [min] | % Sol [H2O, 0.1% TFA] | % Sol [Acetonitril] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

4.5.2 NMR Spectroscopy

Configuration of the Bruker DRX 500 MHz NMR

High performance digital NMR spectrometer, 2-channel microbay console and Windows XP host workstation running Topspin version 1.3.

Equipped with:

Oxford instruments magnet 11.74 Tesla (500 MHz proton resonance frequency)

B-VT 3000 temperature controller

GRASP II gradient spectroscopy accessory for fast acquisition of 2D pulse sequences Deuterium lock switch for gradient shimming 5 mm Broad Band Inverse geometry double resonance probe with automated tuning and matching (BBI ATMA). Allows $^1$H observation with pulsing/decoupling of nuclei in the frequency range $^{15}$N and $^{31}$P with $^2$H lock and shielded z-gradient coils.

Configuration of the Bruker DPX 400 MHz NMR

High performance one bay Bruker 400 MHz digital two channel NMR spectrometer console and Windows XP host workstation running XwinNMR version 3.5.

Equipped with:

Oxford instruments magnet 9.39 Tesla (400 MHz proton resonance frequency)

B-VT 3300 variable temperature controller unit

Four nucleus (QNP) switchable probe for observation of $^1$H, $^{13}$C, $^{19}$F and $^{31}$P with $^2$H lock Configuration of the Bruker 500 MHz NMR High performance digital NMR spectrometer, 2-channel one bay console and Linux host workstation running Topspin version 2.1 PL6.

Equipped with:

Bruker-Biospin AVANCE III 500A magnet 11.75 Tesla (500 MHz proton resonance frequency)

B-VT 3000 temperature controller 5 mm Multinuclear Broad Band fluorine observe (BBFO) probe with digital tuning covering the range from $^{15}$N and $^{31}$P as well as $^{19}$F with $^1$H decoupling.

Configuration of the Bruker DPX 400 MHz NMR

High performance digital NMR spectrometer, 2-channel microbay console and Linux host workstation running Topspin version 2.1 PL6

Equipped with:

Bruker-Biospin AVANCE III DPX400C magnet 9.40 Tesla (400 MHz proton resonance frequency)

B-VT 3200 variable temperature controller unit 5 mm Multinuclear Broad Band fluorine observe (BBFO) probe with digital tuning covering the range from $^{15}$N and $^{31}$P as well as $^{19}$F with $^1$H decoupling.

5. EXAMPLES

The following Examples were prepared analogously to the methods of synthesis described above. These compounds are suitable as SYK inhibitors and have $IC_{50}$-values with regard to SYK-inhibition of less than or equal to 1 µmol. Additionally these compounds exhibit a very good SYK-selectivity which means that—whereas SYK is inhibited effectively—other kinases such as Aurora B (AURB), FLT-3 and GSK 3β are not or almost not inhibited at all. Consequently undesired side effects of these effective SYK-inhibitors of the invention are minimized.

AURB phosphorylates Ser10 and Ser28 on histone H3, a key event in mitosis and cellular proliferation. Inhibition of AURB therefore has the potential to block cellular proliferation, and could compromise tissues that exhibit a high cellular turnover, such as the intestine or the bone marrow. It is therefore desired to avoid parallel AURB inhibition of an effective SYK inhibitor to improve the overall clinical safety profile of the compound. Consequently all example compounds show $IC_{50}$-values with regard to Aurora B inhibition of more than 1 µM, preferably more than 6 µM, more preferably more than 10 µM, more preferably more than 30 µM, more preferably of more than 45 µM, particularly preferably more than 50 µM. The AURB-$IC_{50}$/SYK-$IC_{50}$-ratios of all example compounds are preferably more than 30, more preferably more than 100.

FLT-3 is a tyrosine kinase receptor. When an FLT-3 ligand binds to the receptor, the intrinsic tyrosine kinase activity of the receptor is activated, which in turn phosphorylates and activates signal transduction molecules (such as SHC) which in turn propagates the signal in the cell. Signaling through FLT-3 plays a role in cell survival, proliferation, and differentiation and is important for lymphocyte (B cell and T cell) development. It is therefore desired to avoid parallel FLT-3 inhibition of an effective SYK inhibitor to improve the overall clinical safety profile of the compound. Consequently all example compounds of the instant invention show $IC_{50}$-values with regard to FLT-3 inhibition of more than 0.30 µM, preferably more than 1 µM, more preferably more than 10 µM, particularly preferably more than 30 µM. The FLT-3-$IC_{50}$/SYK-$IC_{50}$-ratios of all example compounds are preferably more than 10, more preferably more than 30.

Glycogen synthase kinase 3 beta (GSK 3β) is a proline-directed serine-threonine kinase that is prominent in the TGF-β and Wnt intracellular signalling pathways. GSK 3β facilitates a number of intracellular signalling pathways including the activation of β-catenin complex. In adults, GSK 3β is involved in cellular proliferation and energy metabolism, whilst in neonates is involved in neuronal cell development and body pattern formation. It is therefore desired to avoid parallel GSK3β inhibition of an effective SYK inhibitor to improve the overall clinical safety profile of the compound. Consequently all example compounds of the invention show $IC_{50}$-values with regard to GSK 3β inhibition of more than 1 µM, preferably of more than 10 µM.

Further it is desirable for an SYK-inhibitor to have certain human liver microsomal stability (corresponding to CI<60% $Q_h$; % $Q_h$=percentage of liver blood flow). Otherwise it will be difficult to reach an adequate plasma level of the SYK-inhibitor in the patient to be treated.

The $IC_{50}$-values with respect to SYK-inhibition, with respect to Aurora B inhibition, with respect to FLT3-inhibition and with respect to GSKbeta-inhibition as well as the human liver microsomal stablities (CI [% $Q_h$]) for each of the individual example substances are shown in the following Table 1 and were experimentally determined as follows:

5.1 Syk Kinase Test

Recombinant human Syk (amino acids 342-635) was expressed as a fusion protein with an N-terminal GST tag, affinity-purified and deep-frozen at a concentration of approx. 50-100 µM in storage buffer (25 mM HEPES pH7.5; 25 mM $MgCl_2$; 5 mM $MnCl_2$; 50 mM KCl; 0.2% BSA; 0.01% CHAPS; 100 µM $Na_3VO_4$; 0.5 mM DTT, 10% glycerol) at −80° C. until use.

The catalytic activity of the GST-Syk kinase fusion protein was determined using the Kinase Glo® Luminescence Kinase test (Promega; V6712). In this homogeneous test the amount of ATP remaining after the kinase reaction is quantified by a luciferin-luciferase reaction using luminescence. The luminescence signal obtained correlates with the amount of ATP still present and thus correlates inversely with the activity of the kinase.

Method

The test compounds were dissolved in 100% DMSO at a concentration of 10 mM and diluted in DMSO to a concentration of 1 mM. Serial Dilution is done in 100% DMSO. All further dilutions of the substances were carried out with test buffer (25 mM HEPES pH7.5; 25 mM $MgCl_2$; 5 mM $MnCl_2$; 50 mM KCl; 0.2% HSA; 0.01% CHAPS; 100 µM $Na_3VO_4$; 0.5 mM DTT). Dilution steps and concentration range were adapted according to need. 7 µl aliquots of these dilutions were transferred into a 384-well Optiplate (Perkin Elmer, #6007290). GST-Syk was diluted to 12 nM in the test buffer and 5 µl of this dilution were used in the kinase test (final concentration of Syk=4 nM in a total volume of 15 µl). After 15 minutes incubation at room temperature 3 µl of a mixture of 750 nM ATP and 100 µg/ml poly (L-Glutamic acid L-Tyrosine 4:1), Fluka #81357) in test buffer were added to each well and the incubation was continued for a further 60 minutes at room temperature.

Positive controls are the reaction mixtures that contain no test substance; negative controls (blanks) are reaction mixtures that contain no kinase.

After 60 minutes, 10 µl Kinase-Glo® solution (Promega, Cat. # V6712) (heated to room temperature) were added to each well and incubation was continued for a further 15 minutes. The plates were read in Envision Luminescence Reader (Perkin-Elmer).

Data Evaluation and Calculation:

The output file of the reader is a csv file that contains the well number and measured relative light units (RLU). For data evaluation and calculation, the measurement of the negative control was set as 100% ctrl and the measurement of the positive control was set as 0% ctrl. Based on this values the % value for the measurement of each substance concentration was calculated using an Assay Explorer software (Accelrys). Normally, the % ctrl values calculated are between 0% and 100% values but may also occur outside these limits in individual cases based on variability or compound characteristics. The $IC_{50}$ values were calculated from the % ctrl values using Assay Explorer software. Calculation:$[y=(a-d)/(1+(x/c)^b)+d]$ a=low value, d=high value; x=conc M; c=IC50 M; b=hill; y=% ctrl.

5.2 Aurora B Kinase Test

Recombinant human Aurora B (amino acids 1-344, clone number DU1773, Molecular weight 40.2 kDa, University of Dundee) was expressed as a fusion protein with an N-terminal His tag, affinity-purified and deep-frozen at a concentration of approx. 0.25-0.5 mg/ml in storage buffer (50 mM Tris-HCl pH 8; 25 mM Na-β-glycerophosphat; 0.1 mM EGTA; 150 mM NaCl; 0.03% Brij-35; 1 mM DTT and 10% glycerol) at −80° C. until use.

The activity of the Aurora B kinase protein was determined using the ADP Glo® Luminescence Kinase test (Promega; V9103X). In this homogeneous test the amount of ADP remaining after the kinase reaction is quantified by a luciferin-luciferase reaction using luminescence. The luminescence signal obtained correlates with the amount of ADP still present and thus correlates with the activity of the protein kinase.
Method The test compounds were dissolved in 100% DMSO at a concentration of 10 mM and diluted in DMSO to a concentration of 5 mM. Serial Dilution is done in 1:10 steps in 100% DMSO. All further dilutions of the substances were carried out with test buffer (50 mM Hepes, pH 7.5, 10 mM MgCl2, 1 mM EGTA, 60 µM Ultra Pure ATP, 0.01% Brij35, 0.1% BSA, 5 mM β-Glycerophosphate) until a concentration was reached which was 2.5 times above the final test concentration (final concentration of the compounds: 50 µM to 0.005 nM). 4 µl aliquots of these dilutions were transferred into a 384-well Optiplate (Perkin Elmer, #6007290). His-Aurora B was diluted to 125 nM in the test buffer and 4 µl of this dilution were used in the kinase test (final concentration of Aurora B=50 nM in a total volume of 10 µl). After 15 minutes incubation at room temperature 2 µl of 250 µM substrate ([LRRLSLGLRRLSLGLRRLSLGLR-RLSLG]; University of Dundee) in test buffer were added to each well and the incubation was continued for a further 60 minutes at room temperature.

Positive controls are the reaction mixtures that contain no test substance; negative controls (blanks) are reaction mixtures that contain no kinase.

After 60 minutes, 10 µl ADP-Glo® solution (ADP-Glo Reagent #V912B Promega) (heated to room temperature) were added to each well and incubation was continued for a further 40. minutes. Then 20 µl Kinase detection mix (Detection Buffer #V913B Promega; Kinase Detection Substrate #V914B Promega) were added and incubated for 40 minutes at room temperature. The plates were read in Envision Luminescence Reader (Perkin-Elmer).
Data Evaluation and Calculation:

The output file of the reader is a csv file that contains the well number and measured RLU. For data evaluation and calculation, the measurement of the negative control was set as 0% ctrl and the measurement of the positive control was set as 100% ctrl. Based on this values the % value for the measurement of each substance concentration was calculated using an Assay Explorer software (Accelrys). Normally, the % ctrl values calculated are between 0% and 100% values but may also occur outside these limits in individual cases based on variability or compound characteristics. The $IC_{50}$ values were calculated from the % ctrl values using Assay Explorer software. Calculation: [y=(a−d)/(1+(x/c)^b)+d], a=low value, d=high value; x=conc M; c=IC50 M; b=hill; y=% ctrl.
5.3 FLT3 Kinase Test FLT3 is obtained from Invitrogen in 50 mM Tris (pH7.5); 100 mM NaCl; 0.05 mM EDTA, 0.05% NP-40, 2 mM DTT; 50% Glycerol # PV3182; Lot 286671; sequence see below). The enzyme is diluted to 720 nM (35 µg/ml) in enzyme dilution buffer and 10 µl aliquots are stored at −80° C.

The activity of FLT3 is measured using the Z'-LYTE™ assay technology from Invitrogen (#PV3191)
Method The assay is performed in 384 black plates from Corning (#3676) in a final volume of 10 µl by adding 5 µl of kinase peptide mix and 2.5 µl of compound dilution. The reaction is started by addition of 2.5 µl of the 4×ATP solution.

Final concentration in assay: FLT3 2 nM, Tyr2 peptide 4 µM, ATP 470 µM (ATP Km for FLT3)

Positive controls are reaction mixtures containing no test compound; negative controls (blanks) are reaction mixtures containing no kinase. As a further control, the phosphopeptide solution is added to wells without kinase (=100% phosphorylation control). The non inhibited kinase reaction will result in a phosphorylation corresponding to 20%-30% of the phosphorylation control.

The reaction is performed for 1 h at room temperature before 5 µl of the development solution is added. After a further incubation for 1 h at room temperature 5 µl of the stop reagent is added. The plates are read on a Flex Station II 384 (Molecular Devices).

To control for any potential inhibition of the protease present in the development solution, the phosphopeptide is incubated with the development solution in the presence of the highest concentration of the test compound (usually 100 µM or 10 µM).
Data Evaluation and Calculation:

The output text file is evaluated in an "MS-Excel—VB-Makro" and "GraphPadPrism" (Version 5) (GraphPad Software Inc.) is used to calculate the results. Data for the inhibition of FLT3 are reported in M. data for the inhibition of the protease are reported in % CTL.
5.4 GSK 30 Kinase-Test Human GSK3beta (expressed and prified from SF21 cells) is obtained from the University Dundee/Scotland (Dr. James Hastie—Dept. of Biochemistry) in 50 mM Tris (pH7.5); 150 mM NaCl; 0.1 mM EGTA, 270 mM Succrose, 0.1% β-mercaptoethanol, 1 mM benzamidine, 0.2 mM PMSF; sequence see below). The enzyme is diluted to 3.56 µM (168 µg/ml) in enzyme dilution buffer and 6 µl aliquots are stored at −80° C.

The activity of GSK3 kinase protein is measured using the Z'-LYTE™ assay technology from Invitrogen (# PV3324).
Method:

The assay is performed in 384 black plates from Corning (#3676) in a final volume of 10 µl by adding 5 µl of kinase peptide mix and 2.5 µl of compound dilution. The reaction is started by addition of 2.5 µl of the 4×ATP solution.

Final concentration in assay: GSK3β 5 nM, Ser/Thr9 peptide 2 µM, ATP 7 µM (ATP Km for GSK3β)

Positive controls are reaction mixtures containing no test compound; negative controls (blanks) are reaction mixtures containing no ATP. As a further control, the phosphopeptide solution is added to wells without kinase and without ATP (=100% phosphorylation control).

The non inhibited kinase reaction will result in a phosphorylation corresponding to 20%-30% of the phosphorylation control.

The reaction is performed 1 h at room temperature. After 1h 5 µl of the development solution is added. After a further incubation for 1 h at room temperature 5 µl of the stop reagent is added. Finally the plates are read on a Flex Station II 384 (Molecular Devices).

To control for any potential inhibition of the protease present in the development solution, the phosphopeptide is incubated with the development solution in the presence of the highest concentration of the test compound (usually 100 µM).
Data Evaluation and Calculation:

The output text file is evaluated in an "MS-Excel—VB-Makro" and "GraphPadPrism" (Version 5) (GraphPad Software Inc.) is used to calculate the results. Data for the inhibition of GSK3beta are reported in M. data for the inhibition of the protease are reported in % CTL.
5.5 Human Liver Microsomal Stability Test Further it is desirable for an SYK-inhibitor that is sufficiently SYK-specific as described above to have certain human liver microsomal stability (corresponding to CI<60%

$Q_h$; % $Q_h$=percentage of liver blood flow). Otherwise it will be difficult to reach an adequate plasma level of the SYK-inhibitor in the patient to be treated.

Method:

The metabolic degradation for a specific SYK-inhibitor is performed at 37° C. with pooled human liver microsomes (human liver microsomes are commercially available as "BD UltraPool™" by Corning Life Sciences, Fogostraat 12, 1060 LJ Amsterdam, The Netherlands). The final incubation volume of 100 μl per time point contains TRIS buffer pH 7.6 at RT (0.1 M), magnesium chloride (5 mM), microsomal protein (1 mg/ml) and the test compound at a final concentration of 1 μM.

Following a short preincubation period at 37° C., the reaction is initiated by addition of beta-nicotinamide adenine dinucleotide phosphate in its reduced form (NADPH, 1 mM) and terminated by transfering an aliquot into solvent after different time points. Additionally, the NADPH-independent degradation is monitored in incubations without NADPH, terminated at the last time point.

The quenched (terminated) incubations are then pelleted by centrifugation (10000 g, 5 min).

An aliquot of the supernatant is assayed by LC-MS/MS for the remaining amount of parent compound. The half-life (t1/2 INVITRO) is determined by the slope of the semilogarithmic plot of the concentration-time profile.

Data Evaluation and Calculation:

The intrinsic clearance (CL_INTRINSIC) is calculated by considering the amount of protein in the incubation:

$$CL\_INTRINSIC[\mu l/min/mg\ protein]=(Ln\ 2/(t1/2\ INVITRO[min]*protein\ content[mg/ml]))*1000$$

The protein content [mg/ml] was determined with the "Bicinchoninic Acid Kit" of Sigma Aldrich (commercially available).

The upscaled intrinsic Clearance (CL_UP_INT) is calculated by considering the liver weight [g liver/kg body weight] and the microsomal recovery [mg protein/g liver]:

$$CL\_UP\_INT[ml/min/kg]= 0.001*CL\_INTRINSIC*liver\ weight*microsomal\ recovery$$

with microsomal recovery=45 mg protein/g liver
with liver weight=25.7 g liver/kg body weight The percent hepatic blood flow (% $Q_h$) is finally calculated by considering the human liver blood flow Q [ml/min/kg]:

$$\%\ Q_h[\%]=((Q*CL\_UP\_INT)/(Q+CL\_UP\_INT)/Q)*100$$

with liver blood flow (Q)=20.7 ml/min/kg.

TABLE 1

| Example No. | Structure | SYK-inhibition IC$_{50}$-value [μM] | AURB-inhibition IC$_{50}$-value [μM] | FLT3-inhibition IC$_{50}$-value [μM] |
|---|---|---|---|---|
| 1 | 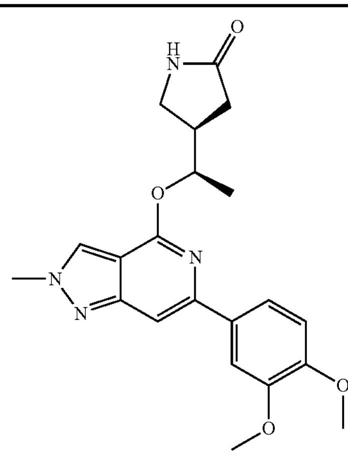 | 0.0160 | >50 | 3.99 |
| 2 | 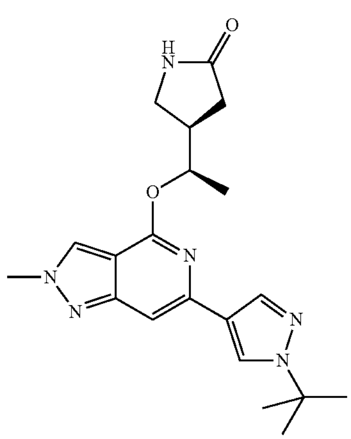 [SMILES: C[C@@H](Oc1nc(-c2cnn(C(C)(C)C)c2)cc2nn(C)cc12)[C@H]1CNC(=O)C1] | 0.0144 | >50 | 14.84 |

TABLE 1-continued
| Example No. | Structure | | SYK-inhibition IC$_{50}$-value [μM] | AURB-inhibition IC$_{50}$-value [μM] | FLT3-inhibition IC$_{50}$-value [μM] |
|---|---|---|---|---|---|
| 3 | 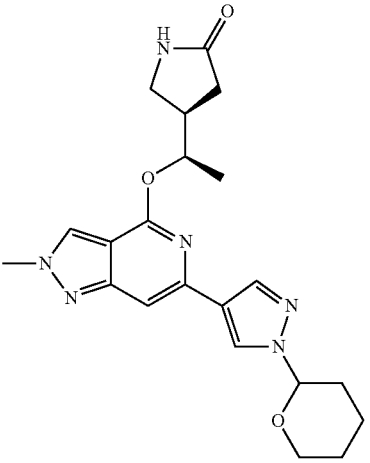 [SMILES: C[C@@H](Oc1nc(-c2cnn(C3CCCCO3)c2)cc2nn(C)cc12)[C@H]1CNC(=O)C1] | | 0.0466 | >50 | 17.45 |
| 4 | not defined | | not defined | not defined | not defined |
| 5 | not defined | | not defined | not defined | not defined |
| 6 | not defined | | not defined | not defined | not defined |
| 7 | 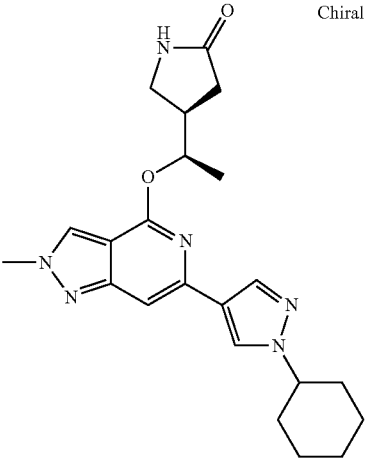 [SMILES: C[C@@H](Oc1nc(-c2cnn(C3CCCCC3)c2)cc2nn(C)cc12)[C@H]1CNC(=O)C1] | Chiral | 0.0147 | 37.30 | 5.77 |
| 8 | 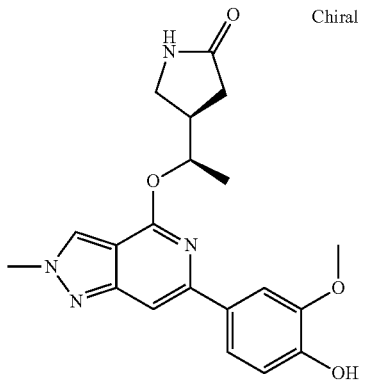 | Chiral | 0.0274 | >50 | 13.50 |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
|---|---|---|---|---|---|
| 9 | 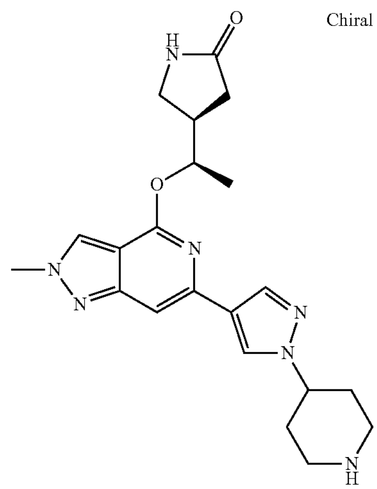 [SMILES: C[C@@H](Oc1nc(-c2cnn(C3CCNCC3)c2)cc2nn(C)cc12)[C@H]1CNC(=O)C1] | Chiral | 0.0424 | >50 | 3.67 |
| 10 | 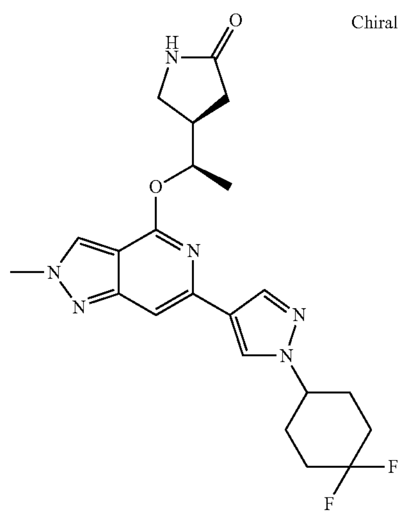 [SMILES: C[C@@H](Oc1nc(-c2cnn(C3CCC(F)(F)CC3)c2)cc2nn(C)cc12)[C@H]1CNC(=O)C1] | Chiral | 0.0218 | 36.00 | 8.03 |
| 11 | 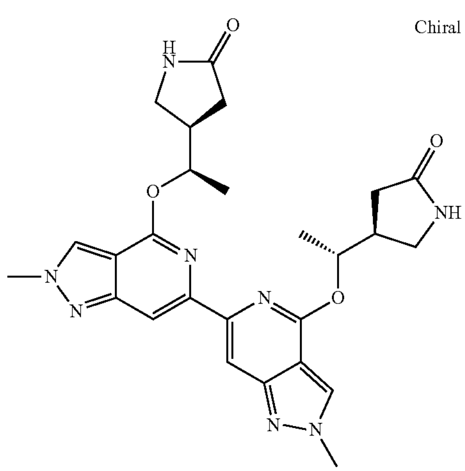 [SMILES: C[C@@H](Oc1nc(-c2cc3nn(C)cc3c(O[C@H](C)[C@H]3CNC(=O)C3)n2)cc2nn(C)cc12)[C@@H]1CNC(=O)C1] | Chiral | 0.9352 | >50 | 37.38 |

TABLE 1-continued

| Example No. | Structure | SYK-inhibition IC$_{50}$-value [μM] | AURB-inhibition IC$_{50}$-value [μM] | FLT3-inhibition IC$_{50}$-value [μM] |
|---|---|---|---|---|
| 12 | Chiral | 0.0123 | 34.09 | 8.33 |
| 13 | Chiral | 0.8310 | >50 | >50 |
| 14 | Chiral | 0.0421 | >50 | 40.80 |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
|---|---|---|---|---|---|
| 15 | 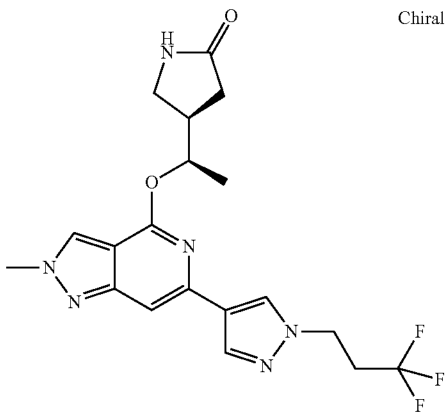 [SMILES: C[C@@H](Oc1nc(-c2cnn(CCC(F)(F)F)c2)cc2nn(C)cc12)[C@H]1CNC(=O)C1] | Chiral | 0.0187 | 33.40 | 10.08 |
| 16 | 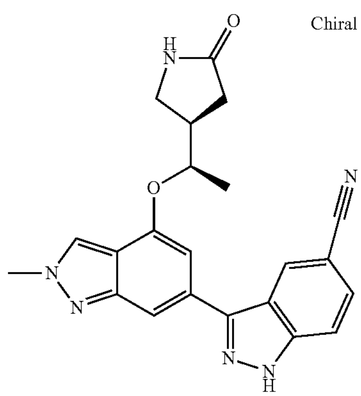 [SMILES: C[C@@H](Oc1cc(-c2n[nH]c3ccc(C#N)cc23)cc2nn(C)cc12)[C@H]1CNC(=O)C1] | Chiral | 0.0065 | >50 | 10.60 |
| 17 | 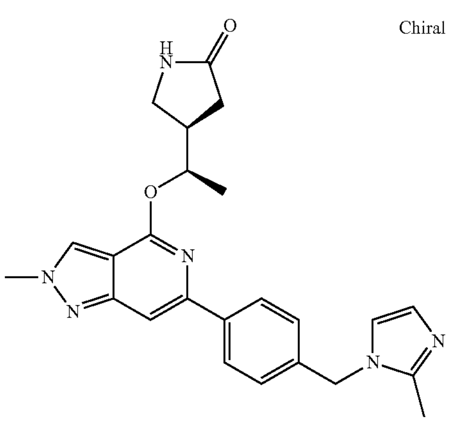 [SMILES: Cc1nccn1Cc1ccc(-c2cc3nn(C)cc3c(O[C@H](C)[C@H]3CNC(=O)C3)n2)cc1] | Chiral | 0.0316 | >50 | 1.61 |

TABLE 1-continued

| Example No. | Structure | | SYK-inhibition IC$_{50}$-value [µM] | AURB-inhibition IC$_{50}$-value [µM] | FLT3-inhibition IC$_{50}$-value [µM] |
|---|---|---|---|---|---|
| 18 | (structure) | Chiral | 0.0046 | >50 | 13.40 |
| 19 | not defined | | not defined | not defined | not defined |
| 20 | not defined | | not defined | not defined | not defined |
| 21 | not defined | | not defined | not defined | not defined |
| 22 | (structure) | Chiral | 0.0128 | 46.90 | 1.17 |
| 23 | not defined | | not defined | not defined | not defined |
| 24 | not defined | | not defined | not defined | not defined |
| 25 | not defined | | not defined | not defined | not defined |
| 26 | (structure) | Chiral | 0.0258 | >50 | 0.95 |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
|---|---|---|---|---|---|
| 27 | 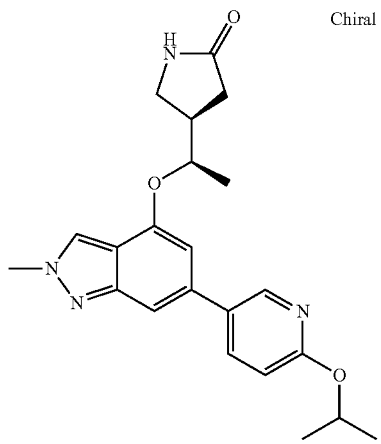 [SMILES: CC(C)Oc1ccc(-c2cc(O[C@H](C)[C@H]3CNC(=O)C3)c3cn(C)nc3c2)cn1] | Chiral | 0.1382 | >50 | 26.64 |
| 28 | 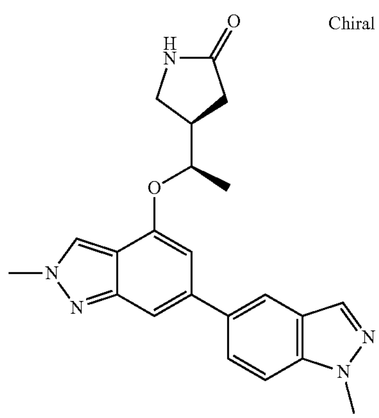 [SMILES: C[C@@H](Oc1cc(-c2ccc3c(cnn3C)c2)cc2nn(C)cc12)[C@H]1CNC(=O)C1] | Chiral | 0.0335 | >50 | 3.69 |
| 29 | 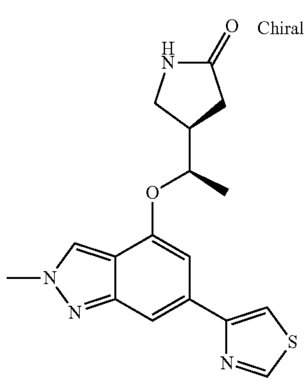 [SMILES: C[C@@H](Oc1cc(-c2cscn2)cc2nn(C)cc12)[C@H]1CNC(=O)C1] | Chiral | 0.0492 | >50 | 20.56 |
| 30 | not defined | | not defined | not defined | not defined |
| 31 | not defined | | not defined | not defined | not defined |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
|---|---|---|---|---|---|
| 32 | 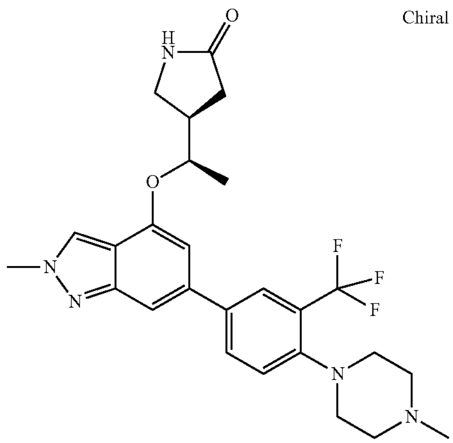 | Chiral | 0.0272 | >50 | 2.35 |
| 33 | 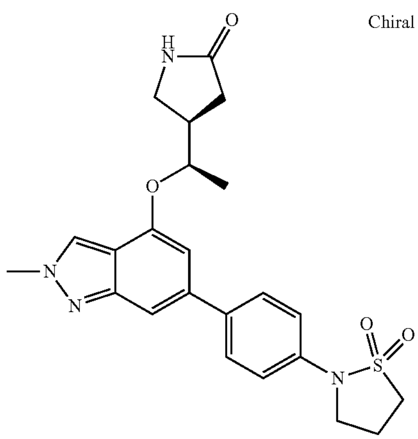 [SMILES: C[C@@H](Oc1cc(-c2ccc(N3CCCS3(=O)=O)cc2)cc2nn(C)cc12)[C@H]1CNC(=O)C1] | Chiral | 0.0245 | >50 | 3.88 |
| 34 | not defined | | not defined | not defined | not defined |
| 35 | 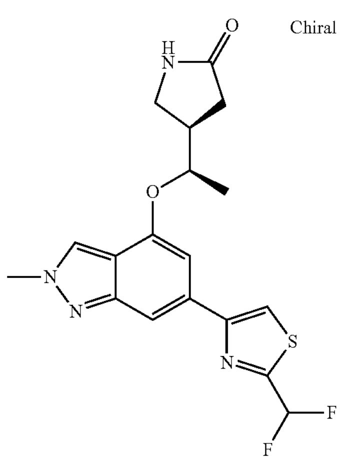 [SMILES: C[C@@H](Oc1cc(-c2csc(C(F)F)n2)cc2nn(C)cc12)[C@H]1CNC(=O)C1] | Chiral | 0.0345 | >50 | 19.66 |

TABLE 1-continued

| Example No. | Structure | SYK-inhibition IC$_{50}$-value [μM] | AURB-inhibition IC$_{50}$-value [μM] | FLT3-inhibition IC$_{50}$-value [μM] |
| --- | --- | --- | --- | --- |
| 36 | Chiral | 0.0172 | 35.22 | 2.39 |
| 37 | not defined | not defined | not defined | not defined |
| 38 | Chiral | 0.0609 | 47.10 | 11.35 |
| 39 | not defined | not defined | not defined | not defined |
| 40 | Chiral | 0.0343 | 31.43 | 8.95 |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
|---|---|---|---|---|---|
| 41 | 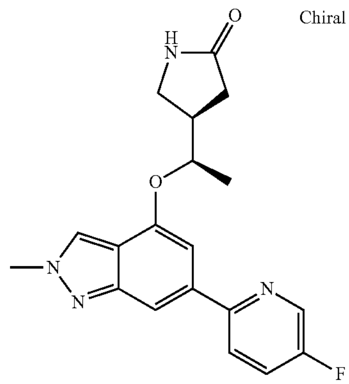 [SMILES: C[C@@H](Oc1cc(-c2ccc(F)cn2)cc2nn(C)cc12)[C@H]1CNC(=O)C1] | Chiral | 0.1638 | >50 | 42.82 |
| 42 | 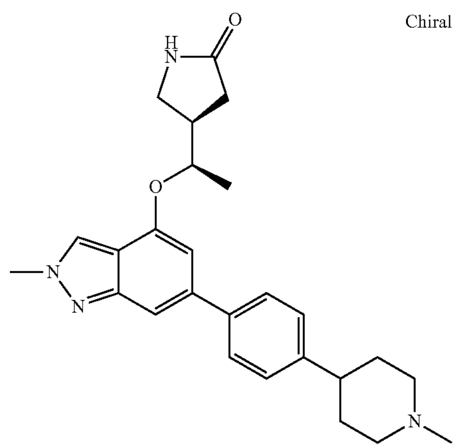 | Chiral | 0.0167 | >50 | 0.55 |
| 43 | 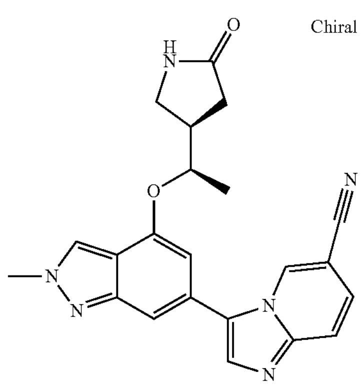 [SMILES: C[C@@H](Oc1cc(-c2cnc3ccc(C#N)cn23)cc2nn(C)cc12)[C@H]1CNC(=O)C1] | Chiral | 0.0649 | >50 | 15.05 |
| 44 | not defined | | not defined | not defined | not defined |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
|---|---|---|---|---|---|
| 45 | (structure) | Chiral | 0.0147 | 45.21 | 2.04 |
| 46 | not defined | | not defined | not defined | not defined |
| 47 | (structure) | Chiral | 0.0067 | 25.97 | 4.77 |
| 48 | (structure) | Chiral | 0.0556 | >50 | 16.86 |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
| --- | --- | --- | --- | --- | --- |
| 49 | 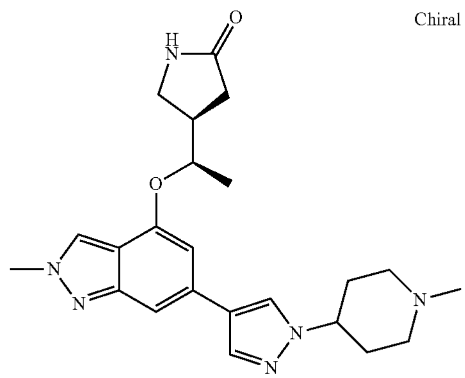 | Chiral | 0.0148 | >50 | 2.78 |
| 50 | 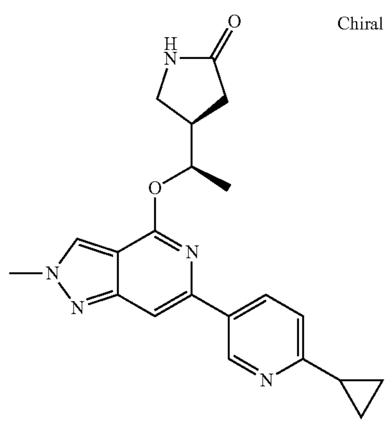 [SMILES: C[C@@H](Oc1nc(-c2ccc(C3CC3)nc2)cc2nn(C)cc12)[C@H]1CNC(=O)C1] | Chiral | 0.0554 | 47.95 | 9.52 |
| 51 | 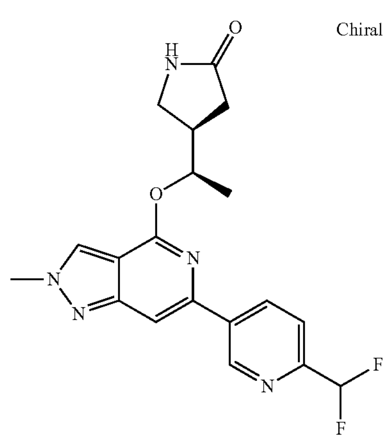 [SMILES: C[C@@H](Oc1nc(-c2ccc(C(F)F)nc2)cc2nn(C)cc12)[C@H]1CNC(=O)C1] | Chiral | 0.3660 | 49.83 | 20.87 |

TABLE 1-continued

| Example No. | Structure | SYK-inhibition IC$_{50}$-value [μM] | AURB-inhibition IC$_{50}$-value [μM] | FLT3-inhibition IC$_{50}$-value [μM] |
| --- | --- | --- | --- | --- |
| 52 | Chiral | 0.0413 | >50 | >50 |
| 53 | Chiral | 0.0139 | >50 | 34.12 |
| 54 | Chiral | 0.0892 | >50 | 16.00 |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
| --- | --- | --- | --- | --- | --- |
| 55 | 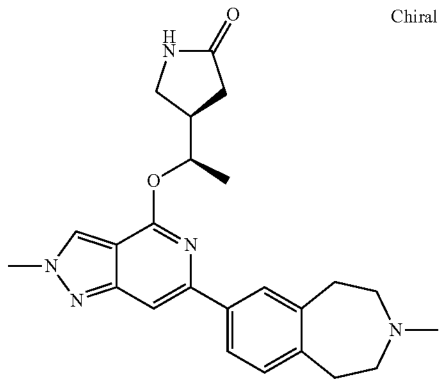 | Chiral | 0.0436 | >50 | 3.07 |
| 56 | 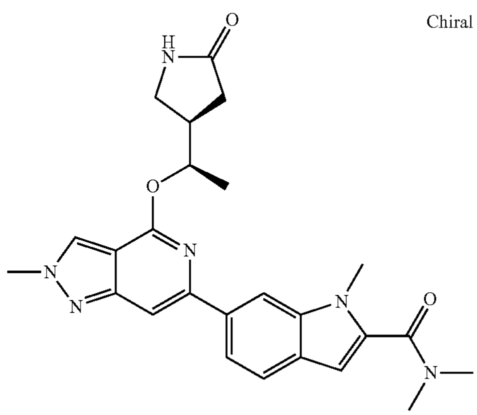 | Chiral | 0.0939 | >50 | 8.94 |
| 57 | 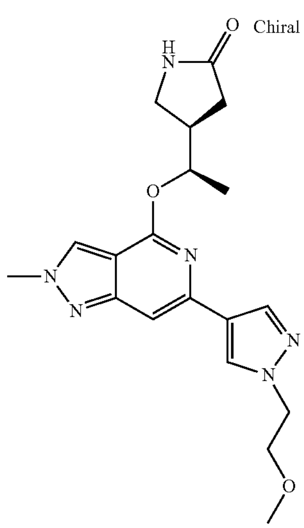 [SMILES: COCCn1cc(-c2cc3nn(C)cc3c(O[C@H](C)[C@H]3CNC(=O)C3)n2)cn1] | Chiral | 0.0901 | >50 | 31.97 |

TABLE 1-continued

| Example No. | Structure | SYK-inhibition IC$_{50}$-value [μM] | AURB-inhibition IC$_{50}$-value [μM] | FLT3-inhibition IC$_{50}$-value [μM] |
|---|---|---|---|---|
| 58 | Chiral | 0.0366 | >50 | 17.10 |
| 59 | Chiral | 0.1437 | >50 | 46.20 |
| 60 | Chiral | 0.1448 | 34.70 | 9.75 |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
| --- | --- | --- | --- | --- | --- |
| 61 | 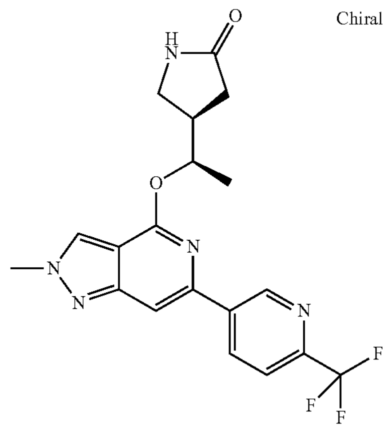 [SMILES: C[C@@H](Oc1nc(-c2ccc(C(F)(F)F)nc2)cc2nn(C)cc12)[C@H]1CNC(=O)C1] | Chiral | 0.4749 | >50 | 48.10 |
| 62 | 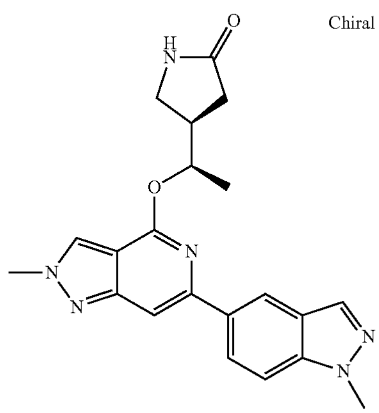 [SMILES: C[C@@H](Oc1nc(-c2ccc3c(cnn3C)c2)cc2nn(C)cc12)[C@H]1CNC(=O)C1] | Chiral | 0.0193 | >50 | 4.78 |
| 63 | 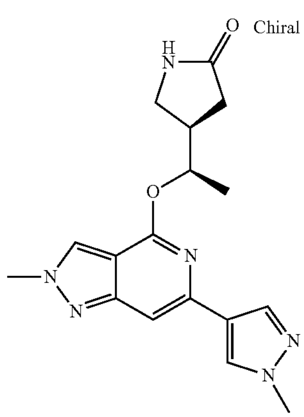 [SMILES: C[C@@H](Oc1nc(-c2cnn(C)c2)cc2nn(C)cc12)[C@H]1CNC(=O)C1] | Chiral | 0.0473 | >50 | 13.24 |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
| --- | --- | --- | --- | --- | --- |
| 64 | 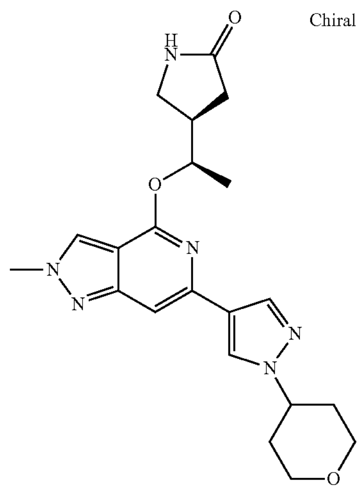 [SMILES: C[C@@H](Oc1nc(-c2cnn(C3CCOCC3)c2)cc2nn(C)cc12)[C@H]1CNC(=O)C1] | Chiral | 0.0258 | >50 | 21.62 |
| 65 | 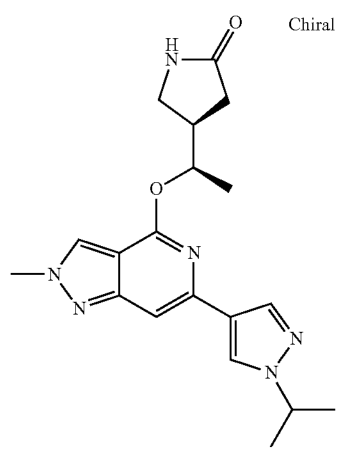 [SMILES: CC(C)n1cc(-c2cc3nn(C)cc3c(O[C@H](C)[C@H]3CNC(=O)C3)n2)cn1] | Chiral | 0.0211 | >50 | 14.85 |
| 66 | 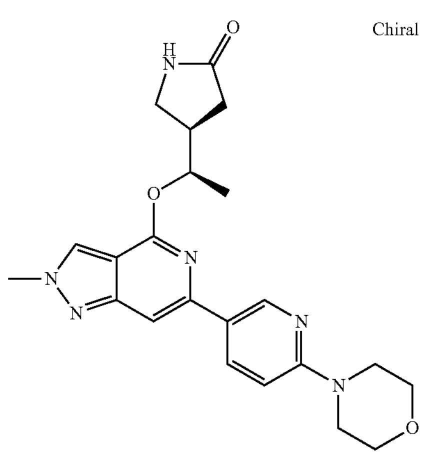 [SMILES: C[C@@H](Oc1nc(-c2ccc(N3CCOCC3)nc2)cc2nn(C)cc12)[C@H]1CNC(=O)C1] | Chiral | 0.0385 | >50 | 4.44 |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
|---|---|---|---|---|---|
| 67 | 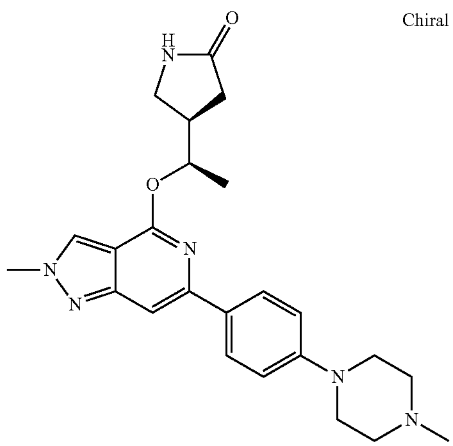 | Chiral | 0.0152 | >50 | 1.68 |
| 68 | 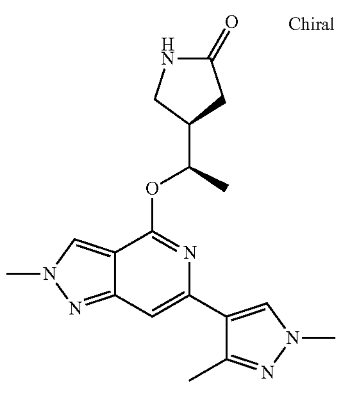 | Chiral | 0.0652 | >50 | 22.43 |
| 69 | 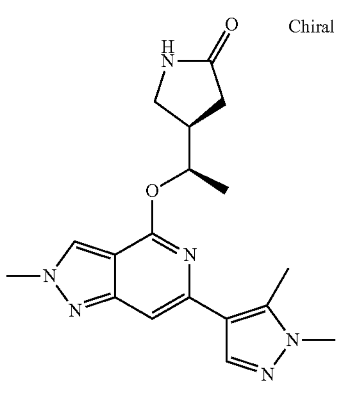 | Chiral | 0.1973 | >50 | 45.15 |

TABLE 1-continued

| Example No. | Structure | SYK-inhibition IC$_{50}$-value [μM] | AURB-inhibition IC$_{50}$-value [μM] | FLT3-inhibition IC$_{50}$-value [μM] |
| --- | --- | --- | --- | --- |
| 70 | Chiral | 0.0345 | >50 | 16.99 |
| 71 | Chiral | 0.0150 | >50 | 7.65 |
| 72 | Chiral | 0.0526 | >50 | 19.59 |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
|---|---|---|---|---|---|
| 73 | 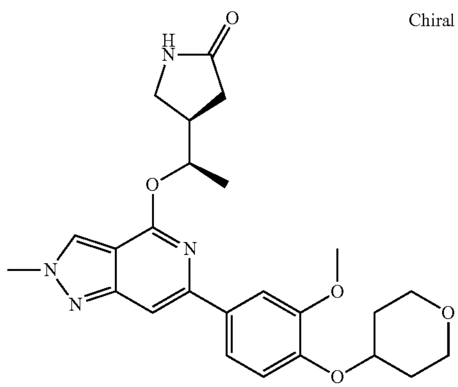 [SMILES: COc1cc(-c2cc3nn(C)cc3c(O[C@H](C)[C@H]3CNC(=O)C3)n2)ccc1OC1CCOCC1] | Chiral | 0.0224 | 49.10 | 4.17 |
| 74 | 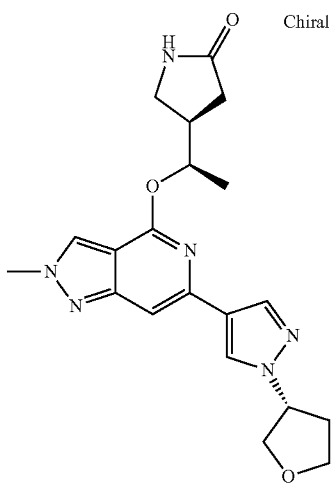 [SMILES: C[C@@H](Oc1nc(-c2cnn([C@@H]3CCOC3)c2)cc2nn(C)cc12)[C@H]1CNC(=O)C1] | Chiral | 0.0322 | >50 | 11.15 |
| 75 | 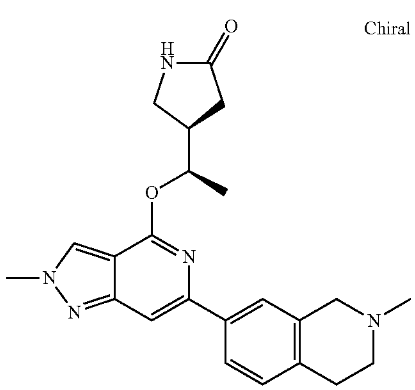 | Chiral | 0.0998 | 8.54 | 1.59 |

TABLE 1-continued

| Example No. | Structure | | SYK-inhibition IC$_{50}$-value [µM] | AURB-inhibition IC$_{50}$-value [µM] | FLT3-inhibition IC$_{50}$-value [µM] |
| --- | --- | --- | --- | --- | --- |
| 76 | 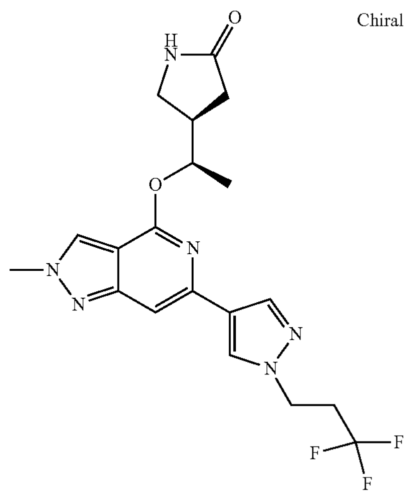 [SMILES: C[C@@H](Oc1nc(-c2cnn(CCC(F)(F)F)c2)cc2nn(C)cc12)[C@H]1CNC(=O)C1] | Chiral | 0.0583 | 46.20 | 14.80 |
| 77 | 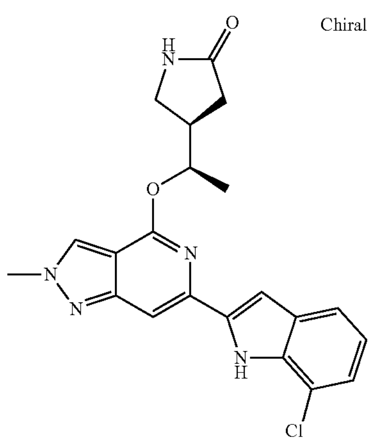 [SMILES: C[C@@H](Oc1nc(-c2cc3cccc(Cl)c3[nH]2)cc2nn(C)cc12)[C@H]1CNC(=O)C1] | Chiral | 0.0498 | 43.38 | 3.75 |
| 78 | 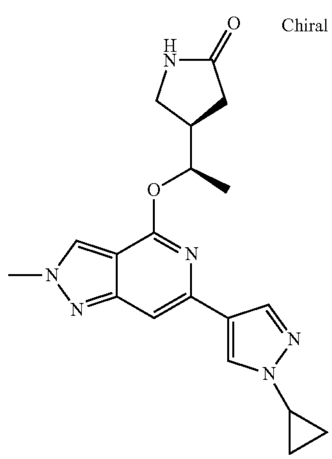 [SMILES: C[C@@H](Oc1nc(-c2cnn(C3CC3)c2)cc2nn(C)cc12)[C@H]1CNC(=O)C1] | Chiral | 0.0359 | >50 | 22.04 |

TABLE 1-continued

| Example No. | Structure | | SYK-inhibition IC$_{50}$-value [μM] | AURB-inhibition IC$_{50}$-value [μM] | FLT3-inhibition IC$_{50}$-value [μM] |
| --- | --- | --- | --- | --- | --- |
| 79 | *(structure)* | Chiral | 0.0364 | >50 | 26.74 |
| 80 | *(structure)* | Chiral | 0.0224 | 39.74 | 1.11 |
| 81 | *(structure)* | Chiral | 0.0240 | 48.40 | 5.24 |

TABLE 1-continued

| Example No. | Structure | | SYK-inhibition IC$_{50}$-value [µM] | AURB-inhibition IC$_{50}$-value [µM] | FLT3-inhibition IC$_{50}$-value [µM] |
|---|---|---|---|---|---|
| 82 | (structure) | Chiral | 0.0483 | >50 | 7.78 |
| 83 | (structure) | Chiral | 0.7324 | >50 | 25.60 |
| 84 | not defined | | not defined | not defined | not defined |

6. COMPARISON OF SYK-INHIBITORY CAPACITY AND OF SYK-SELECTIVITY OF THE COMPOUNDS OF THE INVENTION COMPARED TO SELECTED COMPOUNDS OF WO 2013/014060 AND OF WO 2011/092128

To have an efficient SYK-inhibitory capacity is not the only important aspect which a SYK-inhibitor to be used as a medicament to treat SYK-related diseases must show. Similarly important like the low IC$_{50}$-value with regard to SYK-inhibition (IC$_{50}$ (SYK)≤1 µM) is that the candidate compound does not show undesired inhibitory effects on other kinases which could lead to unwanted or even dangerous side effects. Examples of such other kinases that should not be inhibited by the candidate SYK-inhibitor are AURB, FLT3 and GSKbeta.

Consequently the IC$_{50}$-values with regard to SYK, AURB, FLT3 and GSKbeta for structurally close compounds disclosed in WO 2013/014060 and of WO 2011/092128 have been experimentally determined according to the same assays as described in chapter 5. The measured IC$_{50}$-values with regard to SYK, AURB, FLT3 and GSKbeta of these structurally closest prior art compounds are in the following tables 2a to 6c compared to the respective previously determined IC$_{50}$-values of a representative selection of compounds of the invention (same assay conditions).

Further it is desirable for an SYK-inhibitor that is sufficiently SYK-specific as described above to have certain human liver microsomal stability (corresponding to CI<60% $Q_h$; $Q_h$=liver blood flow). Otherwise it will be difficult to reach an adequate plasma level of the SYK-inhibitor in the patient to be treated. Consequently also the CI-values for structurally close compounds disclosed in WO 2013/014060 and in WO 2011/092128 have been experimentally determined according to the same human liver microsomal-test as described in chapter 5. An experimentally determined CI-value of more than 60% $Q_h$ is regarded to be inacceptable in order to reach an adequate plasma level of the respective SYK-inhibitor in the patient to be treated.

6.1 Comparisons for Compounds with Alkyl-Substituted Pyrazole Structures

Whereas all compounds of the invention (see Table 2a) and of WO 2013/014060 (see Table 2b) with alkyl-substituted pyrazole structures have suitable $IC_{50}$ (SYK)-values of smaller than 1 µM, only the compounds of the invention (see Table 2a) have $IC_{50}$-values with regard to AURB of more than 50 µM (compared to $IC_{50}$-values (AURB) of significantly below 5 µM for the compounds of WO 2013/014060 in Table 2b). Also the $IC_{50}$-values with respect to FLT3 are larger for the compounds of the invention (Table 2a) compared to the compounds of WO 2013/014060 (see Table 2b). Consequently the compounds of the invention with alkyl-substituted pyrazole structures are not only efficient SYK-inhibitors (like the compounds of WO 2013/014060 (see Table 2b)), but also do not have unwanted inhibitory effects on other kinases such as AURB, FLT3 and GSK3beta (unlike the compounds of WO 2013/014060 (see Table 2b)). The compounds of the invention with alkyl-substituted pyrazole structures therefore show a significantly improved SYK-selectivity compared to the structurally closest compounds disclosed in WO2013/014060.

TABLE 2a compounds of the invention with alkyl-substituted pyrazole structures

| Ex. No. | Structure | $IC_{50}$ in µM (SYK-Inhibition) | $IC_{50}$ in µM (AURB-Inhibition) | $IC_{50}$ in µM (FLT3-Inhibition) | $IC_{50}$ in µM (GSK3beta-Inhibition) | microsomal stability Cl [% $Q_h$] |
|---|---|---|---|---|---|---|
| 2 | 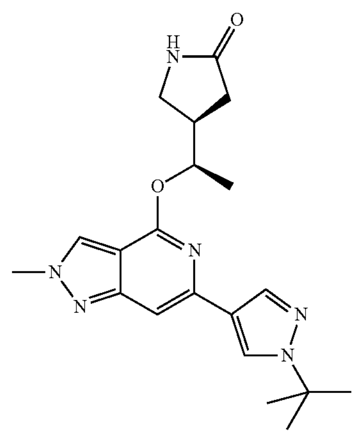 [SMILES: C[C@@H](Oc1nc(-c2cnn(C(C)(C)C)c2)cc2nn(C)cc12)[C@H]1CNC(=O)C1] | 0.0144 | >50 | 14.8 | >10 | <23 |
| 18 | Chiral | 0.0046 | >50 | 13.4 | >10 | <23 | n.d. = not detected

TABELLE 2b

Compounds of WO 2013/014060 with alkyl-substituted pyrazole structures

| Ex. No. | Structure | | IC$_{50}$ in µM (SYK- Inhibition) | IC$_{50}$ in µM (AURB- Inhibition) | IC$_{50}$ in µM (FLT3- Inhibition) | IC$_{50}$ in µM (GSK3beta- Inhibition) | microsomal stability Cl [% Q$_h$] |
|---|---|---|---|---|---|---|---|
| 112 | (structure) | Chiral | 0.006 | 2.96 | 1.25 | >10 | <23 |
| 114 | (structure) | Chiral | 0.0002 | 2.54 | 0.049 | >10 | 26 |
| 115 | (structure) | Chiral | 0.0002 | 0.021 | 0.041 | >10 | <23 |

6.2 Comparisons for Compounds with Optionally Substituted Bicyclic Heteroaryl Structures Whereas all compounds of the invention (see Table 3a) and of WO 2013/014060 (see Table 3b) with optionally substituted bicyclic heteroaryl structures have suitable IC$_{50}$ (SYK)-values of smaller than 1 µM, only the compounds of the invention (see Table 3a) have IC$_{50}$-values with regard to AURB of more than 30 µM, most of them even of more than 50 µM (compared to IC$_{50}$-values (AURB) of mostly below 1 µM for the compounds of WO 2013/014060 in Table 3b).

Consequently the compounds of the invention with optionally substituted bicyclic heteroaryl structures are not only efficient SYK-inhibitors (like the compounds of WO 2013/014060 (see Table 3b)), but also do not have unwanted inhibitory effects on other kinases such as AURB (unlike the compounds of WO 2013/014060 (see Table 3b)).

The compounds of the invention with optionally substituted bicyclic heteroaryl structures therefore show a significantly improved SYK-selectivity compared to the structurally closest compounds disclosed in WO2013/014060.

TABELLE 3a

Compounds of the invention with optionally substituted bicyclic heteroaryl structures

| Ex. No. | Structure | | $IC_{50}$ in µM (SYK-Inhibition) | $IC_{50}$ in µM (AURB-Inhibition) | $IC_{50}$ in µM (FLT3-Inhibition) | $IC_{50}$ in µM (GSK3beta-Inhibition) | microsomal stability Cl [% $Q_h$] |
|---|---|---|---|---|---|---|---|
| 62 | 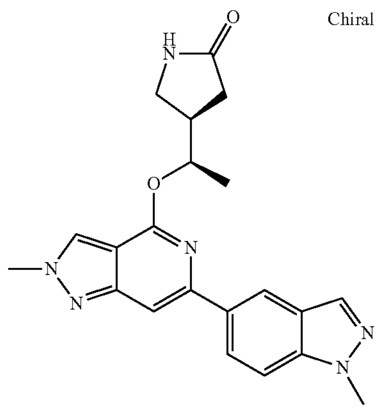 [SMILES: C[C@@H](Oc1nc(-c2ccc3c(cnn3C)c2)cc2nn(C)cc12)[C@H]1CNC(=O)C1] | Chiral | 0.0193 | >50 | 4.78 | >10 | <23 |
| 72 | 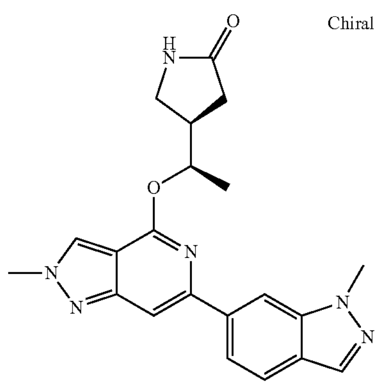 [SMILES: C[C@@H](Oc1nc(-c2ccc3cnn(C)c3c2)cc2nn(C)cc12)[C@H]1CNC(=O)C1] | Chiral | 0.0526 | >50 | 19.6 | 1.45 | <23 |
| 36 | 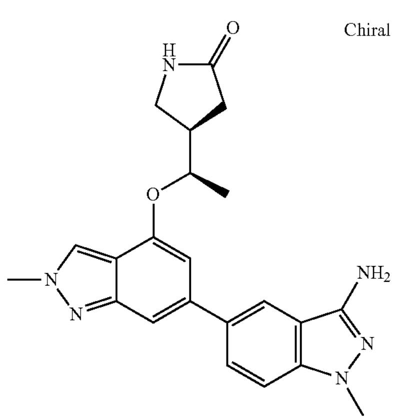 [SMILES: C[C@@H](Oc1cc(-c2ccc3c(c2)c(N)nn3C)cc2nn(C)cc12)[C@H]1CNC(=O)C1] | Chiral | 0.0172 | 35.22 | 2.39 | >10 | <23 |

TABELLE 3a-continued

Compounds of the invention with optionally substituted bicyclic heteroaryl structures

| Ex. No. | Structure | | IC$_{50}$ in µM (SYK- Inhibition) | IC$_{50}$ in µM (AURB- Inhibition) | IC$_{50}$ in µM (FLT3- Inhibition) | IC$_{50}$ in µM (GSK3beta- Inhibition) | microsomal stability Cl [% Q$_h$] |
|---|---|---|---|---|---|---|---|
| 28 | 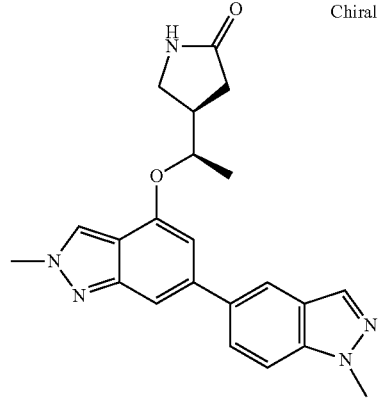 [SMILES: C[C@@H](Oc1cc(-c2ccc3c(cnn3C)c2)cc2nn(C)cc12)[C@H]1CNC(=O)C1] | Chiral | 0.0335 | >50 | 3.69 | >10 | <23 | n.d. = not detected

TABELLE 3b

Compounds of WO 2013/014060 with optionally substituted bicyclic heteroaryl structures

| Ex. No. | Structure | | IC$_{50}$ in µM (SYK- Inhibition) | IC$_{50}$ in µM (AURB- Inhibition) | IC$_{50}$ in µM (FLT3- Inhibition) | IC$_{50}$ in µM (GSK3beta- Inhibition) | microsomal stability Cl [% Q$_h$] |
|---|---|---|---|---|---|---|---|
| 29 | 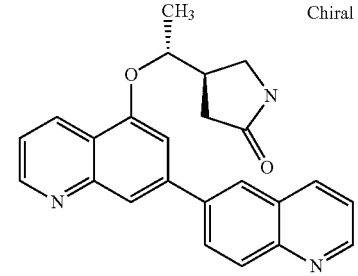 [SMILES: C[C@@H](Oc1cc(-c2ccc3ncccc3c2)cc2ncccc12)[C@H]1CNC(=O)C1] | Chiral | 0.002 | 0.293 | 0.315 | >10 | 44 |
| 41 | 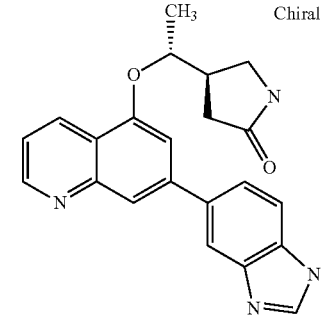 [SMILES: C[C@@H](Oc1cc(-c2ccc3[nH]cnc3c2)cc2ncccc12)[C@H]1CNC(=O)C1] | Chiral | 0.001 | 0.308 | 0.505 | >10 | 37 |

TABELLE 3b-continued

Compounds of WO 2013/014060 with optionally substituted bicyclic heteroaryl structures

| Ex. No. | Structure | | IC$_{50}$ in μM (SYK-Inhibition) | IC$_{50}$ in μM (AURB-Inhibition) | IC$_{50}$ in μM (FLT3-Inhibition) | IC$_{50}$ in μM (GSK3beta-Inhibition) | microsomal stability Cl [% Q$_h$] |
|---|---|---|---|---|---|---|---|
| 42 | *structure* | Chiral | 0.002 | 0.630 | 0.618 | >10 | <23 |
| 61 | *structure* | Chiral | 0.002 | 0.250 | 0.411 | >10 | <23 |
| 81 | *structure* | Chiral | 0.003 | 0.949 | 0.514 | >10 | <23 |
| 85 | *structure* | Chiral | 0.002 | 0.460 | 0.321 | 6.82 | 49 |
| 94 | *structure* | Chiral | 0.001 | 0.298 | 0.267 | n.d. | n.d. |

TABELLE 3b-continued

Compounds of WO 2013/014060 with optionally substituted bicyclic heteroaryl structures

| Ex. No. | Structure | | IC$_{50}$ in µM (SYK- Inhibition) | IC$_{50}$ in µM (AURB- Inhibition) | IC$_{50}$ in µM (FLT3- Inhibition) | IC$_{50}$ in µM (GSK3beta- Inhibition) | microsomal stability Cl [% Q$_h$] |
|---|---|---|---|---|---|---|---|
| 105 | (structure) | Chiral | 0.001 | 0.479 | 0.309 | >10 | 64 |
| 107 | (structure) | Chiral | 0.009 | 1.82 | 1.76 | >10 | 38 |
| 109 | (structure) | Chiral | 0.001 | 0.260 | 0.330 | >10 | 41 |

6.3 Comparisons for Compounds with Alkoxy-Substituted Phenyl Structures

All compounds of the invention (see Table 4a), of WO 2011/092128 (see Table 4b) and of WO 2013/014060 (see Table 4c) with alkoxy-substituted phenyl structures have suitable IC$_{50}$ (SYK)-values of smaller than 1 µM. However, whereas the compounds of the invention (see Table 4a) have IC$_{50}$-values with regard to AURB of more than 45 µM, often even of more than 50 µM, the IC$_{50}$-values (AURB) of WO 2011/092128 (see Table 4b) and of WO 2013/014060 (see Table 4c) are mostly ≤5 µM, often even below 1 µM and consequently the compounds of the invention with alkoxy-substituted phenyl structures have less unwanted inhibitory effects on other kinases such as AURB compared to most of the compounds of WO 2011/092128 (Table 4b) and of WO 2013/014060 (see Table 4c).

Only example 8 of WO 2011/092128 (see Table 4b) also shows an IC$_{50}$-value (with regard to AURB) of more than 50 µM which seems comparable to the compounds of the instant invention, however example 8 of WO 2011/092128 (see Table 4b) shows with CI=77% Q$_h$ a human liver microsomal stability of significantly lower than 60% Q$_h$ that would lead to an inadequately low plasma level of the SYK-inhibitor in a patient to be treated. Also example 2 of WO2013/014060 (see Table 4c) shows with IC$_{50}$ (AURB) =16.9 µM a slightly larger IC$_{50}$-value with respect to AURB than the other prior art compounds, however also here the human liver microsomal stability is with CI=81% Q$_h$ inadequate. In contrast to that the compounds of the invention with alkoxy-substituted phenyl structures (see Table 4a) show acceptable CI-values of lower than 60% Q$_h$ (all CI=<23)% Q$_h$).

The compounds of the invention with alkoxy-substituted phenyl structures therefore show a significantly improved SYK-selectivity and additionally an acceptable human liver microsomal stability compared to all of the structurally closest compounds disclosed in WO2013/014060 and in WO2011/092128.

TABELLE 4a

Compounds of the invention with alkoxy-substituted phenyl structures

| Ex. No. | Structure | | IC$_{50}$ in µM (SYK-Inhibition) | IC$_{50}$ in µM (AURB-Inhibition) | IC$_{50}$ in µM (FLT3-Inhibition) | IC$_{50}$ in µM (GSK3beta-Inhibition) | microsomal stability Cl [% Q$_h$] |
|---|---|---|---|---|---|---|---|
| 1 | 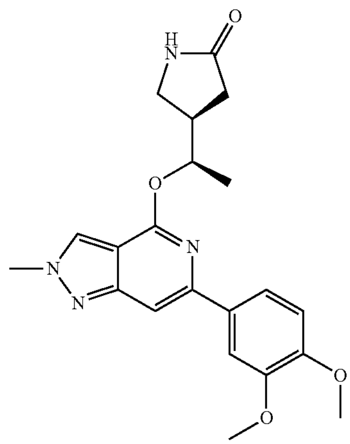 | | 0.0160 | >50 | 3.99 | >10 | <23 |
| 8 | 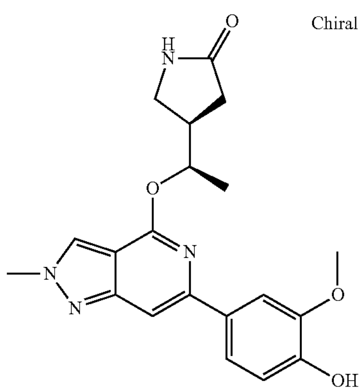 | Chiral | 0.0274 | >50 | 13.50 | >10 | <23 |
| 52 | 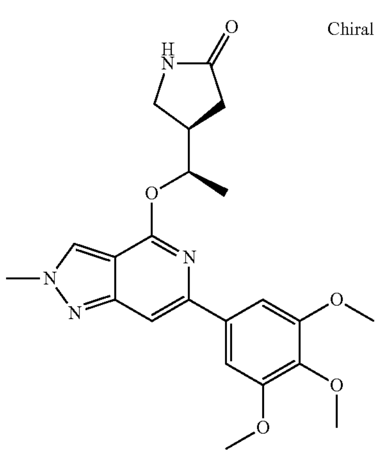 | Chiral | 0.0413 | >50 | >50 | >10 | <23 |

TABELLE 4a-continued

Compounds of the invention with alkoxy-substituted phenyl structures

| Ex. No. | Structure | | IC$_{50}$ in µM (SYK-Inhibition) | IC$_{50}$ in µM (AURB-Inhibition) | IC$_{50}$ in µM (FLT3-Inhibition) | IC$_{50}$ in µM (GSK3beta-Inhibition) | microsomal stability Cl [% Q$_h$] |
|---|---|---|---|---|---|---|---|
| 81 | *(structure)* | Chiral | 0.0240 | 48.40 | 5.24 | >10 | <23 | n.d. = not determined

TABELLE 4b

Compounds of WO 2011/092128 with alkoxy-substituted phenyl structures

| Ex. No. | Structure | | IC$_{50}$ in µM (SYK-Inhibition) | IC$_{50}$ in µM (AURB-Inhibition) | IC$_{50}$ in µM (FLT3-Inhibition) | IC$_{50}$ in µM (GSK3beta-Inhibition) | microsomal stability Cl [% Q$_h$] |
|---|---|---|---|---|---|---|---|
| 35 | *(structure)* | Chiral | 0.001 | 5.21 | 1.18 | >10 | 62 |
| 7 | *(structure)* | Chiral | 0.002 | 2.33 | 0.452 | >10 | 79 |

TABELLE 4b-continued

Compounds of WO 2011/092128 with alkoxy-substituted phenyl structures

| Ex. No. | Structure | | IC$_{50}$ in µM (SYK-Inhibition) | IC$_{50}$ in µM (AURB-Inhibition) | IC$_{50}$ in µM (FLT3-Inhibition) | IC$_{50}$ in µM (GSK3beta-Inhibition) | microsomal stability Cl [% Q$_h$] |
|---|---|---|---|---|---|---|---|
| 8 | *structure* | Chiral | 0.012 | >50 | >50 | >10 | 77 |
| 4 | *structure* | Chiral | 0.003 | 1.85 | 0.633 | >10 | 33 |
| 1 | *structure* | Chiral | 0.009 | 5.09 | 1.53 | >10 | n.d. | n.d. = not determined

TABELLE 4c

Compounds of 2013/014060 with alkoxy-substituted phenyl structures

| Ex. No. | Structure | | IC$_{50}$ in μM (SYK-Inhibition) | IC$_{50}$ in μM (AURB-Inhibition) | IC$_{50}$ in μM (FLT3-Inhibition) | IC$_{50}$ in μM (GSK3beta-Inhibition) | microsomal stability Cl [% Q$_h$] |
|---|---|---|---|---|---|---|---|
| 2 | *structure* | Chiral | 0.007 | 16.9 | 7.39 | >10 | 81 |
| 8 | *structure* | Chiral | 0.001 | 0.643 | 0.369 | >10 | 58 |
| 10 | *structure* | Chiral | 0.001 | 0.271 | 0.312 | >10 | 57 |

TABELLE 4c-continued

| Compounds of 2013/014060 with alkoxy-substituted phenyl structures | | | | | | | |
|---|---|---|---|---|---|---|---|
| Ex. No. | Structure | | IC$_{50}$ in µM (SYK-Inhibition) | IC$_{50}$ in µM (AURB-Inhibition) | IC$_{50}$ in µM (FLT3-Inhibition) | IC$_{50}$ in µM (GSK3beta-Inhibition) | microsomal stability Cl [% Q$_h$] |
| 11 | [structure] | Chiral | 0.002 | 0.752 | 0.738 | >10 | 24 |
| 102 | [structure] | Chiral | 0.013 | 2.63 | 2.27 | >10 | 54 |

6.4 Comparisons for Compounds with Heterocycle-Substituted or Heterocycle-Annulated Phenyl Structures Whereas all compounds of the invention (see Table 5a), of WO 2013/014060 (see Table 5b) with heterocycle-substituted or heterocycle-annulated phenyl structures have suitable IC$_{50}$ (SYK)-values of smaller than 1 µM, only the compounds of the invention (see Table 5a) have IC$_{50}$-values with regard to AURB of mostly more than 45 µM, mostly of more than 50 µM (compared to IC$_{50}$-values (AURB) of below 1 µM for the compounds of WO 2013/014060 in Table 5b). Consequently the compounds of the invention with heterocycle-substituted or heterocycle-annulated phenyl structures are not only efficient SYK-inhibitors (like the compounds of WO 2013/014060 (see Table 5b)), but also do not have unwanted inhibitory effects on other kinases such as AURB (unlike the compounds of WO 2013/014060 (see Table 5b)).

The compounds of the invention with heterocycle-substituted or heterocycle-annulated phenyl structures therefore show a significantly improved SYK-selectivity compared to the structurally closest compounds disclosed in WO2013/014060.

Tabelle 5a: Compounds of the invention with heterocycle-substituted or heterocycle-annulated phenyl structures

| Ex. No. | Structure | | IC$_{50}$ in µM (SYK-Inhibition) | IC$_{50}$ in µM (AURB-Inhibition) | IC$_{50}$ in µM (FLT3-Inhibition) | IC$_{50}$ in µM (GSK3beta-Inhibition) | microsomal stability Cl [% Q$_h$] |
|---|---|---|---|---|---|---|---|
| 22 | 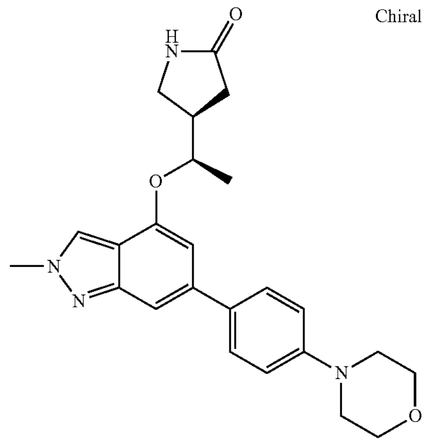 [SMILES: C[C@@H](Oc1cc(-c2ccc(N3CCOCC3)cc2)cc2nn(C)cc12)[C@H]1CNC(=O)C1] | Chiral | 0.0128 | 46.90 | 1.17 | >10 | 25 |
| 26 | 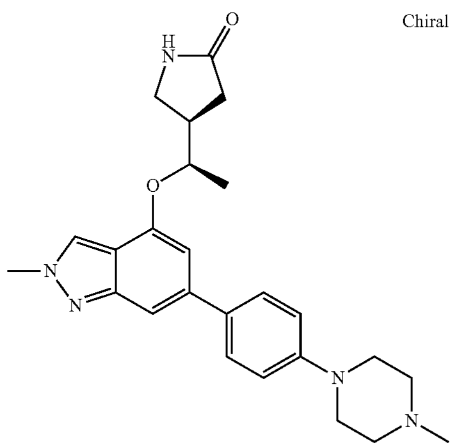 | Chiral | 0.0258 | >50 | 0.95 | >10 | <23 |
| 42 | 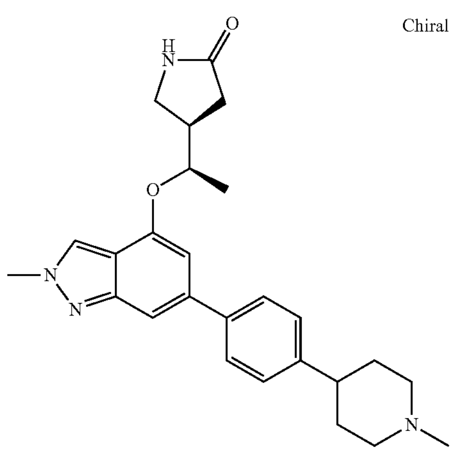 | Chiral | 0.0167 | >50 | 0.55 | >10 | <23 |

Tabelle 5a: Compounds of the invention with heterocycle-substituted or heterocycle-annulated phenyl structures

| Ex. No. | Structure | | $IC_{50}$ in μM (SYK-Inhibition) | $IC_{50}$ in μM (AURB-Inhibition) | $IC_{50}$ in μM (FLT3-Inhibition) | $IC_{50}$ in μM (GSK3beta-Inhibition) | microsomal stability Cl [% $Q_h$] |
|---|---|---|---|---|---|---|---|
| 67 | (structure) | Chiral | 0.0152 | >50 | 1.68 | >10 | 34 |

Tabelle 5b: Compounds of WO 2013/014060 with heterocycle-substituted or heterocycle-annulated phenyl structures

| Ex. No. | Structure | | $IC_{50}$ in μM (SYK-Inhibition) | $IC_{50}$ in μM (AURB-Inhibition) | $IC_{50}$ in μM (FLT3-Inhibition) | $IC_{50}$ in μM (GSK3beta-Inhibition) | microsomal stability Cl [% $Q_h$] |
|---|---|---|---|---|---|---|---|
| 43 | (structure) | Chiral | 0.001 | 0.144 | 0.157 | n.d. | <23 |
| 76 | (structure) | Chiral | 0.002 | 0.075 | 0.169 | >10 | <23 |

Tabelle 5b: Compounds of WO 2013/014060 with heterocycle-substituted or heterocycle-annulated phenyl structures

| Ex. No. | Structure | | IC$_{50}$ in µM (SYK-Inhibition) | IC$_{50}$ in µM (AURB-Inhibition) | IC$_{50}$ in µM (FLT3-Inhibition) | IC$_{50}$ in µM (GSK3beta-Inhibition) | microsomal stability Cl [% Q$_h$] |
|---|---|---|---|---|---|---|---|
| 101 | 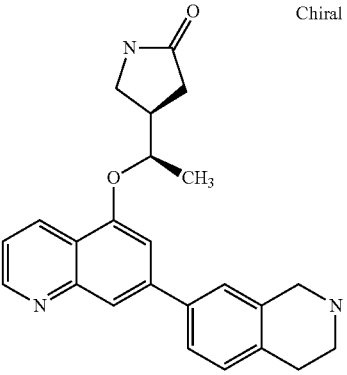 [SMILES: C[C@@H](Oc1cc(-c2ccc3c(c2)CNCC3)cc2ncccc12)[C@H]1CNC(=O)C1] | Chiral | 0.002 | 1.05 | 0.140 | >10 | <23 |

6.5 Comparisons for Compounds with Optionally Substituted Pyridine Structures

Whereas all compounds of the invention (see Table 6a), of WO 2011/092128 (see Table 6b) and of WO 2013/014060 (see Table 6c) with optionally substituted pyridine structures have suitable IC$_{50}$ (SYK)-values of smaller than 1 µM, only the compounds of the invention (see Table 6a) have IC$_{50}$-values with regard to AURB of more than 49 µM, mostly even of more than 50 µM (compared to IC$_{50}$-values (AURB) of around 1 µM for the compounds of WO 2011/092128 in Table 6b and of WO 2013/014060 in Table 6c). Consequently the compounds of the invention with optionally substituted pyridine structures are not only efficient SYK-inhibitors (like the compounds of WO 2011/092128 (Table 6b) and of WO 2013/014060 (see Table 6c)), but also do not have unwanted inhibitory effects on other kinases such as AURB (unlike the compounds of WO 2011/092128 (Table 6b) and of WO 2013/014060 (see Table 6c)).

The compounds of the invention with optionally substituted pyridine structures therefore show a significantly improved SYK-selectivity compared to the structurally closest compounds disclosed in WO 2011/092128 or in WO2013/014060.

TABLE 6a

Compounds of the invention with optionally substituted pyridine structures

| Ex. No. | Structure | | IC$_{50}$ in µM (SYK-Inhibition) | IC$_{50}$ in µM (AURB-Inhibition) | IC$_{50}$ in µM (FLT3-Inhibition) | IC$_{50}$ in µM (GSK3beta-Inhibition) | microsomal stability Cl [% Q$_h$] |
|---|---|---|---|---|---|---|---|
| 59 | 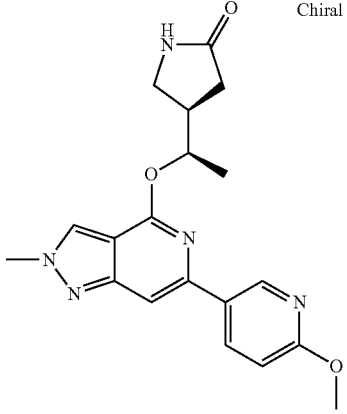 | Chiral | 0.1437 | >50 | 46.20 | >10 | <23 |

TABLE 6a-continued
Compounds of the invention with optionally substituted pyridine structures
| Ex. No. | Structure | | IC$_{50}$ in μM (SYK- Inhibition) | IC$_{50}$ in μM (AURB- Inhibition) | IC$_{50}$ in μM (FLT3- Inhibition) | IC$_{50}$ in μM (GSK3beta- Inhibition) | microsomal stability Cl [% Q$_h$] |
|---|---|---|---|---|---|---|---|
| 61 | 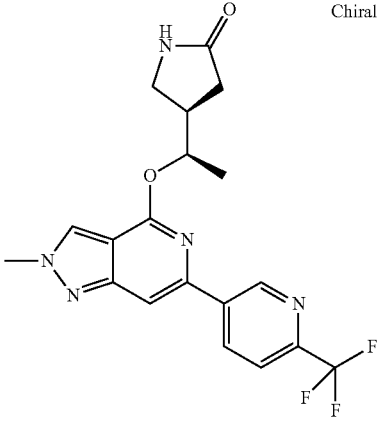 [SMILES: C[C@@H](Oc1nc(-c2ccc(C(F)(F)F)nc2)cc2nn(C)cc12)[C@H]1CNC(=O)C1] | Chiral | 0.4749 | >50 | 48.10 | >10 | <23 |
| 51 | 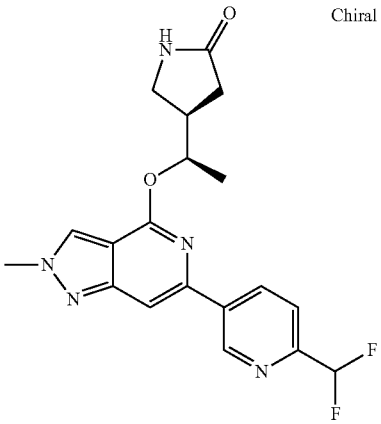 [SMILES: C[C@@H](Oc1nc(-c2ccc(C(F)F)nc2)cc2nn(C)cc12)[C@H]1CNC(=O)C1] | Chiral | 0.3660 | 49.83 | 20.87 | >10 | <23 |
| 41 | 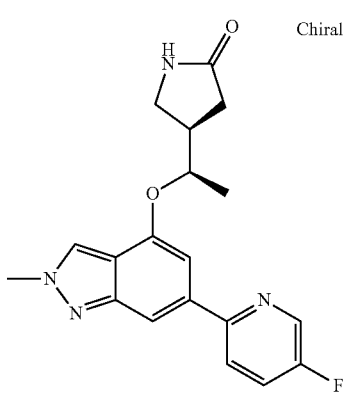 [SMILES: C[C@@H](Oc1cc(-c2ccc(F)cn2)cc2nn(C)cc12)[C@H]1CNC(=O)C1] | Chiral | 0.1638 | >50 | 42.82 | >10 | <23 |

TABLE 6a-continued

Compounds of the invention with optionally substituted pyridine structures

| Ex. No. | Structure | | IC$_{50}$ in µM (SYK-Inhibition) | IC$_{50}$ in µM (AURB-Inhibition) | IC$_{50}$ in µM (FLT3-Inhibition) | IC$_{50}$ in µM (GSK3beta-Inhibition) | microsomal stability Cl [% Q$_h$] |
|---|---|---|---|---|---|---|---|
| 27 | (structure) | Chiral | 0.1382 | >50 | 26.64 | >10 | <23 | n.d. = not determined

TABLE 6b

Compound of WO 2011/092128 with optionally substituted pyridine structure

| Ex. No. | Structure | | IC$_{50}$ in µM (SYK-Inhibition) | IC$_{50}$ in µM (AURB-Inhibition) | IC$_{50}$ in µM (FLT3-Inhibition) | IC$_{50}$ in µM (GSK3beta-Inhibition) | microsomal stability Cl [% Q$_h$] |
|---|---|---|---|---|---|---|---|
| 3 | (structure) | Chiral | 0.0122 | 1.04 | 1.82 | >10 | 24 |
| 45 | (structure) | Chiral | 0.0002 | 0.086 | 0.100 | >10 | 53 |

TABLE 6c

Compound of WO 2013/014060 with optionally substituted pyridine structure

| Ex. No. | Structure | IC$_{50}$ in µM (SYK-Inhibition) | IC$_{50}$ in µM (AURB-Inhibition) | IC$_{50}$ in µM (FLT3-Inhibition) | IC$_{50}$ in µM (GSK3beta-Inhibition) | microsomal stability Cl [% $Q_h$] |
|---|---|---|---|---|---|---|
| 6 | 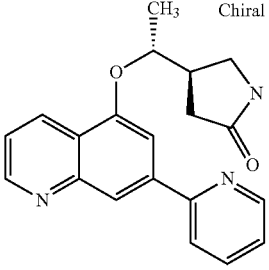 [SMILES: C[C@@H](Oc1cc(-c2ccccn2)cc2ncccc12)[C@H]1CNC(=O)C1] Chiral | 0.004 | 1.03 | 0.640 | >1 | 24 |

6. INDICATIONS

As has been found, the compounds of formula 1 are characterised by their range of applications in the therapeutic field. Particular mention should be made of those applications for which the compounds of formula 1 according to the invention are preferably used on the basis of their pharmaceutical activity as Syk-inhibitors. Examples include respiratory complaints, allergic diseases, osteoporosis, gastrointestinal diseases or complaints, immune or autoimmune diseases, allergic diseases, inflammatory diseases, e.g. inflammatory diseases of the joints, skin and eyes and diseases of the peripheral or central nervous system.

Particular mention should be made of the prevention and treatment of respiratory tract and pulmonary diseases which are accompanied by increased mucus production, inflammation and/or obstructive diseases of the airways. Examples of these include asthma, paediatric asthma, ARDS (Adult Respiratory Distress Syndrome), acute, allergic or chronic bronchitis, autoimmune haemolytic anemia, chronic obstructive bronchitis (COPD) (including the treatment of Rhinovirus-induced exacerbations), coughs, allergic rhinitis or sinusitis, allergic rhinoconjunctivitis, chronic rhinitis or sinusitis, alveolitis, farmers lung, hyperreactive airways, infectious bronchitis or pneumonitis, bronchiectasis, pulmonary arterial hypertension, pulmonary fibrosis, bronchial oedema, pulmonary oedema, pneumonia or interstitial pneumonia triggered by various causes such as aspiration, inhalation of toxic gases or bronchitis, pneumonia or interstitial pneumonia triggered by cardiac insufficiency, radiation, chemotherapy, cystic fibrosis or mucoviscidosis, alpha 1-antitrypsin deficiency.

The compounds according to the invention are preferably also suitable for the treatment of allergic diseases such as for example allergic rhinitis, allergic rhinoconjunctivitis, allergic conjunctivitis, and contact dermatitis, urticaria/angiooedema and allergic dermatitis.

Mention should also preferably be made of the treatment of inflammatory diseases of the gastrointestinal tract. Examples of these are Crohn's disease and ulcerative colitis.

The compounds according to the invention are preferably also suitable for the treatment of inflammatory diseases of the joints, of the blood vessels and of the kidney or inflammatory diseases of the skin and eyes. Examples of these are rheumatoid arthritis, antibody-based glomerulonephritis, psoriasis, Kawasaki syndrome, coeliac disease (sprue), arteriosclerosis and Wegener's granulomatosis, osteoarthritis, systemic scleroderma, ankylosing spondylitis.

The compounds according to the invention are preferably also suitable for the treatment of autoimmune diseases. Examples of these are hepatitis (autoimmune-based), lupus erythematodes, lupus nephritis, systemic lupus, Systemic lupus erythematosus, discoid lupus, cutaneous lupus erythematosus (acute, subacute, chronic), anti-phospholipid syndrome, Berger's disease, Evans's syndrome, immunohaemolytic anaemia, ITP (idiopathic thrombocytopenic purpura; adult, neonatal and paediatric), myasthenia gravis, Sjögren's syndrome, sclerodermy, Bullous pemphigoid and Pemphigus vulgaris.

The compounds according to the invention are preferably also suitable for the treatment of B-cell lymphomas, like chronic lymphocytic leukaemia and non-Hodgkin's lymphomas or T cell lymphomas.

The compounds according to the invention are preferably also suitable for the treatment of Graft-versus-host disease.

Mention may preferably also be made of the prevention and treatment of diseases of the peripheral or central nervous system. Examples of these are acute and chronic multiple sclerosis or non-familial lateral sclerosis.

Mention may preferably also be made of the prevention and treatment of osteoporotic diseases such as for example disease-associated osteopenia, osteoporosis and osteolytic diseases.

The present invention relates particularly preferably to the use of compounds of formula 1 for preparing a pharmaceutical composition for the treatment of diseases selected from among asthma, COPD, allergic rhinitis, Adult Respiratory Distress Syndrome, bronchitis, allergic dermatitis, contact dermatitis, ITP, rheumatoid arthritis, systemic lupus erythematosus, lupus nephritis, and allergic rhinoconjunctivitis.

Most preferably, the compounds of formula 1 may be used for the treatment of a disease selected from among asthma, allergic rhinitis, rheumatoid arthritis, systemic lupus erythematosus, lupus nephritis, allergic dermatitis and COPD.

7. COMBINATIONS

The compounds of formula 1 may be used on their own or in conjunction with other active substances of formula 1 according to the invention. The compounds of formula 1 may optionally also be used in conjunction with other pharmacologically active substances. Preferably the active substances used here may be selected for example from among the betamimetics, anticholinergics, corticosteroids, PDE4-inhibitors, LTD4-antagonists, EGFR-inhibitors, MRP4-inhibitors, dopamine agonists, H1-antihistamines, PAF-antagonists, iNos-inhibitos, HMG-CoA reductase inhibitors (statins), PI3-kinase-inhibitors, CCR3-antagonists, CCR2-antagonists, CCR1-antagonists, IKK2-inhibitors, A2a agonists, alpha-4-integrin-inhibitors, CRTH2-antagonists, histamine 1, combined H1/H3-antagonists, p38 kinase inhibitors, methylxanthines, ENaC-inhibitors, CXCR1-antagonists, CXCR2-antagonists, ICE-inhibitors, LTB4-antagonists, 5-LO antagonists, FLAP-antagonists. LTB4-antagonists; cromoglycine, dissociated glucocorticoid mimetics, immunesuppressive agents, cytostatica, non-steroidal anti-inflammatory drugs (NSAIDs), chloroquine, hydroxychloroquine, anti-TNF-antibodies, anti-GM-CSF antibodies, anti-CD46-antibodies, anti-IL-1-antibodies, anti-IL-2-antibodies, anti-IL-4-antibodies, anti-IL-5-antibodies, anti-1L6 antibodies, anti-IL6 receptor antibodies, anti-IL-13-antibodies, anti-IL_18 antibodies, anti-CD30 L antibodies, anti-Ox40L-antibodies, anti-IL-4/IL-13-antibodies, anti-IL-23 (p19) antibodies, anti-IL-12/IL-23 (p40) antibodies, anti-CD3 antibodies, anti-CD4 antibodies, anti-CD154 antibodies, CD89 antibodies, anti-IL-2 receptor/CD25 antibodies, anti-CD22 antibodies, anti-interferon antibodies, anti-ICOS antibodies, anti-ICOS antibodies, anti-CD20 antibodies, anti-CD40 antibodies, anti-BAFF/BLyS antibodies, anti-CD18 antibodies, anti-CD62L antibodies, anti-CD147 antibodies, anti-integrin antibodies, agents interfering with LFA-1, IL-36 pathway modulators, M-CSF/c-fms antagonists, CTLA-4 fusions, mTor modulators, Toll like receptors 7 inhibitors (TLR7 inhibitor), Toll like receptor 9 inhibitors (TLR9 inhibitors), T cell-costimulatory modulators such as CTLA-4 fusions, JAK inhibitors, IRF modulators, CX3 chemokine receptor antagonists (CX3CR1 antagonists), IRAK inhibitors (in particular IRAK1- and IRAK4-inhibitors), Sphingosine-1-phosphate modulators (S1P pathway modulators), or double or triple combinations thereof, such as for example combinations of one, two or three compounds selected from among the Syk-inhibitors of formula 1, betamimetics, corticosteroids, EGFR-inhibitors and PDE4-antagonists, Syk-inhibitors of formula 1, anticholinergics, betamimetics, corticosteroids, EGFR-inhibitors and PDE4-antagonists, Syk-inhibitors of formula 1, PDE4-inhibitors, corticosteroids and EGFR-inhibitors, Syk-inhibitors of formula 1, EGFR-inhibitors and PDE4-inhibitors, Syk-inhibitors of formula 1 and EGFR-inhibitors, Syk-inhibitors of formula 1, betamimetics and anticholinergics Syk-inhibitors of formula 1, anticholinergics, betamimetics, corticosteroids and PDE4-inhibitors, Syk-inhibitors of formula 1, anticholinergics, betamimetics, corticosteroids, iNOS inhibitors, HMG-CoA reductase inhibitors.

Combinations of three active substances each taken from one of the above-mentioned categories of compounds are also an object of the invention.

Suitable betamimetics used are preferably compounds selected from among arformoterol, carmoterol, formoterol, indacaterol, salmeterol, albuterole, bambuterol, bitolterol, broxaterol, carbuterol, clenbuterol, fenoterol, hexoprenalin, ibuterol, isoetharin, isoprenalin, levosalbutamol, mabuterol, meluadrin, metaproterenol, milveterol, orciprenalin, pirbuterol, procaterol, reproterol, rimiterol, ritodrin, salmefamol, soterenol, sulphonterol, terbutalin, tiaramide, tolubuterol, zinterol,6-Hydroxy-8-{1-hydroxy-2-[2-(4-methoxy-phenyl)-1,1-dimethyl-ethylamino]-ethyl}-4H-benzo[1,4]oxazine-3-one; 8-{2-[2-(2,4-Difluor-phenyl)-1,1-dimethyl-ethylamino]-1-hydroxy-ethyl}-6-hydroxy-4H-benzo[1,4]oxazine-3-one; 8-{2-[2-(3,5-Difluor-phenyl)-1,1-dimethyl-ethylamino]-1-hydroxy-ethyl}-6-hydroxy-4H-benzo[1,4]oxazine-3-one; 8-{2-[2-(4-Ethoxy-phenyl)-1,1-dimethyl-ethylamino]-1-hydroxy-ethyl}-6-hydroxy-4H-benzo [1,4]oxazine-3-one; 8-{2-[2-(4-Fluor-phenyl)-1,1-dimethyl-ethylamino]-1-hydroxy-ethyl}-6-hydroxy-4H-benzo[1,4]oxazine-3-one; N-(5-{2-[3-(4,4-Diethyl-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-fluoro-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-methoxy-2-oxo-4H-benzo[d][1,3]oxazine-1-yl)-, 1-dimethyl-propylamino]-1-hydroxy-ethyl}-2-hydroxy-phenyl)-methansulfonamide; N-(5-{2-[1,1-Dimethyl-3-(2-oxo-4,4-dipropyl-4H-benzo[d][1,3]oxazine-1-yl)-propylamino]-1-hydroxy-ethyl}-2-hydroxy-phenyl)-methansulfonamide; 8-{2-[1,1-Dimethyl-3-(2-oxo-2,3-dihydro-benzoimidazol-1-yl)-propylamino]-1-hydroxy-ethyl}-6-hydroxy-4H-benzo[1,4]oxazine-3-one; 8-{2-[1,1-Dimethyl-3-(6-methyl-2-oxo-2,3-dihydro-benzoimidazole-1-yl)-propylamino]-1-hydroxy-ethyl}-6-hydroxy-4H-benzo [1,4]oxazine-3-one; 8-{2-[1,1-Dimethyl-3-(2-oxo-5-trifluormethyl-2,3-dihydro-benzoimidazol-1-yl)-propylamino]-1-hydroxy-ethyl}-6-hydroxy-4H-benzo[1,4] oxazine-3-one; 8-{2-[1,1-Dimethyl-3-(3-methyl-2-oxo-2,3-dihydro-benzoimidazol-1-yl)-propylamino]-1-hydroxy-ethyl}-6-hydroxy-4H-benzo[1,4]oxazine-3-one; N-[2-Hydroxy-5-((1R)-1-hydroxy-2-{2-[4-(2-hydroxy-2-phenyl-ethylamino)-phenyl]-ethylamino}-ethyl)-phenyl]-formamide; 8-Hydroxy-5-((1R)-1-hydroxy-2-{2-[4-(6-methoxy-biphenyl-3-ylamino)-phenyl]-ethylamino}-ethyl)-1H-quinoline-2-one; 8-Hydroxy-5-[(1R)-1-hydroxy-2-(6-phenethylamino-hexylamino)-ethyl]-1H-quinoline-2-one; 5-[(1R)-2-(2-{4-[4-(2-Amino-2-methyl-propoxy)-phenylamino]-phenyl}-ethylamino)-1-hydroxy-ethyl]-8-hydroxy-1H-quinoline-2-one; [3-(4-{6-[(2R)-2-Hydroxy-2-(4-hydroxy-3-hydroxymethyl-phenyl)ethylamino]-hexyloxy}-butyl)-5-methyl-phenyl]-urea; 4-((1R)-2-{6-[2-(2,6-Dichlor-benzyloxy)-ethoxy]-hexylamino}-1-hydroxy-ethyl)-2-hydroxymethyl-phenol; 3-(4-{6-[(2R)-2-Hydroxy-2-(4-hydroxy-3-hydroxymethyl-phenyl)-ethylamino]-hexyloxy}-butyl)-benzenesulfonamide; 3-(3-{7-[(2R)-2-Hydroxy-2-(4-hydroxy-3-hydroxymethyl-phenyl)-ethylamino]-heptyloxy}-propyl)-benzenesulfonamide; 4-((1R)-2-{6-[4-(3-Cyclopentanesulfonyl-phenyl)-butoxy]-hexylamino}-1-hydroxy-ethyl)-2-hydroxymethyl-phenol, 4-(2-{6-[2-(2,6-dichloro-benzyloxy)-ethoxy]-hexylamino}-1-hydroxy-ethyl)-2-hydroxymethyl-phenol; Vilanterol; N-1-Adamantanyl-2-{3-[(2R)-2-({(2R)-2-hydroxy-2-[4-hydroxy-3-(hydroxymethyl)phenyl]ethyl}amino)propyl]phenyl}acetamide; 2-(3-{2-[2-hydroxy-3-methanesulfonylamino-phenyl)-ethylamino]-propyl}-phenyl)-N-[4-(4-hydroxy-phenyl)-2-vinyl-penta-2,4-dienyl]-acetamide; (1R)-5-{2-[6-(2,2-Difluor-2-phenyl-ethoxy)-hexylamino]-1-hydroxy-ethyl}-8-hydroxy-1H-quinoline-2-one; (R,S)-4-(2-{[6-(2,2-Difluor-4-phenylbutoxy) hexyl]amino}-1-hydroxy-ethyl)-2-(hydroxymethyl) phenol; (R,S)-4-(2-{[6-(2,2-Difluor-2-phenylethoxy)hexyl]amino}-1-hydroxy-ethyl)-2-(hydroxymethyl)phenol; (R,S)-4-(2-{[4,4-Difluor-6-(4-phenylbutoxy)hexyl]amino}-1-hydroxy-ethyl)-2-

(hydroxymethyl)phenol; (R,S)-4-(2-{[6-(4,4-Difluor-4-phenylbutoxy)hexyl]amino}-1-hydroxy-ethyl)-2-(hydroxymethyl)phenol; (R,S)-5-(2-{[6-(2,2-Difluor-2-phenylethoxy)hexyl]amino}-1-hydroxy-ethyl)-8-hydroxyquinoline-2(1H)-one; (R,S)-[2-({6-[2,2-Difluor-2-(3-methylphenyl) ethoxy]hexyl}amino)-1-hydroxyethyl]-2-(hydroxymethyl)phenol; 4-(1R)-2-{[6-(2,2-Difluor-2-phenylethoxy)hexyl]amino}-1-hydroxyethyl)-2-(hydroxymethyl)phenol; (R,S)-2-(Hydroxymethyl)-4-(1-hydroxy-2-{[4,4,5l5-tetrafluor-6-(3-phenylpropoxy)-hexyl]amino}ethyl)phenol; (R,S)-[5-(2-{[6-(2,2-Difluor-2-phenylethoxy)hexyl]amino}-1-hydroxy-ethyl)-2-hydroxyphenyl]formamide; (R,S)-4-[2-({6-[2-(3-Bromophenyl)-2,2-difluoroethoxy]hexyl}amino)-1-hydroxyethyl]-2-(hydroxymethyl)phenol; (R,S)—N-[3-(1,1-Difluor-2-{[6-({2-hydroxy-2-[4-hydroxy-3-(hydroxymethyl) phenyl]-ethyl}amino)hexyl]oxy}ethyl)phenyl]-urea; 3-[3-(1,1-Difluor-2-{[6-({2-hydroxy-2-[4-hydroxy-3-(hydroxymethyl) phenyl]ethyl}amino)hexyl]oxy}ethyl)phenyl]imidazolidine-2,4-dione; (R,S)-4-[2-({6-[2,2-Difluor-2-(3-methoxyphenyl)ethoxy]hexyl}amino)-1-hydroxyethyl]-2-(hydroxymethyl)phenol; 5-((1R)-2-{[6-(2,2-Difluor-2-phenylethoxy)hexyl]amino}-1-hydroxyethyl)-8-hydroxyquinoline-2(1H)-one; 4-((1R)-2-{[4,4-Difluor-6-(4-phenylbutoxy)hexyl]amino}-1-hydroxy-ethyl)-2-(hydroxymethyl) phenol; (R,S)-4-(2-{[6-(3,3-Difluor-3-phenylpropoxy)hexyl]amino}-1-hydroxy-ethyl)-2-(hydroxymethyl)phenol; (R,S)-(2-{[6-(2,2-Difluor-2-phenylethoxy)-4,4-difluorohexyl]amino}-1-hydroxyethyl)-2-(hydroxymethyl)phenol; (R,S)-4-(2-{[6-(2,2-Difluor-3-phenylpropoxy)hexyl]amino}-1-hydroxy ethyl)-2-(hydroxymethyl)phenol; 3-[2-(3-Chlor-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide; N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide; 7-[2-(2-{3-[2-(2-Chlor-phenyl)-ethylamino]-propylsulfanyl}-ethylamino)-1-hydroxy-ethyl]-4-hydroxy-3H-benzothiazol-2-one, optionally in the form of the racemates, enantiomers, diastereomers and optionally in the form of the pharmacologically acceptable acid addition salts, solvates or hydrates thereof.

According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among
tiotropium salts, particularly the bromide salt, oxitropium salts, particularly the bromide salt, flutropium salts, particularly the bromide salt, ipratropium salts, particularly the bromide salt, Aclidinium salts, particularly the bromide salt, glycopyrronium salts, particularly the bromide salt, trospium salts, particularly the chloride salt, tolterodin, (3R)-1-Phenethyl-3-(9H-xanthene-9-carbonyloxy)-1-azoniabicyclo [2.2.2]octan-salts; 2,2-Diphenyl propionic acid tropenole ester-methobromide; 2,2-Diphenyl propionic acid scopine ester-methobromide; 2-Fluor-2,2-Diphenyl acetic acid scopine ester-methobromide; 2-Fluor-2,2-Diphenyl acetic acid tropenole ester-methobromide; 3,3',4,4'-Tetrafluor benzilic acid tropenole ester-methobromide; 3,3',4,4'-Tetrafluor benzilic acid scopine ester-methobromide; 4,4'-Difluor benzilic acid tropenole ester-methobromide; 4,4'-Difluor benzilic acid scopine ester-methobromide; 3,3'-Difluor benzilic acid tropenole ester-methobromide; 3,3'-Difluor benzilic acid scopine ester-methobromide; 9-Hydroxy-fluorene-9-carboxylic acid tropenole ester-methobromide; 9-Fluor-fluorene-9-carboxylic acid tropenole ester-methobromide; 9-Hydroxy-fluorene-9-carboxylic acid scopine ester-methobromide; 9-Fluor-fluorene-9-carboxylic acid scopine ester-methobromide; 9-Methyl-fluorene-9-carboxylic acid tropenole ester-methobromide; 9-Methyl-fluorene-9-carboxylic acid scopine ester-methobromide; Benzilic acid cyclopropyltropine ester-methobromide; 2,2-Diphenyl propionic acid cyclopropyltropine ester-methobromide; 9-Hydroxy-xanthene-9-carboxylic acid cyclopropyltropine ester-methobromide; 9-Methyl-fluorene-9-carboxylic acid cyclopropyltropine ester-methobromide; 9-Methyl-xanthene-9-carboxylic acid cyclopropyltropine ester-methobromide; 9-Hydroxy-fluorene-9-carboxilic acid cyclopropyltropine ester-methobromide; 4,4'-Difluor benzilic acid methyl ester cyclopropyltropine ester-methobromide; 9-Hydroxy-xanthene-9-carboxylic acid tropenole ester-methobromide; 9-Hydroxy-xanthene-9-carboxylic acid scopine ester-methobromide; 9-Methyl-xanthene-9-carboxylic acid tropenole ester-methobromide; 9-Methyl-xanthene-9-carboxylic acid scopine ester-methobromide; 9-Ethyl-xanthene-9-carboxylic acid tropenole ester-methobromide; 9-Difluormethyl-xanthene-9-carboxylic acid tropenole ester-methobromide; 9-Hydroxymethyl-xanthene-9-carboxylic acid scopine ester-methobromide;
3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide;
N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide;
7-[2-(2-{3-[2-(2-Chloro-phenyl)-ethylamino]-propylsulfanyl}-ethylamino)-1-hydroxy-ethyl]-4-hydroxy-3H-benzothiazol-2-one and Darotropium;
optionally in the form of the solvates or hydrates thereof.

In the above-mentioned salts the cations tiotropium, oxitropium, flutropium, ipratropium, glycopyrronium, aclidinium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among
beclomethasone, betamethasone, budesonide, butixocort, ciclesonide, deflazacort, dexamethasone, etiprednole, flunisolide, fluticasone, loteprednole, mometasone, prednisolone, prednisone, rofleponide, triamcinolone, tipredane; Pregna-1,4-diene-3,20-dione, 6-fluoro-11-hydroxy-16,17-[(1-methylethylidene) bis(oxy)]-21-[[4-[(nitrooxy)methyl]benzoyl]oxy]-, (6-alpha, 11-beta, 16-alpha)-(9CI); 16,17-butylidenedioxy-6,9-difluoro-1-hydroxy-17-(methylthio)androst-4-en-3-one; 6,9-Difluor-17-[(2-furanylcarbonyl)oxy]-1-hydroxy-16-methyl-3-oxo-androsta-1,4-dien-17-carbothione acid (S)-fluoromethylester; (S)-fluoromethyl 6,9-difluoro-17-[(2-furanylcarbonyl)oxy]-11-hydroxy-16-methyl-3-oxo-androsta-1,4-diene-17-carbothionate; 6-alpha,9-alpha-difluoro-11-beta-hydroxy-16alpha-methyl-3-oxo-17alpha-(2,2,3,3-tetramethylcyclopropylcarbonyl)oxy-androsta-1,4-diene-17beta-carboxylic acid cyanomethyl ester, each optionally in the form of the racemates, enantiomers or diastereomers thereof and optionally in the form of the salts and derivatives, solvates and/or hydrates thereof.

Particularly preferably the steroid is selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulfobenzoates, phosphates, isonicotinates, acetates, propionates, dihydrogen phosphates, palmitates, pivalates or furoates thereof.

PDE4 inhibitors which may be used are preferably compounds selected from among enprofyllin, theophyllin, roflumilast, ariflo (cilomilast), tofimilast, pumafentrin, lirimilast, apremilast, arofyllin, atizoram, oglemilast, tetomilast; 5-[(N-(2,5-dichloro-3-pyridinyl)-carboxamide]-8-methoxy-Quinoline (D-4418); 5-[N-(3,5-dichloro-1-oxido-4-pyridinyl)-carboxamide]-8-methoxy-2-(trifluoromethyl)-Quinoline (D-4396 (Sch-351591)); N-(3,5-dichloropyrid-4-yl)-[1-(4-fluorobenzyl)-5-hydroxy-indol-3-yl]glyoxylic acid amide (AWD-12-281 (GW-842470)); 9-[(2-fluorophenyl)methyl]-N-methyl-2-(trifluoromethyl)-9H-Purin-6-amine (NCS-613); 4-[(2R)-2-[3-(cyclopentyloxy)-4-methoxyphenyl]-2-phenylethyl]-Pyridine (CDP-840); N-[(3R)-3,4,6,7-tetrahydro-9-methyl-4-oxo-1-phenylpyrrolo[3,2,1-jk][1,4]benzodiazepin-3-yl]-4-Pyridinecarboxamide (PD-168787); 4-[6,7-diethoxy-2,3-bis(hydroxymethyl)-1-naphthalenyl]-1-(2-methoxyethyl)-2(1H)-Pyridinone (T-440); 2-[4-[6,7-diethoxy-2,3-bis(hydroxymethyl)-1-naphthalenyl]-2-pyridinyl]-4-(3-pyridinyl)-(2H)-Phthalazinone (T-2585); (3-(3-cyclopenyloxy-4-methoxybenzyl)-6-ethylamino-8-isopropyl-3H-purine (V-11294A); beta-[3-(cyclopentyloxy)-4-methoxyphenyl]-1,3-dihydro-1,3-dioxo-2H-Isoindole-2-propanamide (CDC-801); Imidazo[1,5-a]pyrido[3,2-e]pyrazine-6(5H)-one, 9-ethyl-2-methoxy-7-methyl-5-propyl-(D-22888); 5-[3-(cyclopentyloxy)-4-methoxyphenyl]-3-[(3-methylphenyl)methyl]-, (3S,5S)-2-Piperidinon (HT-0712); 4-[1-[3,4-bis(difluoromethoxy)phenyl]-2-(3-methyl-1-oxido-4-pyridinyl)ethyl]-alpha,alpha-bis(trifluoromethyl)-Benzenemethanol (L-826141); N-(3,5-Dichloro-1-oxo-pyridin-4-yl)-4-difluormethoxy-3-cyclopropylmethoxybenzamide; (−)p-[(4aR*,10bS*)-9-Ethoxy-1,2,3,4,4a,10b-hexahydro-8-methoxy-2-methyl-benzo[s][1,6]naphthyridin-6-yl]-N,N-diisopropylbenzamide; (R)-(+)-1-(4-Brombenzyl)-4-[(3-cyclopentyloxy)-4-methoxyphenyl]-2-pyrrolidon; 3-(Cyclopentyloxy-4-methoxyphenyl)-1-(4-N'—[N-2-cyano-S-methyl-isothioureido]benzyl)-2-pyrrolidon; cis[4-Cyano-4-(3-cyclopentyloxy-4-methoxyphenyl)cyclohexan-1-carboxylic acid]; 2-carbomethoxy-4-cyano-4-(3-cyclopropylmethoxy-4-difluoromethoxyphenyl) cyclohexan-1-one; cis[4-Cyano-4-(3-cyclopropylmethoxy-4-difluormethoxyphenyl)cyclohexan-1-ol]; (R)-(+)-Ethyl[4-(3-cyclopentyloxy-4-methoxyphenyl)pyrrolidin-2-yliden]acetat; (S)-(−)-Ethyl[4-(3-cyclopentyloxy-4-methoxyphenyl)pyrrolidin-2-yliden]acetat; 9-Cyclopentyl-5,6-dihydro-7-ethyl-3-(2-thienyl)-9H-pyrazolo[3,4-c]-1,2,4-triazolo[4,3-a]pyridin; 9-Cyclopentyl-5,6-dihydro-7-ethyl-3-(tert-butyl)-9H-pyrazolo[3,4-c]-1,2,4-triazolo[4,3-a]pyridin, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast; (E)-8-[2-[4-[4-(4-Fluorophenyl)butoxy]phenyl]ethenyl]-2-(1H-tetrazol-5-yl)-4H-1-benzopyran-4-one (MEN-91507); 4-[6-Acetyl-3-[3-(4-acetyl-3-hydroxy-2-propylphenylthio)propoxy]-2-propylphenoxy]-butyric acid (MN-001); 1-(((R)-(3-(2-(6,7-Difluor-2-quinolinyl)ethenyl)phenyl)-3-(2-(2-hydroxy-2-propyl)phenyl)thio)methylcyclopropane-acetic acid; 1-(((1(R)-3(3-(2-(2,3-Dichlorthieno[3,2-b]pyridin-5-yl)-(E)-ethenyl)phenyl)-3-(2-(1-hydroxy-1-methylethyl)phenyl) propyl)thio)methyl)cyclopropane acetic acid; [2-[[2-(4-tert-Butyl-2-thiazolyl)-5-benzofuranyl]oxymethyl]phenyl] acetic acid, optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholine-4-yl)-1-oxo-2-butene-1-yl]amino}-7-cyclopropylmethoxy-quinazoline, 4-[(3-chloro-4-fluorophenyl)amino]-6-{[4-(N,N-diethylamino)-1-oxo-2-butene-1-yl]amino}-7-cyclopropylmethoxy-quinazoline, 4-[(3-chloro-4-fluorophenyl)amino]-6-{[4-(N,N-dimethylamino)-1-oxo-2-butene-1-yl]amino}-7-cyclopropylmethoxy-quinazoline, 4-[(R)-(1-phenyl-ethyl)amino]-6-{[4-(morpholine-4-yl)-1-oxo-2-butene-1-yl]amino}-7-cyclopentyloxy-quinazoline, 4-[(3-chloro-4-fluoro-phenyl)amino]-6-{[4-((R)-6-methyl-2-oxo-morpholine-4-yl)-1-oxo-2-butene-1-yl]amino}-7-cyclopropylmethoxy-quinazoline, 4-[(3-chloro-4-fluoro-phenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholine-4-yl)-1-oxo-2-butene-1-yl]amino}-7-cyclopropylmethoxy-quinazoline, 4-[(3-chloro-4-fluoro-phenyl)amino]-6-[2-((S)-6-methyl-2-oxo-morpholine-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2-butene-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-butene-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-butene-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(R)-(1-Phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2-butene-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-butene-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-butene-1-yl}amino)-7-cyclopentyloxy-quinazoline, 4-[(3-chloro-4-fluorophenyl)amino]-6-{[4-(N-cyclopropyl-N-methyl-amino)-1-oxo-2-butene-1-yl]amino}-7-cyclopentyloxy-quinazoline, 4-[(3-chloro-4-fluorophenyl)amino]-6-{[4-(N,N-dimethylamino)-1-oxo-2-butene-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-butene-1-yl]amino}-7-[(S)-(tetrahydrofuran-2-yl)methoxy]-quinazoline, 4-[(3-ethynyl-phenyl)amino]-6.7-bis-(2-methoxy-ethoxy)-quinazoline, 4-[(3-chloro-4-fluorophenyl)amino]-7-[3-(morpholine-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-butene-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholine-4-yl)-1-oxo-2-butene-1-yl]amino}-7-methoxy-quinazoline, 4-[(3-chloro-4-fluorophenyl)amino]-6-{[4-(morpholine-4-yl)-1-oxo-2-butene-1-yl]-amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-butene-1-yl}amino)-7-[(tetrahydrofuran-2-yl)methoxy]-quinazoline, 4-[(3-ethynyl-phenyl)amino]-6-{[4-(5.5-dimethyl-2-oxo-morpholine-4-yl)-1-oxo-2-butene-1-yl]amino}-quinazoline, 4-[(3-chloro-4-fluoro-phenyl)amino]-6-[2-(2.2-dimethyl-6-oxo-morpholine-4-yl)-ethoxy]-7-methoxy-quinazoline, 4-[(3-chloro-4-fluoro-phenyl)amino]-6-[2-(2.2-dimethyl-6-oxo-morpholine-4-yl)-ethoxy]-7-[(R)-(tetrahydrofuran-2-yl)methoxy]-quinazoline, 4-[(3-chloro-4-fluoro-phenyl)amino]-7-[2-(2.2-dimethyl-6-oxo-morpholine-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholine-4-yl)-piperidine-1-yl]-ethoxy}-7-methoxy-quinazoline, 4-[(3-chloro-4-fluoro-phenyl)amino]-6-[1-(tert.-butyloxycarbonyl)-piperidine-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidine-4-yloxy)-7-methoxy-quinazoline, 4-[(3-chloro-4-fluoro-phenyl)amino]-6-{1-[(morpholine-4-yl)carbonyl]-piperidine-4-yloxy}-7-methoxy-quinazoline, 4-[(3-chloro-4-fluoro-phenyl)amino]-6-{1-[(methoxymethyl)carbonyl]-piperidine-4-yloxy}-7-methoxy-quinazoline, 4-[(3-chloro-4-fluoro-phenyl)amino]-6-(piperidine-3-yloxy)-7-methoxy-quinazoline, 4-[(3-chloro-4-fluoro-phenyl)amino]-6-[1-(2-acetylamino-ethyl)-piperidine-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino-cyclohexan-1-yloxy}-7-methoxy-quinazoline, 4-[(3-chloro-4-fluoro-phenyl)amino]-6-{trans-4-[(morpholine-4-yl)carbonylamino]-cyclohexan-1-yloxy}-7-methoxy-quinazoline, 4-[(3-chloro-4-fluoro-phenyl)amino]-6-{trans-4-[(morpholine-4-yl)sulphonylamino-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidine-1-yl)carbonyl]-piperidine-4-yloxy}-7-methoxy-quinazoline, 4-[(3-chloro-4-fluoro-phenyl)amino]-6-(1-aminocarbonylmethyl-piperidine-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholine-4-yl)carbonyl]-N-methyl-amino}-cyclohexan-1-yloxy)-7-methoxy-quinazolin; 4-{2-[4-(3-chloro-4-fluoro-phenylamino)-7-methoxy-quinazolin-6-yloxy]-ethyl}-6-methyl-morpholine-2-one, 4-{4-[4-(3-chloro-2-fluoro-phenylamino)-7-methoxy-quinazolin-6-yloxy]-cyclohexyl}-1-methyl-piperazine-2-one, 4-[(3-chloro-4-fluoro-phenyl)amino]-6-(cis-4-{N-[(morpholine-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidine-4-yloxy)-7-ethoxy-quinazoline, 4-[(3-chloro-4-fluoro-phenyl)amino]-6-(1- methanesuphonyl-piperidine-4-yloxy)-7-(2-methoxy-ethoxy)-quinazoline, 4-[(3-chloro-4-fluoro-phenyl)amino]-6-[1-(2-methoxy-acetyl)-piperidine-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert-butyloxycarbonyl)-piperidine-4-yloxy-7-methoxy-quinazoline, 4-[(3-ethynyl-phenyl)amino]-6-(tetrahydropyran-4-yloxy]-7-methoxyquinazoline, 4-[(3-chloro-4-fluoro-phenyl)amino]-6-(cis-4-{N-[(piperidine-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazine-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholine-4-yl)carbonylamino-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidine-4-yloxy}-7-methoxy-quinazoline, 4-[(3-chloro-4-fluoro-phenyl)amino]-6-{1-[(morpholine-4-yl)carbonyl]-piperidine-4-yloxy}-7-(2-methoxy-ethoxy)-quinazoline, 4-[(3-ethynyl-phenyl)amino]-6-(1-acetyl-piperidine-4-yloxy)-7-methoxy-quinazoline, 4-[(3-ethynyl-phenyl)amino]-6-(1-methyl-piperidine-4-yloxy)-7-methoxy-quinazoline, 4-[(3-ethynyl-phenyl)amino]-6-(1-methanesulphonyl-piperidine-4-yloxy)-7-methoxy-quinazoline, 4-[(3-chloro-4-fluoro-phenyl)amino]-6-(1-methyl-piperidine-4-yloxy)-7(2-methoxy-ethoxy)-quinazoline, 4-[(3-chloro-4-fluoro-phenyl)amino]-6-(1-isopropyloxycarbonyl-piperidine-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl) amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidine-4-yloxy)-7-methoxy-quinazoline, 4-[(3-ethynyl-phenyl)amino]-6-[1-(2-methoxy-acetyl)-piperidine-4-yloxy]-7-methoxy-quinazoline, 4-[(3-ethynyl-phenyl)amino]-6-{1-[(morpholine-4-yl)carbonyl]-piperidine-4-yloxy}-7-methoxy-quinazoline, 4-[(3-chloro-4-fluoro-phenyl)amino]-6-{1-[(cis-2,6-dimethyl-morpholine-4-yl)carbonyl]-piperidine-4-yloxy}-7-methoxy-quinazoline, 4-[(3-chloro-4-fluoro-phenyl)amino]-6-{1-[(2-methyl-morpholine-4-yl)carbonyl]-piperidine-4-yloxy}-7-m ethoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidine-4-yloxy}-7-methoxy-quinazoline, 4-[(3-chloro-4-fluoro-phenyl)amino]-6-{1-[(N-methyl-N-2-methoxyethyl-amino)carbonyl]-piperidine-4-yloxy}-7-methoxy-quinazoline, 4-[(3-chloro-4-fluoro-phenyl)amino]-6-(1-ethyl-piperidine-4-yloxy)-7-methoxy-quinazoline, 4-[(3-chloro-4-fluoro-phenyl)amino]-6-{1-[(2-methoxyethyl)carbonyl]-piperidine-4-yloxy}-7-methoxy-quinazoline, 4-[(3-chloro-4-fluoro-phenyl)amino]-6-{1-[(3-methoxypropyl-amino)-carbonyl]-piperidine-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholine-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholine-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidine-4-yloxy)-7-methoxy-quinazoline, 4-[(3-chloro-4-fluoro-phenyl)amino]-6-(1-cyano-piperidine-4-yloxy)-7-methoxy-quinazoline, 3-Cyano-4-[(3-chlor-4-fluorphenyl)amino]-6-{[4-(N,N-dimethylamino)-1-oxo-2-butene-1-yl]amino}-7-ethoxy-quinoline, [4-[(3-chloro-4-fluoro-phenyl)amino]-6-{[4-(homo-morpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-7-(2-{4-[(S)-(2-oxo-tetrahydrofuran-5-yl)carbonyl]-piperazine-1-yl}-ethoxy)-6-[(vinylcarbonyl)amino]-quinazoline, 4-[(3-chloro-4-fluoro-phenyl)amino]-7-[2-((S)-6-methyl-2-oxo-morpholine-4-yl)-ethoxy]-6-[(vinylcarbonyl)amino]-quinazoline, 4-[(3-chloro-4-fluoro-phenyl)amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, 4-[(3-chloro-4-fluoro-phenyl)amino]-7-(2-{4-[(S)-(2-oxo-tetrahydrofuran-5-yl)carbonyl]-piperazine-1-yl}-ethoxy)-6-[(vinylcarbonyl)amino]-quinazoline, 4-[(3-chloro-4-fluoro-phenyl)amino]-7-[2-((S)-6-methyl-2-oxo-morpholine-4-yl)-ethoxy]-6-[(vinylcarbonyl)amino]-quinazoline, 4-[(3-chloro-4-fluoro-phenyl)amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, cetuximab, trastuzumab, panitumumab (=ABX-EGF), Mab ICR-62, gefitinib, pelitinib, canertinib and erlotinib, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, olopatadine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among lexipafant, 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpholinyl) carbonyl]-4H,7H-cyclo-penta-[4,5]thieno-[3,2-f][1,2,4] triazolo[4,3-a][1,4]diazepines. Any reference to the above-mentioned above-mentioned PAF-antagonists includes within the scope of the present invention a reference to any pharmacologically acceptable acid addition salts thereof which may exist.

Examples of non-steroidal anti-inflammatory drugs (NSAIDs) preferably include compounds selected from among Aceclofenac, Acemetacin, Acetylsalicylsaure, Alclofenac, Alminoprofen, Amfenac, Ampiroxicam, Antolmetinguacil, Anirolac, Antrafenin, Azapropazon, Benorilat, Bermoprofen, Bindarit, Bromfenac, Bucloxinsäure, Bucolom, Bufexamac, Bumadizon, Butibufen, Butixirat, Carbasalatcalcium, Carprofen, Cholin Magnesium Trisalicylat, Celecoxib, Cinmetacin, Cinnoxicam, Clidanac, Clobuzarit, Deboxamet, Dexibuprofen, Dexketoprofen, Diclofenac, Diflunisal, Droxicam, Eltenac, Enfenaminsäure, Etersalat, Etodolac, Etofenamat, Etoricoxib, Feclobuzon, Felbinac, Fenbufen, Fenclofenac, Fenoprofen, Fentiazac, Fepradinol, Feprazon, Flobufen, Floctafenin, Flufenaminsaure, Flufenisal, Flunoxaprofen, Flurbiprofen, Flurbiprofenaxetil, Furofenac, Furprofen, Glucametacin, Ibufenac, Ibuprofen, Indobufen, Indometacin, Indometacinfarnesil, Indoprofen, Isoxepac, Isoxicam, Ketoprofen, Ketorolac, Lobenzarit, Lonazolac, Lornoxicam, Loxoprofen, Lumiracoxib, Meclofenaminsaure, Meclofen, Mefenaminsaure, Meloxicam, Mesalazin, Miroprofen, Mofezolac, Nabumeton, Naproxen, Nifluminsaure, Olsalazin, Oxaprozin, Oxipinac, Oxyphenbutazon, Parecoxib, Phenylbutazon, Pelubiprofen, Pimeprofen, Pirazolac, Priroxicam, Pirprofen, Pranoprofen, Prifelon, Prinomod, Proglumetacin, Proquazon, Protizininsaure, Rofecoxib, Romazarit, Salicylamid, Salicylsaure, Salmistein, Salnacedin, Salsalat, Sulindac, Sudoxicam, Suprofen, Talniflumat, Tenidap, Tenosal, Tenoxicam, Tepoxalin, Tiaprofensaure, Taramid, Tilnoprofenarbamel, Timegadin, Tinoridin, Tiopinac, Tolfenaminsaure, Tolmetin, Ufenamat, Valdecoxib, Ximoprofen, Zaltoprofen und Zoliprofen.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-beta-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, glycolithocholic acid sulphate, ibuprofen, indomethacin, indoprofen, ketoprofen, lithocholic acid sulphate, methotrexate,((E)-3-[[[3-[2-(7-chloro-2-quinolinyl)ethenyl]phenyl]-[[3-dimethylamino)-3-oxopropyl]thio]methyl]thio]-propanoic acid), alpha-naphthyl-beta-D-glucuronide, nitrobenzyl mercaptopurine riboside, probenecid, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

Examples of JAK inhibitors preferably include compounds selected from among Tofacitinib and Ruxolitinib.

Examples of immunesuppressive agents preferably include compounds selected from among mycophenolate mofetil, mycophenolic acid, azathioprine, cyclosporine, tacrolimus, pimecrolimus, abetimus, gusperimus and leflunomide.

An example of a cytostaticum is cyclophosphamide.

The invention relates more preferably to the use of MRP4-inhibitors for preparing a pharmaceutical composition for treating respiratory complaints, containing the Syk-inhibitors of formula 1 and MRP4-inhibitors according to the invention, the MRP4-inhibitors preferably being selected from among dehydroepiandrosterone 3-sulphate, estradiol 3,17-disulphate, flurbiprofen, indomethacin, indoprofen, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the Syk-inhibitors of formula 1, MRP4-inhibitors and another active substance according to the invention, such as, for example, an anticholinergic, a PDE4 inhibitor, a steroid, an LTD4-antagonist or a betamimetic, and the preparation thereof and the use thereof for treating respiratory complaints.

Compounds which may be used as iNOS inhibitors are compounds selected from among: S-(2-aminoethyl)isothiourea, aminoguanidine, 2-aminomethylpyridine, 5,6-dihydro-6-methyl-4H-1,3-Thiazine-2-amine (=AMT), L-canavanine, 2-iminopiperidine, S-isopropylisothiourea, S-methylisothiourea, S-ethylisothiourea, S-methyltiocitrullin, S-ethylthiocitrulline, L-NA (N$^\omega$-nitro-L-arginine), L-NAME (N$^\omega$-nitro-L-argininemethylester), L-NMMA (N$^G$-monomethyl-L-arginine), L-NIO (N$^\omega$-iminoethyl-L-ornithine), L-NIL (N$^\omega$-iminoethyl-lysine), (S)-6-acetimidoylamino-2-aminohexanoic acid (1H-tetrazol-5-yl)-amide (SC-51) (*J. Med. Chem.* 2002, 45, 1686-1689), N-[[3-(aminomethyl)phenyl] methyl]-Ethanimidamide (=1400W), (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-trifluoromethyl-nicotinonitrile (WO 2004/041794), 2-((1R,3S)-3-amino-4-hydroxy-1-thiazol-5-yl-butylsulphanyl)-4-chloro-benzonitrile (WO 2004/041794), 2-((1R.3S)-3-amino-4-hydroxy-1-thiazol-5-yl-butylsulphanyl)-5-chloro-benzonitrile (WO 2004/041794), (2S.4R)-2-amino-4-(2-chloro-5-trifluoromethyl-phenylsulphanyl)-4-thiazol-5-yl-butan-1-ol (WO 2004/041794), 2-((1R.3S)-3-amino-4-hydroxy-1-thiazol-5-ylbutylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamine such as e.g. (1 S.5S.6R)-7-chloro-5-methyl-2-azabicyclo[4.1.0]hept-2-en-3-ylamine (ONO-1714) (*Biochem. Biophys. Res. Commun.* 2000, 270, 663-667), (4R,5R)-5-ethyl-4-methyl-thiazolidin-2-ylideneamine (*Bioorg. Med. Chem.* 2004, 12, 4101), (4R,5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chloro-phenyl)-N-(1-{2-oxo-2-[4-(6-trifluoromethyl-pyrimidin-4-yloxy)-piperidine-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-ylmethyl-phenoxy)-ethoxy]-2-phenyl-pyridine (PPA250) (*J. Pharmaco Exp. Ther.* 2002, 303, 52-57), 3-{[(benzo[1,3]dioxol-5-ylmethyl)-carbamoyl]-methyl}-4-(2-imidazol-1-yl-pyrimidin-4-yl)-piperazine-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1,3]dioxol-5-yl-ethyl)-amide (BBS-2) (*Drugs Future* 2004, 29, 45-52) and the pharmaceutical salts, prodrugs or solvates thereof.

Examples of iNOS-inhibitors within the scope of the present invention may also include antisense oligonucleotides, particularly those antisense oligonucleotides which bind iNOS-coding nucleic acids. For example, WO 01/52902 describes antisense oligonucleotides, particularly antisense oligonucleotides, which bind iNOS coding nucleic acids, for modulating the expression of iNOS. iNOS-antisense oligonucleotides as described particularly in WO 01/52902 may therefore also be combined with the PDE4-inhibitors of the present invention on account of their similar effect to the iNOS-inhibitors.

Suitable HMG-CoA reductase inhibitors (also called statins) which may be preferably used in double or triple combinations with the compounds of formula 1 are selected from among Atorvastatin, Cerivastatin, Flurvastatin, Lovastatin, Pitavastatin, Pravastatin, Rosuvastatin, Simvastatin, optionally in form of their pharmaceutically available acid addition salts, prodrugs, solvates or hydrates thereof.

8. FORMULATIONS

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain the compounds of formula 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, together with a imidazolyl-pyrimidine according to formula 1 and one or more combination partners selected from those described above.

The invention claimed is:
1. A compound, which is

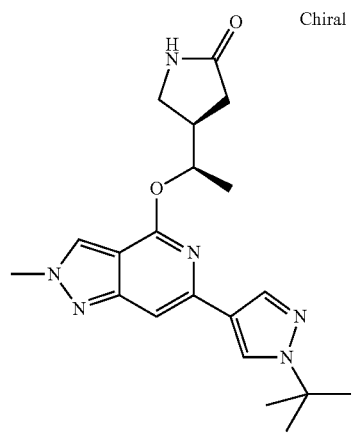 [SMILES: C[C@@H](Oc1nc(-c2cnn(C(C)(C)C)c2)cc2nn(C)cc12)[C@H]1CNC(=O)C1]

or a pharmaceutically acceptable salt thereof.

2. A compound, which is

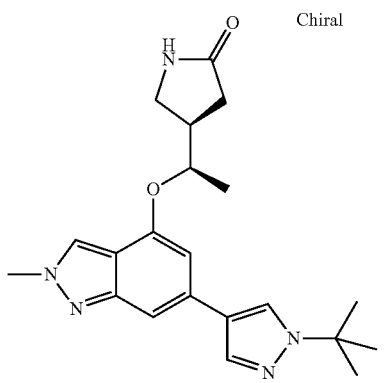 [SMILES: C[C@@H](Oc1cc(-c2cnn(C(C)(C)C)c2)cc2nn(C)cc12)[C@H]1CNC(=O)C1]

or a pharmaceutically acceptable salt thereof.

3. A method of treating asthma comprising the step of administering to a person in need thereof the compound according to claim 1 or a pharmaceutically acceptable salt thereof.

4. A method of treating COPD comprising the step of administering to a person in need thereof the compound according to claim 1 or a pharmaceutically acceptable salt thereof.

5. A pharmaceutical formulation comprising the compound according to claim 1 or a pharmaceutically acceptable salt thereof, and a pharmaceutically acceptable excipient.

6. A pharmaceutical formulation comprising the compound according to claim 2 or a pharmaceutically acceptable salt thereof, and a pharmaceutically acceptable excipient.

7. A method of treating asthma comprising the step of administering to a person in need thereof the compound according to claim 2 or a pharmaceutically acceptable salt thereof.

8. A method of treating COPD comprising the step of administering to a person in need thereof the compound according to claim 2 or a pharmaceutically acceptable salt thereof.

9. A pharmaceutical formulation comprising the compound according to claim 1, or a pharmaceutically acceptable salt thereof, in combination with an active substance selected from the group consisting of anticholinergics, betamimetics, corticosteroids, PDE4-inhibitors, EGFR-inhibitors, LTD4-antagonists, CCR3-inhibitors, iNOS-inhibitors, CRTH2-antagonists, HMG-CoA reductase inhibitors and NSAIDs.

10. A pharmaceutical formulation comprising the compound according to claim 2, or a pharmaceutically acceptable salt thereof, in combination with an active substance selected from the group consisting of anticholinergics, betamimetics, corticosteroids, PDE4-inhibitors, EGFR-inhibitors, LTD4-antagonists, CCR3-inhibitors, iNOS-inhibitors, CRTH2-antagonists, HMG-CoA reductase inhibitors and NSAIDs.

* * * * *